(12) United States Patent
Wood et al.

(10) Patent No.: US 11,427,616 B2
(45) Date of Patent: Aug. 30, 2022

(54) PCSK9 ANTAGONIST COMPOUNDS

(71) Applicant: Merck Sharp & Dohme LLC, Rahway, NJ (US)

(72) Inventors: Harold B. Wood, Westfield, NJ (US); Hubert B. Josien, Jersey City, NJ (US); Thomas Joseph Tucker, North Wales, PA (US); Angela Dawn Kerekes, Plainfield, NJ (US); Ling Tong, Warren, NJ (US); Abbas M. Walji, Lansdale, PA (US); Anilkumar G. Nair, Rahway, NJ (US); Fa-Xiang Ding, Staten Island, NJ (US); Elisabetta Bianchi, Rome (IT); Danila Branca, Pomezia (IT); Chengwei Wu, Ambler, PA (US); Yusheng Xiong, Plainsboro, NJ (US); Sookhee Nicole Ha, Warren, NJ (US); Jian Liu, Edison, NJ (US); Sobhana Babu Boga, Karnataka (IN)

(73) Assignee: Merck Sharp & Dohme LLC, Rahway, NJ (US)

( * ) Notice: Subject to any disclaimer, the term of this patent is extended or adjusted under 35 U.S.C. 154(b) by 229 days.

(21) Appl. No.: 16/446,940

(22) Filed: Jun. 20, 2019

(65) Prior Publication Data
US 2019/0389909 A1    Dec. 26, 2019

Related U.S. Application Data

(60) Provisional application No. 62/687,913, filed on Jun. 21, 2018.

(51) Int. Cl.
| | | |
|---|---|---|
| C07K 7/64 | (2006.01) | |
| A61P 3/06 | (2006.01) | |
| A61K 38/00 | (2006.01) | |

(52) U.S. Cl.
CPC .................. C07K 7/64 (2013.01); A61P 3/06 (2018.01); *A61K 38/00* (2013.01)

(58) Field of Classification Search
CPC .. C07K 7/56; A61K 38/00; A61P 3/06; C07D 487/18; C07D 498/22
See application file for complete search history.

(56) References Cited

U.S. PATENT DOCUMENTS

| | | | |
|---|---|---|---|
| 4,393,046 | A | 7/1983 | Baylis et al. |
| 2010/0041102 | A1 | 2/2010 | Sitlani et al. |
| 2012/0219558 | A1 | 8/2012 | Ni et al. |
| 2013/0158021 | A1 | 6/2013 | Dong et al. |
| 2013/0281366 | A1 | 10/2013 | Pingali et al. |
| 2017/0081383 | A1 | 3/2017 | Gruber |
| 2017/0189470 | A1 | 7/2017 | Wang et al. |
| 2018/0023071 | A1 | 1/2018 | Basak |
| 2021/0069288 | A1 | 3/2021 | Josien et al. |

FOREIGN PATENT DOCUMENTS

| | | |
|---|---|---|
| WO | WO 2010/144038 A1 | 12/2010 |
| WO | 2012/040259 A2 | 3/2012 |
| WO | WO 2012/177741 A1 | 12/2012 |
| WO | WO 2014/140210 A1 | 9/2014 |
| WO | WO 2014/150326 A1 | 9/2014 |
| WO | 2017/181061 A1 | 10/2017 |
| WO | 2017/220701 A1 | 12/2017 |
| WO | WO 2018/053517 A1 | 3/2018 |
| WO | 2019/246352 A1 | 12/2019 |
| WO | 2019/246386 A1 | 12/2019 |

(Continued)

OTHER PUBLICATIONS

Josephson et al, Drug Discovery Today, vol. 19, No. 4, Apr. 2014, 388-399 (Year: 2014).*
Zhang et al, Nature structure & molecular biology, vol. 24, No. 10, Oct. 2017, 848-856 (Year: 2017).*
Zhang et al, The Journal of Biological Chemistry, vol. 289, No. 2, Jan. 10, 2014, 942-955 (Year: 2014).*
PCT/US19/38220/WO 2019/246386, Jun. 20, 2019/Dec. 26, 2019, Alonso Ricardo.
PCT/US19/38221/WO 2019/246387, Jun. 20, 2019/Dec. 26, 2019, Alonso Ricardo.
PCT/US19/38247/WO 2020/009805, Jun. 20, 2019/Apr. 2, 2019, Alonso Ricardo.

(Continued)

*Primary Examiner* — Sudhakar Katakam
(74) *Attorney, Agent, or Firm* — Lathrop GPM LLP; Brian C. Trinque

(57) ABSTRACT

Disclosed are compounds of Formula I, or a salt thereof:

Formula I

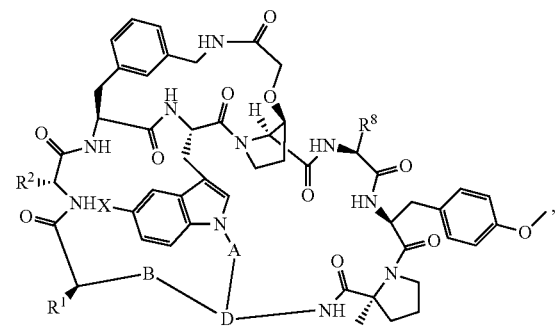

where A, B, D, X, $R^1$, $R^2$ and $R^8$ are as defined herein, which compounds have properties for antagonizing PCSK9. Also described are pharmaceutical formulations comprising the compounds of Formula I or their salts, and methods of treating cardiovascular disease and conditions related to PCSK9 activity, e.g. atherosclerosis, hypercholesterolemia, coronary heart disease, metabolic syndrome, acute coronary syndrome, or related cardiovascular disease and cardiometabolic conditions.

48 Claims, No Drawings

(56) References Cited

FOREIGN PATENT DOCUMENTS

| WO | 2019/246387 A1 | 12/2019 |
| WO | 2019/246405 A1 | 12/2019 |
| WO | WO 2019/246349 A1 | 12/2019 |
| WO | 2020/009805 A3 | 4/2020 |

OTHER PUBLICATIONS

PCT/US19/38250/WO 2019/246405, Jun. 20, 2019/Dec. 26, 2019, Alonso Ricardo.
PCT/US19/38158/WO 2019/246352, Jun. 20, 2019/Dec. 26, 2019, Harold B. Wood.
International Search Report and Written Opinion in related PCT Application No. PCT/US2020/048342, dated Nov. 18, 2020, 11 pages.
Elbitar et al., Proprotein convertase subtilisin/kexin 9 (PCSK9) inhibitors and the future of dyslipidemia therapy: an updated patent review (2011-2015), Expert Opinion on Therapeutic Patents, 2016. 26(12): 1377-1392.
Chaudhary et al., "PCSK9 inhibitors: A new era of lipid lowering therapy", World Journal of Cardiology, vol. 9, No. 2, pp. 76-91, Feb. 26, 2017.
He et al. "Lowering serum lipids via PcSK9-targeting drugs: current advances and future perspectives", ACTA Pharmacologica Sinica, vol. 38, No. 3, Jan. 23, 2017.
International Search Report and Written Opinion in related PCT Application No. PCT/US2019/038220, dated Nov. 5, 2019 (6 pages).
International Search Report and Written Opinion in related PCT Application No. PCT/US2019/038155, dated Nov. 15, 2019 (5 pages).
Umemura, M et al. "Characterization of the biosynthetic gene cluster for the ribosomally 1, 14 synthesized cyclic peptide ustiloxin B in Aspergillus flavus", Fungal Genetics and Biology, vol. 68, pp. 23-30, May 16, 2014.
International Search Report and Written Opinion in related PCT Application No. PCT/US2019/038221, dated Nov. 18, 2019 (4 pages).
Zhang, Y et al., "Identification of a Small Peptide That Inhibits PCSK9 Protein Binding to the Low Density Lipoprotein Receptor." Journal of Biological Chemistry. vol. 289, No. 2; pp. 942-955; p. 943, col. 1, paragraphs 3, 5, Jan. 13, 2014.
International Search Report and Written Opinion in related PCT Application No. PCT/US2019/038247, dated Apr. 20, 2020 (4 pages).
International Search Report and Written Opinion in related PCT Application No. PCT/US2019/038250, dated Sep. 17, 2019 (3 pages).
International Search Report and Written Opinion in related PCT Application No. PCT/US2019/038158, dated Dec. 26, 2019 (3 pages).
U.S. Appl. No. 17/253,764, filed Dec. 18, 2020, Alonso Ricardo.
PCT/US2019/038220 / WO 2019/246386, Jun. 20, 2019 / Dec. 26, 2019, Alonso Ricardo.
U.S. Appl. No. 17/253,774, filed Dec. 18, 2020, Alonso Ricardo.
PCT/US2019/038221 / WO 2019/246387, Jun. 20, 2019 / Dec. 26, 2019, Alonso Ricardo.
U.S. Appl. No. 17/253,783 2021/0163538, filed Dec. 18, 2020 Jun. 3, 2021, Alonso Ricardo.
PCT/US2019/038247 / WO 2020/009805, Jun. 20, 2019 / Apr. 2, 2019, Alonso Ricardo.
U.S. Appl. No. 17/253,864 2021/0284694, filed Dec. 18, 2020 Sep. 16, 2021, Alonso Ricardo.
PCT/US2019/038250 / WO 2019/246405, Jun. 20, 2019 / Dec. 26, 2019, Alonso Ricardo.
PCT/US2019/038155 / WO 2019/246349, Jun. 20, 2019 / Dec. 26, 2019, Harold B. Wood.
U.S. Appl. No. 17/253,815 2021/0214395, Dec. 18, 2020 Jul. 15, 2021, Yusheng Xiong.
PCT/US2019/038158 / WO 2019/246352, Jun. 20, 2019 / Dec. 26, 2019, Harold B. Wood.
U.S. Appl. No. 17/005,686 2021/0069288, filed Aug. 28, 2020 Mar. 11, 2021, Hubert Josien.
PCT/US2020/048342 WO 2021/041770, Aug. 28, 2020 / Mar. 4, 2021, Hubert Josien.
PCT/US2020/066046 WO 2021/127460, Dec. 18, 2020 Jun. 24, 2021, Hubert Josien.

* cited by examiner

PCSK9 ANTAGONIST COMPOUNDS

CROSS REFERENCE TO RELATED APPLICATION

This application claims priority to U.S. Application No. 62/687,913, filed Jun. 21, 2018, which is incorporated herein by reference in its entirety.

BACKGROUND OF THE INVENTION

The identification of compounds and/or agents that are effective in the treatment of cardiovascular affliction is highly desirable. In clinical trials, reductions in LDL cholesterol levels have been directly related to the rate of coronary events; Law et al., 2003 *BMJ* 326:1423-1427. The moderate lifelong reduction in plasma LDL cholesterol levels was found to correlate with a substantial reduction in the incidence of coronary events; Cohen et al., 2006 *N. Engl. J. Med.* 354:1264-1272. This was the case even in populations with a high prevalence of non-lipid-related cardiovascular risk factors; supra. Accordingly, there is great benefit to be reaped from the managed control of LDL cholesterol levels.

Proprotein convertase subtilisin-kexin type 9 (hereinafter called "PCSK9"), also known as neural apoptosis-regulated convertase 1 ("NARC-1"), is a proteinase K-like subtilase identified as the 9th member of the secretory subtilase family; see Seidah et al., 2003 *PNAS* 100:928-933. PCSK9 belongs to the mammalian proprotein convertase family of serine proteases and contains an N-terminal signal sequence, a prodomain, a catalytic domain, and a C-terminal domain; see Seidah et al., 2012 *Nat. Rev. Drug Discov.* 11:367-383. A study of PCSK9 transcriptional regulation demonstrated that it is regulated by sterol regulatory element-binding proteins ("SREBP"), as seen with other genes involved in cholesterol metabolism; Maxwell et al., 2003 *J. Lipid Res.* 44:2109-2119, as is typical of other genes implicated in lipoprotein metabolism; Dubuc et al., 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

While in the endoplasmic reticulum, PCSK9 performs as its only catalytic activity an autocleavage between residues Gln-152 and Ser-153, see Naureckiene et al., 2003 *Arch. Biochem. Biophys.* 420:55-67; Seidah et al., 2003 *Proc. Natl. Acad. Sci. U.S.A.* 100:928-933. The prodomain remains tightly associated with the catalytic domain during subsequent trafficking through the trans-Golgi network. The maturation via autocleavage has been demonstrated to be critical for PCSK9 secretion and subsequent extracellular function (see Benjannet et al., 2012 *J. Biol. Chem.* 287:33745-33755). Accordingly, several lines of evidence demonstrate that PCSK9, in particular, lowers the amount of hepatic LDLR protein and thus compromises the livers ability to remove LDL cholesterol from the circulation.

Adenovirus-mediated overexpression of PCSK9 in the liver of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park et al., 2004 *J. Biol. Chem.* 279:50630-50638; and Lalanne et al., 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 *PNAS* 102:5374-5379; and Graham et al., 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

Thus, identification of compounds and/or agents effective in the treatment of cardiovascular affliction is highly desirable, including antagonism of PCSK9's role in LDL regulation, however, in general, because PCSK9 circulates in blood and has modest binding affinity to cell surface LDL receptors here-to-fore attempts to utilize this mechanism in treatment of diseases related to high serum LDL levels have been focused on the use of large biomolecules, for example, antibodies. Accordingly, there is scant publication reflecting activity toward this target using small peptides or small molecules to inhibit PCSK9, see for example, Zhang et al., 2014 J. Biol. Chemistry, 289(2): 942-955. Moreover, there is a paucity of compounds which are amenable to formulation into a dosage form for utilizing an oral administration route of dosing such compounds, a route which would be highly desirable for the provision of therapy for conditions in which regulation of the activities of PCSK9 could play a role.

The present invention advances these interests by providing antagonists of PCSK9 which are believed to be of use for inhibiting the activities of PCSK9 and the corresponding role PCSK9 plays in various conditions for which the administration of a PCSK9 antagonist provides therapy.

SUMMARY OF THE INVENTION

In one aspect the invention provides a compound of Formula I:

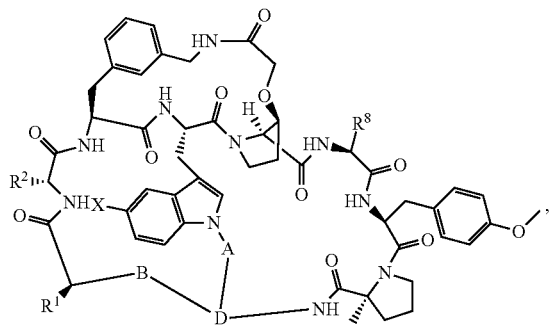

Formula I wherein:
X is H, F, Cl or Br;
$R^1$ is selected from:
(a) —H; or
(b) —(CH$_2$)$_z$—R$^{14A}$, wherein: z is 1-6, and R$^{14A}$ is:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$, or —N$^+$(CH$_3$)$_3$;
  (vi) —NH—C(O)—[(CH$_2$)$_{y12}$—O—]$_2$—(CH$_2$)$_{y13}$R$^{14B}$
  wherein:
    y12 and y13 are not both 2 and are independently 2 to 4; and
    R$^{14B}$ is: —NH$_2$; —N$^+$H$_3$; —N(CH$_3$)$_2$, or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{za}$—N$^+$(CH$_3$)$_3$, wherein za is 3 or 4; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$,
    (aii) —N$^+$(CH$_3$)$_3$, or
    (aiii) a moiety of the formula:

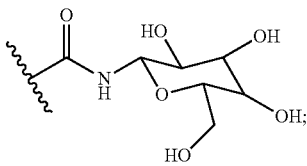 [SMILES: *C(=O)NC1OC(CO)C(O)C(O)C1O]

$R^2$ is selected from:
(a) —H; and
(b) —(CH$_2$)$_z$—R$^{14A}$, wherein: z is 1-6, and R$^{14A}$ is selected from:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$, or —N$^+$(CH$_3$)$_3$;
  (vi) —NH—C(O)—[(CH$_2$)$_{y12}$—O—]$_2$—(CH$_2$)$_{y13}$R$^{14B}$
  wherein:
    y12 and y13 are not both 2 and are independently 2 to 4; and
    R$^{14B}$ is: —NH$_2$; —N$^+$H$_3$; —N(CH$_3$)$_2$, or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{zb}$—N$^+$(CH$_3$)$_3$, wherein zb is 3 or 4; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$;
    (aii) —N$^+$(CH$_3$)$_2$R$^{14ca}$, wherein R$^{14ca}$ is —CH$_3$ or —(CH$_2$)$_{1-4}$—OCH$_3$;
    (aiii) a moiety of the formula:

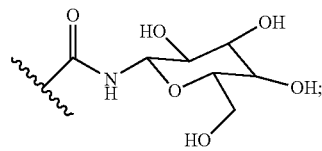 [SMILES: *C(=O)NC1OC(CO)C(O)C(O)C1O]

or
(aiv) a moiety of the formula:

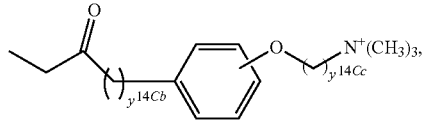

where R$^{14Cb}$ and R$^{14Cc}$ are 1 to 4; or
$R^1$ and $R^2$ may be bonded together to form a moiety of the formula:

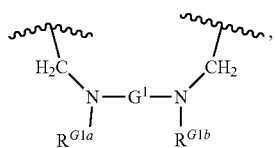

wherein:
$G^1$, $R^{G1a}$ and $R^{G1b}$ are defined as follows:
(a) $G^1$ is a linker moiety of the formula:

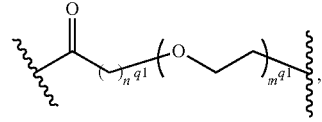

wherein $n^{q1}$ is 1 to 6, $m^{q1}$ is 0, 1 or 2 and together the value of $n^{q1}$ and $m^{q1}$ are selected such that the length of the linker moiety they define does not exceed a total of 8 carbon and/or oxygen atoms comprising the chain including the carbon atom in the chain that forms the carbonyl moiety;
$R^{G1a}$ is selected from: (i) —H; and (ii) alkyl of up to 4 carbon atoms; and $R^{G1b}$ is selected from:
(i) a moiety of the formula:

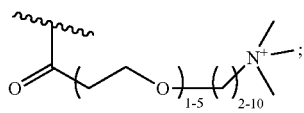

and
(ii) a moiety of the formula:

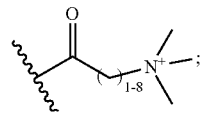

or
(b) $G^1$ is a linker moiety of the formula:

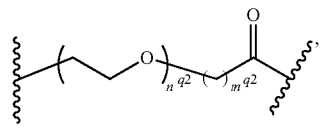

wherein $n^{q2}$ is 0, 1 or 2, $m^{q2}$ is 1 to 6, and together the value of $n^{q2}$ and $m^{q2}$ are selected such that the length of the linker moiety they define does not exceed a total of 8 carbon and/or oxygen atoms comprising the chain including the carbon atom in the chain that forms the carbonyl moiety;
$R^{G1a}$ is selected from:
(i) a moiety of the formula:

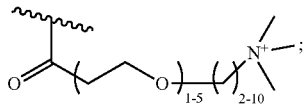

and
(ii) a moiety of the formula:

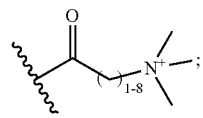

and
$R^{G1b}$ is selected from: (i) —H; and (ii) alkyl of up to 4 carbon atoms;
$R^8$ is —$CH_3$ or a moiety of the formula:

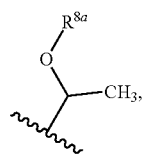

wherein $R^{8a}$ is —H, or a linear, branched or cyclic alkyl of up to four carbon atoms;
A is selected from:
(a) a moiety of the formula:

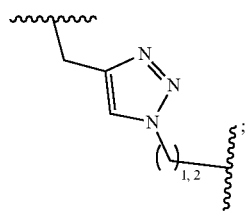

(b) —$CH_2$—$(CH_2)_y$—$CH_2$—, wherein y is 1 to 6;
(c) a moiety of the formula:

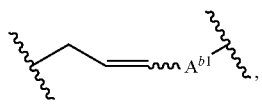

wherein $A^{b1}$ is:
(i) a moiety of the formula:

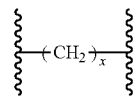

wherein x is 1 to 6; or
(ii) a moiety of the formula:

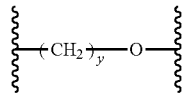

wherein y is 1 to 5;
(d) a moiety of the formula: —$CH_2$—$(CH_2)_m$—O—$(CH_2)_n$—, wherein m=1 to 5, and n=0 or 1 to 4;
B is:
(a) a bond;
(b) —$(CH_2)_{1-4}$, or
(c) a moiety of the formula:

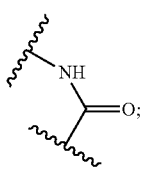 [SMILES: *NC(*)=O]

D is:
(a) a moiety of the Formula:

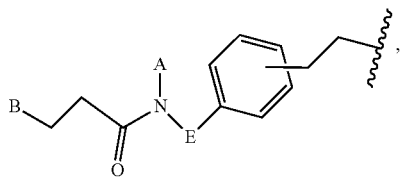

wherein E is —CH$_2$— or —(CH$_2$)$_{2-4}$—O—, and A and B are as defined above;
(b) a moiety of the formula:

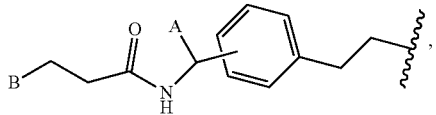

wherein A and B are as defined above;
(c) a moiety of the formula:

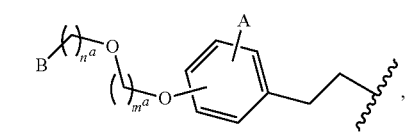

wherein n$^a$ is 1, 2, or 3, m$^a$ is 2, 3, or 4, and n$^a$+m$^a$ is ≥3, and wherein A and B are as defined above;
(d) a moiety of the formula:

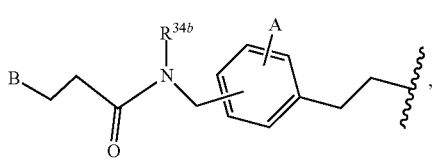

wherein, R$^{34b}$ is —H or a liner, branched or cyclic alkyl of up to four carbon atoms, and A and B are as defined above,
or a pharmaceutically acceptable salt of any thereof.

In a further embodiment, the invention provides a compound of Formula I, wherein X is F, or a pharmaceutically acceptable salt of any thereof. In some embodiments, it is preferred for D to be a moiety of the formula:

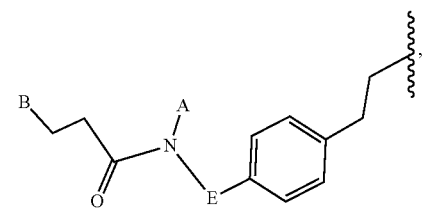

wherein, E is —CH$_2$— or —(CH$_2$)$_2$—O—, and A and B are as defined herein.

In some embodiments, it is preferred for D to be a moiety of the formula:

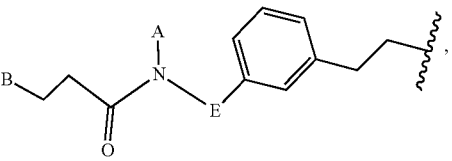

wherein, E is —CH$_2$— or —(CH$_2$)$_2$—O—, and A and B are as defined herein.

In some embodiments it is preferred for D to be a moiety of the Formula:

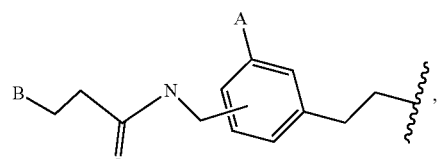

wherein A and B are as defined herein.

In some embodiments, it is preferred for D to be a moiety of the formula:

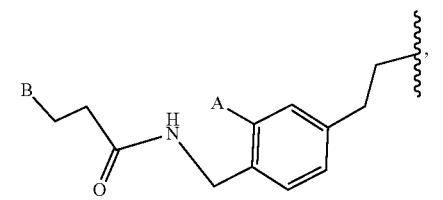

wherein A and B are as defined herein.

In some embodiments, it is preferred for D to be a moiety of the formula:

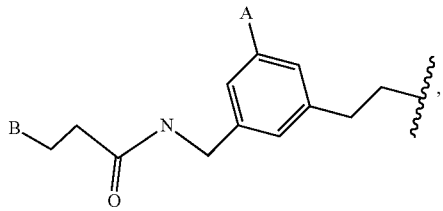

wherein A and B are as defined herein.

In some embodiments, it is preferred for D to be a moiety of the formula:

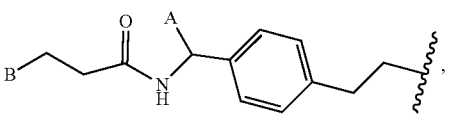

wherein A and B are as defined herein.

In some embodiments, it is preferred for D to be a moiety of the formula:

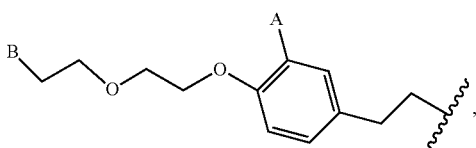

wherein A and B are as defined herein.

In some embodiments, it is preferred for D to be a moiety of the formula:

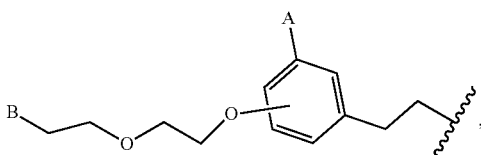

wherein A and B are as defined herein.

In some embodiments wherein $R^1$ and $R^2$ are joined together, along with the peptide ring to which they are attached forming thereby a cyclic structure, it is preferred for $R^1$ and $R^2$ to form a moiety of the structure:

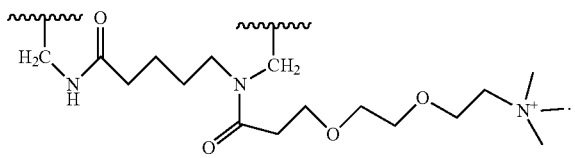 [SMILES: *CNC(=O)CCCCN(C*)C(=O)CCOCCOCC[N+](C)(C)C]

In one embodiment the present invention provides pharmaceutical compositions comprising a compound of the invention, for example, a compound of Formula I, and at least one pharmaceutical excipient, preferably a composition directed to oral administration.

In one aspect the present invention provides a method of antagonizing PCSK9 in the provision of therapy for disease states related to PCSK9 activity, for example, atherosclerosis, hypercholesterolemia, coronary heart disease, metabolic syndrome, acute coronary syndrome, or related cardiovascular disease and cardiometabolic conditions, by administering to a subject in need thereof a therapeutically effective amount of a compound of Formula I, or a salt thereof, preferably in the form of a pharmaceutical composition.

DETAILED DESCRIPTION OF THE INVENTION

In the description that follows conventional structural representation is employed and includes conventional stereochemical notation for certain asymmetric carbon centers.

Thus, structural representation of compounds of the invention includes conventional stereochemical notation for some asymmetric carbon centers shown in the example compounds. Accordingly, in such instances, solid black "wedge" bonds represent bonds projecting from the plane of the reproduction medium, "hashed wedge" bonds representing descending bonds into the plane of the reproduction medium, and a "wavy" line appended to a carbon bearing a double bond indicates both possible cis and trans orientations are included. As is conventional, plain solid lines represent all spatial configurations for the depicted bonding. Accordingly, where no specific stereochemical notation is supplied, the representation contemplates all stereochemical and spatial orientations of the structural features.

As is shown in the examples of the invention, and mentioned above, particular asymmetric carbon centers are structurally represented using conventional "Solid Wedge" and "Hash Wedge" bonding representation. For the most part, absolute configuration has not been determined for the example compounds, but has been assigned by analogy to specific example compounds of known stereochemical configurations (determined by X-ray crystallography) prepared using the same or analogous reaction conditions and starting reagents and isolated under the same chromatographic conditions. Accordingly, specific assignment of the configurations structurally represented herein is meant to identify the specific compounds prepared has having an excess of one particular stereoisomer and is not put forth herein necessarily as being a statement of the absolute determination of the stereochemical structure of said compound unless otherwise noted in the data presented.

It will be appreciated that where isomeric mixtures are obtained, the preparation of individual stereoisomers in significant percentages of enantiomeric excess can be carried out, if desired, by separation of the mixture using customary methods, for example by chromatography or crystallization, or by the use of stereochemically uniform starting materials for the synthesis described, or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product.

Where indicated herein, absolute stereochemistry is determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. The present invention is meant to include all suitable isotopic variations of the compounds of Formula I.

Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$, and $^{125}I$. It will be appreciated that other isotopes may be incorporated by known means also.

In particular, certain isotopically-labeled compounds of the invention (e.g., those labeled with $^3H$, $^{11}C$, and $^{14}C$) are recognized as being particularly useful in compound and/or substrate tissue distribution assays using a variety of known techniques. Additionally, compounds of the invention contemplate isotopic substitution include different isotopic forms of hydrogen (H), including protium ($^1H$) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Where a wavy line terminates a conventional bond (as opposed to connecting two atoms within a structure) it indicates a point of bonding to a structure, e.g.:

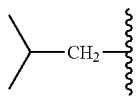

indicates a the secondary-butyl moiety is bonded via the methylene group via the bond terminated with the wavy line. Where an alphabetical notation is used to depict a substituent moiety, a dash is employed to indicate the point of bonding to the indicated substrate, e.g.: —CH$_2$—C(O)—CH$_2$Cl indicates the acetyl chloride moiety is bonded via the methylene portion of the moiety.

When any variable (e.g., n, R$^a$, R$^b$, etc.) occurs more than one time in any constituent or in Formula I, its definition on each occurrence is independent of its definition at every other occurrence unless otherwise specified at the point of definition. One of ordinary skill in the art will recognize that choice of combinations of the various substituents defined in a structural representation, i.e. R$^1$, R$^4$, etc., are to be chosen in conformity with well-known principles of chemical structure connectivity and stability, and combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Where any variable or moiety is expressed in the form of a range, e.g. (—CH$_2$—)$_{1-4}$, both of the extremes of the specified range are included (i.e. 1 and 4 in the example) as well as all of the whole number values in between (i.e. 2 and 3 in the example).

The term "halogen" includes fluorine, chlorine, bromine and iodine unless specified otherwise at the point of use.

As the term is used herein, "subjects" (alternatively "patients") refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In some embodiments the subject is preferably a human. As used herein, the term "administration" and variants thereof (e.g., "administering" a compound) in reference to a compound of Formula I means providing the compound, or a pharmaceutically acceptable salt thereof, to a subject in need of treatment.

As mentioned above, in one aspect the present invention includes the provision of compounds of Formula I, or a pharmaceutically acceptable salt thereof, which have properties that antagonize PCSK9 function.

In an embodiment, the compounds of Formula I have the structure of Formula IA:

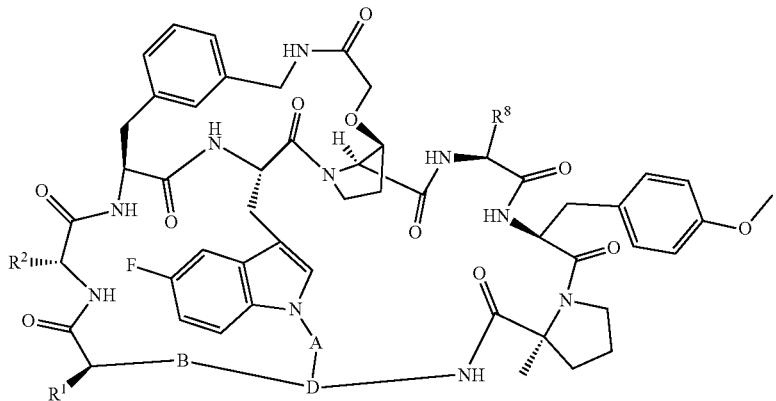

Formula IA wherein:
R$^1$ is selected from:
(a) —H; or
(b) —(CH$_2$)$_z$—R$^{14A}$, wherein: z is 1-6, and R$^{14A}$ is:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$, or —N$^+$(CH$_3$)$_3$;
  (vi) —NH—C(O)—[(CH$_2$)$_{y12}$—O—]$_{1-4}$—(CH$_2$)$_{y13}$R$^{14B}$, preferably —NH—C(O)—[(CH$_2$)$_{y12}$—O—]$_2$—(CH$_2$)$_{y13}$R$^{14B}$ wherein:
    y12 and y13 are not both 2 and are independently 2 to 4; and
    R$^{14B}$ is: —NH$_2$; —N$^+$H$_3$; —N(CH$_3$)$_2$; or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{za}$—N$^+$(CH$_3$)$_3$, wherein za is 3 or 4; and
  (viii) —NH—C(O)—(CH$_2$)$_y$R$^{14C}$, wherein, y=1 to 6 and R$^{14C}$ is:

(ai) —O—(CH$_2$)$_2$—N$^+$(CH$_3$)$_3$;
(aii) —N$^+$(CH$_3$)$_3$; or
(aiii) a moiety of the formula:

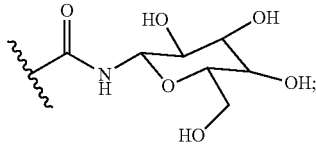

R$^2$ is selected from:
(a) —H; and
(b) —(CH$_2$)$_z$—R$^{14A}$, wherein: z is 1-6, and R$^{14A}$ is selected from:
(i) —H;
(ii) —NH$_2$;
(iii) —N$^+$H$_3$;
(iv) —N$^+$(H$_3$C)$_3$;
(v) —NH—C(O)—[(CH$_2$)$_2$—O—]$_{1-4}$—(CH$_2$)$_2$R$^{14B}$, preferably —NH—C(O)—[(CH$_2$)$_2$—O—]$_2$—(CH$_2$)$_2$R$^{14B}$ wherein R$^{14B}$ is: —NH$_2$; —N(CH$_3$)$_2$, or —N$^+$(CH$_3$)$_3$;
(vi) —NH—C(O)—[(CH$_2$)$_2$—O—]$_{1-4}$—(CH$_2$)$_{y13}$R$^{14B}$ wherein:
y12 and y13 are not both 2 and are independently 2 to 4; and
R$^{14B}$ is: —NH$_2$; —N(CH$_3$)$_2$, or —N$^+$(CH$_3$)$_3$;
(vii) —NH—C(O)—(CH$_2$)$_y$R$^{14C}$, wherein, y=1 to 6 and R$^{14C}$ is —O—(CH$_2$)$_{zb}$—N$^+$(CH$_3$)$_3$, wherein zb is 3 or 4; and
(viii) —NH—C(O)—(CH$_2$)$_y$R$^{14C}$, wherein, y=1 to 6 and R$^{14C}$ is:
(ai) —O—(CH$_2$)$_2$—N$^+$(CH$_3$)$_3$;
(aii) —N$^+$(CH$_3$)$_2$R$^{14ca}$, wherein R$^{14ca}$ is —CH$_3$ or —(CH$_2$)$_{1-4}$—OCH$_3$;
(aiii) a moiety of the formula:

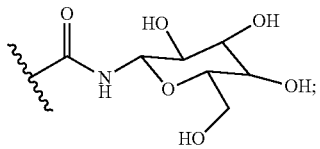 [SMILES: *C(=O)NC1OC(CO)C(O)C(O)C1O]

or
(aiv) a moiety of the formula:

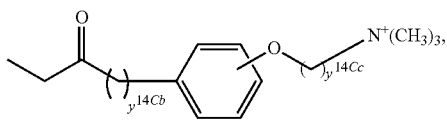

where Y$^{14Cb}$ and Y$^{14Cc}$ are 1 to 4; or
R$^1$ and R$^2$ may be bonded together to form a moiety of the formula:

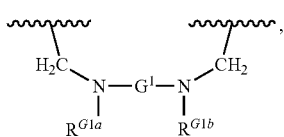

wherein:
G$^1$, R$^{G1a}$ and R$^{G1b}$ are defined as follows:
(a) G$^1$ is a linker moiety of the formula:

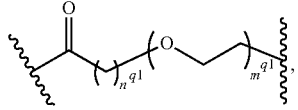

wherein n$^{q1}$ is 1 to 6, m$^{q1}$ is 0, 1 or 2 and together the value of n$^{q1}$ and m$^{q1}$ are selected such that the length of the linker moiety they define does not exceed a total of 8 carbon and/or oxygen atoms comprising the chain including the carbon atom in the chain that forms the carbonyl moiety;
R$^{G1a}$ is selected from: (i) —H; and (ii) alkyl of up to 4 carbon atoms; and
R$^{G1b}$ is selected from:
(i) a moiety of the formula:

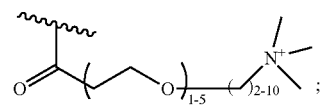

and
(ii) a moiety of the formula:

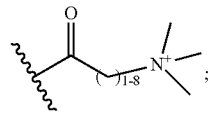

or
(b) G$^1$ is a linker moiety of the formula:

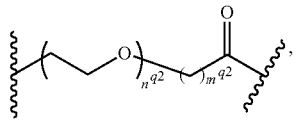

wherein n$^{q2}$ is 0, 1 or 2, m$^{q2}$ is 1 to 6, and together the value of n$^{q2}$ and m$^{q2}$ are selected such that the length of the linker moiety they define does not exceed a total of 8 carbon and/or oxygen atoms comprising the chain including the carbon atom in the chain that forms the carbonyl moiety;
R$^{G1a}$ is selected from:
(i) a moiety of the formula:

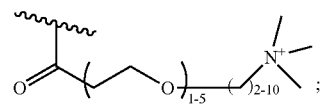

and
(ii) a moiety of the formula:

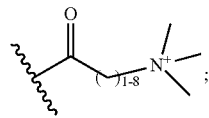

and
$R^{G1b}$ is selected from: (i) —H; and (ii) alkyl of up to 4 carbon atoms;
$R^8$ is —CH$_3$ or a moiety of the formula:

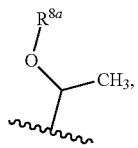

wherein $R^{8a}$ is —H, or a linear, branched or cyclic alkyl of up to four carbon atoms;
A is selected from:
(a) a moiety of the formula:

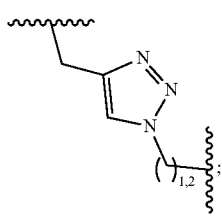

(b) —CH$_2$—(CH$_2$)$_y$—CH$_2$—, wherein y is 1 to 6;
(c) a moiety of the formula:

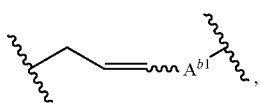

wherein $A^{b1}$ is:
(i) a moiety of the formula:

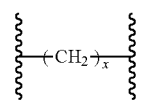

wherein x is 1 to 6; or
(ii) a moiety of the formula:

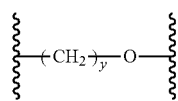

wherein y is 1 to 5;
(d) a moiety of the formula: —CH$_2$—(CH$_2$)$_m$—O—(CH$_2$)$_n$—, wherein m=1 to 5, and n=0 or 1 to 4;

B is:
(a) a bond;
(b) —(CH$_2$)$_{1-4}$, or
(c) a moiety of the formula:

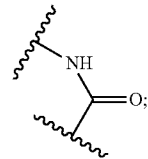 [SMILES: *NC(*)=O]

D is:
(a) a moiety of the Formula:

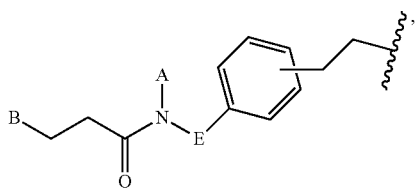

wherein E is —CH$_2$— or —(CH$_2$)$_{2-4}$—O—, and A and B are as defined above;
(b) a moiety of the formula:

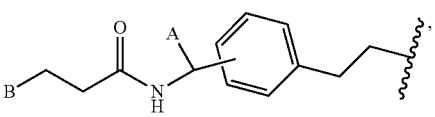

wherein A and B are as defined above;
(c) a moiety of the formula:

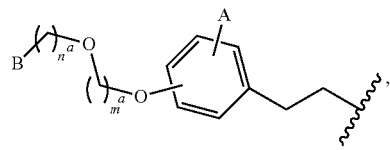

wherein $n^a$ is 1, 2, or 3, $m^a$ is 2, 3, or 4, and $n^a+m^a$ is at least 3, and wherein A and B are as defined above;
(d) a moiety of the formula:

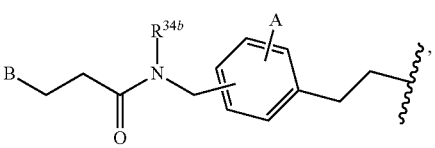

wherein, $R^{34b}$ is —H or a liner, branched or cyclic alkyl of up to four carbon atoms, and A and B are as defined above,
or a pharmaceutically acceptable salt of any thereof.
In an embodiment of the compounds of Formula IA, $R^1$ is —(CH$_2$)$_z$—$R^{14A}$, wherein: z is 1-6, and $R^{14A}$ is:
(i) —H;
(ii) —NH$_2$;
(iii) —N$^+$H$_3$; or
(iv) —N$^+$(H$_3$C)$_3$;

$R^2$ is —$(CH_2)_z$—$R^{14A}$, wherein: z is 1-6, and $R^{14A}$ is selected from:
- (i) —H;
- (ii) —$NH_2$;
- (iii) —NH—C(O)—$[(CH_2)_2$—O—$]_{1-4}$—$(CH_2)_2R^{14B}$, preferably —NH—C(O)—$[(CH_2)_2$—O—$]_2$—$(CH_2)_2$ $R^{14B}$ wherein $R^{14B}$ is: —$NH_2$; —$N^+H_3$; —$N(CH_3)_2$, or —$N^+(CH_3)_3$;
- (iv) —NH—C(O)—$[(CH_2)_{y12}$—O—$]_2$—$(CH_2)_{y13}R^{14B}$ wherein:
  - y12 and y13 are not both 2 and are independently 2 to 4; and
  - $R^{14B}$ is: —$NH_2$; —$N^+H_3$; —$N(CH_3)_2$, or —$N^+(CH_3)_3$;
- (v) —NH—C(O)—$(CH_2)_yR^{14C}$, wherein, y=1 to 6 and $R^{14C}$ is —O—$(CH_2)_{zb}$—$N^+(CH_3)_3$, wherein zb is 3 or 4; and
- (vi) —NH—C(O)—$(CH_2)_yR^{14C}$, wherein, y=1 to 6 and $R^{14C}$ is:
  - (ai) —O—$(CH_2)_2$—$N^+(CH_3)_3$;
  - (aii) —$N^+(CH_3)_2R^{14ca}$, wherein $R^{14ca}$ is —$CH_3$ or —$(CH_2)_{1-4}$—$OCH_3$;
  - (aiii) a moiety of the formula:

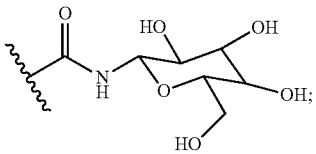 [SMILES: *C(=O)NC1OC(CO)C(O)C(O)C1O]

or
  - (aiv) a moiety of the formula:

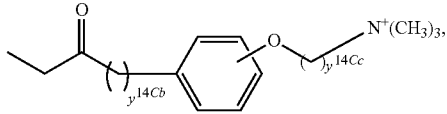

where $Y^{14Cb}$ and $Y^{14Cc}$ are 1 to 4; or
$R^8$ is —$CH_3$ or a moiety of the formula:

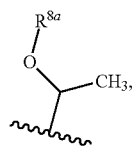

wherein $R^{8a}$ is —H, or a linear, branched or cyclic alkyl of up to four carbon atoms;

A is selected from:
- (a) a moiety of the formula:

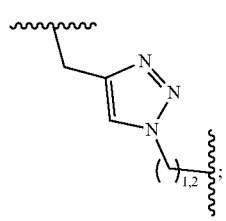

- (b) —$CH_2$—$(CH_2)_y$—$CH_2$—, wherein y is 1 to 6;
- (c) a moiety of the formula:

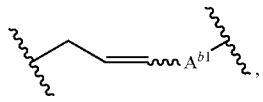

wherein $A^{b1}$ is:
- (i) a moiety of the formula:

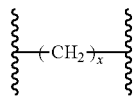

wherein x is 1 to 6; or
- (ii) a moiety of the formula:

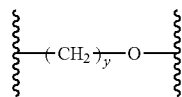

wherein y is 1 to 5; and
- (d) a moiety of the formula: —$CH_2$—$(CH_2)_m$—O—$(CH_2)_n$—, wherein m=1 to 5, and n=0 or 1 to 4;

B is:
- (a) —$(CH_2)_{1-4}$, or
- (b) a moiety of the formula:

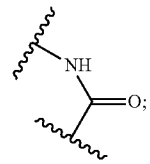 [SMILES: *NC(*)=O]

D is:
- (a) a moiety of the Formula:

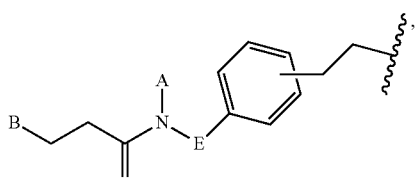

wherein E is —$CH_2$— or —$(CH_2)_{2-4}$—O—, and A and B are as defined above;
- (b) a moiety of the formula:

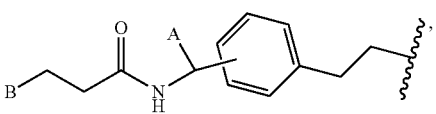

wherein A and B are as defined above; or (c) a moiety of the formula:

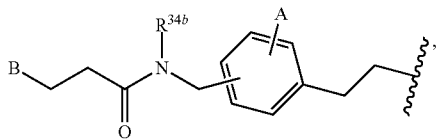

wherein, $R^{34b}$ is —H or a liner, branched or cyclic alkyl of up to four carbon atoms, and A and B are as defined above,
or a pharmaceutically acceptable salt of any thereof.

In an embodiment of the compound of Formula IA, D is a moiety of the formula:

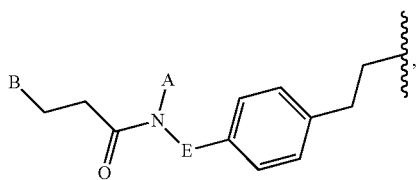

wherein, E is —CH$_2$— or —(CH$_2$)$_2$—O—, and A and B are as defined above in Formula IA.

In an embodiment of the compound of Formula IA, A is:
(a) —(CH$_2$)$_6$,
(b) a moiety of the formula:

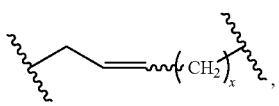

wherein x is 1 to 3; or
(c) a moiety of the formula:

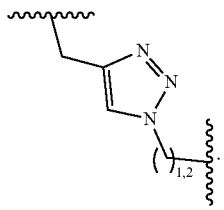

In another embodiment of the compound of Formula IA, $R^2$ is:
(a) —(CH$_2$)$_z$—R$^{14A}$, wherein: z is 1-6, and R$^{14A}$ is:
   (a) —H;
   (b) —CH$_3$;
   (c) —NH$_2$;
   (d) —N$^+$H$_3$;
   (e) —N$^+$(H$_3$C)$_3$;
   (f) —NH—C(O)—[(CH$_2$)$_{2-4}$—O—]$_{2-4}$—(CH$_2$)$_{2-4}$R$^{14B}$ wherein R$^{14B}$ is: —NH$_2$; —N$^+$H$_3$; —N(CH$_3$)$_2$, or —N$^+$(CH$_3$)$_3$;
   (g) —NH—C(O)—[(CH$_2$)$_y$R$^{14C}$, wherein, y=1 to 6 and R$^{14C}$ is:
      (ai) —O—(CH$_2$)$_{2-4}$—N$^+$(CH$_3$)$_3$;
      (aii) —N$^+$(CH$_3$)$_3$; or (aiii) a moiety of the formula:

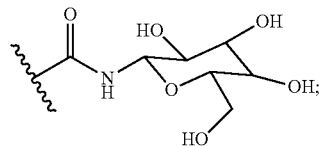 [SMILES: *C(=O)NC1OC(CO)C(O)C(O)C1O]

or
(b) a moiety of the formula

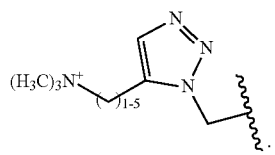

In a further embodiment of the compound of Formula IA, $R^1$ is selected from:
(a) —H;
(b) —(CH$_2$)$_z$—R$^{14A}$, wherein: z is 1-6, and R$^{14A}$ is:
   (i) —H;
   (ii) —N$^+$H$_3$; or
   (iii) —NH—C(O)—[(CH$_2$)$_2$—O—]$_2$—(CH$_2$)$_2$—N$^+$(CH$_3$)$_3$.

In yet another embodiment of the compound of Formula IA, A is —CH$_2$—(CH$_2$)$_y$—CH$_2$—, wherein y is 3-5. In a further embodiment, A is —(CH$_2$)$_6$.

In another embodiment of the compound of Formula IA, B is a moiety of the formula:

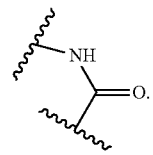 [SMILES: *NC(*)=O]

In another embodiment of the compound of Formula IA, $R^1$ is —(CH$_2$)$_z$—R$^{14A}$, wherein: z is 1-6, and R$^{14A}$ is —H. In another embodiment of the compound of Formula IA, $R^1$ is —(CH$_2$)$_z$—R$^{14A}$, wherein: z is 1, and R$^{14A}$ is —H.

In another embodiment of the compound of Formula IA, $R^2$ is —(CH$_2$)$_z$—R$^{14A}$, wherein: z is 1-6, and R$^{14A}$ is —NH—C(O)—(CH$_2$)$_y$R$^{14C}$, wherein y=1 to 6 and R$^{14C}$ is —N$^+$(CH$_3$)$_2$R$^{14ca}$, wherein R$^{14ca}$ is —CH$_3$.

In another embodiment of the compound of Formula IA, $R^8$ is a moiety of the formula:

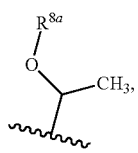

wherein $R^{8a}$ is —H or linear alkyl of up to four carbon atoms. In a further embodiment, $R^8$ is a moiety of the formula:

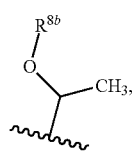

wherein $R^{8b}$ is —H, —CH$_3$, or —C(CH$_3$)$_3$.

In some embodiments, it is preferred for the compounds of Formula I to have the structure of Formula II or Formula IIA, or a pharmaceutically acceptable salt thereof:

Formula II

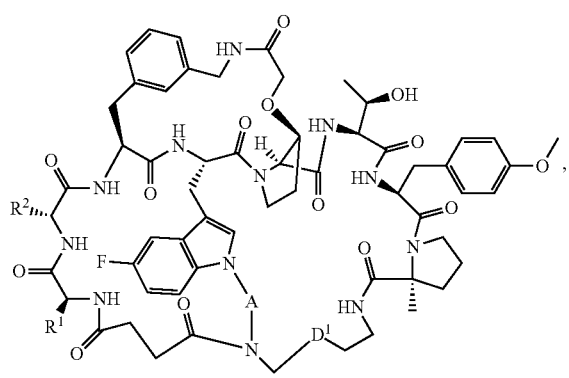

Formula IIA

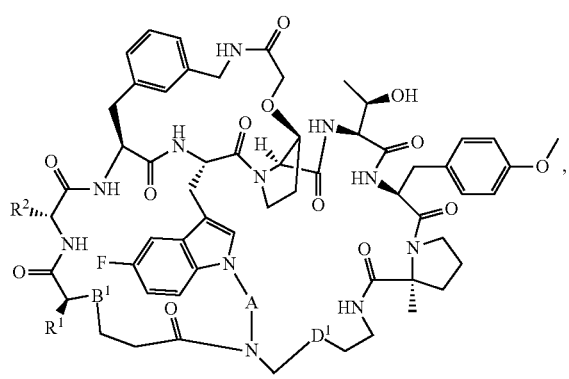

wherein, A, $R^1$ and $R^2$ are as defined above in Formula IA and $B^1$ is —(CH$_2$)$_{0-2}$, and $D^1$ is selected from:

a) a moiety of the formula:

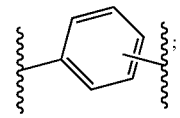

and b) a moiety of the formula:

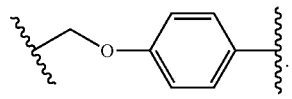 [SMILES: *COc1ccc(*)cc1]

In some embodiments of Formula II or Formula IIA, it is preferred for $D^1$ to be a moiety of the formula:

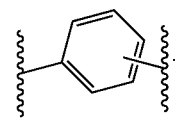

In some embodiments Formula II or Formula IIA, it is preferred for $D^1$ to be a moiety of the formula:

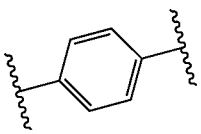 [SMILES: *c1ccc(*)cc1]

In some embodiments of Formula II or Formula IIA, it is preferred for $D^1$ to be a moiety of the formula:

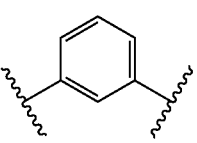 [SMILES: *c1cccc(*)c1]

In some embodiments of Formula II or Formula IIA, it is preferred for $D^1$ to be a moiety of the formula:

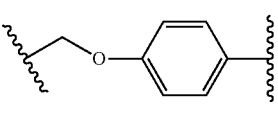 [SMILES: *COc1ccc(*)cc1]

In some embodiments, the compound of Formula I is preferably a compound of Formula III:

Formula III

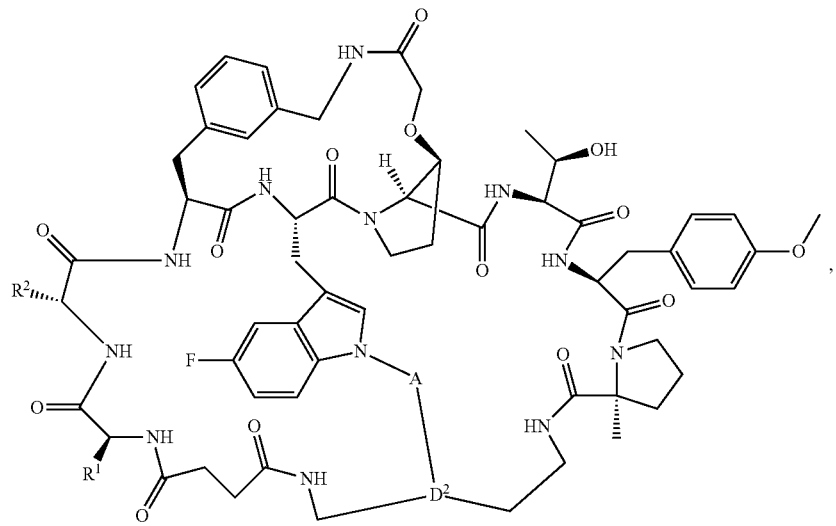

wherein, A, R$^1$ and R$^2$ are as defined above in Formula IA and D$^2$ is a moiety of the formula:

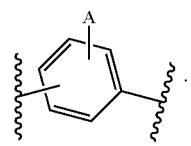

In some embodiments of Formula III, it is preferred for D$^2$ to be a moiety of the formula:

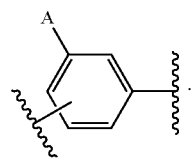

In some embodiments of Formula III, it is preferred for D$^2$ to be a moiety of the formula:

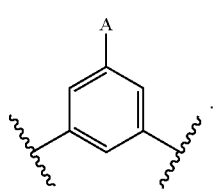

In some embodiments of Formula III, it is preferred for D$^2$ to be a moiety of the formula:

In some embodiments, it is preferred for the compounds of Formula I to have the structure of Formula IID, or a pharmaceutically acceptable salt thereof:

Formula IID

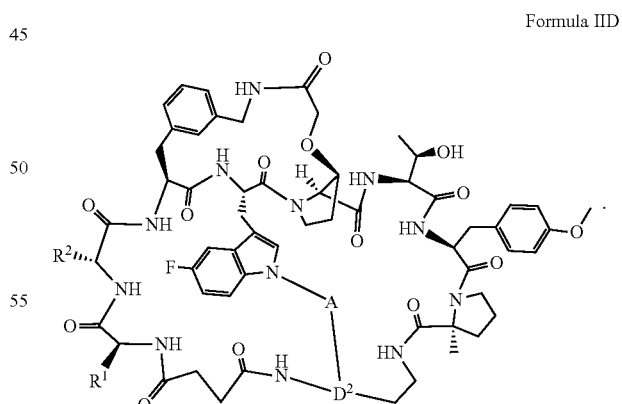

In some embodiments, it is preferred for the compounds of Formula I to have the structure of Formula IIE, or a pharmaceutically acceptable salt thereof:

Formula IIE
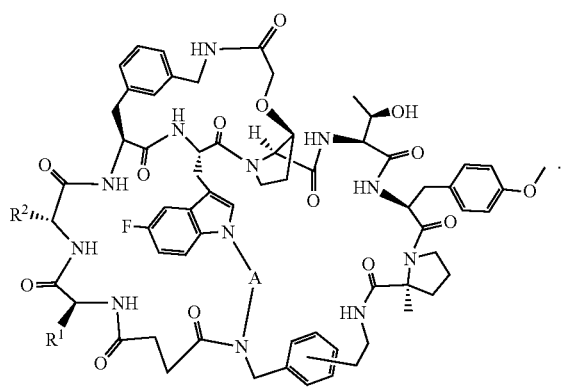
In some embodiments, the compound of Formula I is preferably a compound of Formula IV:
Formula IV
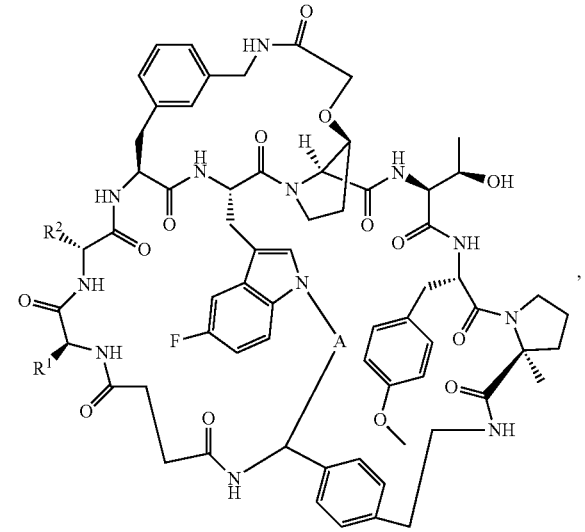
wherein, A, R¹ and R² are as defined above in Formula IA.
In some embodiments the compound of Formula I is a compound of Formula V:
Formula V
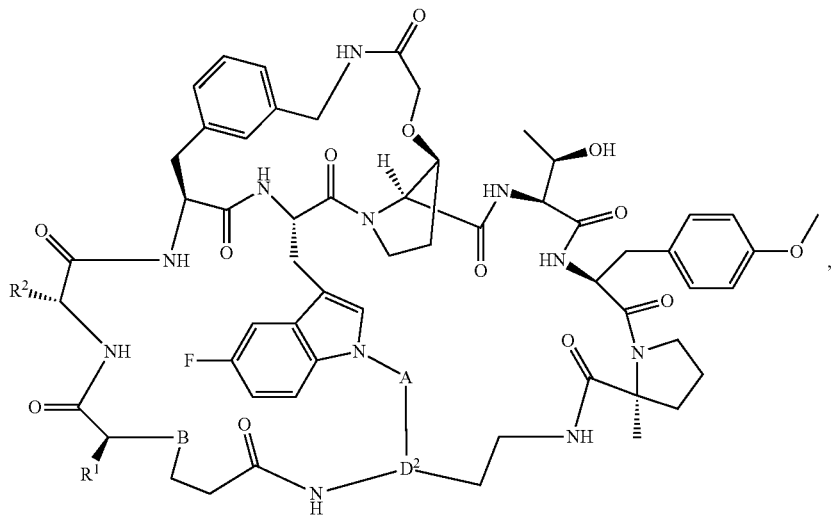
wherein
A, B, R¹ and R² are as defined above in Formula IA; and D² is:
(a) a moiety of the formula:
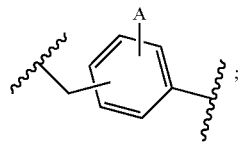
(b) a moiety of the formula:
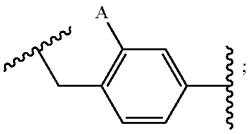

(c) a moiety of the formula:

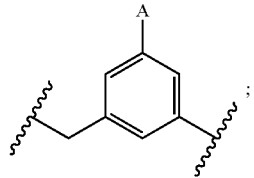

or (d) a moiety of the formula:

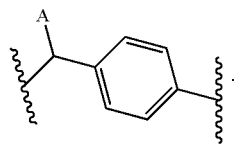

In some embodiments of Formula I, Formula IA, Formula II, Formula IIA, Formula III, Formula IV, or Formula V, it is preferred for A to be a moiety of the formula: $—(CH_2)_{ya}—$, wherein ya is 4 to 6. In some embodiments of Formula I, Formula IA, Formula II, or Formula IIA, it is preferred for A to be a moiety of the formula: $—CH_2—(CH_2)_{ma}—O—(CH_2)_{na}—$, wherein ma is 2 or 3 and na is 0 or 1. In some embodiments of Formula III, Formula IV, or Formula V, it is preferred for A to be a moiety of the formula: $—CH_2—(CH_2)_{ma}—O—(CH_2)_{na}—$, wherein ma is 2 or 4 and na is 0, 1, or 2. In some embodiments of Formula I, Formula IA, Formula II, Formula IIA, Formula III, Formula IV, or Formula V, it is preferred for A to be a moiety of the formula:

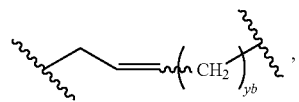

wherein yb is 1 to 3. In some embodiments of Formula I, Formula IA, Formula II, Formula IIA, Formula III, Formula IV, or Formula V, it is preferred for A to be a moiety of the formula:

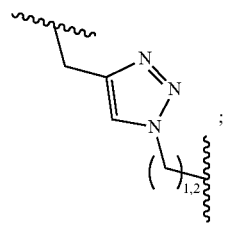

Also provided herein as compounds of Formula I are compounds Ex-1, Ex-2, Ex-3, Ex-4, Ex-5, Ex-6, Ex-7, Ex-8, Ex-9, Ex-10, Ex-11, Ex-12, Ex-13, Ex-14, Ex-15, Ex-16, Ex-17, Ex-18, Ex-19, Ex-20, Ex-21, Ex-22, Ex-23, Ex-24, Ex-25, Ex-26, Ex-27, Ex-28, Ex-29, Ex-31, Ex-35, Ex-36, Ex-38, Ex-39, Ex-40, Ex-41, Ex-44, Ex-47, Ex-48, Ex-49, Ex-50, Ex-51, Ex-52, Ex-53, Ex-54, Ex-55, Ex-56, Ex-57, Ex-58, Ex-59, Ex-60, and Ex-61, or any pharmaceutically acceptable salt thereof. These compounds, which are disclosed in Table 1, are also referred to herein as "compounds of the invention."

TABLE 1

| Ex No | Structure |
|---|---|
| Ex-01 | 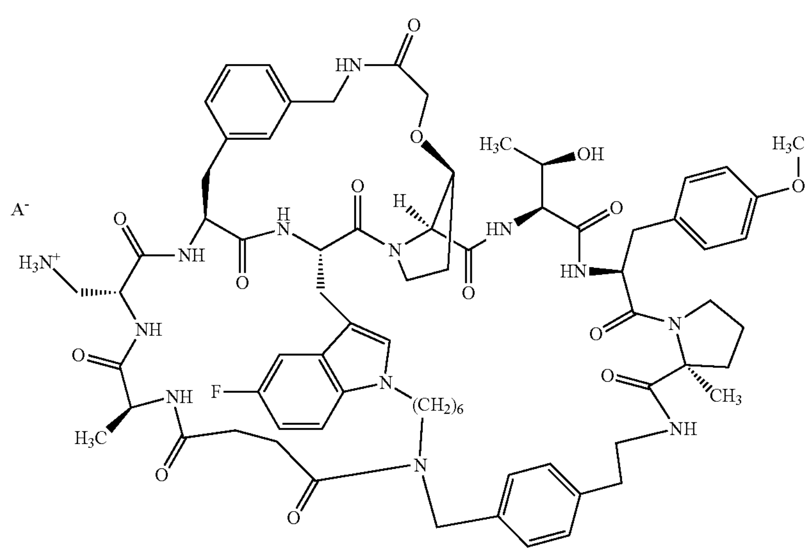 |

TABLE 1-continued
| Ex No | Structure |
|---|---|
| Ex-02 | 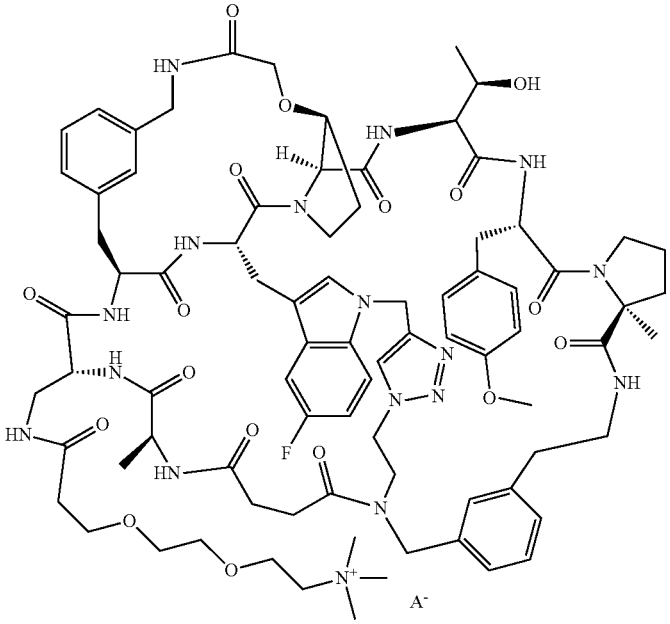 |
| Ex-03 | 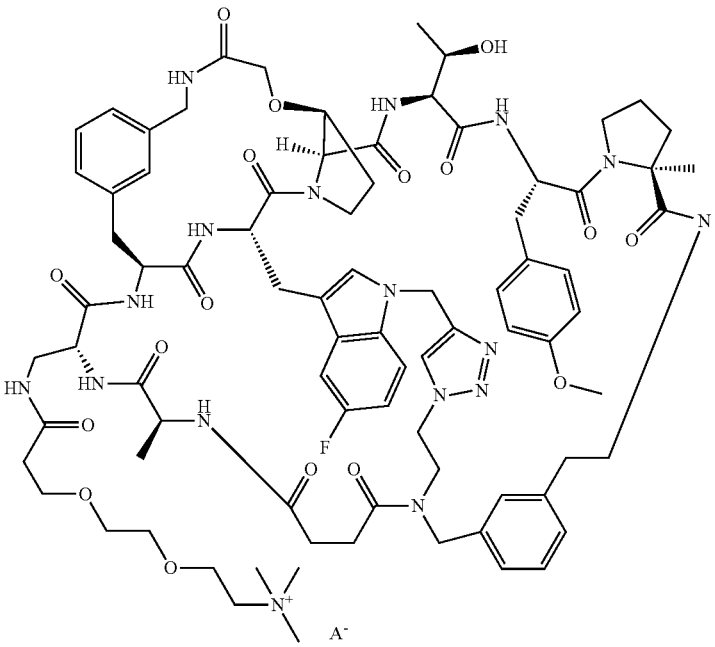 |

TABLE 1-continued
| Ex No | Structure |
|---|---|
| Ex-04 | 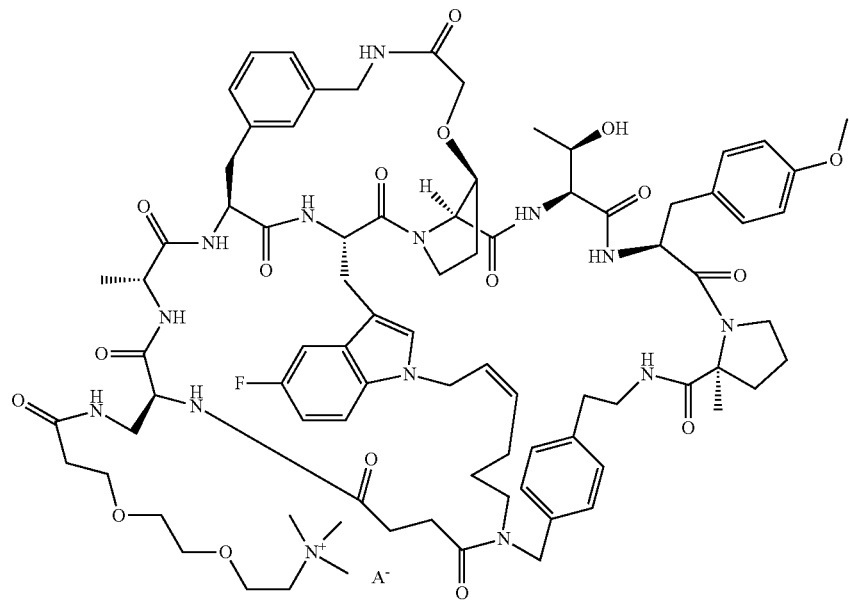 |
| Ex-05 | 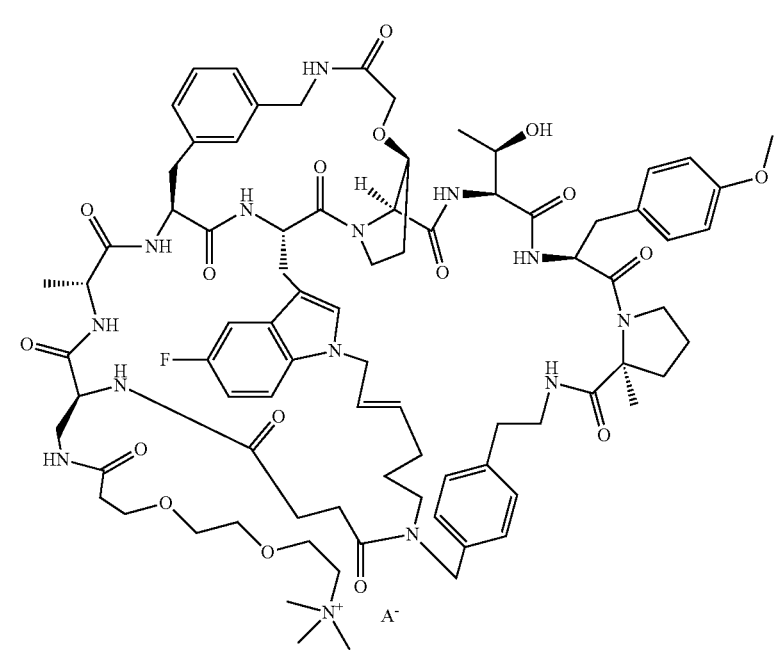 |

| Ex No | Structure |
|---|---|
| Ex-06 | 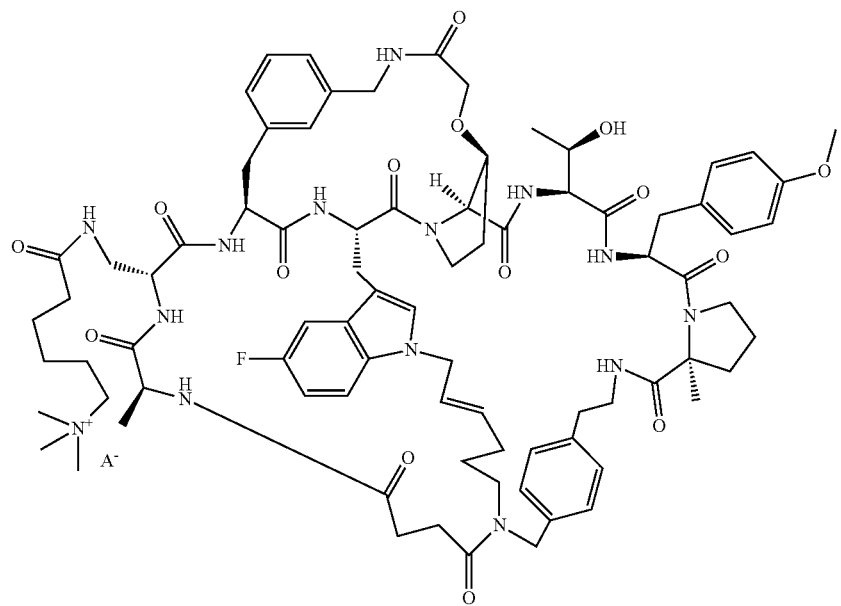 |
| Ex-07 | 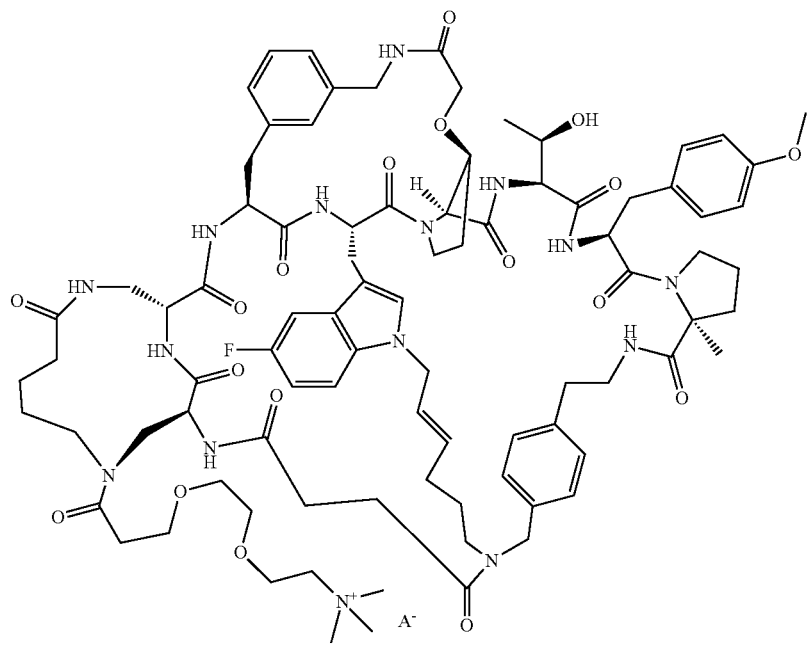 |

TABLE 1-continued
| Ex No | Structure |
|---|---|
| Ex-08 | 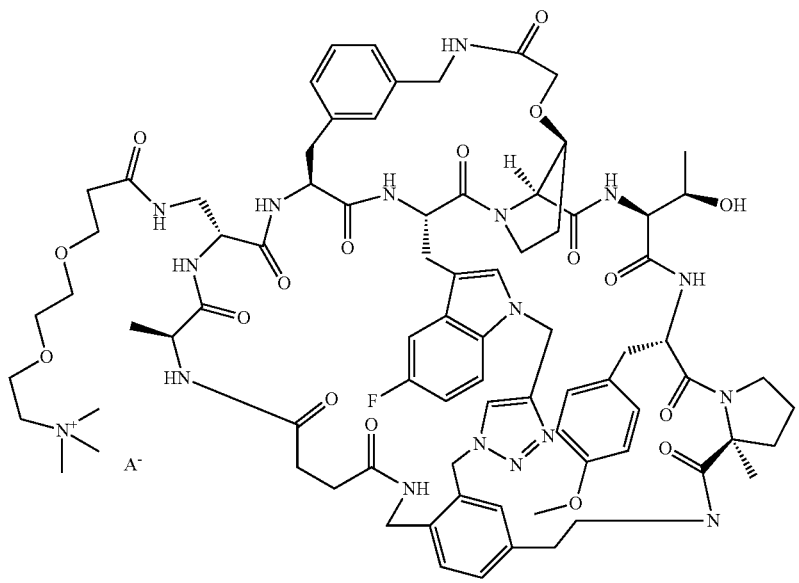 |
| Ex-09 | 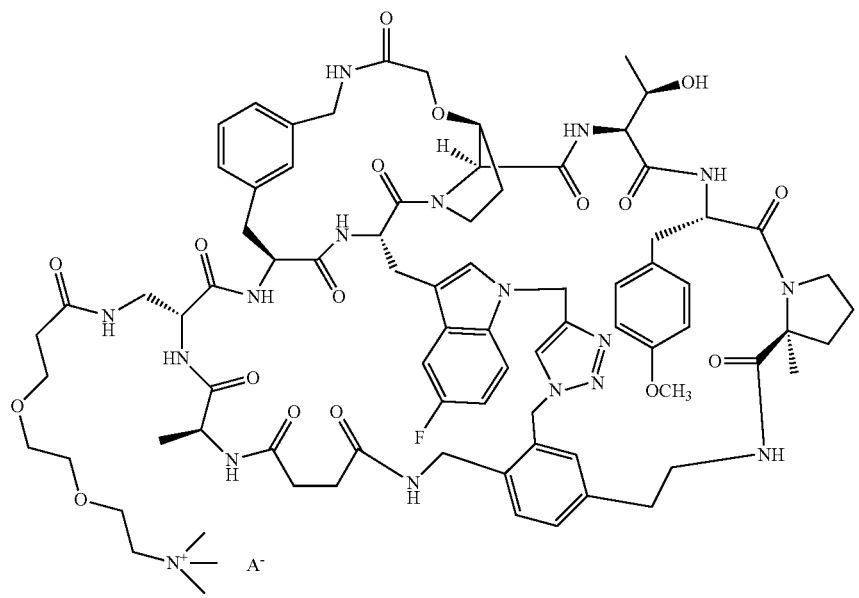 |

TABLE 1-continued
| Ex No | Structure |
|---|---|
| Ex-10 | 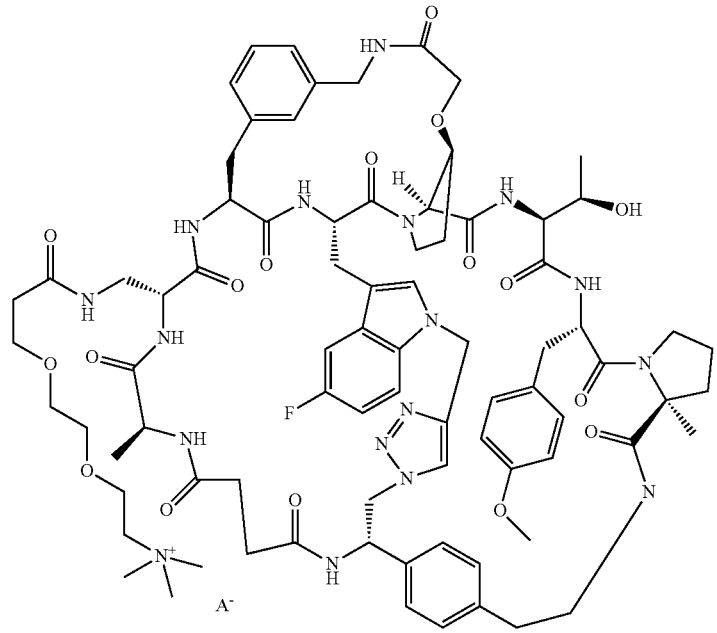 |
| Ex-11 | 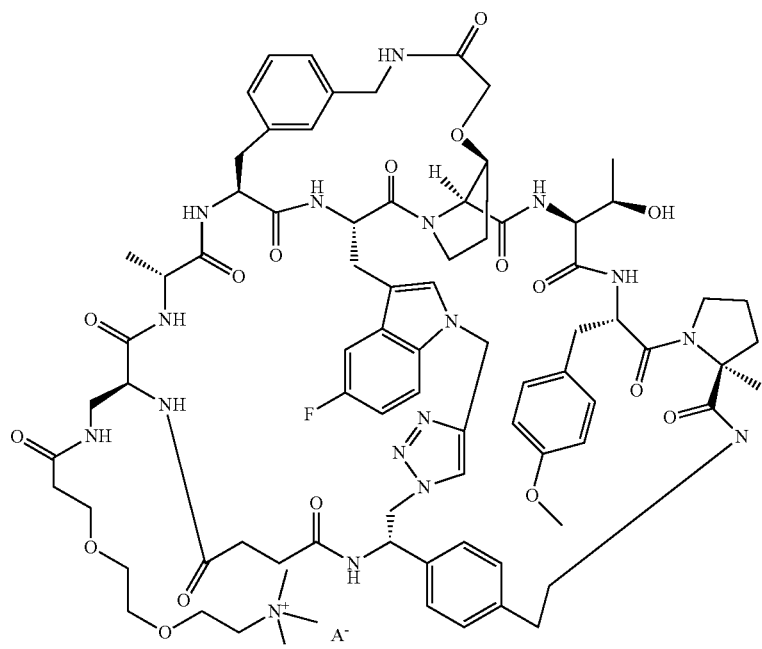 |

TABLE 1-continued
| Ex No | Structure |
|---|---|
| Ex-12 | 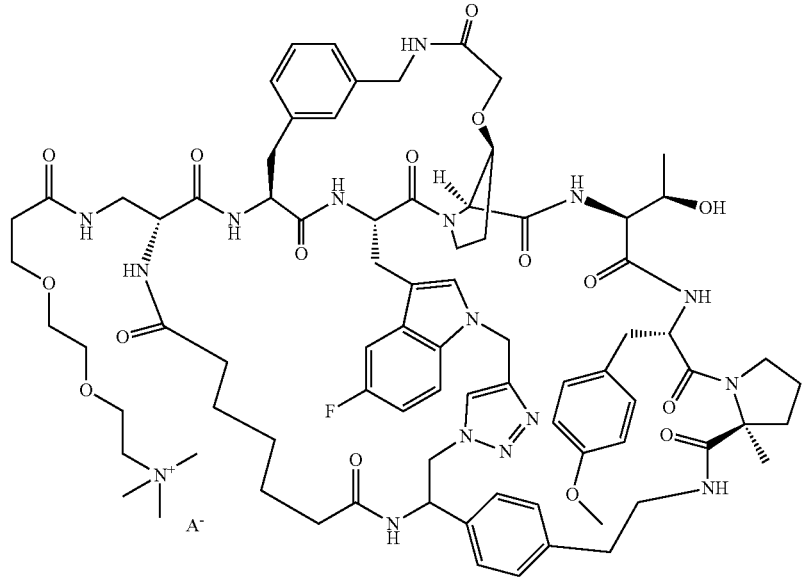 |
| Ex-13 | 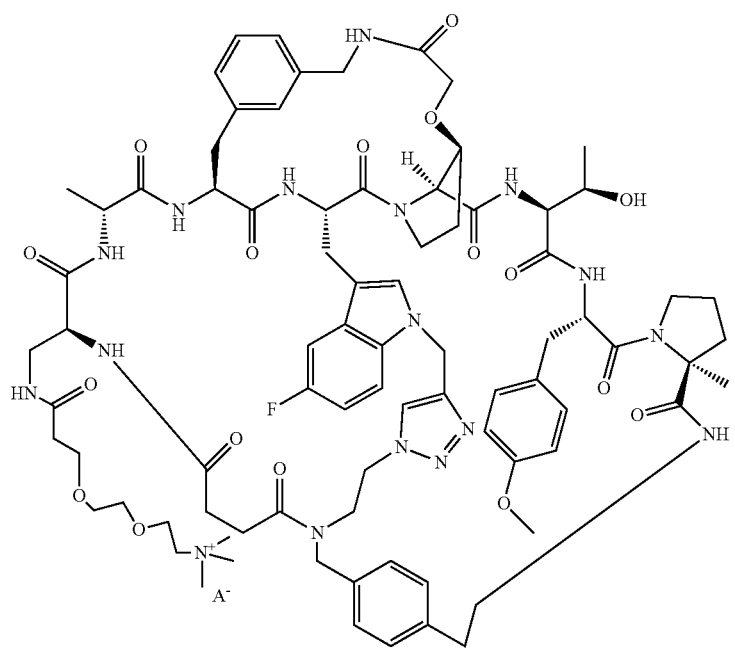 |

TABLE 1-continued
| Ex No | Structure |
|---|---|
| Ex-14 | 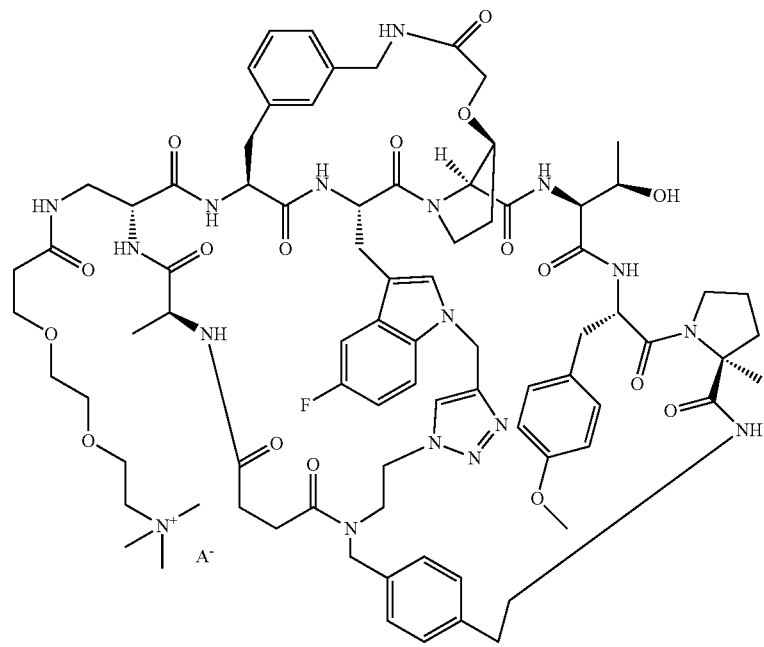 |
| Ex-15 | 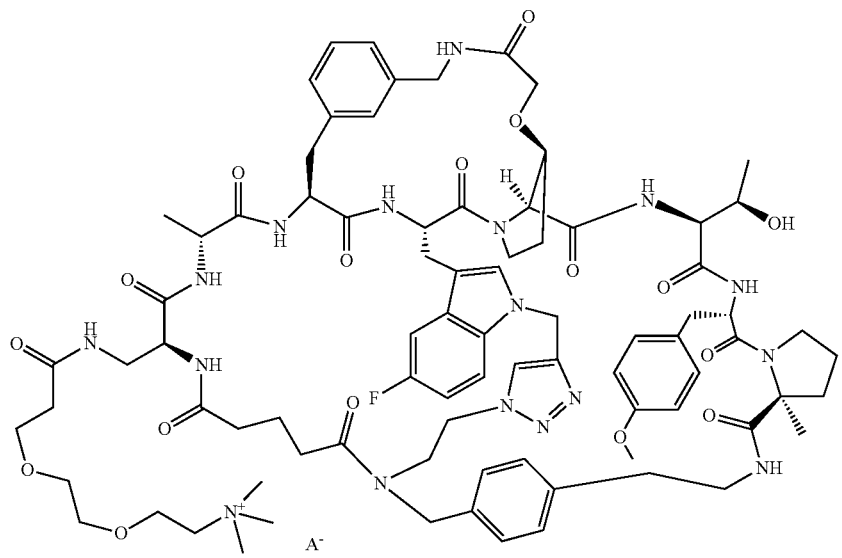 |

TABLE 1-continued
| Ex No | Structure |
|---|---|
| Ex-16 | 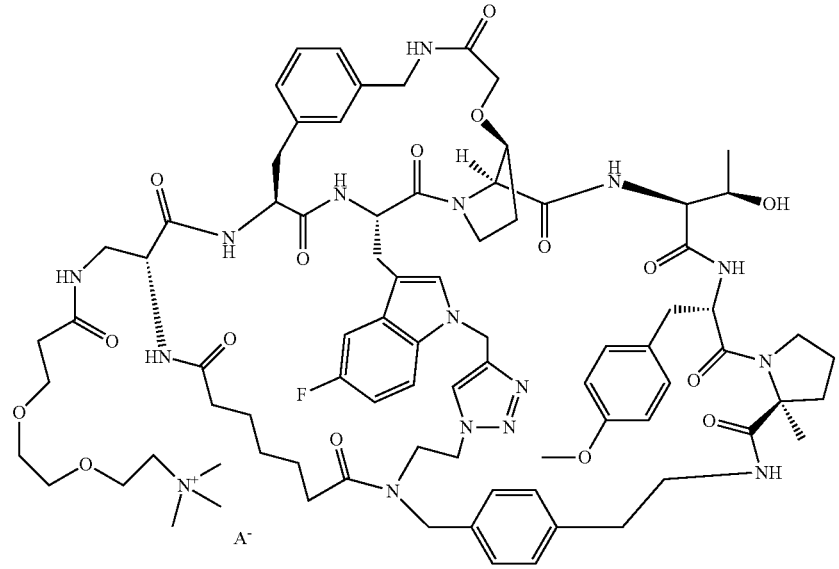 |
| Ex-17 | 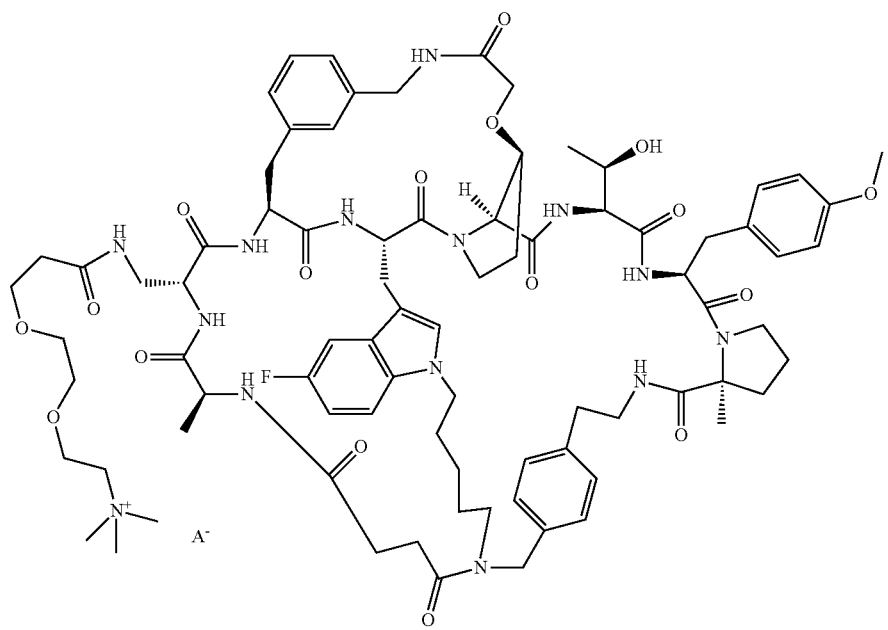 |

TABLE 1-continued
| Ex No | Structure |
|---|---|
| Ex-18 | 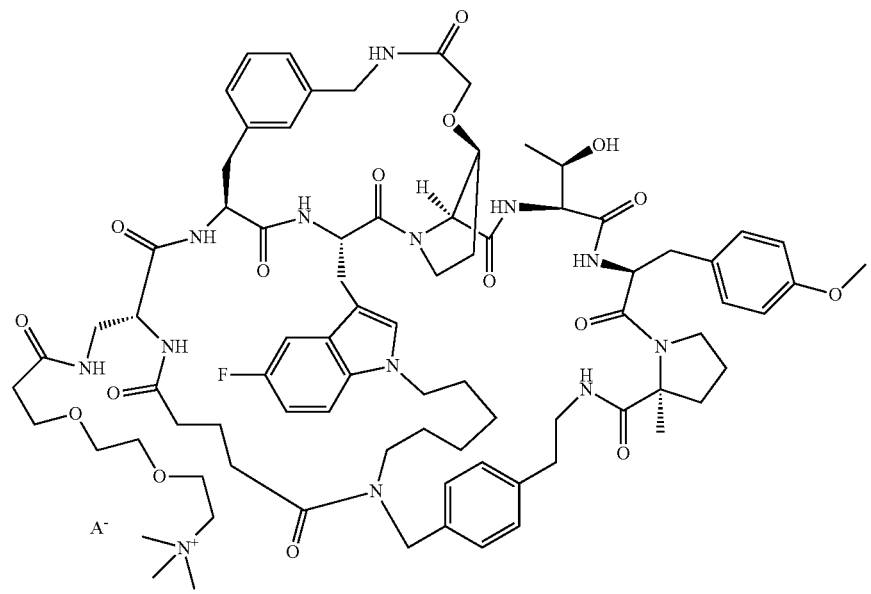 |
| Ex-19 | 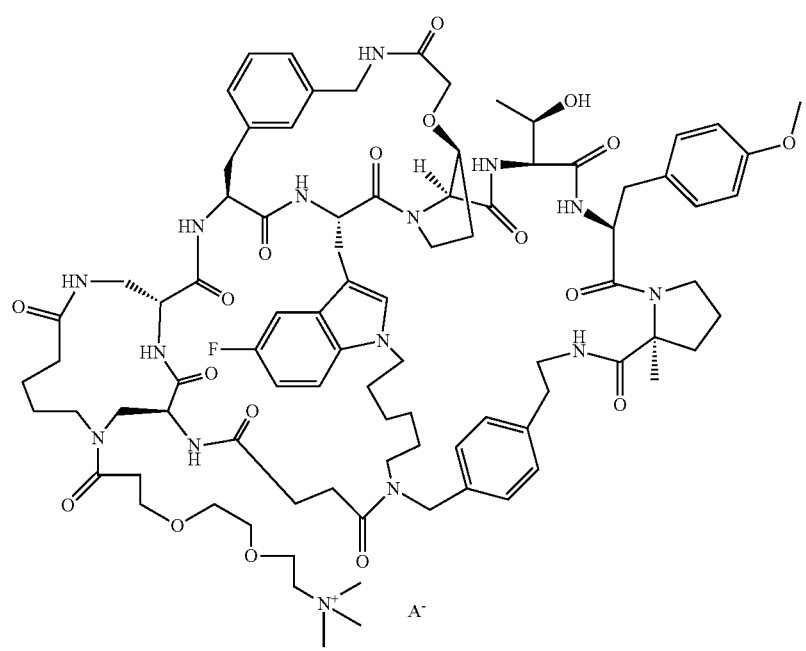 |

TABLE 1-continued
| Ex No | Structure |
|---|---|
| Ex-20 | 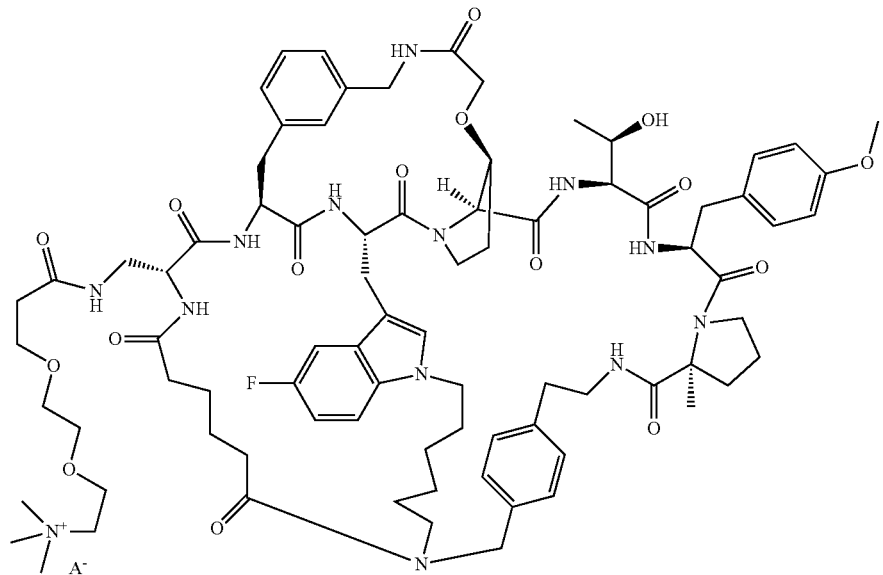 |
| Ex-21 | 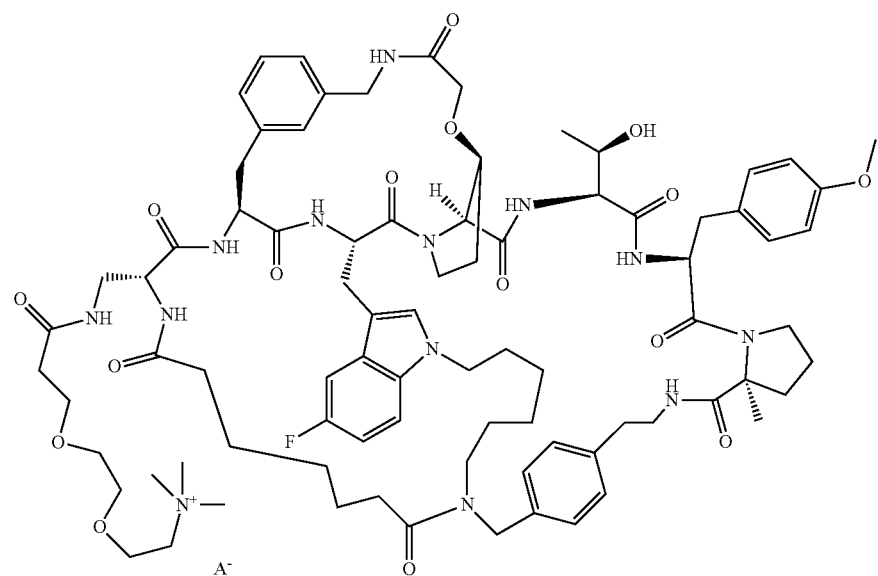 |

TABLE 1-continued
| Ex No | Structure |
|---|---|
| Ex-22 | 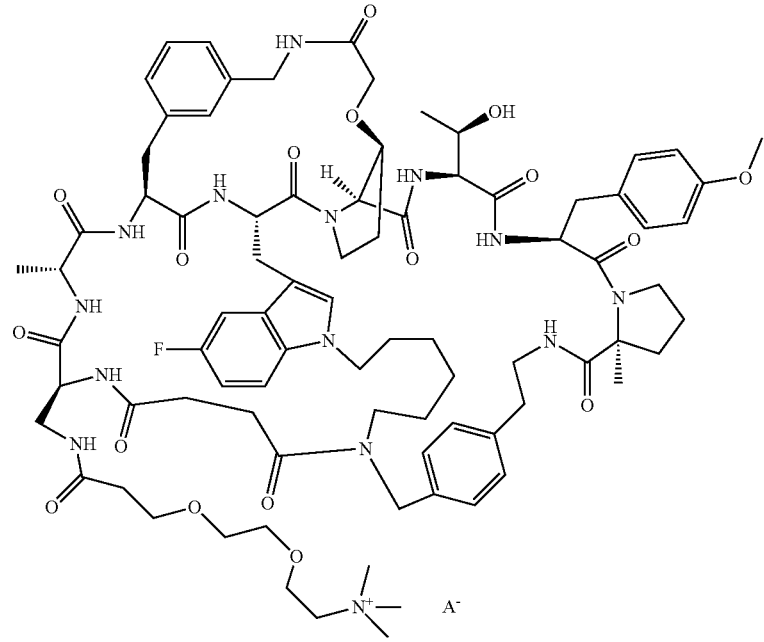 |
| Ex-23 | 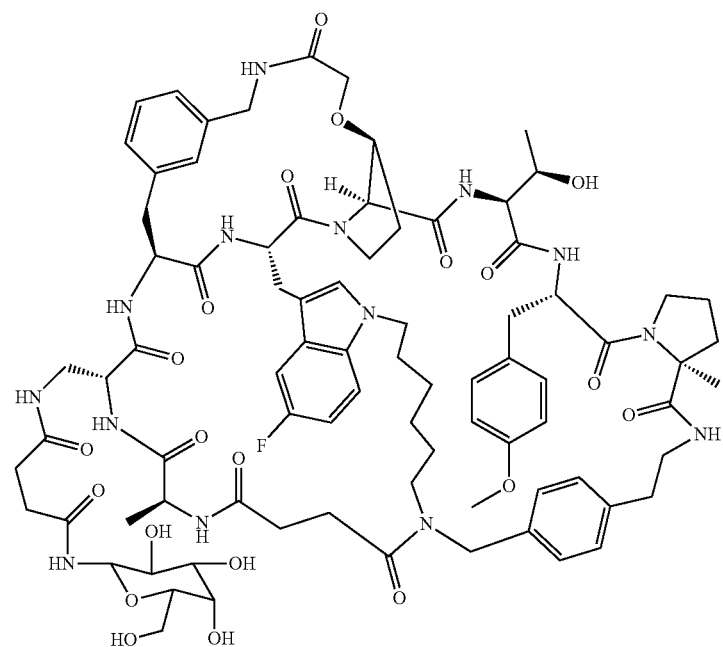 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCC(=O)NC2OC(CO)C(O)C(O)C2O)C(=O)N[C@@H](Cc2cccc(c2)CNC(=O)CO4)C(=O)N3)cc1] |

TABLE 1-continued
| Ex No | Structure |
|---|---|
| Ex-24 | 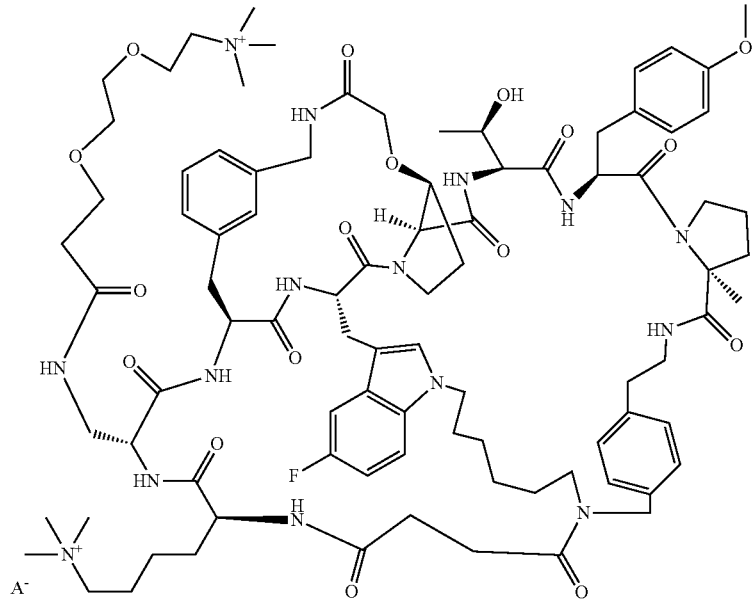 |
| Ex-25 | 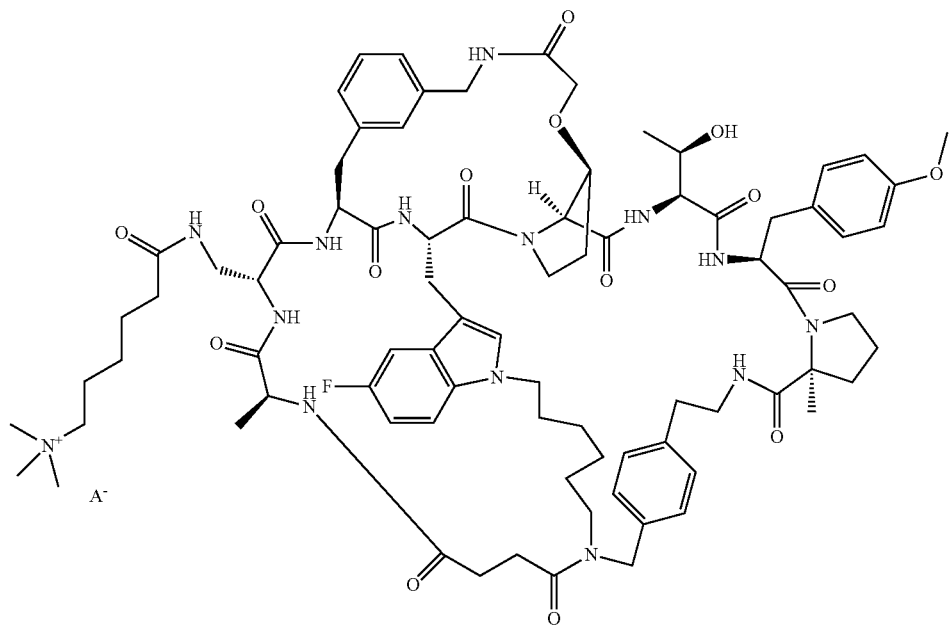 |

| Ex No | Structure |
|---|---|
| Ex-26 | 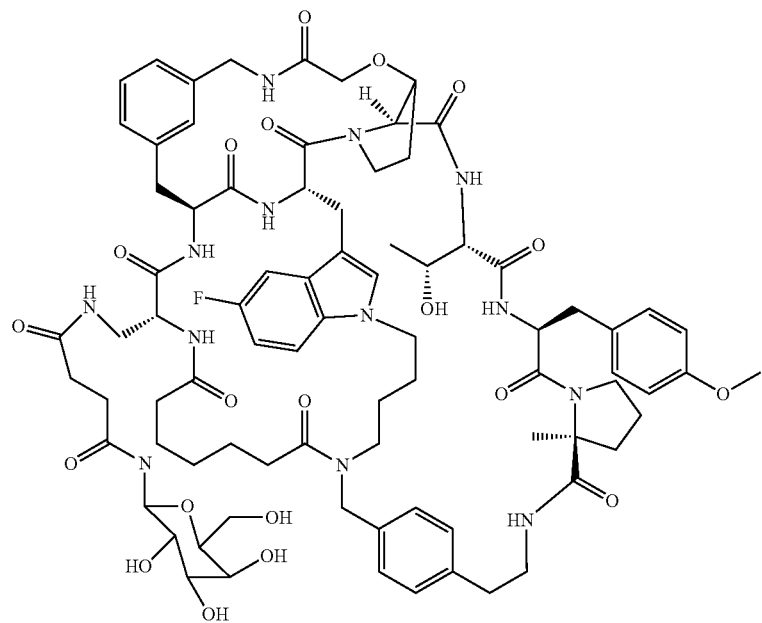 [SMILES: COc1ccc(C[C@@H]2NC(=O)[C@H]([C@@H](C)O)NC(=O)[C@@H]3C4CCN3C(=O)[C@@H]3Cc5cn(c6ccc(F)cc56)CCCCN(Cc5ccc(cc5)CCNC(=O)[C@]5(C)CCCN5C2=O)C(=O)CCCCCC(=O)N[C@H](CNC(=O)CCC(=O)NC2OC(CO)C(O)C(O)C2O)C(=O)N[C@@H](Cc2cccc(c2)CNC(=O)CO4)C(=O)N3)cc1] |
| Ex-27 | 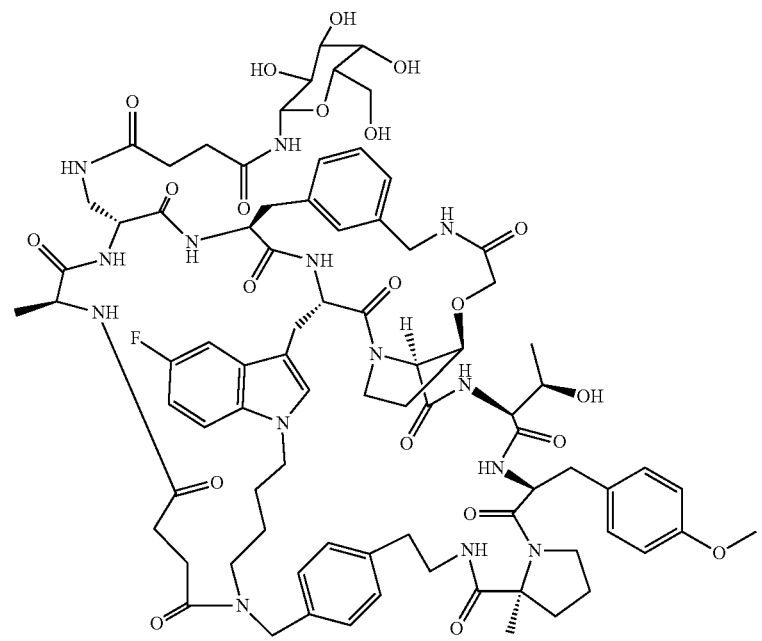 |

TABLE 1-continued
| Ex No | Structure |
|---|---|
| Ex-28 | 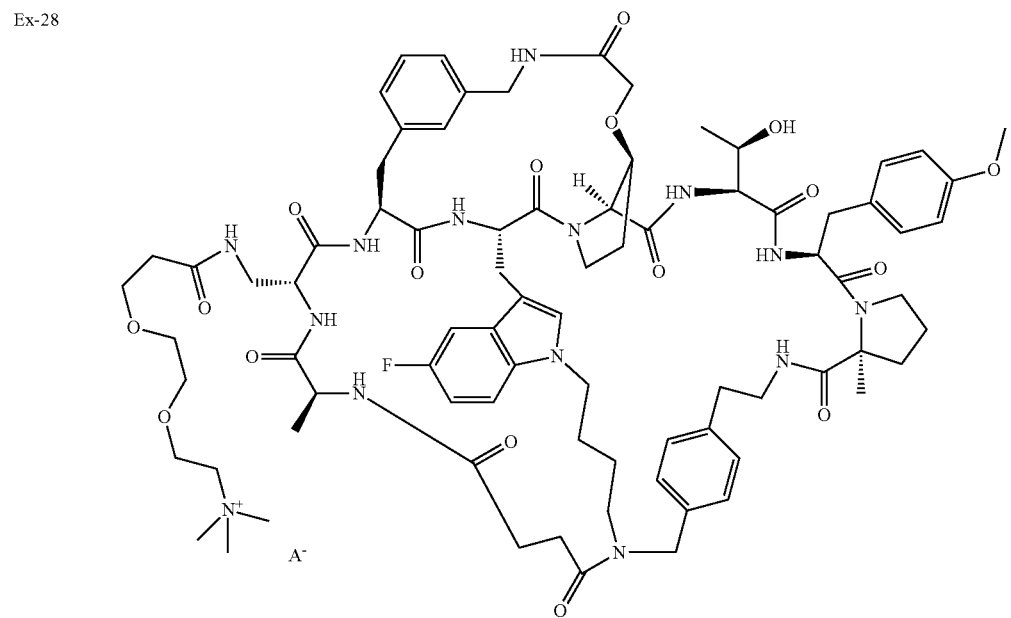 |
| Ex-29 | 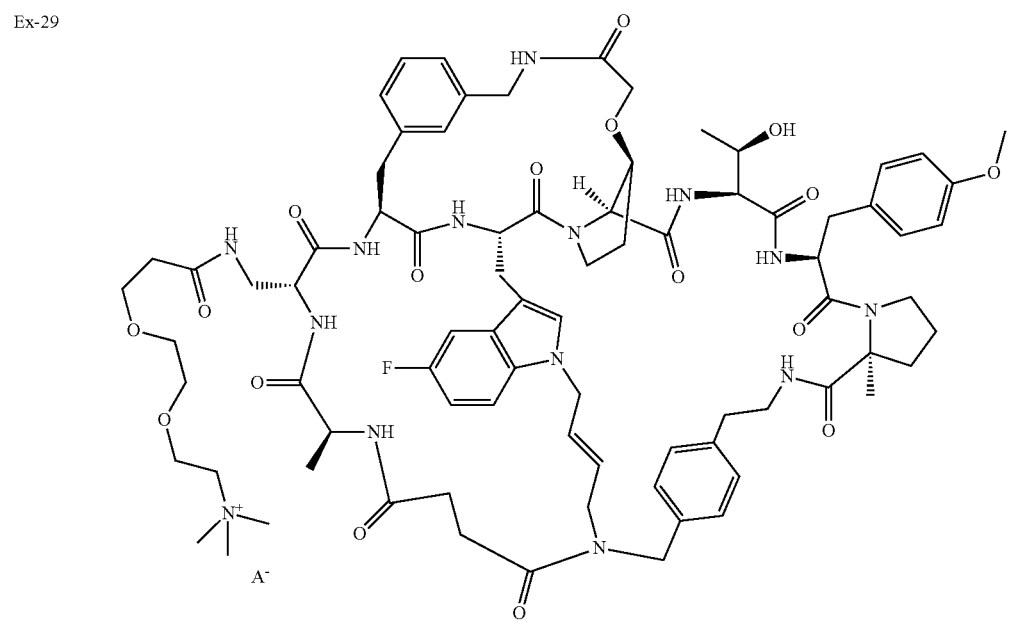 |

TABLE 1-continued
| Ex No | Structure |
|---|---|
| Ex-31 | 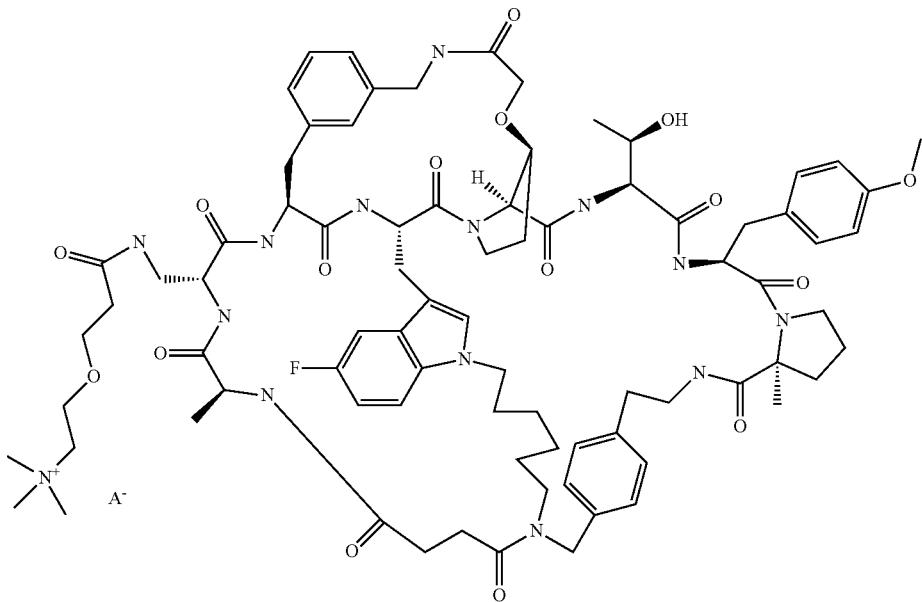 |
| Ex-35 | 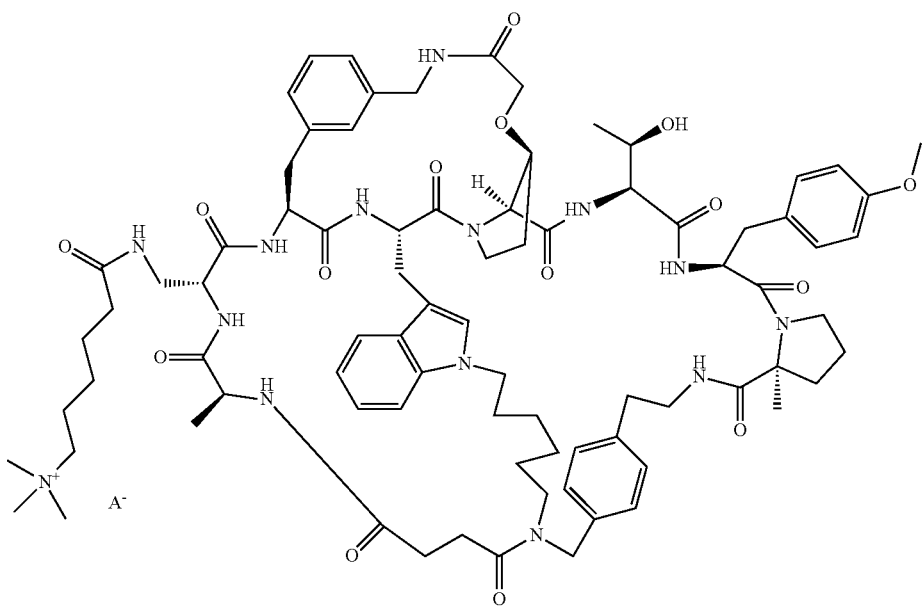 |

TABLE 1-continued
| Ex No | Structure |
|---|---|
| Ex-36 | 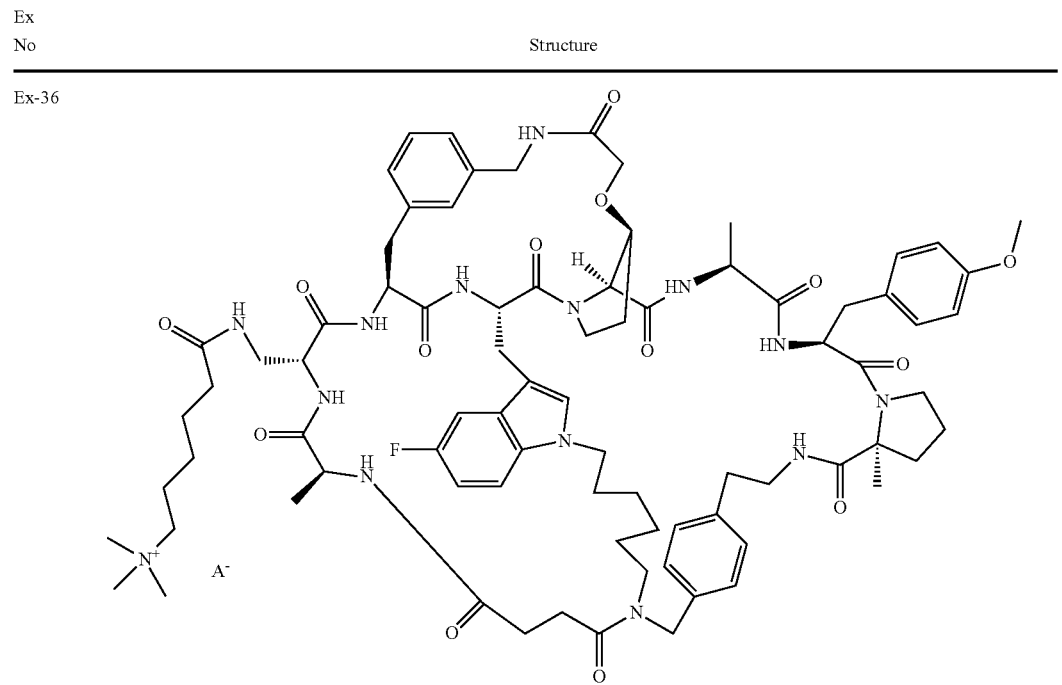 |
| Ex-38 | 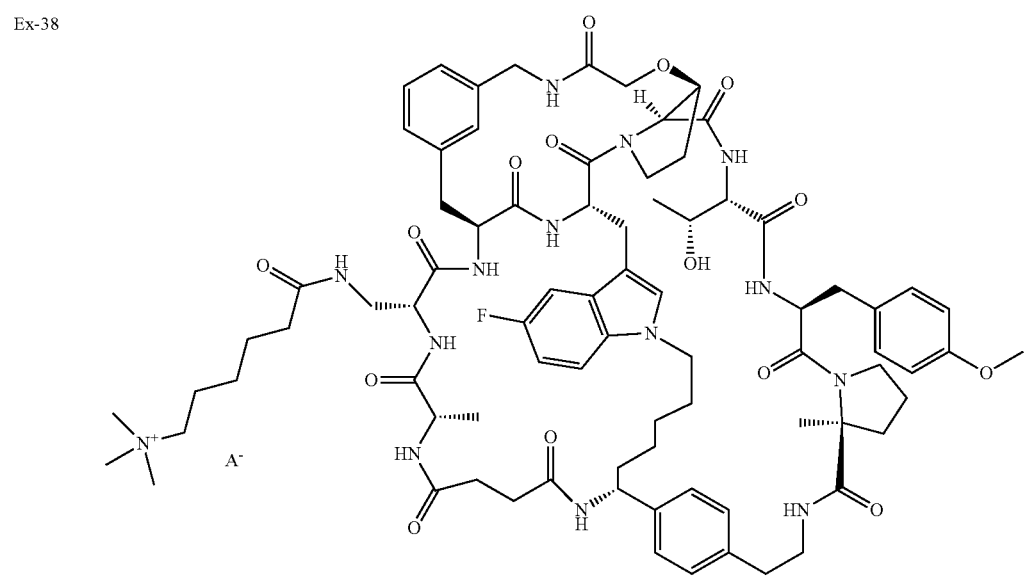 |

TABLE 1-continued
| Ex No | Structure |
|---|---|
| Ex-39 | 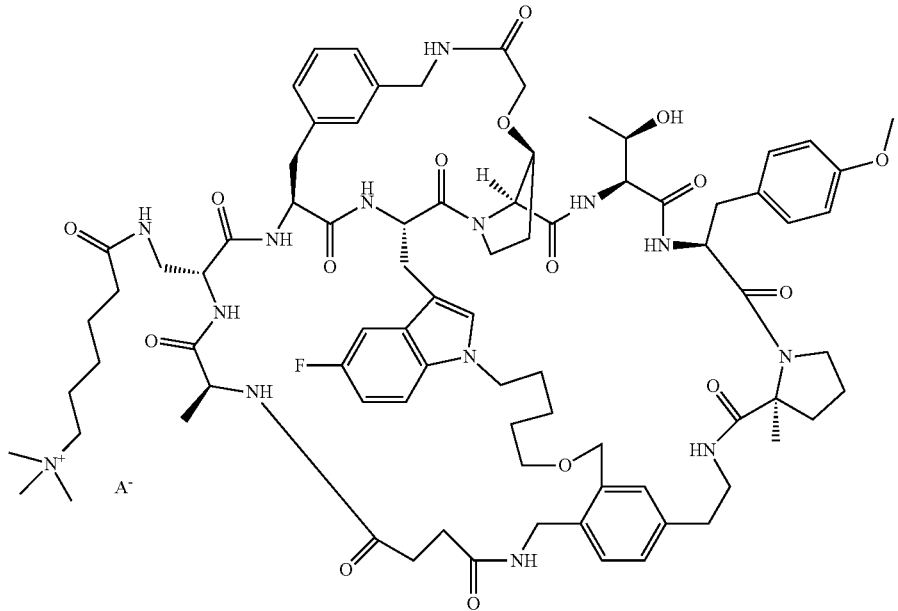 |
| Ex-40 | 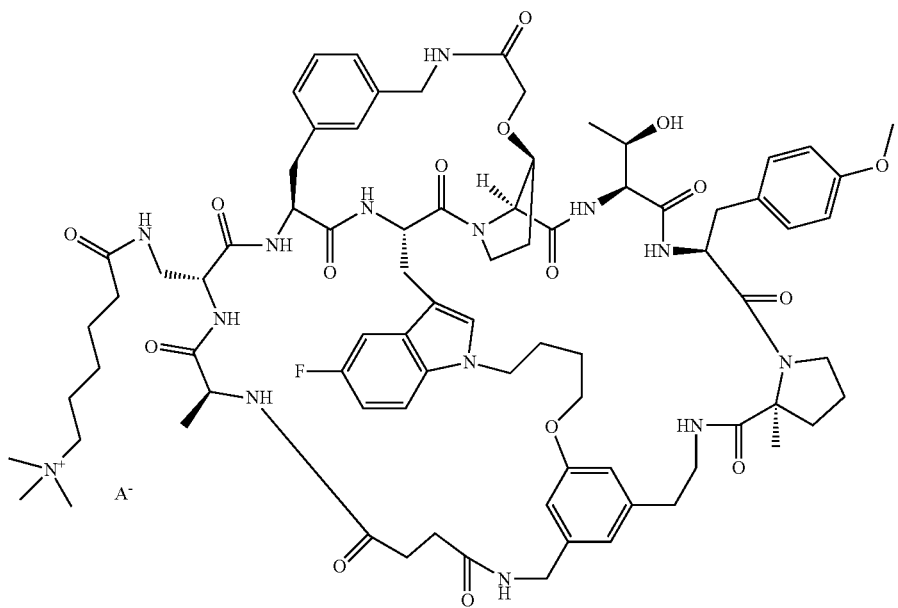 |

| Ex No | Structure |
|---|---|
| Ex-41 | 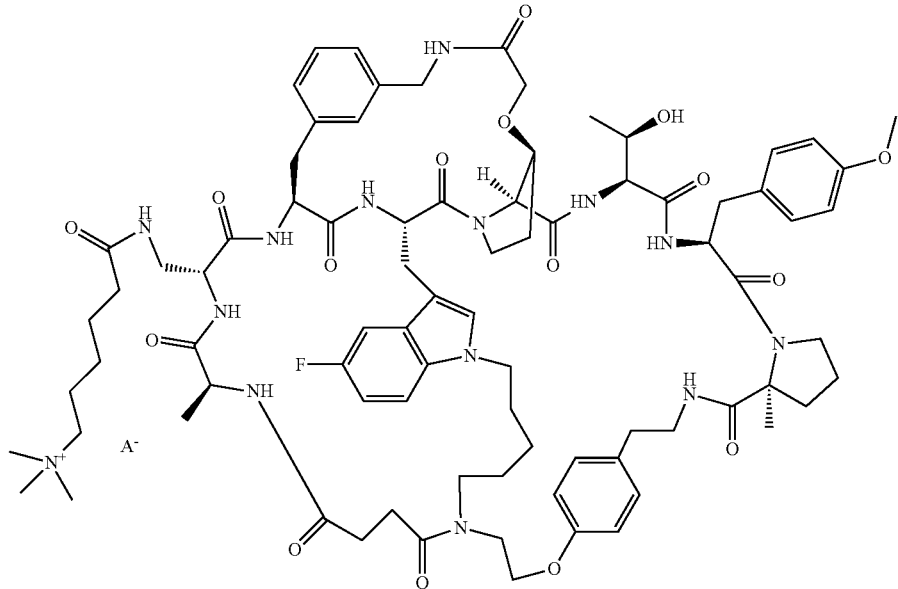 |
| Ex-44 | 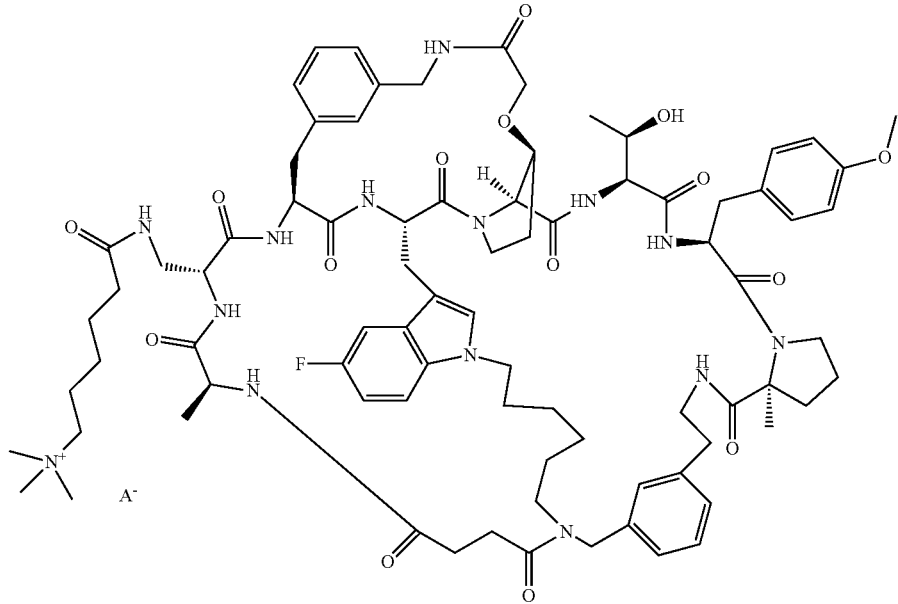 |

TABLE 1-continued
| Ex No | Structure |
|---|---|
| Ex-47 | 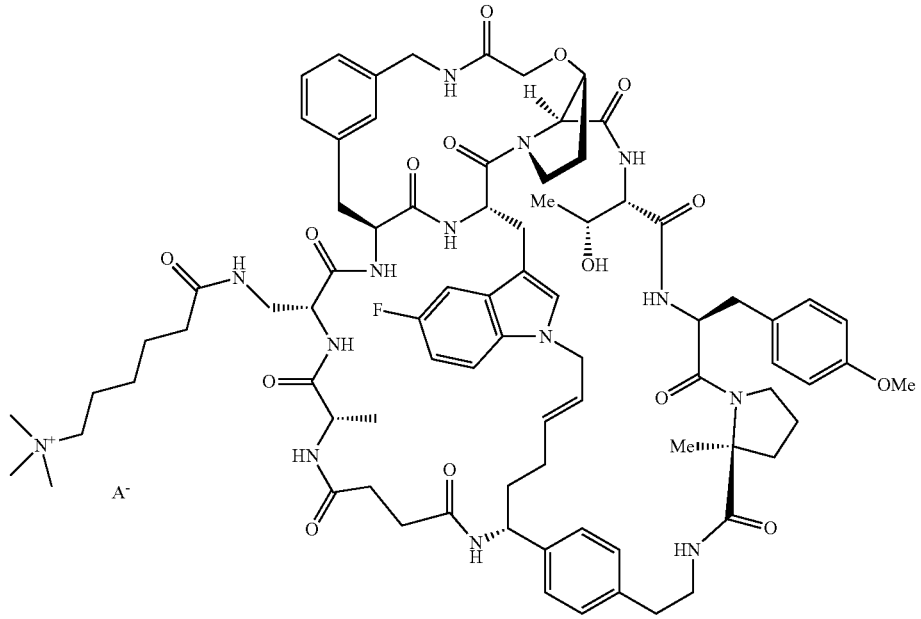 |
| Ex-48 | 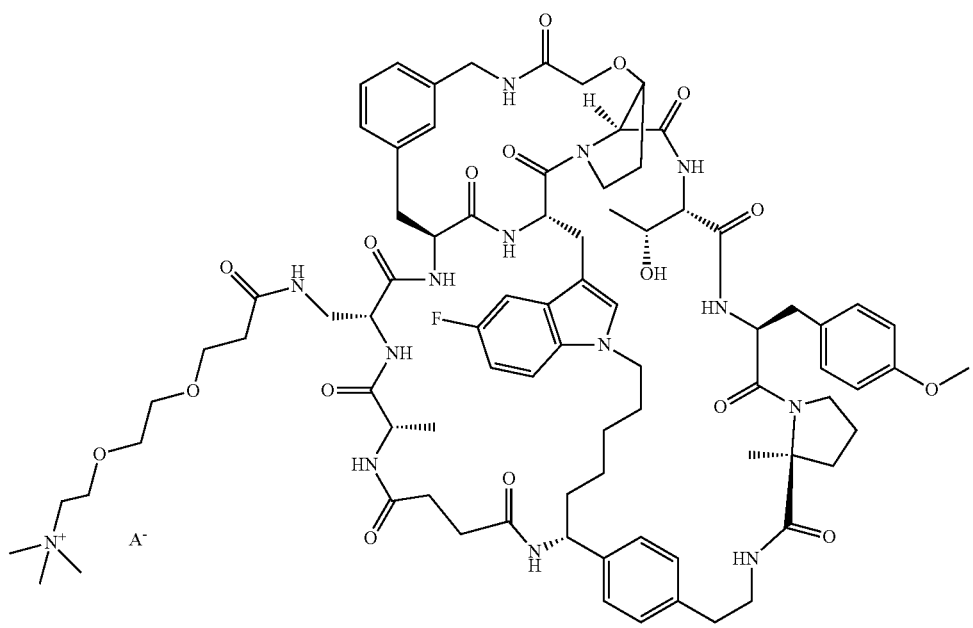 |

TABLE 1-continued
| Ex No | Structure |
|---|---|
| Ex-49 | 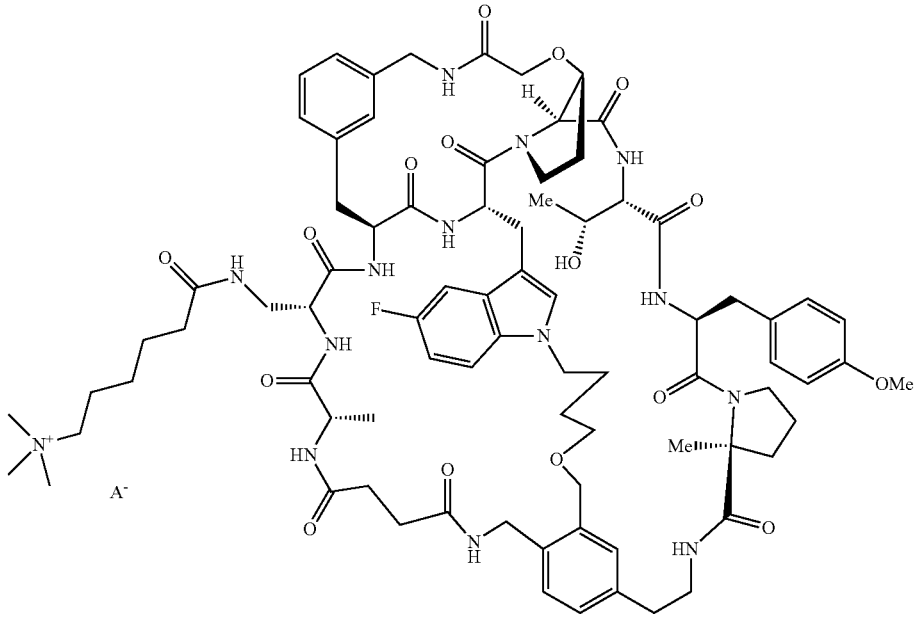 |
| Ex-50 | 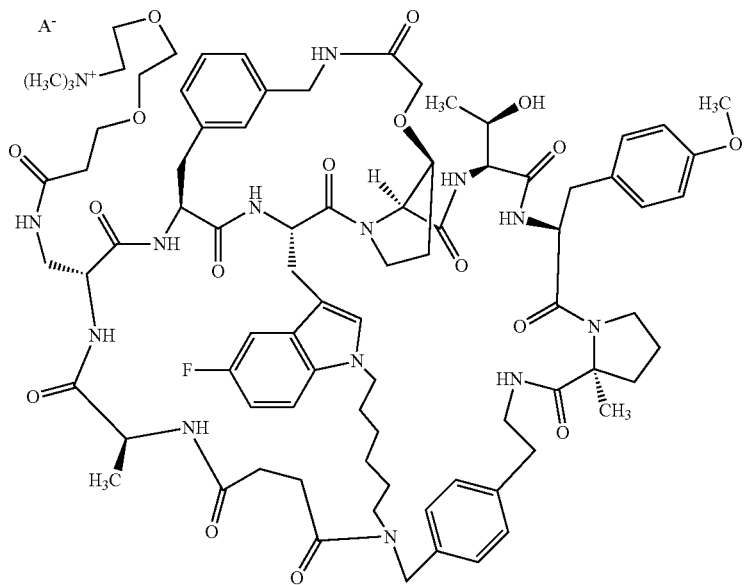 |

TABLE 1-continued
| Ex No | Structure |
|---|---|
| Ex-51 | 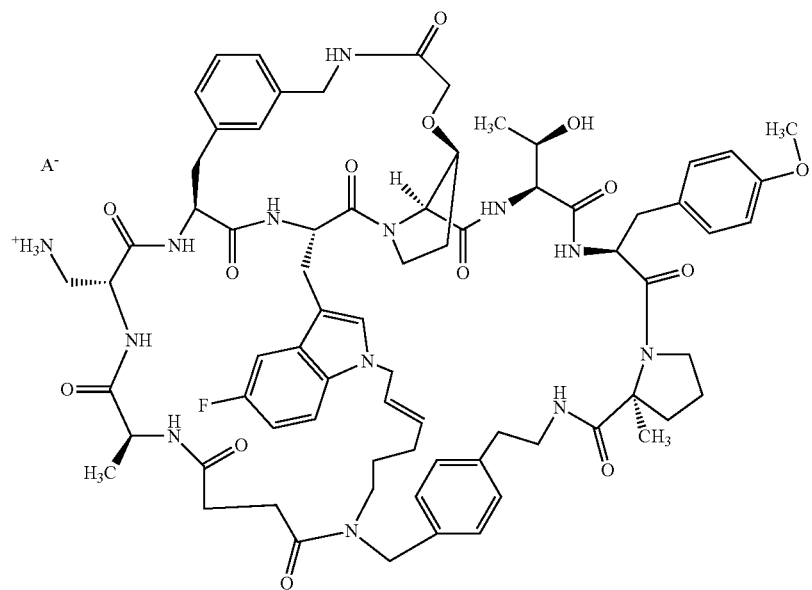 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)C/C=C/CCCN(Cc5ccc(cc5)CCNC(=O)[C@]5(C)CCCN5C2=O)C(=O)CCC(=O)N[C@@H](C)C(=O)N[C@H](C[NH3+])C(=O)N[C@@H](Cc2cccc(c2)CNC(=O)CO4)C(=O)N3)cc1 ; "A-"] |
| Ex-52 | 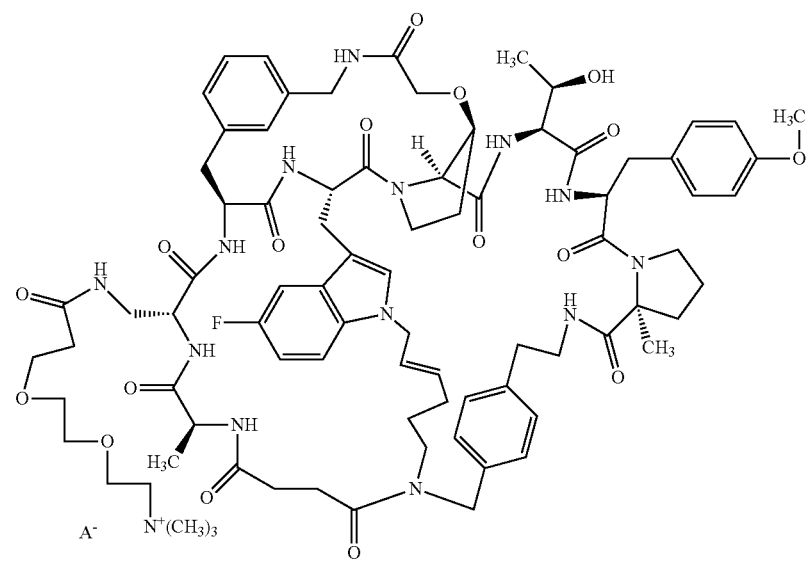 |

TABLE 1-continued
| Ex No | Structure |
|---|---|
| Ex-53 | 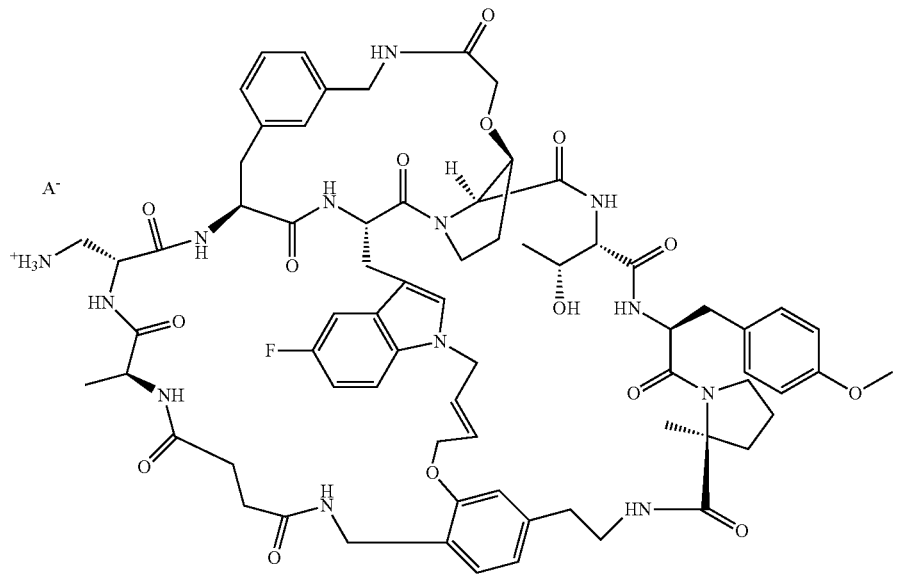 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)C/C=C/COc5cc(ccc5CNC(=O)CCC(=O)N[C@@H](C)C(=O)N[C@H](C[NH3+])C(=O)N[C@@H](Cc5cccc(c5)CNC(=O)CO4)C(=O)N3)CCNC(=O)[C@]3(C)CCCN3C2=O)cc1 ; "A-"] |
| Ex-54 | 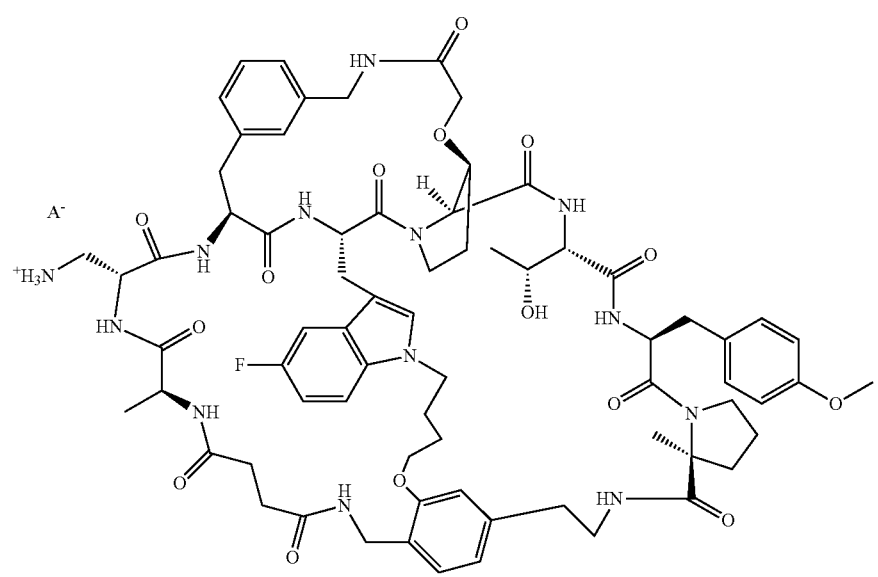 |

TABLE 1-continued
| Ex No | Structure |
|---|---|
| Ex-55 | 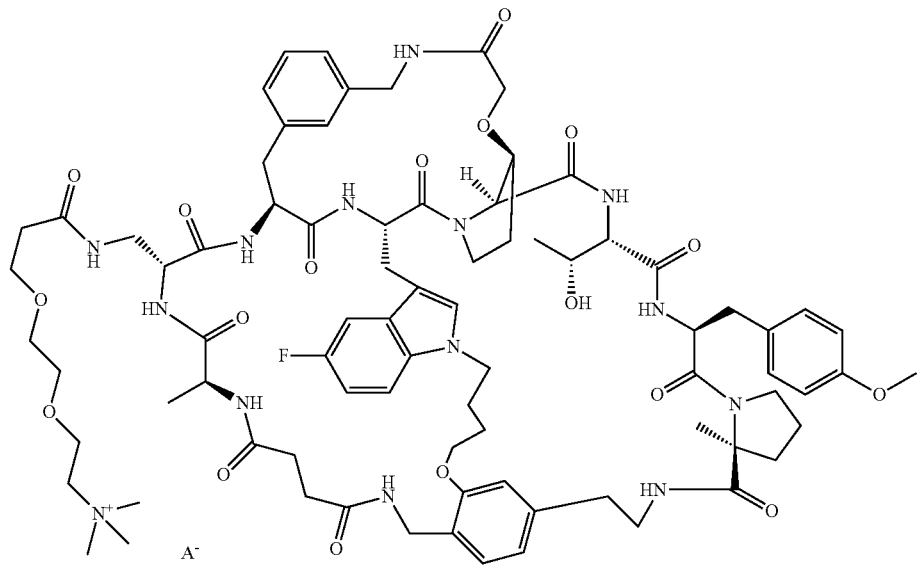 |
| Ex-56 | 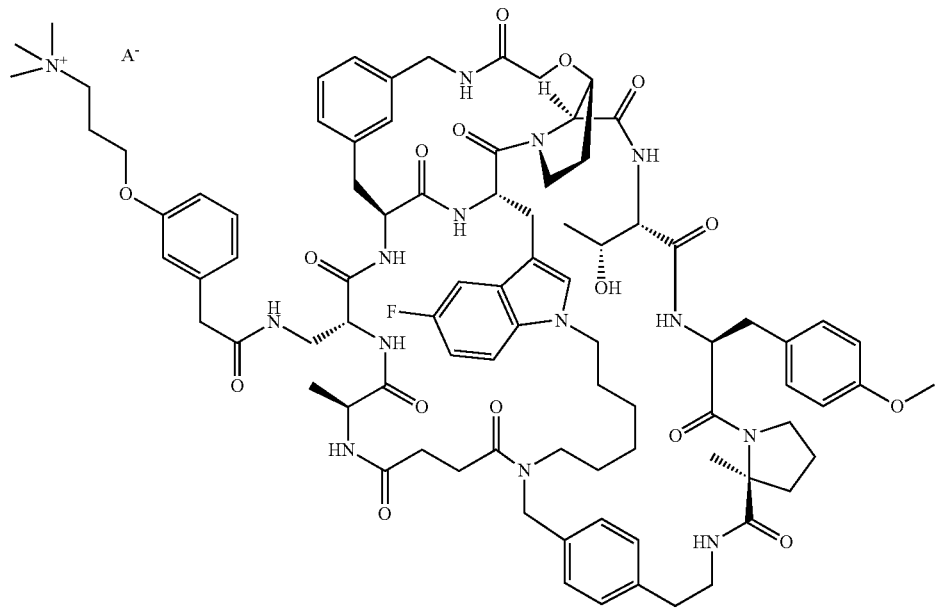 |

TABLE 1-continued
| Ex No | Structure |
|---|---|
| Ex-57 | 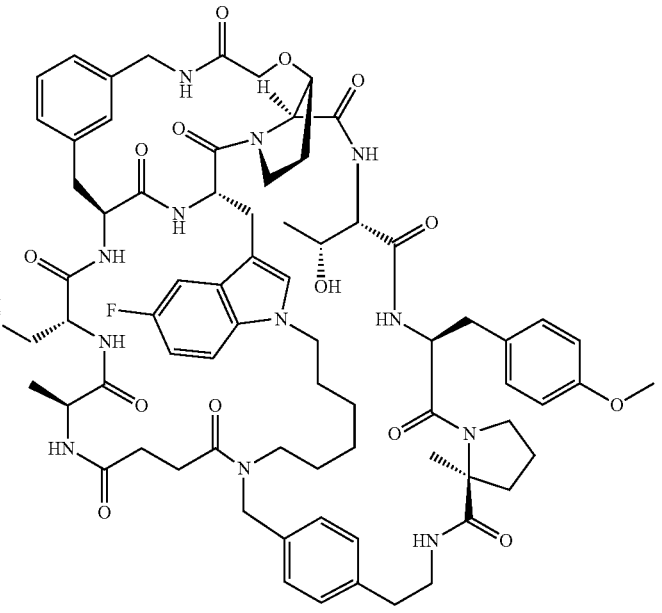 |
| Ex-58 | 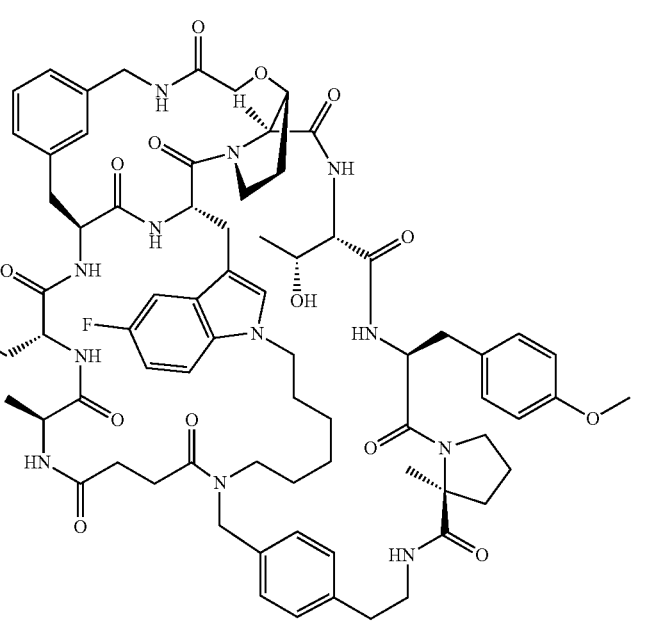 |

| Ex No | Structure |
|---|---|
| Ex-59 | 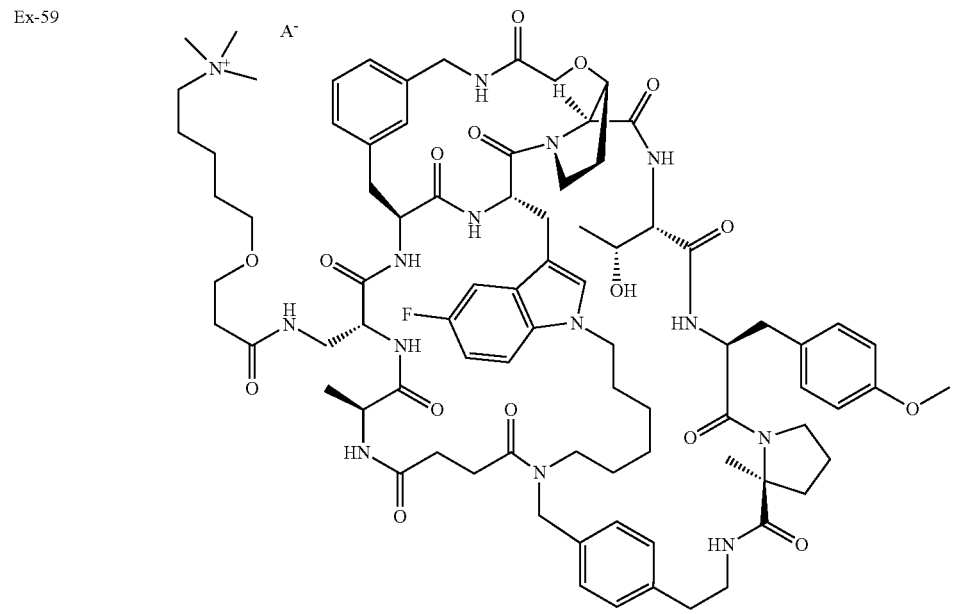 |
| Ex-60 | 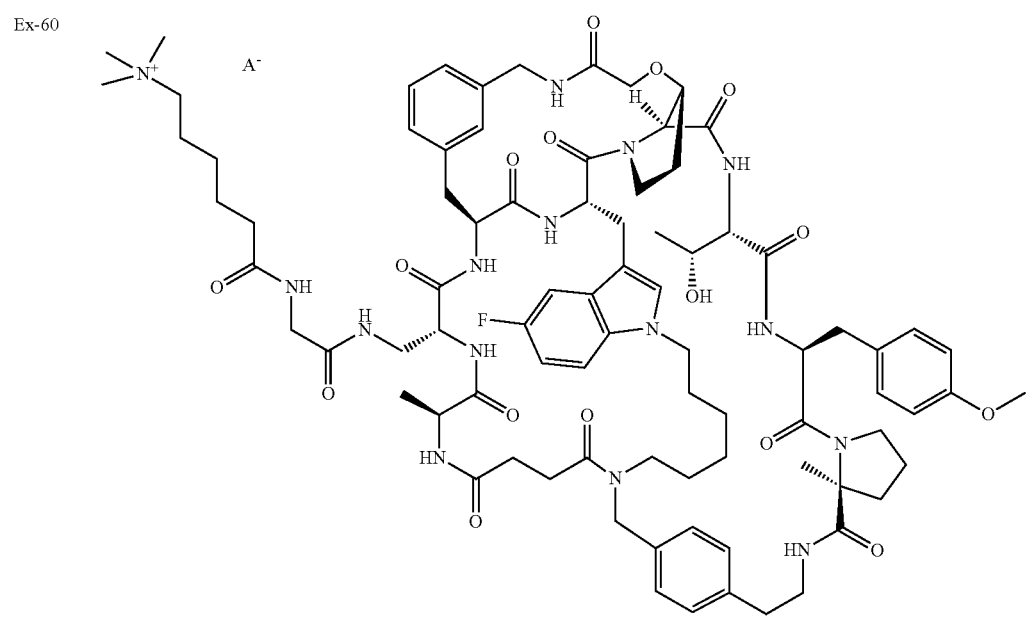 |

TABLE 1-continued

| Ex No | Structure |
|---|---|
| Ex-61 | [chemical structure] | wherein A⁻ is a pharmaceutically acceptable anion.

The term "salt(s)", and its use in the phrase "pharmaceutically acceptable salts" employed herein, includes any of the following: acidic salts formed with inorganic and/or organic acids, basic salts formed with inorganic and/or organic bases, zwitterionic and quaternary ammonium complexes. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Compounds of the invention contain tri-coordinate nitrogen atoms, for example, primary, secondary or tertiary amino moieties, wherein, as is known, the lone pair of electrons residing on the nitrogen atom may be protonated with an appropriate acid or alkylated with an appropriate reagent, for example, alkyl bromide, under the appropriate reaction conditions to provide tetracoordinate charged nitrogen stabilized by an anion generated in the process, for example, a halogen ion or conjugate base. Accordingly, compounds of the invention may be prepared in the form of a free-base or isolated in the form of a quaternary complex or a salt complex. In some instances where there is an appropriate acidic proton proximal to a basic nitrogen formation of a zwitterionic complex is possible. As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, and quaternary ammonium complexes are included in the scope of the inventive compounds described herein.

Accordingly, structural representation of compounds of the invention, whether in a free-base form, a salt form, a zwitterionic form or a quaternary ammonium form, also include all other forms of such compounds discussed above. Thus, one aspect of the invention is the provision of compounds of the invention in the form of a pharmaceutically acceptable salt, zwitterionic complex or quaternary ammonium complex. Those skilled in the art will recognize those instances in which the compounds of the invention may form such complexes, including where a tetracoordinate nitrogen can be quaternized or protonated and the charged nitrogen form stabilized by an associated anion. The term "pharmaceutically acceptable salt" refers to a salt (including a quaternary ammonium complex and an inner salt such as a zwitterion complex) which possesses effectiveness similar to or greater than a free-base form of the compound and which is not biologically or otherwise undesirable (e.g., is neither toxic nor otherwise deleterious to the recipient thereof).

The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l Union of Pure and Applied Chemistry, pp. 330-331. These disclosures are incorporated herein by reference.

The present invention contemplates both freebase forms of the compounds of the invention and all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts." As will be appreciated, freebase compounds may be prepared by controlling the conditions of isolation of the compound during synthesis or by neutralization and ion exchange from salt forms of compounds of the invention.

Examples of pharmaceutically acceptable acid salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The term "pharmaceutically acceptable anion" refers to an anion suitable for forming a pharmaceutically acceptable salt.

Further examples of pharmaceutically acceptable salts that may be used with the instant invention include, but are not limited to, fluoride, chloride, bromide and iodide.

In general, salts of compounds are intended to be pharmaceutically acceptable salts within the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan. Compounds of the invention include any form of the compound including in situ in a reaction mixture as well as in isolated and purified form obtained by routine techniques. Also included are polymorphic forms of the compounds of the invention and solvates and prodrugs thereof.

Certain compounds of the invention may exist in different tautomeric forms, for example, but are not limited to, ketone/enol tautomeric forms, imine-enamine tautomeric forms, and for example heteroaromatic forms such as the following moieties:

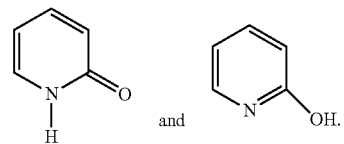 [SMILES: O=c1cccc[nH]1 ; Oc1ccccn1]

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention.

In another aspect, the present invention provides pharmaceutical compositions comprising one or more compounds of the invention. As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts.

As will be appreciated by the ordinarily skilled artisan, excipients are any constituent which adapts the composition to a particular route of administration or aids the processing of a composition into a dosage form without itself exerting an active pharmaceutical effect. In general compositions comprise more than one excipient depending upon the route of administration and the characteristics of the active being administered. Examples of excipients which impart to the composition properties which make it easier to handle or process include, but are not limited to, lubricants or pressing aids in powdered medicaments intended to be tableted, and emulsion stabilizers in compositions in which the active is present in the form of an emulsion. Examples of excipients which adapt a composition to a desired route of administration are, for example, but not limited to, for oral administration, absorption enhancers promoting absorption from the gastrointestinal tract, for transdermal or transmucosal administration, penetration enhancers, for example, those employed in adhesive skin "patch" or compositions for buccal administration.

Notwithstanding the function excipients perform in a composition, excipients are collectively termed herein "a carrier." Typically, formulations may comprise up to about 95 percent active ingredient and the balance carrier, although formulations with different ratios may be prepared. In general, acceptable pharmaceutical compositions contain a suitable concentration of the active that an effective amount of the PCSK9 antagonist can be provided in an individual dosage form of acceptable volume based upon the route of administration such that it can provide a therapeutic serum level of the active for an acceptable period of time in a subject to whom the composition is administered and the composition will retain biological activity during storage within an acceptable temperature range for an acceptable period of time.

Pharmaceutical composition, as used herein, refers both to a bulk composition, that is, formulated material that has not yet been formed into individual dosage units for administration, and the composition contained within individual dosage units.

While compositions of the invention may be employed in bulk form, it will be appreciated that for most applications compositions will be incorporated into a dosage form providing individual units suitable for administration to a patient, each dosage form comprising an amount of the selected composition which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachet or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; (vi) a dosage form adapted for intravenous (IV) infusion, for example, over a prolonged period using an I.V. infusion pump; (vii) a dosage form adapted for intramuscular administration (IM), for example, an injectable solution or suspension, and which may be adapted to form a depot having extended release properties; (viii) a dosage form adapted for drip intravenous administration (IV), for example, a solution or suspension, for example, as an IV solution or a concentrate to be injected into a saline IV bag; (ix) a dosage form adapted for subcutaneous administration, including administration over an extended time period by implanting a rod or other device which diffuses the compound into the surround tissue and thereby provides a continuous serum therapeutic level; or (x) a dosage form adapted for delivery via rectal or vaginal mucosa, for example, a suppository.

Pharmaceutical compositions can be solid, semi-solid or liquid. Solid, semi-solid and liquid form preparations can be adapted to a variety of modes of administration, examples of which include, but are not limited to, powders, dispersible granules, mini-tablets, beads, which can be used, for example, for tableting, encapsulation, or direct administration. In addition, liquid form preparations include, but are not limited to, solutions, suspensions and emulsions which for example, but not exclusively, can be employed in the preparation of formulations intended for ingestion, inhalation or intravenous administration (IV), for example, but not limited to, administration via drip IV or infusion pump, intramuscular injection (IM), for example, of a bolus which is released over an extended duration, direct IV injection, or adapted to subcutaneous routes of administration.

Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in a solid oral dosage form, for example, a tablet or quick-melt mouth-dissolving formulation are preferable routes of administration for a compound of the invention or a salt thereof, a composition of the invention may be formulated for administration via other routes mentioned above. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md. Additional examples of publications addressing formulation issues may be found in: Pharmaceutical compositions may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127.

In another aspect the present invention provides methods of employing PCSK9-specific antagonist compounds described herein for antagonizing PCSK9 function; said methods of which are further described below. Use of the term "antagonizing" throughout the present application refers to providing to the affected tissue(s) a substance which opposes the action of, inhibits, counteracts, neutralizes or curtails one or more functions of PCSK9 in the affected tissues. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen relative to the activity observed when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. In some embodiments of the present invention include such methods wherein the cell is a human cell. Additional embodiments of the present invention include such methods wherein the cell is a murine cell.

In one aspect, the present invention provides a method for antagonizing the activity of PCSK9 in a subject, which comprises administering to the subject a therapeutically effective amount of a PCSK9-specific antagonist of the present invention. In some embodiments, the methods for antagonizing PCSK9 function are for the treatment, as defined herein, of a PCSK9-associated disease, disorder or condition or, alternatively, for providing therapy in a disease, disorder or condition that could benefit from the effects of a PCSK9 antagonist.

The present invention, thus, contemplates the use of PCSK9-specific antagonists described herein in various methods of treatment where antagonizing PCSK9 function is desirable. As used herein, the term "method of treatment" relates to a course of action resulting in a change in at least one symptom of a disease state which can be prophylactic or therapeutic in nature. In some embodiments, the present invention relates to a method of treatment for a condition associated with and/or attributed to PCSK9 activity, or a condition where the functioning of PCSK9 is contraindicated for a particular subject, the method comprising administering to the subject a therapeutically effective amount of a PCSK9-antagonist compound of Formula I, or pharmaceutically acceptable salt thereof. In some embodiments, the condition may be atherosclerosis, hypercholesterolemia, coronary heart disease, metabolic syndrome, acute coronary syndrome or related cardiovascular disease and cardiometabolic conditions, or may be a disease state or condition in which PCSK9 activity is contraindicated.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic and/or prophylactic effect for the period of time desired. The desired effect may be, for example, the alleviation, amelioration, reduction or cessation of at least one symptom associated with the treated condition. These amounts will vary, as the skilled artisan will appreciate, according to various factors, including but not limited to the disease state, age, sex, and weight of the individual, and the ability of the PCSK9-specific antagonist to elicit the desired effect in the individual. The response may be documented by in vitro assay, in vivo non-human animal studies, and/or further supported from clinical trials.

In some embodiments it is preferred to administer a PCSK9 antagonist compound of the invention in the form of a pharmaceutical composition as described herein.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors, for example, but not limited to, those mentioned above, including the condition of the patient, the area being treated, the route of administration, and the treatment desired, for example, prophylaxis or acute treatment and the like. A physician or veterinarian of ordinary skill can readily determine and prescribe the effective therapeutic amount of the antagonist.

The subject may be in need of, or desire, treatment for an existing disease or medical condition. As used herein, the subject "in need" of treatment of an existing condition encompasses both a determination of need by a medical professional as well as the desire of the subject for such treatment. When a compound or a salt thereof is provided in combination with one or more other active agents, "administration" and its variants are each understood to include provision of the compound or its salt and the other agents contemporaneously or simultaneously or over a course of separate administrations over a period of time. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to antagonize PCSK9 and thereby elicit the response being sought (i.e., induce a therapeutic response in the treatment or management of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions in an animal or human).

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. For convenience, the total daily dosage may be divided and administered in portions during the day as required or delivered continuously.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or antiobesity agents may be used in any combination with the compound of Formula I in a single dosage formulation (a fixed dose drug combination), or may be administered to the subject in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), crivastatin, and pitavastatin, a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199), CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2), AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211), inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the treatment of the above-mentioned conditions or disorders including the free-acid, free-base, and pharmaceutically acceptable salt forms of the above active agents where chemically possible.

The compounds of the present invention can be readily prepared according to the following reaction schemes and examples, or modifications thereof, using readily available starting materials, reagents and conventional synthesis procedures. In these reactions, it is also possible to make use of known variants. For purification of the compounds using reverse phase chromatography (either HPLC or MPLC, as noted below), a C18 column was used. Other methods for preparing compounds of the invention will be readily apparent to the person of ordinary skill in the art in light of the following reaction schemes and examples. Abbreviations listed below may used in the exemplary schemes and/or examples herein.

ACN is acetonitrile
AcOH is acetic acid
AcO⁻NH₄ is ammonium acetate
Boc₂O is di-tert-butyl dicarbonate
Bn is benzyl
BnBr is benzyl bromide
BzCl is benzoyl chloride
CBr₄ is perbromomethane
Cbz-Cl is benzyl chloroformate
DBU is 1,8-Diazabicyclo[5.4.0]undec-7-ene
DCC is dicyclohexylcarbodiimide
DCE is 1,2-dichloroethane
DCM is dichloromethane
DEA is N,N-diethylamine
DIAD is (E)-diisopropyl diazene-1,2-dicarboxylate
DIEA or DIPEA is N,N-diisopropylethylamine
DMAP is 4-dimethylaminopyridine
DMF is N,N-dimethylformamide
DMSO is dimethyl sulfoxide
EA or EtOAc is ethyl acetate
EtOH is ethanol
Et₂O is diethyl ether
Fmoc is fluorenylmethyloxycarbonyl protecting group
Fmoc-Cl is (9H-fluoren-9-yl)methyl carbonochloridate
Fmoc-D-Dap(Boc)-OH is N-alpha-(9-Fluorenylmethyloxycarbonyl)-N-beta-t-butyloxycarbonyl-D-2,3-diaminopropionic acid
Fmoc-Osu is Fmoc N-hydroxysuccinimide ester
HATU is 1-[bis(dimethylamino)methylene]-1H-1,2,3-triazolo[4,5-b]pyridinium 3-oxid hexafluorophosphate
HPLC is High Performance Liquid Chromatography
IPA is isopropyl alcohol
LiOH is lithium hydroxide
LC/MS is Liquid chromatography-mass spectrometry
Me₃N is trimethyl amine
MeOH is methanol
MPLC is Medium pressure liquid chromatography
MsCl is methanesulfonyl chloride
NaBH(OAc)₃ is sodium triacetoxyborohydride
NMR is Nuclear Magnetic Resonance
NsCl is 4-nitrobenzene-1-sulfonyl chloride
PE is petroleum ether
Pd₂(dba)₃(HCCl₃) is tris(dibenzylideneacetone)dipalladium (0)-chloroform adduct
PPh₃ is triphenylphosphine
PdCl₂(dppf) or Pd(ii)(dppf)Cl₂ is dichloro[1,1'-bis(diphenylphosphino)ferrocene]palladium(II)
Pd(dppf)Cl₂·CH₂Cl₂ is dichloro[1,1'-bis(diphenylphosphino)ferrocene]palladium(II) dichloromethane adduct
Pd(PPh₃)₄ is tetrakis(triphenylphosphine)palladium
PPT$_s$ is pyridinium p-toluenesulfonate
[Rh(OAc)₂]₂ is rhodium(II) acetate dimer
RT or r.t. or rt is room temperature
tBuOAc is tert-butyl acetate
TEA is triethylamine
TFA is trifluoroacetic acid
TFE is tetrafluoroethylene
THF is tetrahydrofuran
Tf₂O is trifluoromethanesulfonic anhydride
Teoc-OSu is 2,5-dioxopyrrolidin-1-yl (2-(trimethylsilyl)ethyl) carbonate
TBAF is tetrabutylammonium fluoride
TMS is tetramethylsilane
Zhan's catalyst 1B is dichloro(1,3-bis(2,4,6-trimethylphenyl)-2-imidazolidinylidene)((5-(((dimethylamino)sulfonyl)-2-(1-methylethoxy-O)phenyl)methylene-C)ruthenium(II) [also described as 1,3-Bis(2,4,6-trimethylphenyl)-4,5-dihydroimidazol-2-ylidene[2-(i-propoxy)-5-(N,N-dimethylaminosulfonyl)phenyl[methyleneruthenium (II) dichloride]

Example 1 Preparation of Ex-01 and Ex-51
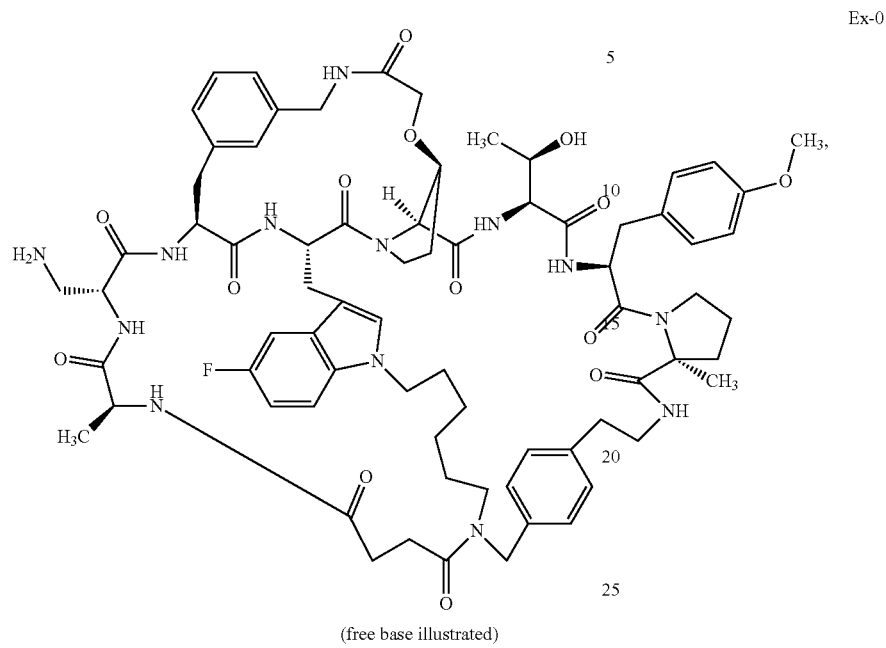
Ex-01
(free base illustrated)
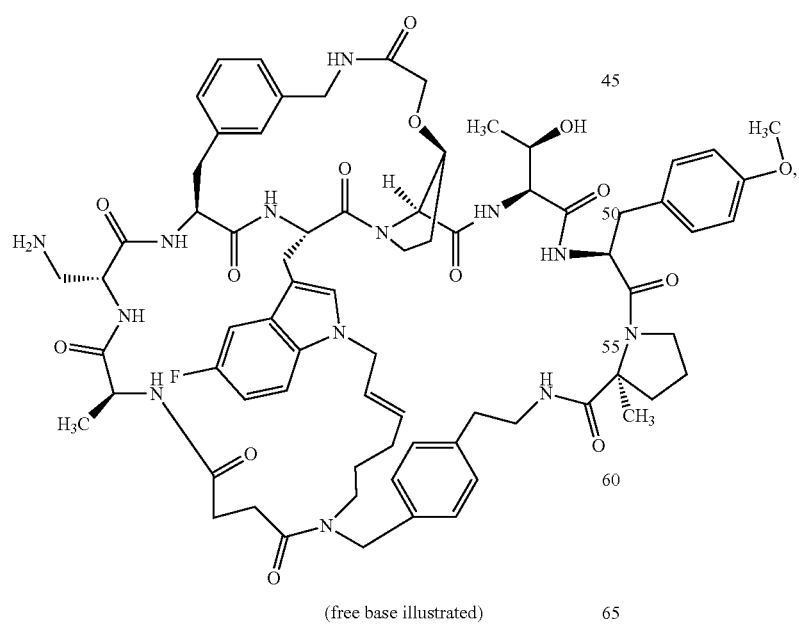
Ex-51
(free base illustrated)

Salt forms of compounds Ex-01 and Ex-51 were prepared from intermediates 76 and 86 (preparation following) in accordance with the following scheme:
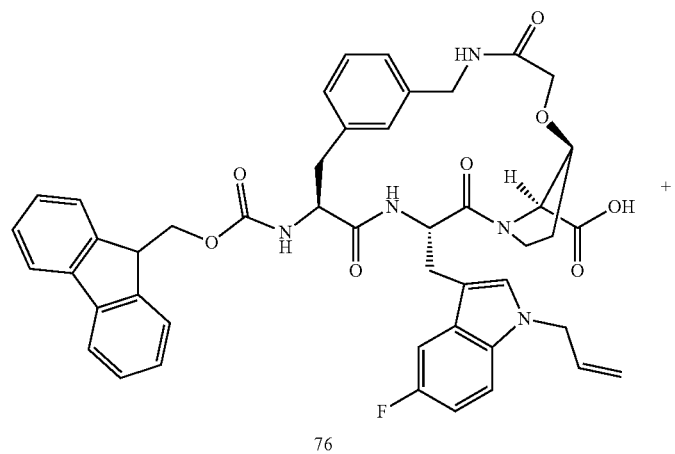
76
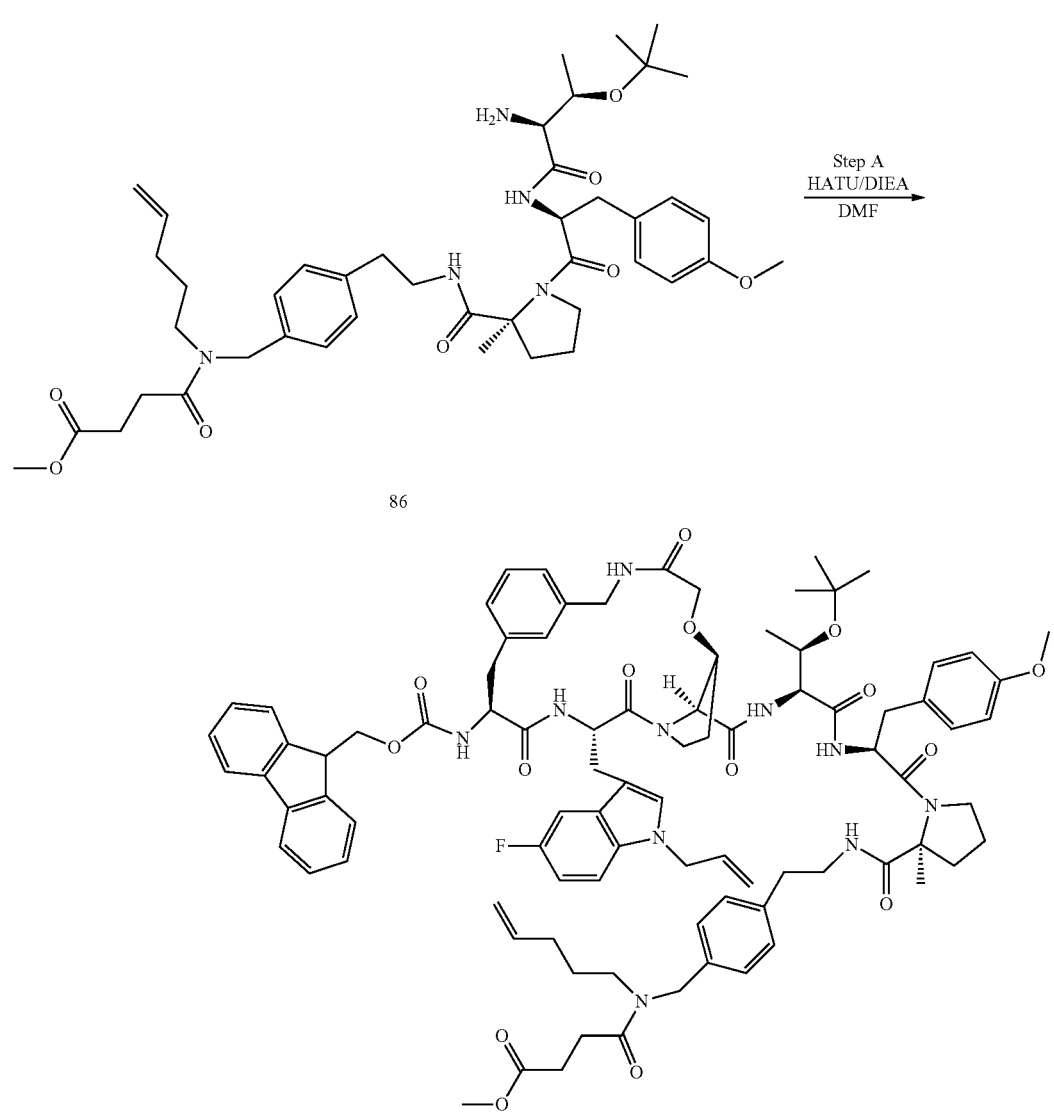
86
89

-continued
89 →(Step B, Zhan Catalyst, DCM/AcOH)
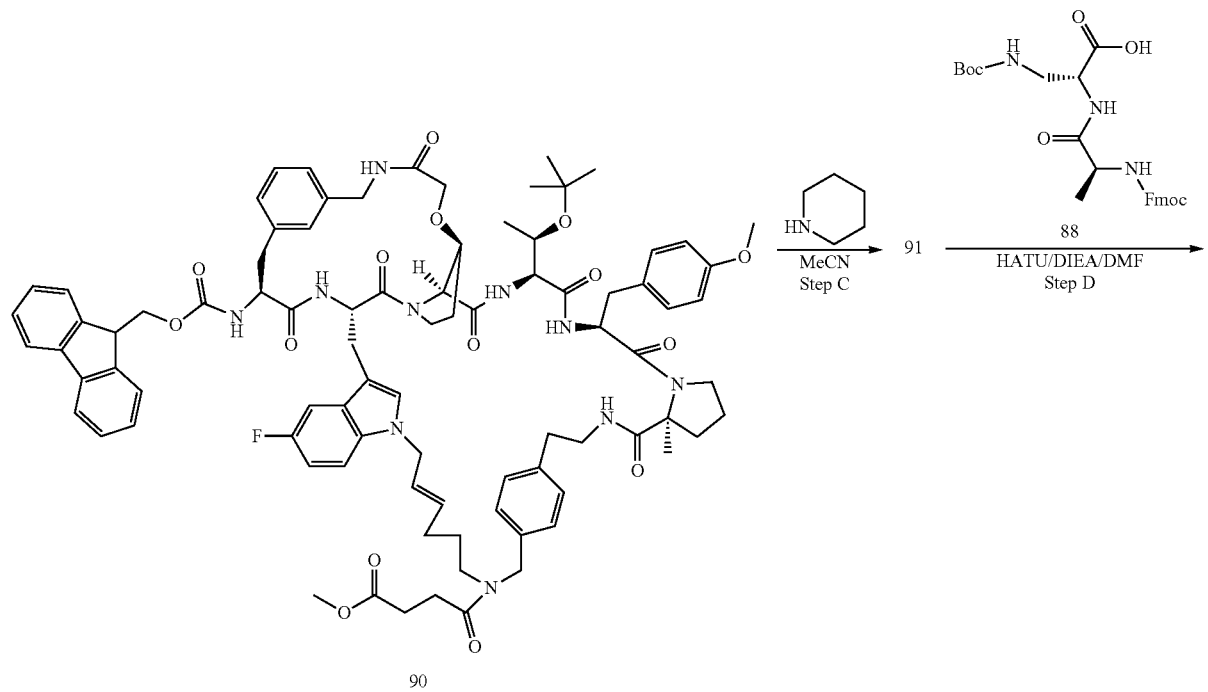
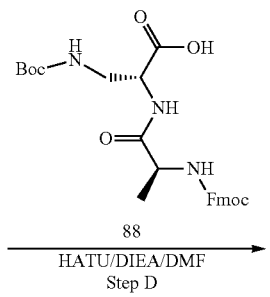
90 →(piperidine, MeCN, Step C) 91 →(88, HATU/DIEA/DMF, Step D)
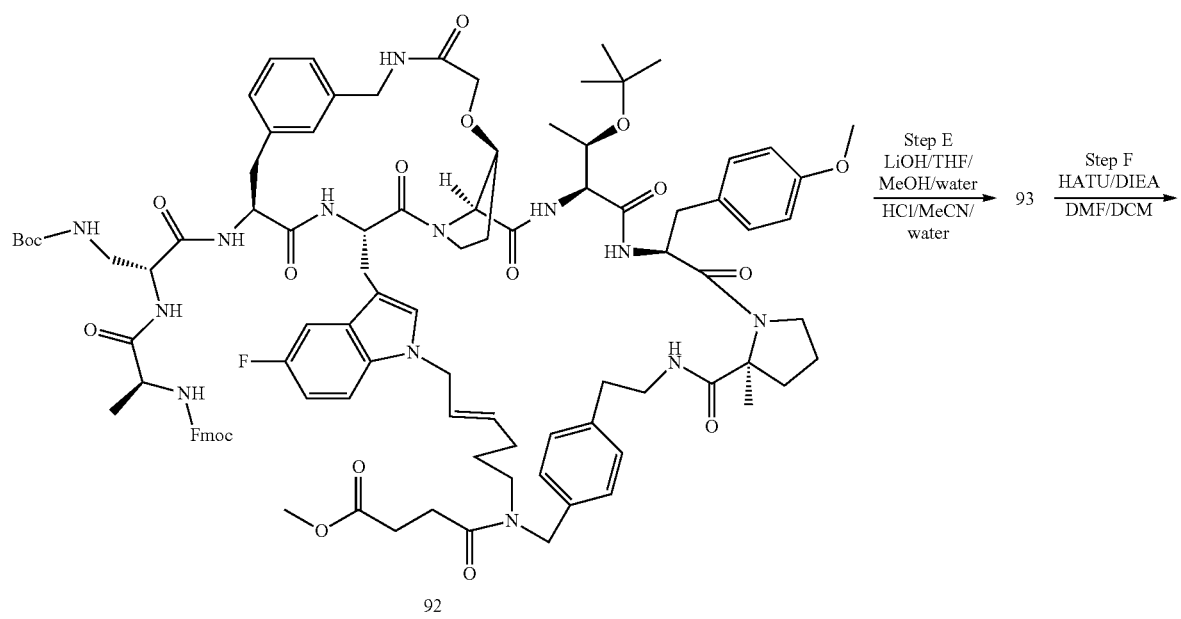
92 →(Step E, LiOH/THF/MeOH/water, HCl/MeCN/water) 93 →(Step F, HATU/DIEA, DMF/DCM)

-continued

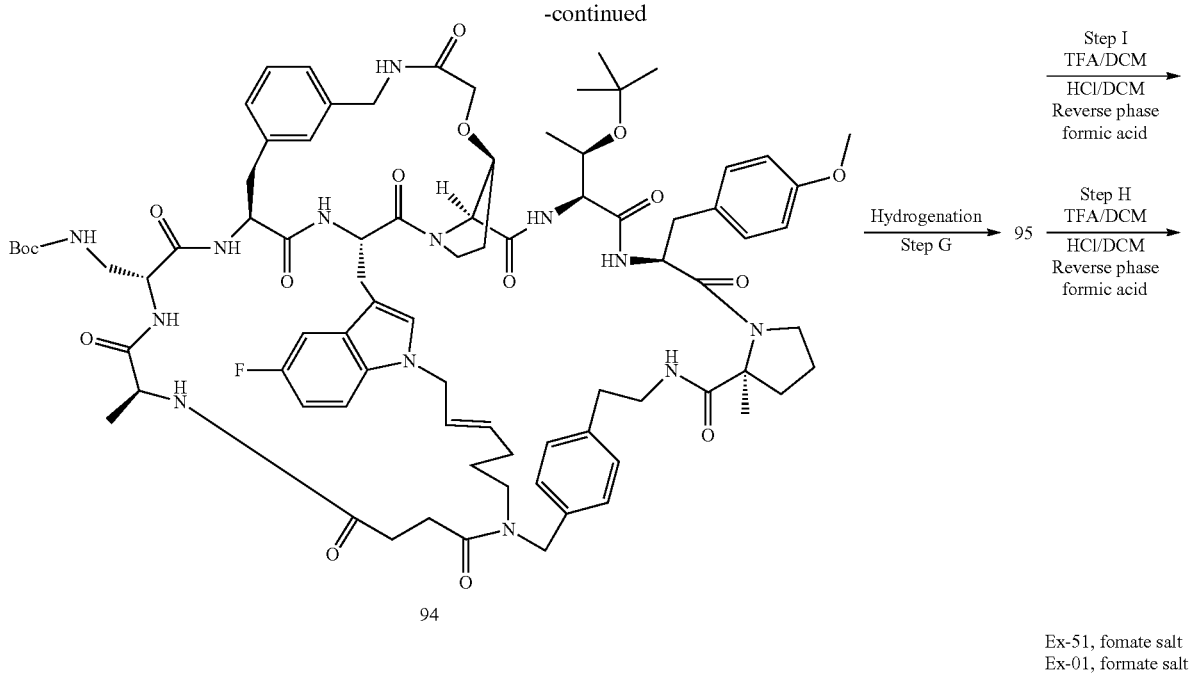

94

Step I
TFA/DCM
→
HCl/DCM
Reverse phase
formic acid

Hydrogenation
Step G
→ 95

Step H
TFA/DCM
→
HCl/DCM
Reverse phase
formic acid

Ex-51, formate salt
Ex-01, formate salt

Step A: Preparation of Intermediate 89

To a solution of 76 (1.56 g, 1.917 mmol, preparation following) and 86 (1.506 g, 1.936 mmol, preparation following) in DMF (40 ml) was added HATU (0.802 g, 2.108 mmol) and DIEA (0.670 ml, 3.83 mmol). The resulting solution was stirred at rt for 50 min, then partitioned between EtOAc (300 mL) and brine (100 mL). The organic phase was washed with brine (2×100 mL), dried over $Na_2SO_4$, concentrated and the residue was purified on silica gel column using MeOH/DCM as eluting solvents to give 89. LC/MS: (M+1)+: 1573.8.

Step B: Preparation of Intermediate 90

A solution of 89 (0.68 g, 0.432 mmol) in DCM (500 ml) and acetic acid (40 mL) was bubbled with $N_2$ for 20 min followed by addition of Zhan catalyst-1b (0.222 g, 0.302 mmol). The resulting mixture was further bubbled with $N_2$ for 20 min, then heated at 55° C. for 5 h. After cooling to rt the mixture was filtered through celite, the filtrate was concentrated, and the residue was purified on silica gel column using MeOH/DCM as eluting solvents to give 90 (cis/trans mixture). LC/MS: $(M+1)^+$: 1545.7.

Step C: Preparation of Intermediate 91

To a solution of 90 (cis/trans mixture) (65 mg, 0.042 mmol) in acetonitrile (2 ml) was added piperidine (0.042 ml, 0.420 mmol). The resulting solution was stirred at rt for 1 h, then concentrated and the residue was dissolved in acetonitrile (4 mL) and concentrated again. The residue was further dried under high vacuum for 30 min to give 91 (cis and trans mixture). LC/MS: $(M+1)^+$: 1324.0.

Step D: Preparation of Intermediate 92

To a solution of 91 (cis/trans mixture) (548 mg, 0.414 mmol) and 88 (227 mg, 0.455 mmol, preparation following) in DMF (10 ml) at 0° C. was added HATU (181 mg, 0.476 mmol) and DIEA (0.166 ml, 0.952 mmol). The resulting solution was stirred at 0° C. for 1 h, and the solution was purified by reverse phase MPLC over C18 column using acetonitrile (0.05% TFA)/water (0.05% TFA) as eluting solvents to give 92 (cis/trans mixture). LC/MS: $(M+1)^+$: 1803.5.

Step E: Preparation of Intermediate 93

To a solution of 92 (700 mg, 0.388 mmol) in THF (20 ml), MeOH (6 ml), and water (6 ml) at 0° C. was added 1N aqueous LiOH (3.11 ml, 3.11 mmol) dropwise, and the resulting solution was stirred at 0° C. for 23 h. The solution was neutralized by addition of 1N HCl to pH 7-8, the volatile was evaporated, the aqueous phase was acidified to pH 5, and the mixture was purified by reverse phase MPLC over C18 column using acetonitrile (0.05% TFA)/water (0.05% TFA) as eluting solvents to give 93 as TFA salt. To a solution of 93 TFA salt (427 mg, 0.257 mmol)) in water (70 mL) and acetonitrile (70 ml) at 0° C. was added 0.1 N HCl (13.5 ml, 1.350 mmol) dropwise, the resulting solution was stirred at 0° C. for 5 min, then lyophilized to give 93 as HCl salt. LC/MS: $(M+1)^+$: 1567.1.

Step F: Preparation of Intermediate 94

To a solution of 93 as HCl salt (200 mg, 0.125 mmol) in DMF (30 mL) was added HATU (56.9 mg, 0.150 mmol). The resulting solution was stirred at rt for 30 min, then diluted with DCM (400 mL) followed by addition of DIEA (0.065 mL, 0.374 mmol). The resulting solution was stirred at rt for 1 h, the volatile was evaporated on rotary evaporator, and the resulting DMF solution was purified by reverse phase MPLC using acetonitrile (0.05% TFA)/water (0.05% TFA) as eluting solvents to give 94. LC/MS: $(M+1)^+$: 1549.2.

Step G: Preparation of Intermediate 95

To a solution of 94 (14 mg, 9.04 µmol) in MeOH (20 ml) was added 10% Pd/C (1.924 mg, 1.808 µmol) and the resulting mixture was subjected to hydrogenation at rt via $H_2$ balloon for 1 h. The mixture was filtered through celite and the filtrate was concentrated to give intermediate compound 95. LC/MS: $(M+1)^+$: 1550.9.

Step H: Preparation of Ex-01

Intermediate compound 95 prepared in the previous step (26 mg, 0.017 mmol) was dissolved in DCM (2 ml). To this solution was added TFA (6 mL, 78 mmol) and the resulting solution was stirred at rt for 30 min, then concentrated and the residue was dissolved in DCM (3 mL) and treated with 4N HCl in dioxane (0.042 mL, 0.168 mmol), and concentrated again to give Ex-01 as a crude product. The crude Ex-01 was purified by reverse phase HPLC using acetonitrile (0.1% formic acid)/water (0.1% formic acid) as eluting solvents to provide the formate salt form of Ex-01. LC/MS: (M+1)$^+$: 1394.4.

Step I: Preparation of Ex-51

To a solution of intermediate compound 94 (30 mg, 0.019 mmol) in DCM (2 ml) was added TFA (4 ml, 51.9 mmol), and the reaction mixture was stirred at ambient temperature for 30 minutes, then concentrated. The residue was dissolved in DCM (2 mL), treated with HCl (4N in dioxane) (0.048 ml, 0.194 mmol), and concentrated to yield Ex-51 as a HCl salt. The compound was purified by reverse phase HPLC using acetonitrile (0.1% formic acid)/water (0.1% formic acid) as mobile phase to provide the formate salt form of Ex-51. LC/MS: (M+1)$^+$:1392.0.

The following schemes and procedures were used to prepare intermediates 76, 86 and 88 used in the procedures described above.

Preparation of Intermediate 68 Used in the Preparation of Intermediate 76

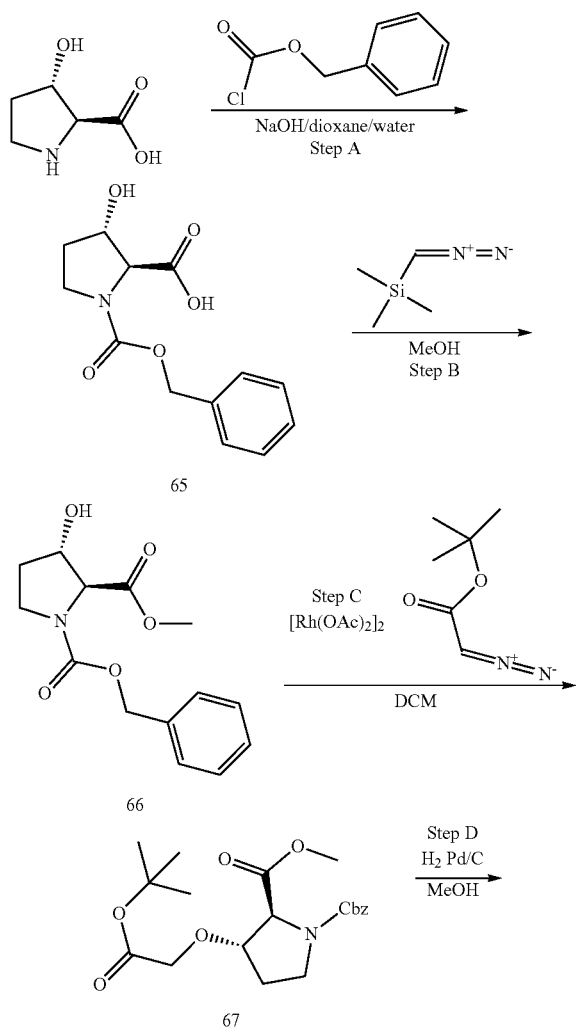

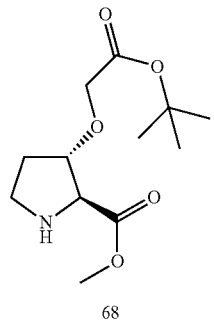

Step A: Preparation of Intermediate Compound 65

To a suspension of (2S,3S)-3-hydroxypyrrolidine-2-carboxylic acid (5.32 g, 40.6 mmol) in dioxane (100 ml) at 0° C. was added sodium hydroxide (122 ml, 122 mmol), followed by addition of benzyl chloroformate (6.50 ml, 44.6 mmol) dropwise. The resulting suspension was stirred at 0° C. for 5 h. After removing the volatile, the aqueous phase was acidified to pH 3, then partitioned between 30% IPA/DCM (200 mL) and brine (50 mL), the aqueous phase was further extracted with 30% IPA/DCM (2×100 mL). Combined organic phases were dried over Na$_2$SO$_4$ and concentrated to give (2S,3S)-1-((benzyloxy)carbonyl)-3-hydroxypyrrolidine-2-carboxylic acid (65). LC/MS: (M+1)$^+$: 266.1.

Step B: Preparation of Intermediate Compound 66

To a solution of 65 (7.48 g, 28.2 mmol) in MeOH (80 ml) was added TMS-Diazomethane (70.5 ml, 141 mmol) dropwise, and the resulting solution was stirred at rt for 10 min then quenched by addition of acetic acid (ca. 400 uL) dropwise. The solution was concentrated, and the residue was purified on silica gel column using EtOAc/hexane as eluting solvents to give 66. LC/MS: (M+1)$^+$: 280.1.

Step C: Preparation of Intermediate Compound 67

A solution of 66 (4.81 g, 17.22 mmol) in DCM (200 mL) was bubbled with N$_2$ for 30 min, followed by addition of rhodium(ii) acetate dimer (0.761 g, 1.722 mmol). The mixture was cooled in a ice-water bath, and tert-butyl diazoacetate (3.58 mL, 25.8 mmol) were added at 0° C. dropwise. The resulting mixture was stirred at 0° C. for 1.5 h. The reaction was quenched by addition of water (100 mL), the mixture was extracted with DCM (3×100 mL), the combined organic phase was dried over Na$_2$SO$_4$, concentrated and the residue was purified by reverse phase MPLC using acetonitrile (0.05% TFA)/water (0.05% TFA) as eluting solvents. The fraction containing the product was concentrated and the aqueous phase was extracted with DCM (2×100 mL). The combined organic phase was dried over Na$_2$SO$_4$ and concentrated to give 67. LC/MS: (M+1)$^+$: 394.2.

Step D: Preparation of Intermediate Compound 68

To a solution of 67 (3.72 g, 9.46 mmol) in MeOH (80 ml) was added 10% Pd/C (0.805 g, 0.756 mmol) and the resulting mixture was subjected to hydrogenation via H$_2$ balloon at ambient temperature for 2 hours, then filtered through celite. The filtrate was concentrated to give 68. LC/MS: (M+1)$^+$: 259.9.

Preparation of Intermediate Compound 76
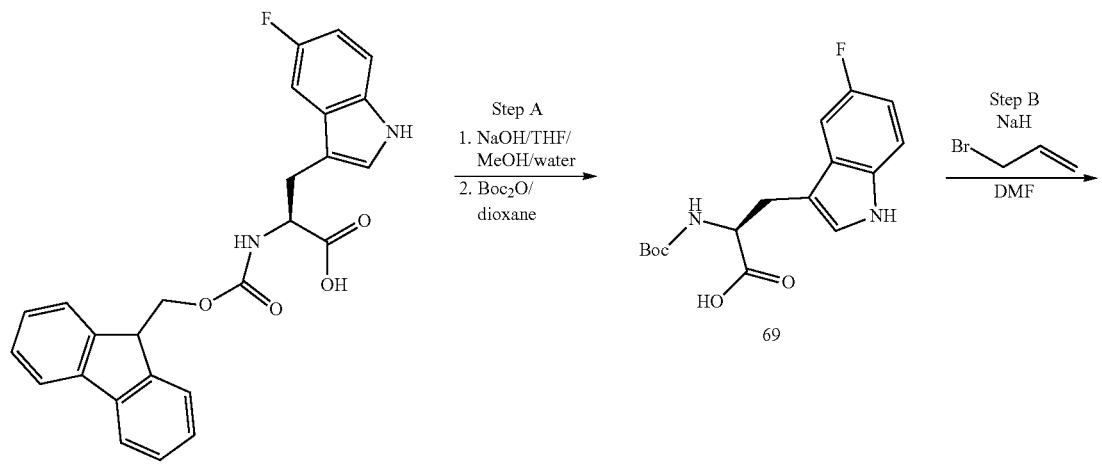
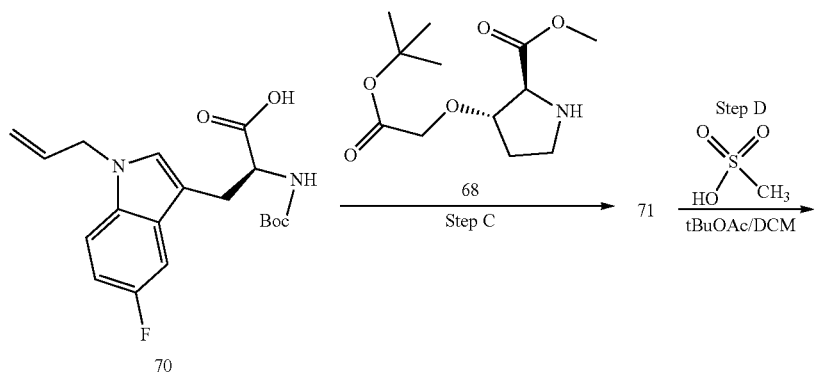
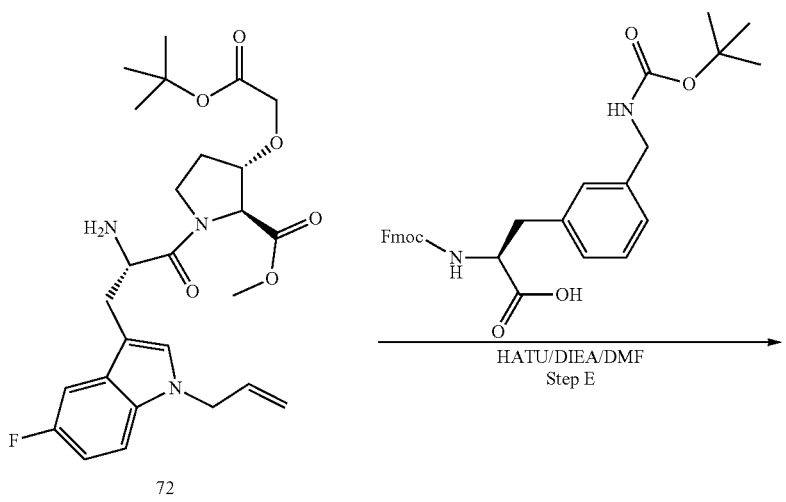

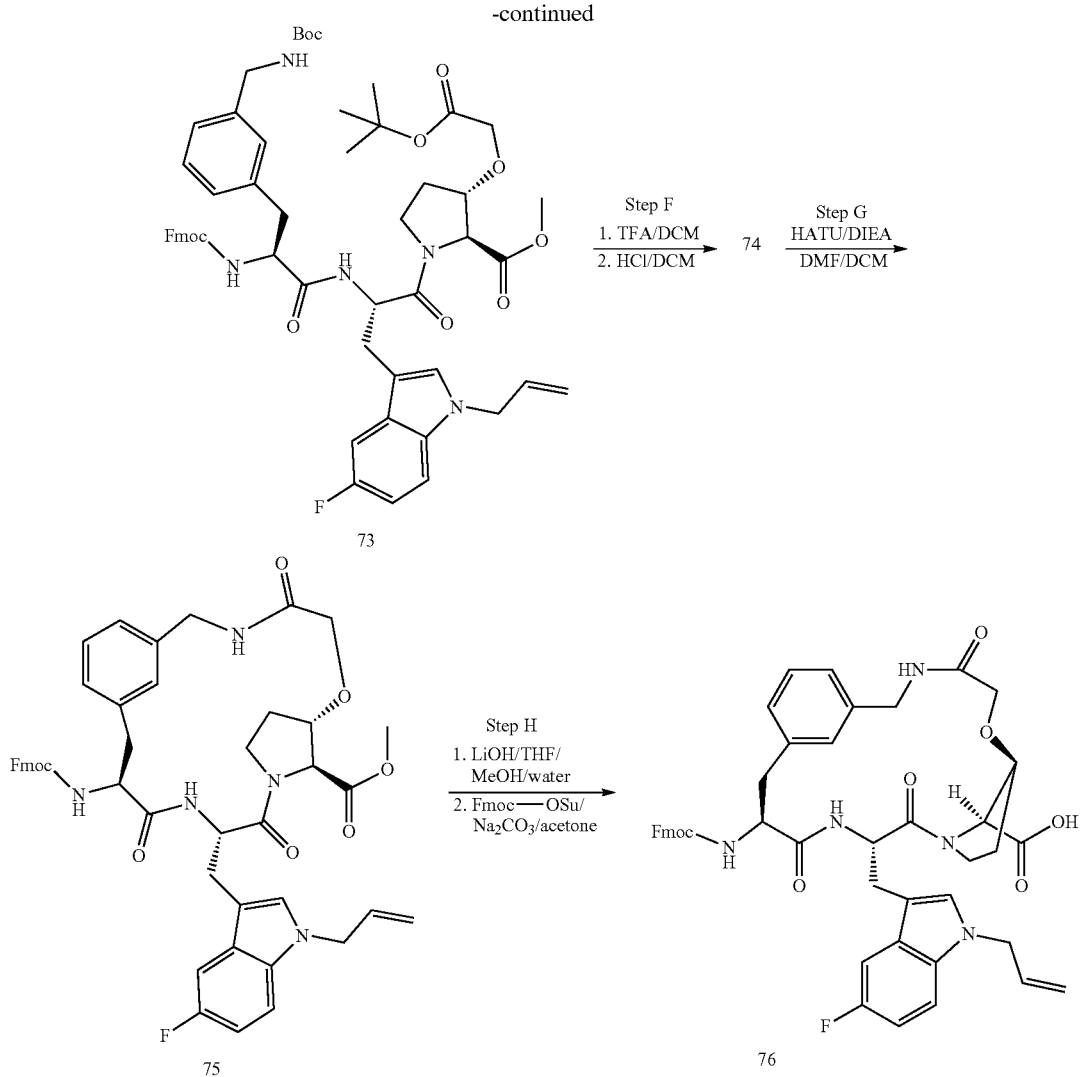

Step A: Preparation of Intermediate 69

To a solution of (S)-2-((((9H-fluoren-9-yl)methoxy)carbonyl)amino)-3-(5-fluoro-1H-indol-3-yl)propanoic acid (3 g, 6.75 mmol) in THF (20 ml), MeOH (10 mL), and water (20.00 ml) at 0° C. was added NaOH (20.25 ml, 20.25 mmol) and the resulting solution was stirred at ambient temperature for 4 hours, then the volatile was evaporated. To the aqueous mixture was added dioxane (50 ml) and water (20 mL), the resulting solution was cooled to 0° C. and Boc$_2$O (1.881 ml, 8.10 mmol) was added to the above solution. The resulting solution was stirred at 0° C. for 3 hours, the volatile was removed and the aqueous phase was extracted with Et$_2$O (3×40 mL), acidified to pH 3, then extracted with DCM (3×100 mL), followed by 30% IPA/DCM (2×80 mL). The combined organic phase was dried over Na$_2$SO$_4$ and concentrated to give 69. LC/MS: (M+1)$^+$: 322.9.

Step B: Preparation of Intermediate 70

To a solution of 69 (2.079 g, 6.45 mmol) in DMF (40 ml) at 0° C. was added 60% NaH in hexane (0.568 g, 14.19 mmol), and the resulting solution was stirred at 0° C. for 50 min followed by addition of allyl bromide (1.172 mL, 13.54 mmol) dropwise. The resulting solution was stirred at 0° C. for 1.5 h, then quenched by addition of 1N HCl (ca. 3.68 mL). The solution was then partitioned between EtOAc (200 mL) and water (100 mL), the organic phase was washed with brine (2×100 mL), dried over Na$_2$SO$_4$, concentrated and the residue was purified on silica gel column using MeOH/DCM as eluting solvents to give 70. LC/MS: (M+1)$^+$: 363.0.

Step C: Preparation of Intermediate 71

To a solution of 70 (2.239 g, 6.18 mmol) and 68 (1.842 g, 7.11 mmol) in DMF (30 ml) was added HATU (2.82 g, 7.41 mmol) and DIEA (2.59 ml, 14.83 mmol), and the resulting solution was stirred at ambient temperature for 1 hour. The mixture was partitioned between EtOAc (200 mL) and brine (100 mL), the organic phase was washed with brine (3×100 mL), dried over Na$_2$SO$_4$, concentrated and the residue was purified on silica gel column using EtOAc/hexane as eluting solvents to give 71. LC/MS: (M+1)$^+$: 604.2.

Step D: Preparation of Intermediate 72

To a solution of 71 (2.83 g, 4.69 mmol) in CH$_2$Cl$_2$ (20 ml) and tBuOAc (30 ml) at 0° C. was added methanesulfonic acid (1.218 ml, 18.75 mmol), and the resulting solution was stirred at 0° C. for 16.5 h, then ambient temperature for 2.5 h. The solution (72) was directly used in the next step. LC/MS: (M+1)$^+$: 504.2.

Step E: Preparation of Intermediate 73

To a solution of (S)-2-((((9H-fluoren-9-yl)methoxy)carbonyl)amino)-3-(3-(((tert-butoxycarbonyl)amino)methyl)phenyl)propanoic acid (2.66 g, 5.16 mmol) in DMF (10 ml) was added HATU (1.961 g, 5.16 mmol) and DIEA (5.32 ml, 30.5 mmol), and the resulting solution was stirred at rt for 30 min then added to an ice-cold bath of the above prepared 72 solution. The resulting solution was stirred at ambient temperature for 1 hour. Volatiles were evaporated on rotary evaporator, and the residue was purified by reverse phase MPLC using acetonitrile (0.05% TFA)/water (0.05% TFA) as eluting solvents. Collected fractions were concentrated on rotary evaporator to give 73. LC/MS: (M+1)$^+$: 1002.1.

Step F: Preparation of Intermediate 74

To a solution of 73 (3.235 g, 3.23 mmol) in DCM (4 ml) was added TFA (7.46 ml, 97 mmol), and the resulting solution was stirred at ambient temperature for 1 hour, then concentrated. The residue was dissolved in DCM (10 mL), treated with 4N HCl in dioxane (3.23 ml, 12.91 mmol), then concentrated and the residue was dissolved in acetonitrile (100 mL)/water (50 mL) and lyophilized to provide 74. LC/MS: (M+1)$^+$: 846.1.

Step G: Preparation of Intermediate 75

To a solution of 74 (2.85 g, 3.23 mmol) in DMF (45 ml) was added HATU (1.474 g, 3.88 mmol), and the resulting solution was stirred at ambient temperature for 30 min, then diluted with DCM (600 ml) followed by addition of DIEA (1.692 ml, 9.69 mmol) dropwise. The resulting solution was stirred at ambient temperature for 1 hour. The solution was concentrated, and the residue was purified by reverse phase MPLC over C18 column using acetonitrile (0.05% TFA)/water (0.05% TFA) as eluting solvents. The fractions containing the product were concentrated and the aqueous layer was partitioned between DCM (200 mL) and sat. NaHCO$_3$ (200 mL). The aqueous phase was extracted with DCM (2×100 mL) and the combined organic phase was dried over Na$_2$SO$_4$ and concentrated to give 75. LC/MS: (M+1)$^+$: 828.1.

Step H: Preparation of Intermediate Compound 76

To a solution of 75 (1.93 g, 2.331 mmol) in THF (60 ml), MeOH (30 ml), and water (20 ml) at 0° C. was added 1N aqueous LiOH (9.9 ml, 9.90 mmol) dropwise, and the resulting solution was stirred at 0° C. for 16 h then quenched by addition of HCl (1N, 9.9 mL). The volatile was evaporated on rotary evaporator and to the solution above at 0° C. was added acetone (60 ml), sodium carbonate (0.371 g, 3.50 mmol), and Fmoc-Osu (0.802 g, 2.378 mmol). The resulting solution was stirred at 0° C. for 6 h, the volatile was evaporated on rotary evaporator, the aqueous phase was acidified to pH 4, then extracted with 30% IPA/DCM (3×100 mL). The combined organic phase was dried over Na$_2$SO$_4$, concentrated and the residue was purified on silica gel column using MeOH/DCM as eluting solvents to give 76. LC/MS: (M+1)$^+$: 814.2.

Alternative Preparation of Intermediate Compound 75b and Intermediate Compound 76B there from:

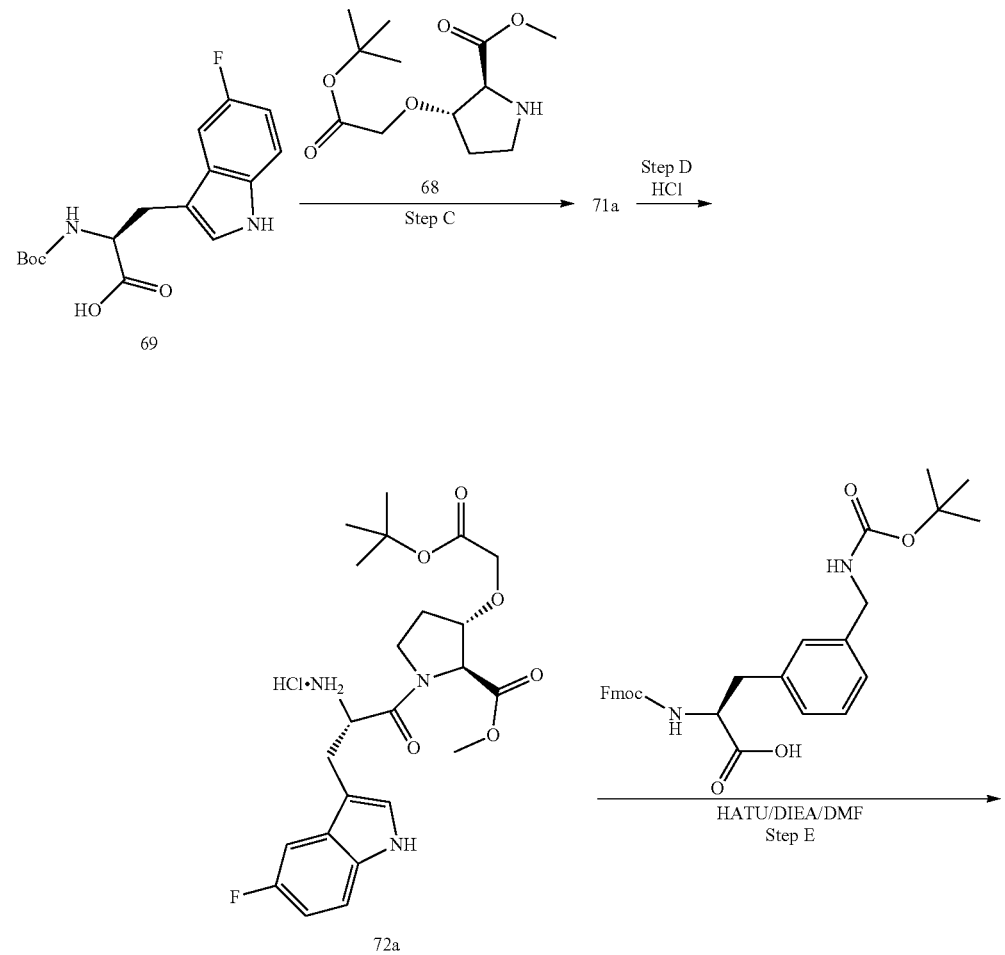

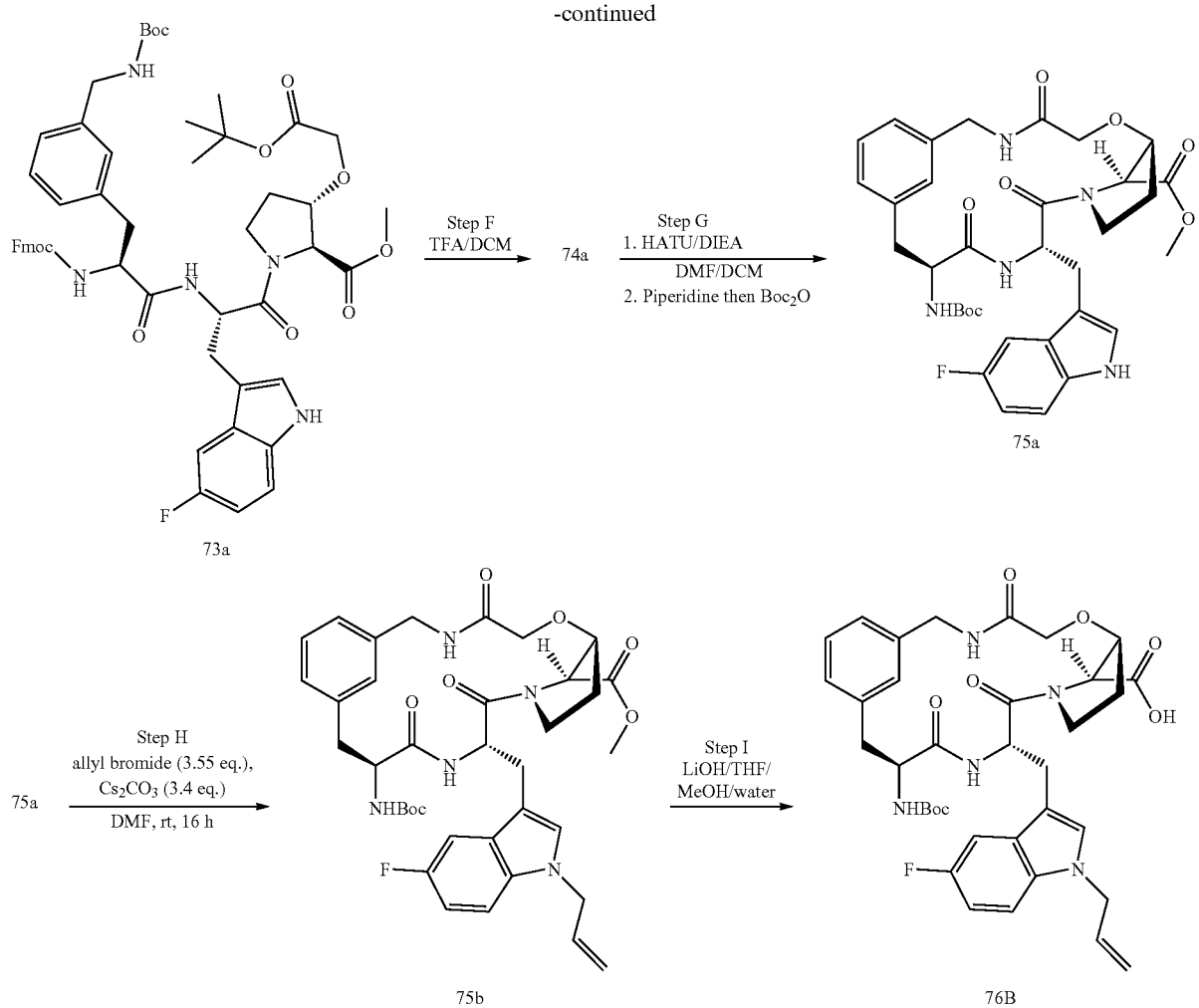

The general procedure described above for the preparation of intermediate compound 75 was generally followed, except that Step B was eliminated and the final step G also included replacing the Fmoc protecting group with a Boc protecting group, thus providing the intermediate compound 75a. The procedures for 75a and 76B are described below.

Step C: Preparation of Intermediate Compound 71a

To a solution of 69 (5.00 g, 15.5 mmol) in DMF (40.0 mL) at −50° C. were added 68, HATU (5.90 g, 15.5 mmol) and DIEA (4.01 g, 31.0 mmol) and the reaction mixture was stirred at −50° C. for 3 h. The final solution was quenched with water (5 mL), concentrated under reduced pressure and the residue was purified by reverse phase column chromatography over C18 (eluting with a gradient of acetonitrile/water+0.01% ammonium bicarbonate) to provide 71a. LCMS (ESI) calc'd for $C_{28}H_{38}FN_3O_8[M+H]^+$: 564.3, found 564.2.

Step D: Preparation of Intermediate Compound 72a

To a solution of 2 N HCl in dioxane (100 mL) and THF (100 mL) at rt was added 71a (8.40 g, 14.9 mmol) and the reaction mixture was stirred for 5 h. The final solution was concentrated under reduced pressure to afford 72a. LCMS (ESI) calc'd for $C_{23}H_{31}ClFN_3O_6[M−HCl+H]+$: 464.2, found 464.3.

Step E: Preparation of Intermediate Compound 73a

To a solution of 72a (800 mg, 1.60 mmol) in DMF (10.0 mL) at −50° C. were added (S)-2-((((9H-fluoren-9-yl)methoxy)carbonyl)amino)-3-(3-(((tert-butoxycarbonyl)amino)methyl)phenyl)propanoic acid (827 mg, 1.60 mmol), HATU (608 mg, 1.60 mmol) and DIEA (620 mg, 4.80 mmol) and the mixture was stirred at −50° C. for 3 h. The resulting solution was diluted with water (50 mL) and the aqueous layer was extracted with EtOAc (3×100 mL). The combined organic layer was washed with brine, dried over anhydrous $Na_2SO_4$ and filtered. The filtrate was concentrated under reduced pressure and the residue was purified by silica gel column chromatography (eluting with a gradient 1%-60% of EtOAc in PE) to give 73a. LCMS (ESI) calc'd for $C_{53}H_{60}FN_5O_{11}[M+H]+$: 962.4, found 962.6.

Step F: Preparation of Intermediate Compound 74a

To a solution of 73a (3.00 g, 3.12 mmol) in DCM (15.0 mL) at rt was added TFA (15.0 mL) and the reaction mixture was stirred for 1 h at room temperature. The resulting solution was concentrated under reduced pressure, co-evaporated with toluene and DCM to give 74a. LCMS (ESI) calc'd for $C_{46}H_{45}F_4N_5O_{11}$ [M−TFA+H]+: 806.3, found 806.7.

Step G: Preparation of Intermediate Compound 75a

To a solution of 74a (4.00 g, 4.35 mmol) in DMF (150 mL) at rt was added HATU (1.65 g, 4.35 mmol) and the reaction solution was stirred for 0.5 h. The solution was diluted with DCM (450 mL) and DIEA (1.69 g, 13.1 mmol) then stirred at rt for 3 h. The resulting solution was quenched with water (5 mL), concentrated under reduced pressure and the residue was purified by reverse phase column chromatography over C18 (eluting with a gradient of acetonitrile/water+0.05% TFA) to provide a Fmoc-protected intermediate. LCMS (ESI) calc'd for $C_{44}H_{42}FN_5O_8$ [M+H]+: 788.3, found 788.9.

To a solution of the Fmoc-protected intermediate just above (200 mg, 0.250 mmol) in DCM (5.00 mL) at rt was added piperidine (1.25 mL) and the reaction solution was stirred for 1 h. The final solution was concentrated under reduced pressure and the residue was purified by silica gel column chromatography (eluting with a gradient 0%-5% of MeOH in DCM) to afford an amine intermediate. LCMS (ESI) calc'd for $C_{29}H_{32}FN_5O_6$ [M+H]+: 566.2, found 566.3.

To a solution of the amine intermediate just above (2.86 g, 5.06 mmol) in THF (30.0 mL) and water (30.0 mL) at rt were added $Boc_2O$ (2.21 g, 10.1 mmol) and sodium bicarbonate (1.70 g, 20.2 mmol) and the reaction was stirred for 3 h. The final solution was diluted with water (50 mL) and extracted with EtOAc (3×100 mL). The combined organic layer was washed with brine (3×100 mL), dried over anhydrous $Na_2SO_4$ and filtered. The filtrate was concentrated under reduced pressure and the residue was purified by silica gel column chromatography (eluting with a gradient 0%-5% MeOH in DCM) to provide 75a. LCMS (ESI) calc'd for $C_{34}H_{40}FN_5O_8$ [M+H]+: 666.3, found 666.5; $^1$H NMR (300 MHz, $CD_3OD$) δ 7.35-7.08 (m, 6H), 6.95-6.79 (m, 2H), 5.01-4.91 (m, 1H), 4.72-4.56 (m, 2H), 4.45-4.38 (m, 1H), 4.45-4.38 (m, 5H), 3.69 (s, 3H), 3.32-2.92 (m, 5H), 2.14-1.82 (m, 2H), 1.47 (s, 9H).

Step H: Preparation of Intermediate Compound 75b

To a solution of 75a (0.665 g, 0.99 mmol) in DMF (0.5 mL) was added $Cs_2CO_3$ (1.11 g, 3.40 mmol) and 3-bromoprop-1-ene (0.43 g, 3.55 mmol) at 0° C. The reaction mixture was stirred at room temperature for 16 hours and poured into 5 mL of 50% sat. brine/10% citric acid solution, then extracted with ethyl acetate (2×20 mL). The organic layer was washed with brine (3×20 mL), dried over anhydrous $MgSO_4$ and filtered. The filtrate was concentrated under reduced pressure. The residue was purified by silica gel column chromatography, eluting with a 1%-5% gradient of MeOH in DCM. The fractions containing intermediate compound 75b were combined and concentrated to afford the title compound. LCMS (ESI) calc'd for $C_{37}H_{44}FN_5O_8$ [M+H]$^+$: 706.3, found 706.3.

Step I: Preparation of Intermediate Compound 76B

Hydrolysis of 75b with LiOH followed conditions similar to the ones described in the preparation of intermediate 93 to provide 76B.

Preparation of Intermediate 77B

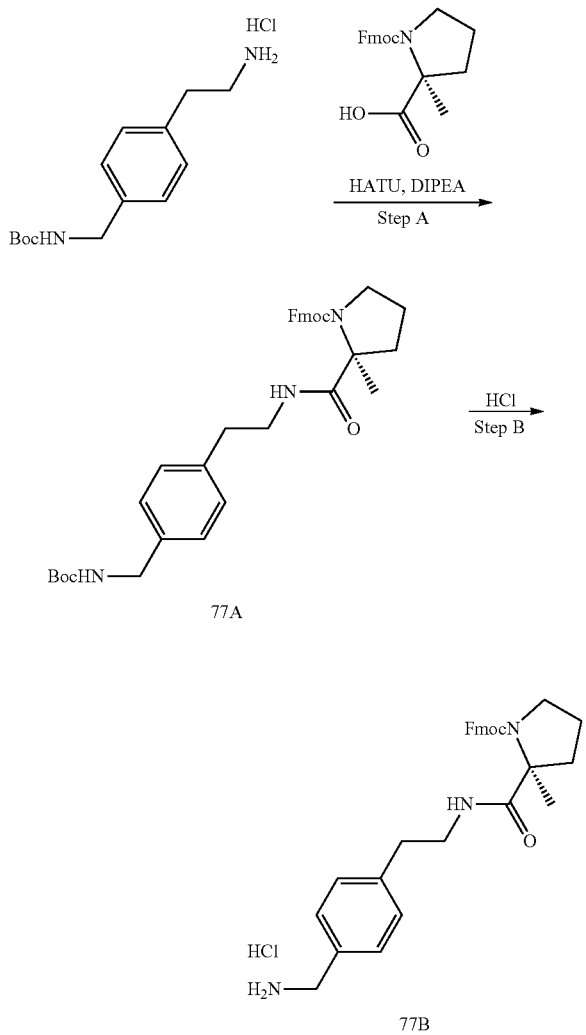

Step A: Preparation of Intermediate 77A

To a solution of (S)-1-(((9H-fluoren-9-yl)methoxy)carbonyl)-2-methylpyrrolidine-2-carboxylic acid (6.16 g, 17.54 mmol) and tert-butyl 4-(2-aminoethyl)benzylcarbamate hydrochloride (5.03 g, 17.54 mmol) in DMF (140 ml) at 0° C. were added HATU (8.00 g, 21.05 mmol) and DIPEA (9.16 ml, 52.6 mmol) then the reaction was allowed to warm to r.t. and stirred for 2 h. The final mixture was diluted with water, extracted with EtOAc, washed with brine, dried over $MgSO_4$, and filtered. The filtrate was concentrated and the residue was purified by column chromatography over silica gel (eluting with a gradient of 0-60% of EtOAc in hexane) to give 77A. MS (ESI): m/z (M+H)+ 584.5.

Step B: Preparation of Intermediate 77B

To a solution of 77A (8.92 g, 15.28 mmol) in DCM (40 ml) was added HCl 4N in dioxane (15.28 ml, 61.1 mmol), and the resulting solution was stirred at r.t. overnight. The mixture was concentrated to give 77B. MS (ESI): m/z (M+H)+ 484.3.

Preparation of Intermediate 86
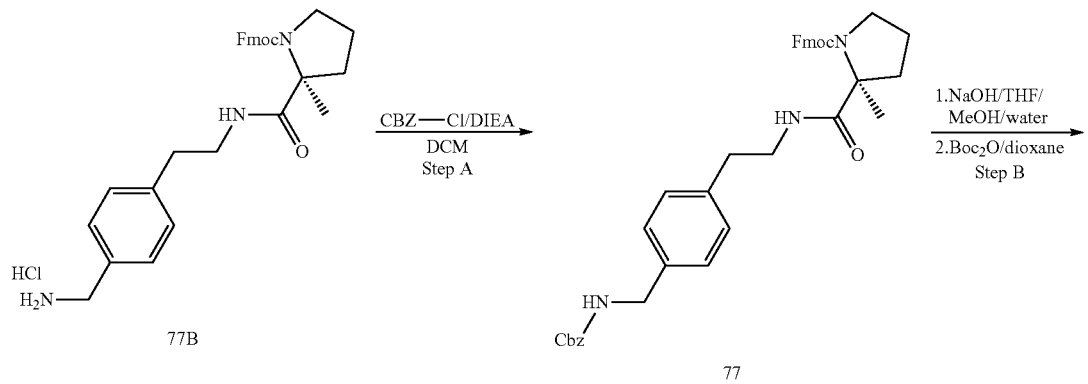
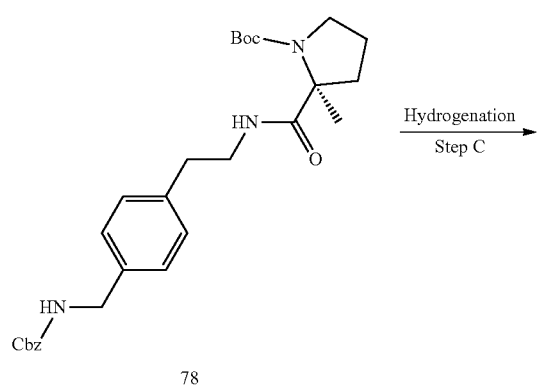
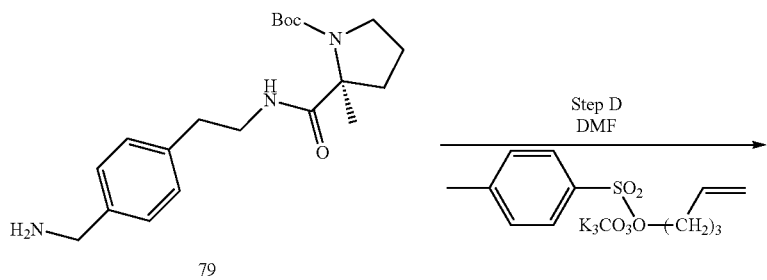
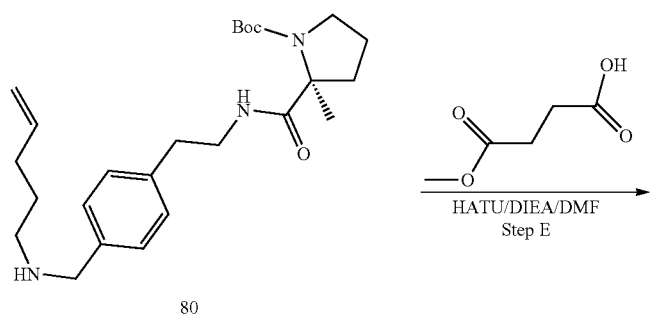

-continued
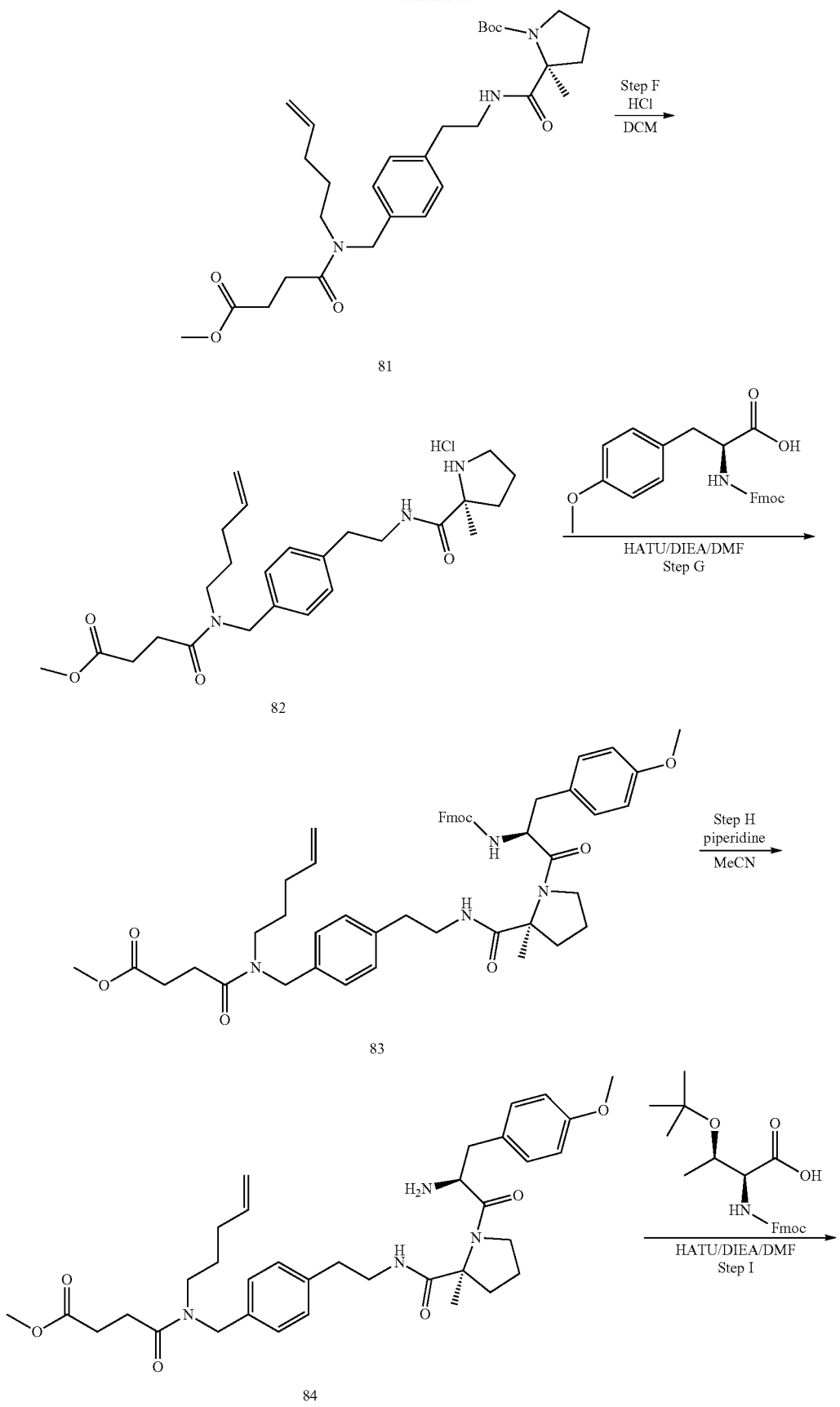

-continued

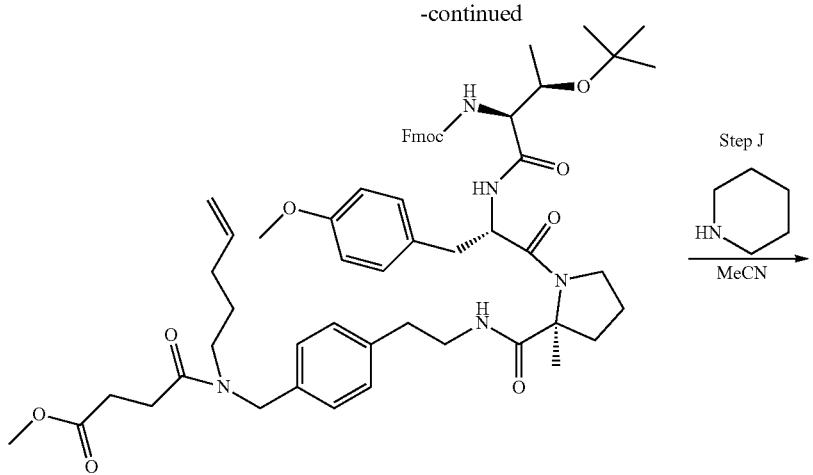

85

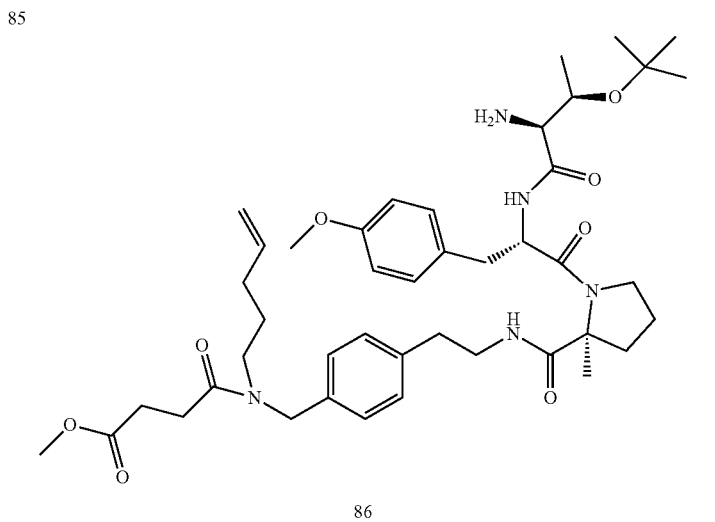

86

Step A: Preparation of Intermediate 77

To a solution of (S)—(9H-fluoren-9-yl)methyl 2-((4-(aminomethyl)phenethyl)carbamoyl)-2-methylpyrrolidine-1-carboxylate hydrochloride (77B) (5.87 g, 11.29 mmol) in DCM (140 ml) at 0° C. was added DIEA (5.91 ml, 33.9 mmol) and CBZ-Cl (1.726 ml, 11.85 mmol) dropwise, and the resulting solution was stirred at 0° C. for 4 h. The reaction solution was partitioned between water (200 mL) and DCM (200 mL), the water phase was extracted with DCM (100 mL), the combined organic phase was dried over $Na_2SO_4$, and the residue was purified on silica gel column using EtOAc/hexane as eluting solvents to give 77. LC/MS: $(M+1)^+$: 618.3.

Step B: Preparation of Intermediate 78

To a solution of 77 (5.56 g, 9.00 mmol) in THF (100 ml), water (50 ml), and MeOH (30 ml) was added 1N aqueous NaOH (45.0 ml, 45.0 mmol), and the resulting solution was stirred at rt for 2 h. The volatile was evaporated, and to the aqueous solution was added dioxane (200 ml), and $Boc_2O$ (2.508 ml, 10.80 mmol) in dioxane (20 mL). The resulting mixture was stirred from 0° C. to rt overnight. The volatile was evaporated on rotary evaporator, and the aqueous phase was extracted with DCM (3×150 mL). The combined organic phase was dried over $Na_2SO_4$, concentrated and the residue was purified on silica gel column using EtOAc/hexane as eluting solvents to give 78. LC/MS: $(M+1)^+$: 496.2.

Step C: Preparation of Intermediate 79

To a solution of 78 (4.04 g, 8.15 mmol) in MeOH (100 ml) was added 10% Pd/C (0.867 g, 0.815 mmol), and the resulting mixture was subjected to hydrogenation via $H_2$ balloon at rt for 1.5 h. The mixture was filtered through Celite, and the filtrate was concentrated to give 79. LC/MS: $(M+1)^+$: 362.2.

Step D: Preparation of Intermediate 80

To a solution of 79 (2.58 g, 7.14 mmol) in DMF (15 ml) was added pent-4-en-1-yl 4-methylbenzenesulfonate (0.858 g, 3.57 mmol) and $K_2CO_3$ (1.973 g, 14.27 mmol), and the resulting mixture was heated at 80° C. for 6 h. After cooling down to rt, the mixture was filtered and the filtrate was purified by reverse phase MPLC using acetonitrile (0.05% TFA)/water (0.05% TFA) as eluting solvents to give the product as TFA salt, which was further partitioned between DCM (100 mL) and 1N aqueous NaOH (50 mL). The aqueous phase was further extracted with DCM (2×50 mL), the combined organic phase was dried over $Na_2SO_4$, and concentrated to give 80. LC/MS: $(M+1)^+$: 430.3.

Step E: Preparation of Intermediate 81

To a solution of 80 (0.95 g, 2.211 mmol) in DMF (15 ml) was added 4-methoxy-4-oxobutanoic acid (0.321 g, 2.433 mmol), HATU (1.009 g, 2.65 mmol), and DIEA (0.927 ml, 5.31 mmol), and the resulting solution was stirred at rt for 1 h. The solution was partitioned between EtOAc (200 mL)

and brine (100 mL), the organic phase was washed with brine (2×100 mL), dried over Na$_2$SO$_4$, concentrated and the residue was purified on silica gel column using EtOAc/hexane as eluting solvents to give 81. LC/MS: (M+1)$^+$: 544.2.

Step F: Preparation of Intermediate 82

To a solution of 81 (1.165 g, 2.143 mmol) in DCM (12 ml) was added HCl (4N in dioxane) (5.36 ml, 21.43 mmol). The resulting solution was stirred at rt for 3 h, and the mixture was concentrated to give 82. LC/MS: (M+1)$^+$: 444.2.

Step J: Preparation of Intermediate 86

To a solution of 85 prepared in the previous step (1.94 g, 1.940 mmol) in acetonitrile (20 ml) was added piperidine (0.960 ml, 9.70 mmol), and the resulting solution was stirred at rt for 30 min, then concentrated. The residue was redissolved in DCM/acetonitrile (1:1, 20 mL), then concentrated again, the cycle was repeated once, and the residue was dried under high vacuum to give 86. LC/MS: (M+1)$^+$: 778.3.

Preparation of Intermediate 88

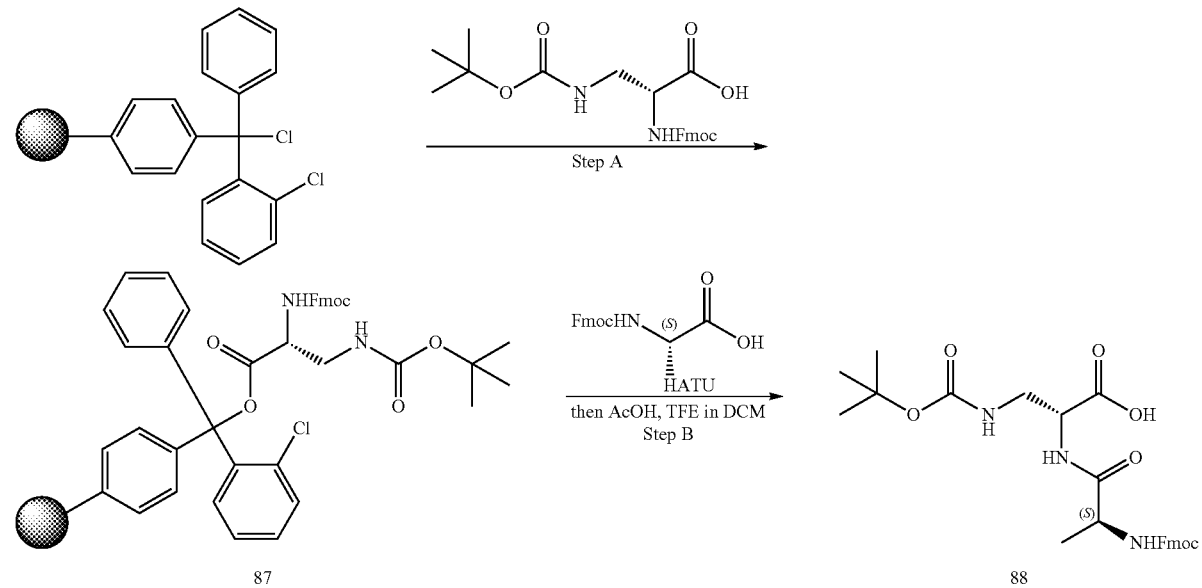

Step G: Preparation of Intermediate 83

To a solution of 82 (1.003 g, 2.089 mmol) in DMF (20 ml) was added Fmoc-L-Tyr(Me)-OH (0.959 g, 2.298 mmol), HATU (0.914 g, 2.403 mmol), and DIEA (1.095 ml, 6.27 mmol), and the resulting solution was stirred at rt for 50 min. The solution was partitioned between EtOAc (200 mL) and brine (100 mL), the organic phase was washed with brine (2×100 mL), the combined organic phase was dried over Na$_2$SO$_4$, concentrated and the residue was purified on silica gel column using EtOAc/hexane as eluting solvents to give 83. LC/MS: (M+1)$^+$: 843.4.

Step H: Preparation of Intermediate 84

To a solution of 83 (1.63 g, 1.934 mmol) in acetonitrile (10 ml) was added piperidine (0.574 ml, 5.80 mmol), and the resulting solution was stirred at rt for 1 h, then concentrated. The residue was resuspended in acetonitrile (20 mL) and concentrated again, the cycle was repeated once, and the residue was further dried under high vacuum to give 84. LC/MS: (M+1)$^+$: 621.3.

Step I: Preparation of Intermediate 85

To a solution of 84 (1.2 g, 1.933 mmol) in DMF (15 ml) was added Fmoc-L-Thr(tBu)-OH (0.922 g, 2.320 mmol), HATU (0.919 g, 2.416 mmol), and DIEA (0.844 ml, 4.83 mmol), and the resulting solution was stirred at rt for 1 h. The solution was partitioned between EtOAc (200 mL) and brine (100 mL), the organic phase was washed with brine (2×100 mL), dried over Na$_2$SO$_4$, concentrated and the residue was purified on silica gel column using EtOAc/hexane as eluting solvents to give 85. LC/MS: (M+1)$^+$: 1000.2.

Step A—Synthesis of Intermediate 87

To 2-chloro-2-chlorotrityl resin 1-1.5 mmol/g (7.0 g, 1-1.5 mmol/g) was added dry DCM (45 ml). The resin was shaken 20 min followed by addition of half of DIPEA 0.17 N in DCM (3.67 ml, 21.00 mmol), Fmoc-D-Dap(Boc)-OH (3.28 g, 7.70 mmol) then the remainder of DIPEA 0.17 N in DCM (3.67 ml, 21.00 mmol). The resin was shaken at room temperature overnight, rinsed with DCM and dried. The resin was then quenched with 5% DIPEA and 10% MeOH in DCM (80 mL), shaken for 2 h then filtered, rinsing with DCM (3×), DMF (3×) and DCM (3×) then dried under vacuum to give resin 87 which was used as is in the next step.

Step B—Synthesis of Intermediate 88

Resin 87 (4.5 g, 2.475 mmol) was manually deprotected with 5% piperidine in DMF (30 ml) for 30 min, filtered, retreated with 5% piperidine in DMF (30 ml) for another 30 min, filtered, then rinsed with DMF and DCM and dried. The resin was then manually coupled with Fmoc-Ala-OH (1.541 g, 4.95 mmol), HATU (1.694 g, 4.46 mmol) and DIPEA (1.729 ml, 9.90 mmol) in DMF (30 ml) for 2 h then filtered, rinsing with DMF and DCM, then dried. The resin was then treated with 10% AcOH and TFE in DCM (60 ml) for 90 min, filtered and the filtrate was concentrated to provide 88. LC/MS: [2M+H]$^+$=995.01.

Example 1A—Alternative Synthesis of Ex-01 and Preparation of Ex-25 Therefrom

Compound Ex-01, presented above, may alternatively be prepared, and compound Ex-25 may be prepared from Ex-01, in accordance with the following Scheme:

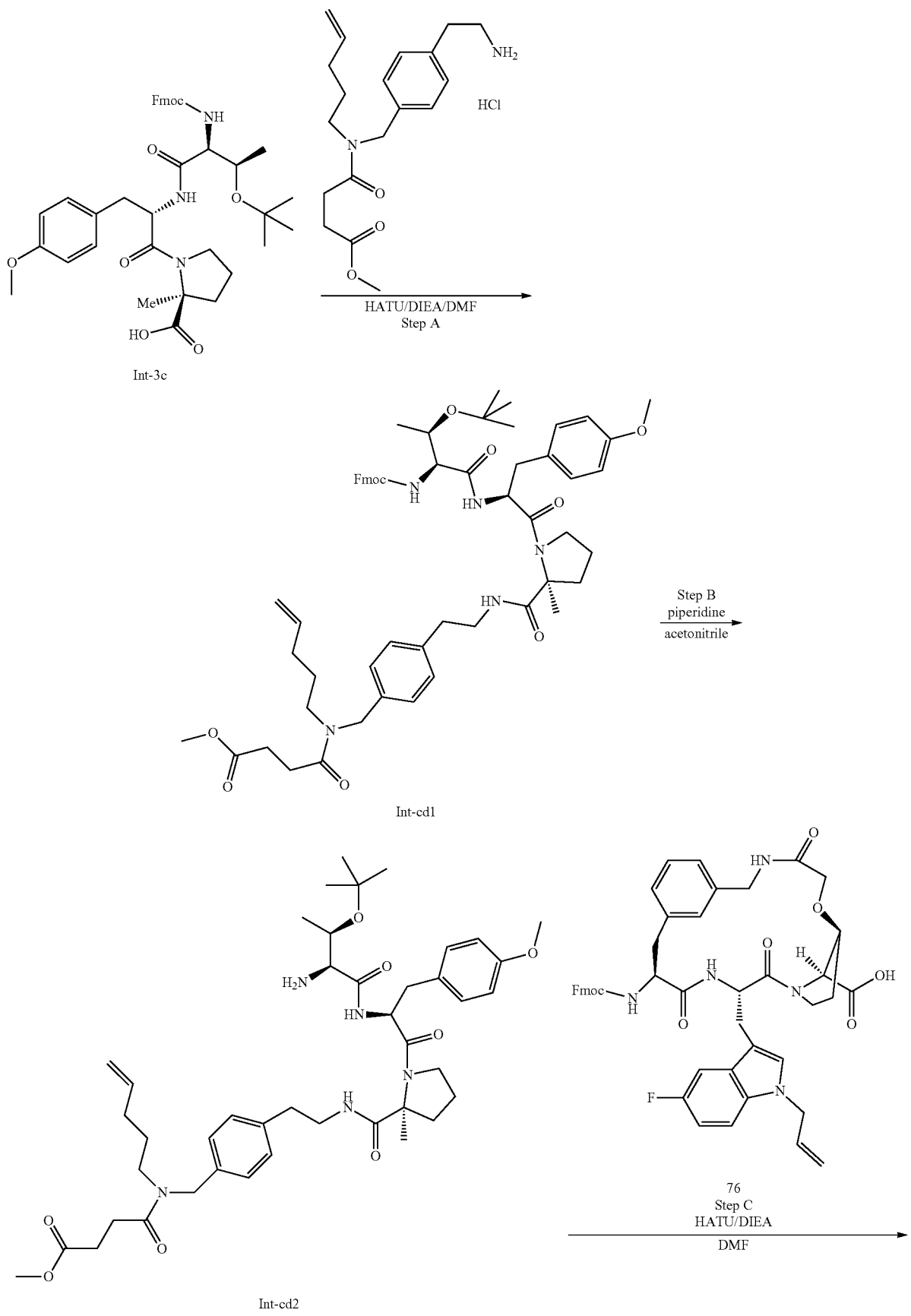

-continued
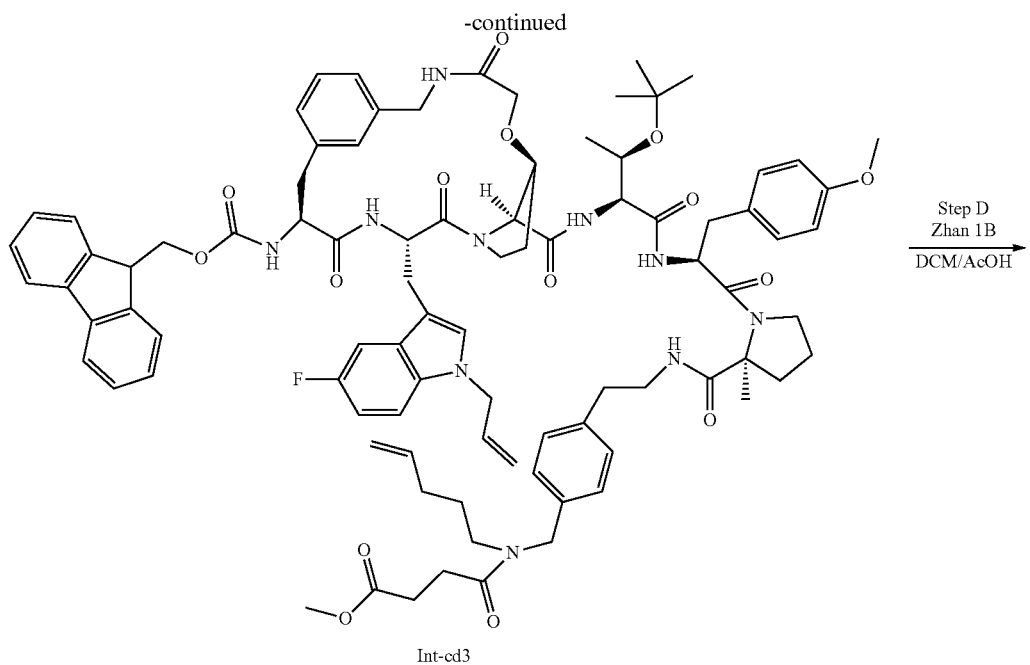
Int-cd3
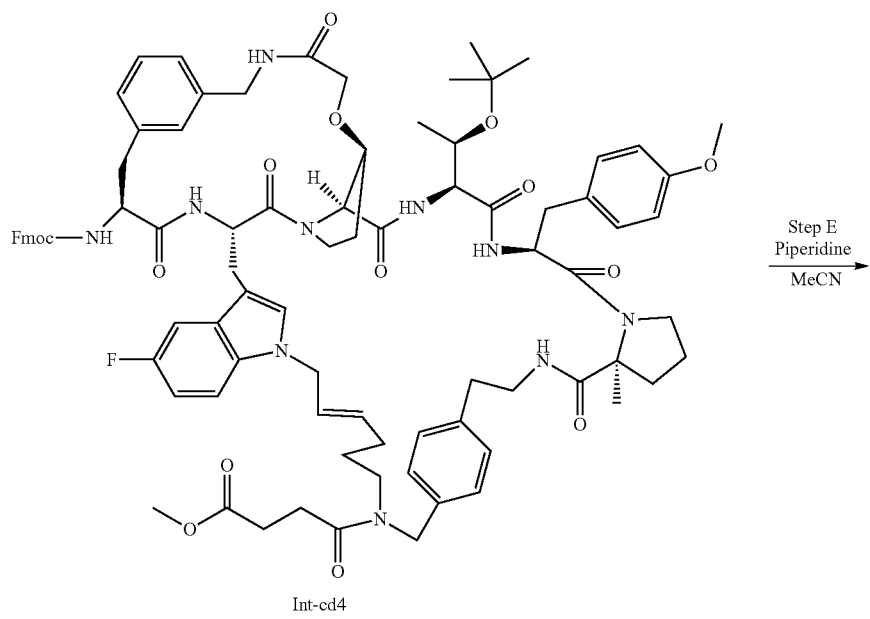
Int-cd4

123
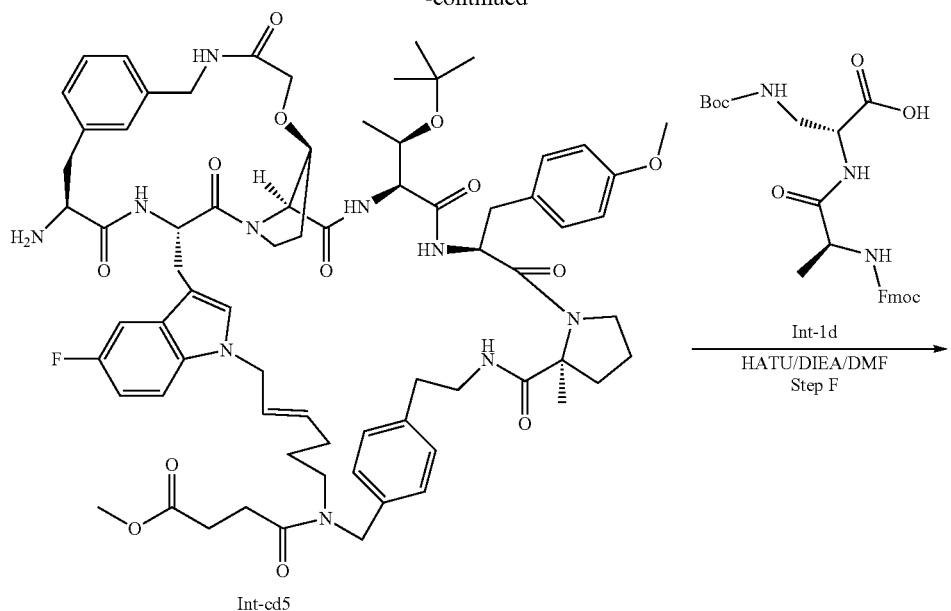
Int-cd5
124
-continued
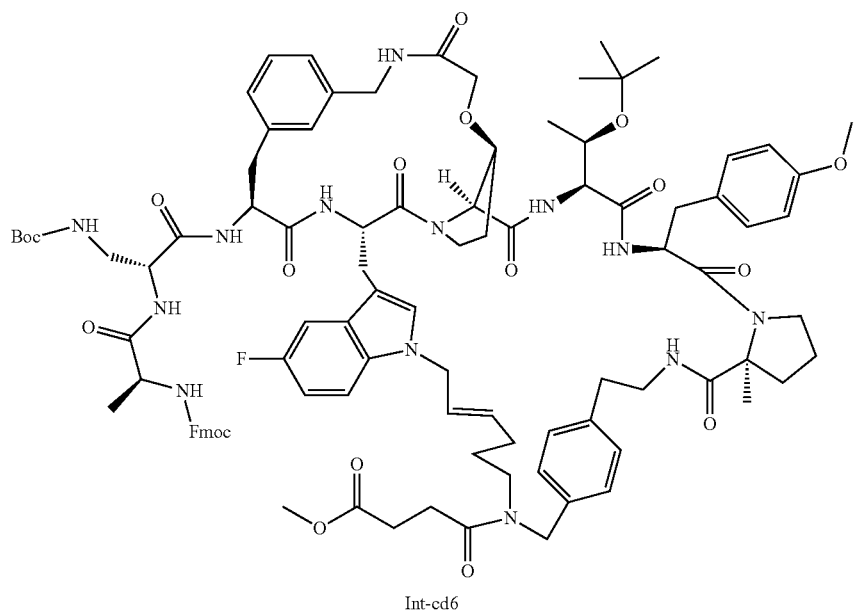
Int-cd6
Int-cd6 →[Step G LiOH THF/MeOH/ H₂O]

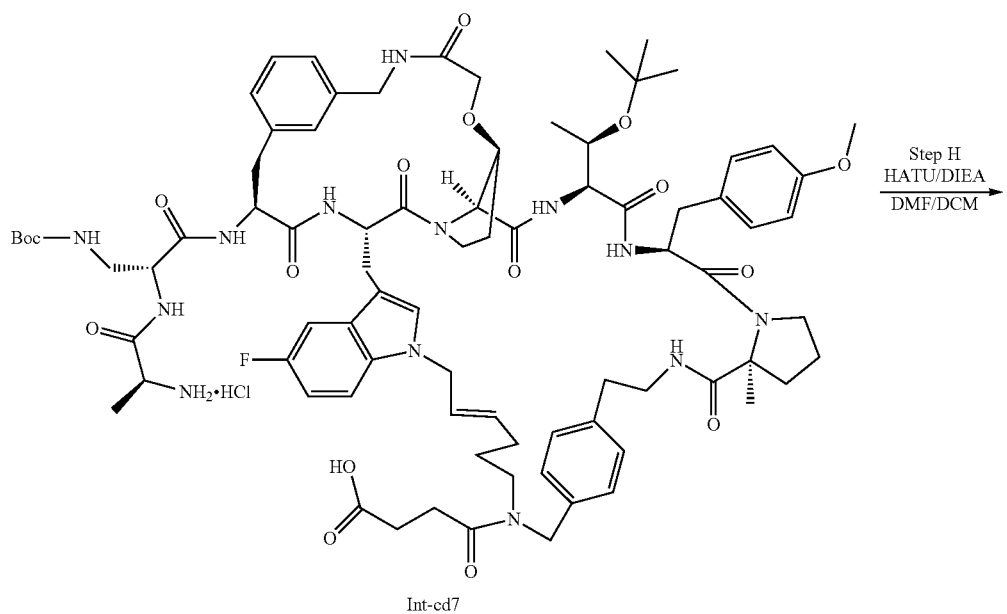
Int-cd7
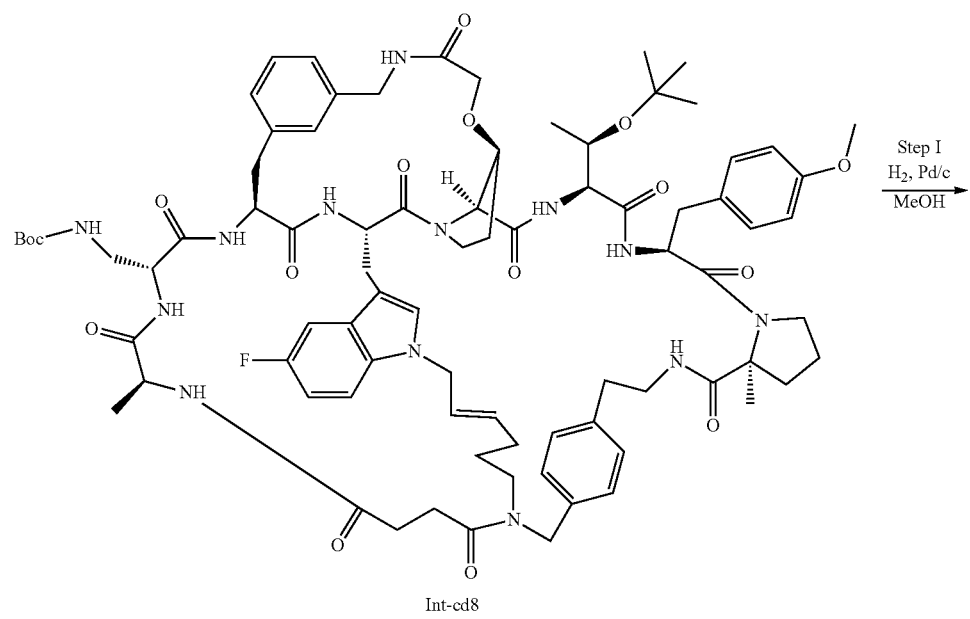
Int-cd8

-continued
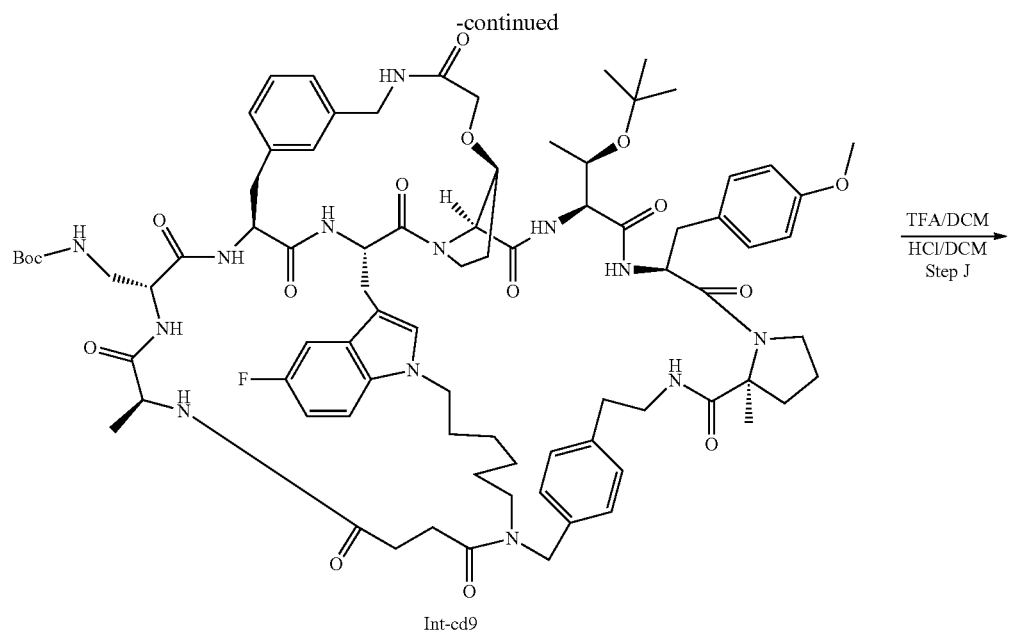
Int-cd9
TFA/DCM
HCl/DCM
Step J
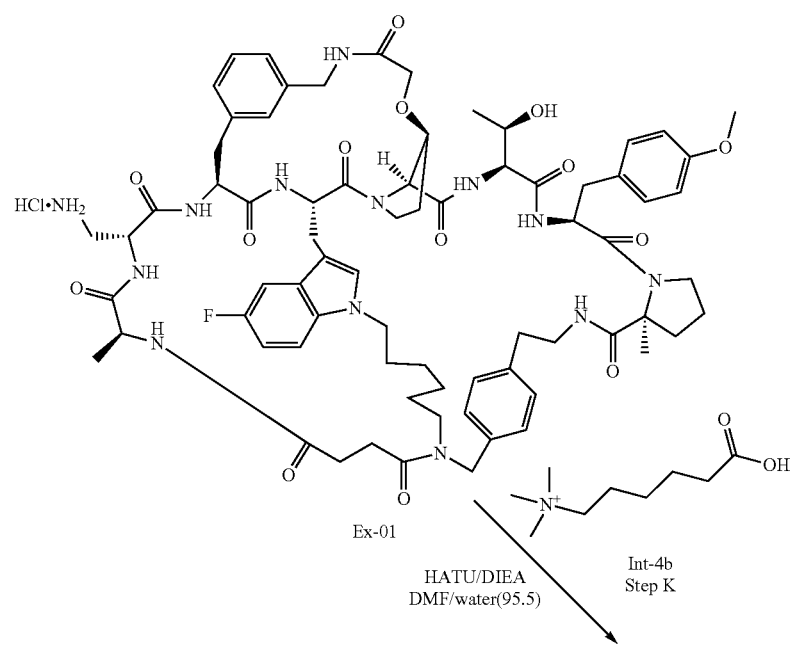
Ex-01
HATU/DIEA
DMF/water(95:5)
Step K
Int-4b -continued

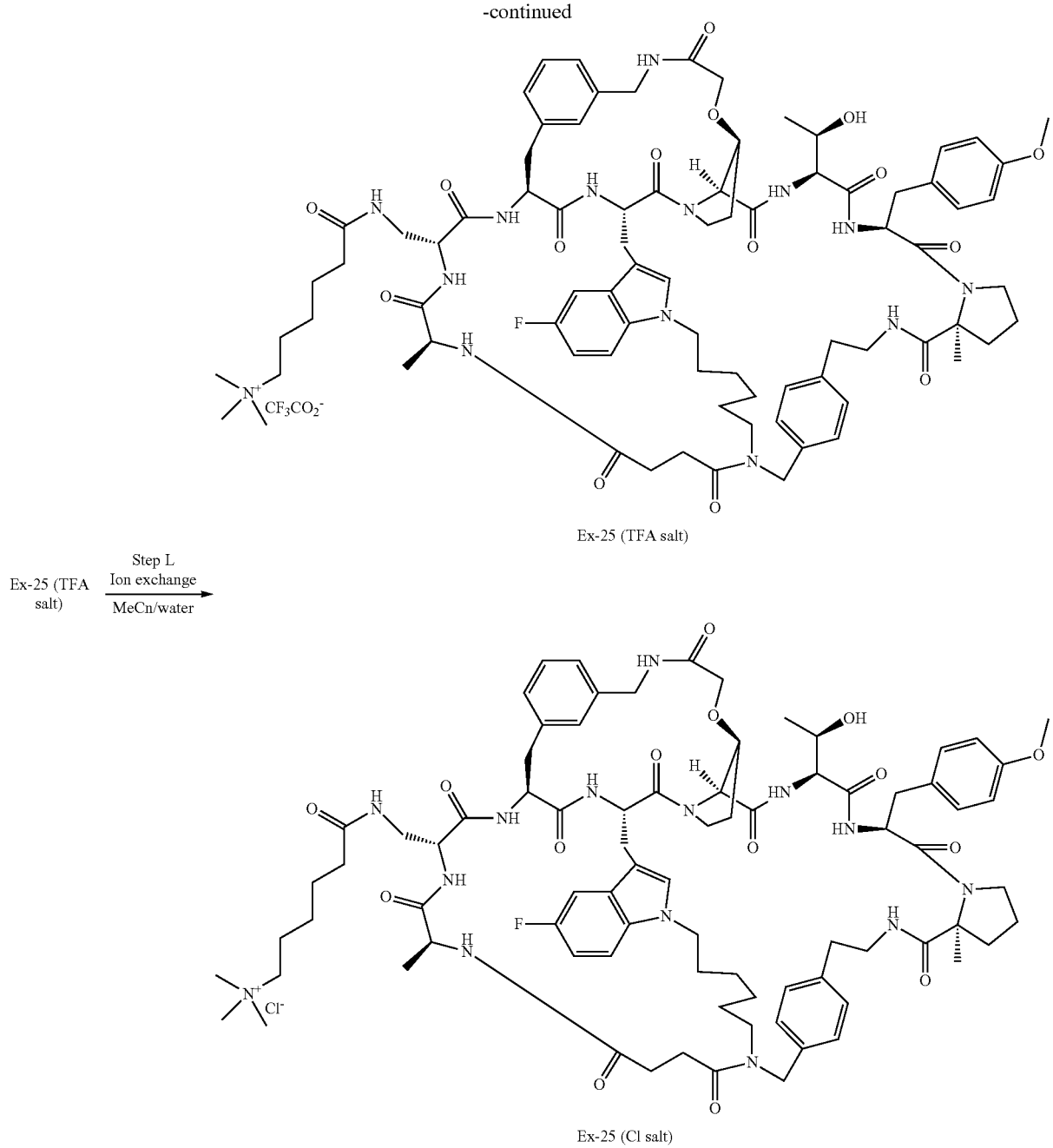

Ex-25 (TFA salt)

Ex-25 (TFA salt) $\xrightarrow[\text{MeCn/water}]{\text{Step L}\ \text{Ion exchange}}$ Ex-25 (Cl salt)

Step A—Synthesis of Intermediate Int-cd1

To a solution of Int-3c (synthesis from intermediate 107 described below) (7.09 g, 10.33 mmol) in DMF (45 ml) at 0° C. was added Int-2d (3.63 g, 9.84 mmol, preparation described below) and HATU (3.74 g, 9.84 mmol)) followed by DIPEA in DMF (6.87 ml, 39.4 mmol) and the mixture was allowed to warm to room temperature and stirred for 1 h. The mixture was quenched at 0° C. with brine and extracted with EtOAc. The combined organic fractions were washed with brine, dried over MgSO$_4$, filtered and concentrated in vacuo. The residue was purified by column chromatography over silica gel (eluting with a gradient of 1% to 80% ethyl acetate in petroleum ether) to give Int-cd1. LC/MS: [M+1]+=1000.5.

Step B—Synthesis of Intermediate Int-cd2

To a solution of Int-cd1 (3.48 g, 3.48 mmol) in acetonitrile (50 ml) was added piperidine (1.72 ml, 17.40 mmol), and the resulting solution was stirred at rt for 3 h. The mixture was concentrated, the residue was re-dissolved in DCM/acetonitrile (1:1, 20 mL), concentrated again and the residue was dried under vacuum to give Int-cd2 as a crude product. LC/MS: (M+1)$^+$=778.5.

Step C—Synthesis of Intermediate Int-cd3

To a solution of 76 (preparation shown in Example 1, above) (2.45 g, 3.01 mmol) and Int-cd2 (2.69 g, 3.46 mmol) in DMF (70 ml) at 0° C. was added HATU (1.37 g, 3.61 mmol) followed by DIEA (1.05 ml, 6.02 mmol). The resulting solution was stirred at rt for 50 min, then partitioned between EtOAc (500 mL) and brine (200 mL). The organic phase was washed with brine (2×200 mL), dried over Na$_2$SO$_4$, concentrated and the residue was purified by column chromatography over silica gel (eluting with a gradient of 1%-5% MeOH in DCM) to give Int-cd3. LC/MS: (M+1)$^+$=1574.7.

Step D—Synthesis of Intermediate Int-cd4

A room temperature solution of Int-cd3 (1.91 g, 1.21 mmol) in DCM (1500 ml) and acetic acid (30 mL) was bubbled with N$_2$ for 30 min followed by addition of Zhan's catalyst-1B (0.445 g, 0.607 mmol). The resulting mixture was further bubbled at room temperature with N$_2$ for 30 min, then heated at 55° C. for 5 h. After cooling to rt the mixture was filtered over Celite, the filtrate was concentrated, and the residue was purified by column chromatography over silica gel (eluting with a gradient of 1%-5% MeOH in DCM) to give Int-cd4 (as mixture of cis and trans olefins). LC/MS: (M+1)$^+$=1546.8.

Step E—Synthesis of Intermediate Int-cd5

To a solution of Int-cd4 (mixture of cis and trans olefins) (5.49 g, 3.55 mmol) in DCM (20 ml) and acetonitrile (50 ml) was added piperidine (1.76 ml, 17.8 mmol). The resulting solution was stirred at rt for 2 h, then concentrated and the residue was suspended in acetonitrile (20 ml) and concentrated again. The residue was then dried under vacuum to give Int-cd5 (as mixture of cis and trans olefins) as a crude mixture. LC/MS: (M+1)$^+$=1323.8.

Step F—Synthesis of Intermediate Int-cd6

To a solution of Int-cd5 (mixture of cis and trans olefins) (4.70 g, 3.55 mmol) and Int-1d (2.21 g, 4.44 mmol, preparation described below) in DMF (70 ml) at 0° C. was added HATU (1.76 g, 4.62 mmol) and DIEA (1.55 ml, 8.88 mmol). The resulting solution was warmed to room temperature and stirred for 1 h, then partitioned between EtOAc (300 mL) and brine (200 mL). The aqueous phase was extracted with EtOAc (200 mL), the EtOAc phase was combined and washed with brine (3×200 mL), dried over Na$_2$SO$_4$, concentrated and the residue was purified by column chromatography over silica gel (eluting with a gradient of 1%-5% MeOH in DCM) to give Int-cd6 (as mixture of cis and trans olefins). LC/MS: (M+1)$^+$=1802.8

Step G—Synthesis of Intermediate Int-cd7

To a solution of Int-cd6 (as mixture of cis and trans olefins) (5.41 g, 3.00 mmol) in THF (100 ml), MeOH (30 ml), and water (30 ml) at 0° C. was added 1N aqueous LiOH (24.0 ml, 24.0 mmol) dropwise, and the resulting solution was stirred at 0° C. for 3 h. The mixture was neutralized at 0° C. by addition of 1N HCl, the volatile was evaporated, and the aqueous layer was neutralized to pH 5 by 1N HCl. The mixture was then frozen and lyophilized, and the residue was purified by column chromatography over C18 (eluting with a gradient of acetonitrile (0.05% TFA)/water (0.05% TFA)) to give Int-cd7 (as mixture of cis and trans olefins) as a TFA salt. To the Int-cd7 TFA salt thus obtained, (as mixture of cis and trans olefins) in acetonitrile (750 mL) and water (450 mL) was added at 0° C. 0.1N aqueous HCl (150 ml, 15.00 mmol) dropwise, then the resulting solution was stirred at 0° C. for 5 min, frozen and lyophilized to give Int-cd7 as a HCl salt (as mixture of cis and trans olefins). LC/MS: (M+1)$^+$=1566.6.

Step H—Synthesis of Intermediate Int-cd8

To a solution of Int-cd7 HCl salt obtained from the previous step (1.01 g, 0.630 mmol) in DMF (50 ml) and DCM (1300 ml) was added DIEA (0.330 ml, 1.890 mmol) and HATU (0.287 g, 0.756 mmol). The resulting solution was stirred at rt for 2 h, the volatile was evaporated, and the residue was partitioned between EtOAc (400 mL) and brine (200 mL). The aqueous phase was extracted with EtOAc (300 mL), the combined organic layers were washed with brine (3×100 mL), dried over Na$_2$SO$_4$, concentrated and the residue was purified by column chromatography over silica gel (eluting with a gradient of 1%-10% MeOH in DCM) to give Int-cd8 (as mixture of cis and trans olefins). LC/MS: (M+1)$^+$=1548.8.

Step I—Synthesis of Intermediate Int-cd9

To a solution of Int-cd8 obtained in the previous step (1.22 g, 0.788 mmol) in MeOH (100 ml) was added 10% Pd/C (0.645 g, 0.607 mmol), and the resulting mixture was hydrogenated at ambient temperature via H$_2$ balloon for 7 hours. After 7 hours the reaction was filtered over Celite, the filtrate was concentrated, and the residue was purified by column chromatography over silica gel (eluting with a gradient of 1%-10% MeOH in DCM) to give Int-cd9. LC/MS: (M+1)$^+$=1550.9.

Step J—Synthesis of Compound Ex-01 as the —HCl Salt

To a solution of Int-cd9 (1.14 g, 0.735 mmol) in DCM (6 ml) was added TFA (12 ml, 156 mmol), and the resulting solution was stirred at ambient temperature for 30 min. The mixture was then concentrated, and the residue was dissolved in DCM (20 mL) and toluene (20 mL). The resulting mixture was concentrated, and the residue was re-dissolved in DCM (20 mL) and treated with HCl (4N in dioxane) (0.919 ml, 3.68 mmol). The resulting mixture was concentrated to give the product as solid. This solid product was re-dissolved in acetonitrile (200 mL) and water (100 mL), and to the above solution at 0° C. was added 1N aqueous HCl (3.68 ml, 3.68 mmol) dropwise. The resulting solution was stirred at 0° C. for 2 min, then frozen and lyophilized to give Ex-01 as a —HCl salt. LC/MS: (M+1)$^+$=1394.7.

Step K—Synthesis of Example Ex-25 as the TFA Salt

To a solution of Ex-01 HCl salt (870 mg, 0.608 mmol) and Int-4b (170 mg, 0.669 mmol, preparation described below) in DMF (1.2 ml) and water (0.6 ml) was added HATU (254 mg, 0.669 mmol) and DIEA (425 µl, 2.433 mmol). The resulting solution was stirred at rt for 1 h then quenched by addition of 1.2 mL water. The mixture was filtered, and the filtrate was purified by column chromatography over C18 (eluting with a gradient of acetonitrile (0.05% TFA)/water (0.05% TFA)) to give Ex-25 as a TFA salt. LC/MS: M$^+$=1550.6.

Step L—Preparation of Example Ex-25 as the Cl Salt

Into two columns was packed 73.6 g of AG MP-1 ion exchange resin chloride form (cat #141-1841 BIO-RAD) for a total of 36.8 g resin in each column. Each column was washed with water (2×80 ml), followed by 20% acetonitrile in water (2×100 ml). A solution of Ex-25 TFA salt prepared in the previous step (737 mg, 0.443 mmol) in 20% acetonitrile in water (100 mL) was loaded evenly onto the two resin columns, then each column was eluted with 20% acetonitrile in water (130 ml). The eluents were combined, frozen and lyophilized to give Ex-25 as the chloride salt. LC/MS: M$^+$=1550.6.

There follows the description of a number of intermediates which are usefully employed in the synthesis of Ex-01 and Ex-25 described immediately preceding.

Preparation of Intermediate Int-1d

Intermediate compound Int-1d was prepared from starting materials in accordance with the following scheme:

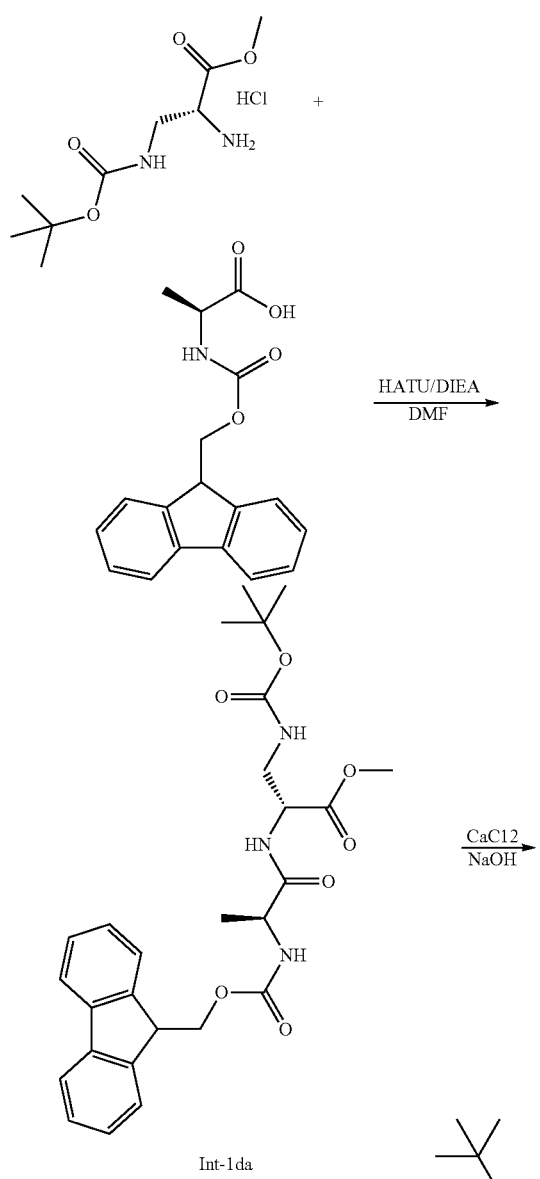

Int-1da

Int-1d

Step A—Synthesis of Int-1da

To a solution of D-Dap(Boc)-OMe HCl salt (4.10 g, 16.10 mmol), Fmoc-Ala-OH (5.01 g, 16.10 mmol) and HATU (6.43 g, 16.90 mmol) in DMF (40 ml) at 0° C. was added DIPEA (7.03 ml, 40.2 mmol) and the mixture was stirred at 0° C. for 2 h then kept in the refrigerator overnight. The mixture was quenched at room temperature with water and extracted with EtOAc. The combined organic fractions were washed with half brine, dried over $Na_2SO_4$, filtered and concentrated in vacuo. The residue was purified by column chromatography over silica gel (eluting with a gradient of Hexanes/EtOAc) to give Int-1da. LC/MS: [M+H]+=512.3.

Step B—Synthesis of Int-1d

To a solution of Int-1da (8.03 g, 15.70 mmol) and 0.8 N calcium chloride (19.62 ml, 15.70 mmol) in water (40 ml) and 2-propanol (120 ml) at room temperature was added solid sodium hydroxide (0.691 g, 17.27 mmol). The mixture was stirred at room temperature overnight. The mixture was concentrated, acidified with 0.5 N to pH ~2 (~40 mL), extracted trice with EtOAc, washed with brine, dried over $Na_2SO_4$ and concentrated. The residue was purified by column chromatography over C18 (eluting with a gradient of acetonitrile/water+0.1% TFA) to give Int-1d. LC/MS: [M+H]+=498.25.

The preparation of intermediate Int-1d is described above for use in the preparation of Ex-01 and Ex-25. This portion of the molecule may be described as a "linker" which cyclizes the lower peptide ring to the higher peptide ring. Other similar "linkers" may be used in place of Int-1d by varying the spacer used in the synthesis, including but not limited to, using Dap and D-Ala.

Preparation of Intermediate Int-2d

Intermediate Int-2d, useful as a "linker" in the preparation of compounds of the invention, was prepared in accordance with the following scheme:

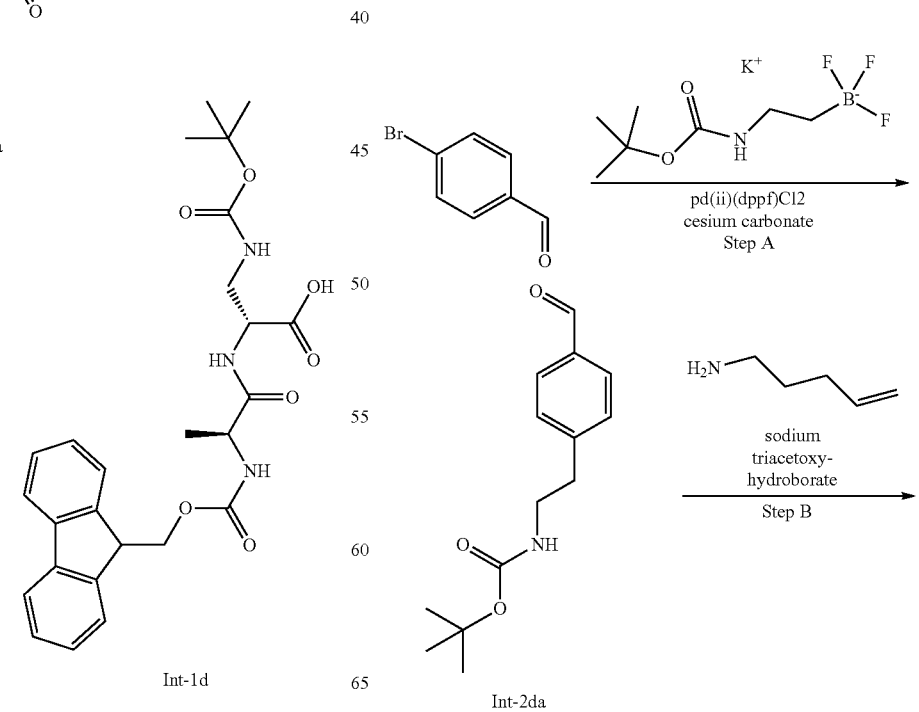

Int-2da

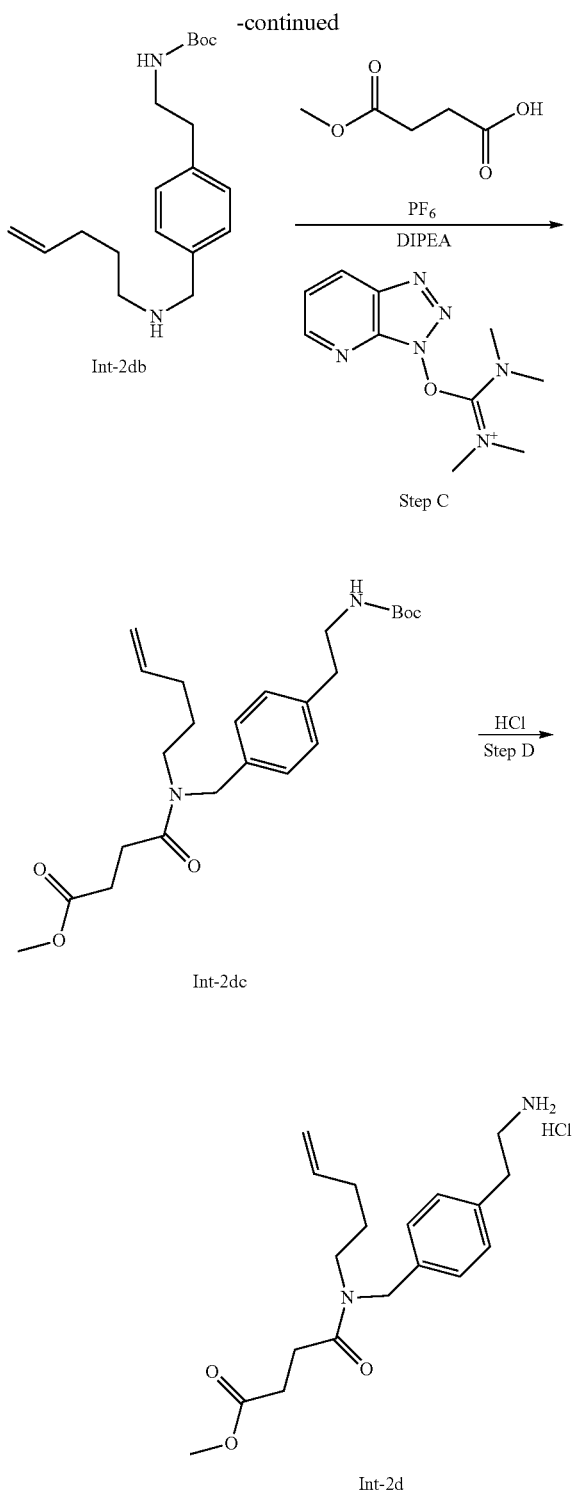

Step A—Synthesis of Int-2da

A solution of 4-bromobenzaldehyde (15.00 g, 81 mmol), potassium tert-butyl N-[2-(trifluoroboranuidyl)ethyl]carbamate (20.97 g, 84 mmol), cesium carbonate (52.8 g, 162 mmol) and 1,1'-bis(diphenylphosphino)ferrocene-palladium(ii)dichloride dichloromethane complex (Pd(II)(dppf)Cl$_2$, 1.99 g, 2.43 mmol) in degassed toluene (250 ml) and water (85 ml) was warmed to 76° C. and stirred overnight. The mixture was quenched at room temperature with half-saturated aqueous ammonium chloride and extracted with EtOAc. The combined organic fractions were washed with brine, dried over Na$_2$SO$_4$, filtered and concentrated in vacuo. The residue was purified by column chromatography over silica gel (eluting with a gradient of DCM/EtOAc) to give Int-2da. LC/MS: (M−56+1)$^+$=193.0.

Step B—Synthesis of Int-2db

To a solution of Int-2da (12.9 g, 51.7 mmol) and pent-4-en-1-amine (6.61 g, 78 mmol) in DCM (120 ml) and AcOH (3 ml) at room temperature in a water bath was added sodium triacetoxyhydroborate (32.9 g, 155 mmol) portion wise and the mixture was stirred for 30 min. The reaction was slowly quenched at 0° C. with 3 ml of water, poured into 1 N NaOH (500 ml), stirred for 15 min then extracted with DCM, dried over Na$_2$SO$_4$, and concentrated. The residue was purified by column chromatography over silica gel (eluting with a gradient of DCM/MeOH) to give Int-2db. LC/MS: (M+1)$^+$=319.2.

Step C—Synthesis of Int-2dc

To a solution of Int-2db (8.48 g, 20.77 mmol) and 4-methoxy-4-oxobutanoic acid (3.02 g, 22.85 mmol) in DMF (40 ml) was added HATU (9.48 g, 24.92 mmol) and DIPEA (8.71 ml, 49.8 mmol). The resulting solution was stirred at room temperature for 1 hour, then quenched with aqueous saturated NaHCO$_3$ (10 mL). The mixture was partitioned between EtOAc (500 mL) and aqueous saturated NaHCO$_3$ (200 mL), the organic phase was washed with brine (3×200 mL), dried over Na$_2$SO$_4$, concentrated and the residue was purified on silica gel column (eluting with a gradient of Hexanes/EtOAc) to give Int-2dc. LC/MS: (M+1)$^+$=433.4.

Step D—Synthesis of Int-2d

To a solution of Int-2dc (2.9 g, 6.70 mmol) in DCM (15 mL) was added 4 M HCl in Dioxane (10 mL) at room temperature. The reaction mixture was stirred at room temperature for 1 h.

The mixture was concentrated under reduced pressure to afford methyl 4-((4-(2-aminoethyl)benzyl)(pent-4-en-1-yl)amino)-4-oxobutanoate hydrochloride (Int-2d). LC/MS [M−HCl+H]$^+$=333.3.

Preparation of Int-3c from 107 Used in the Synthesis of Ex-01 and Ex-25 Described Above Intermediate Int-3c was prepared in accordance with the following scheme:

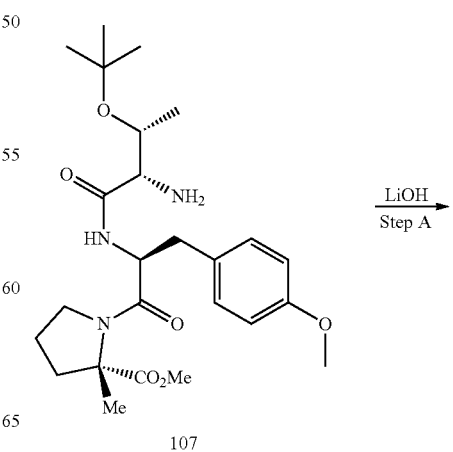

107

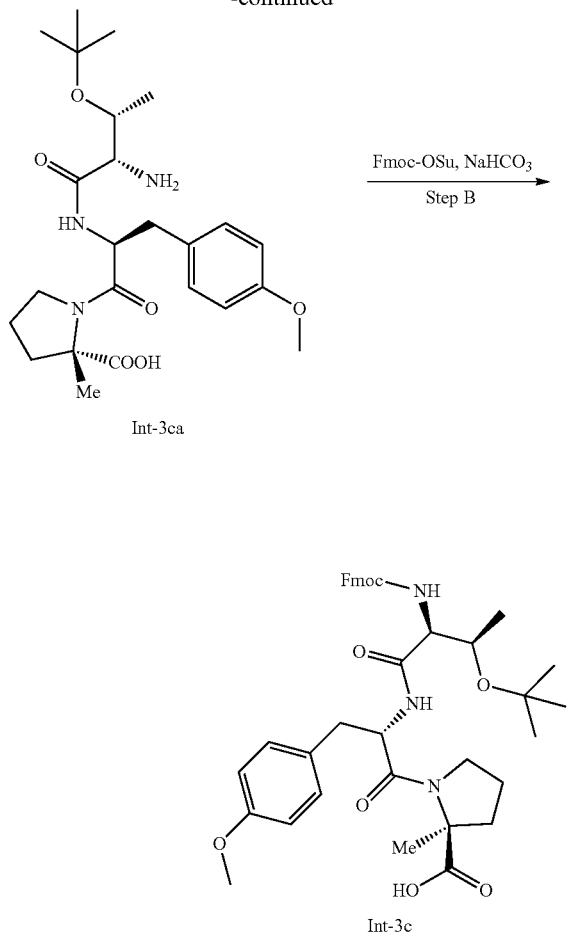

Int-3ca

Int-3c

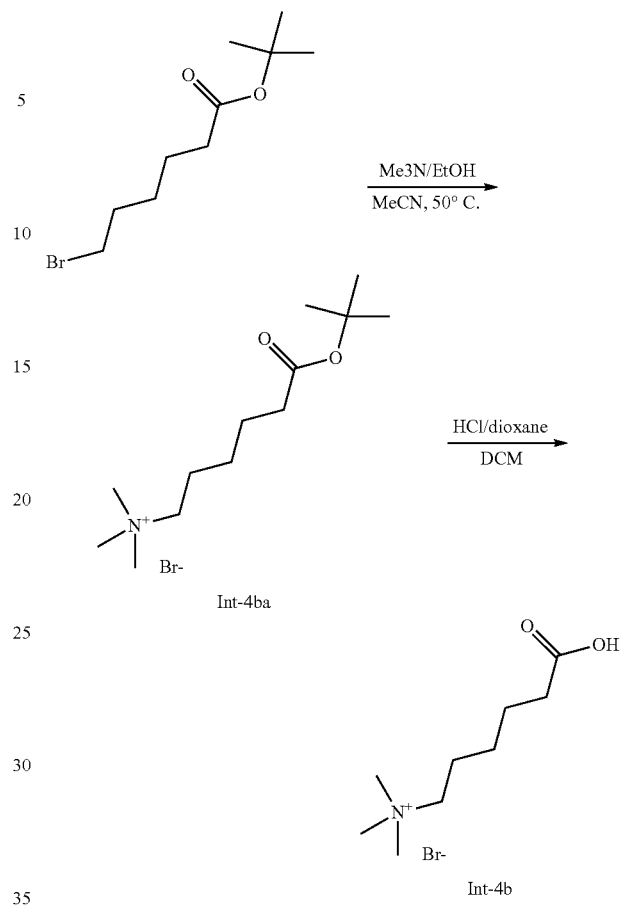

Int-4ba

Int-4b

Step A—Synthesis of Int-3ca

Into a solution of 107 (the preparation of which is presented in the synthesis of 109 and later used for 116, which intermediate compound is used in the synthesis of Ex-53, Ex-54 and Ex-55 in Example 3 below) (10.34 g, 21.65 mmol) in THF (100 ml) at room temperature, was added 2 N lithium hydroxide monohydrate (43.3 ml, 87 mmol) and the mixture was warmed to 45° C. and stirred overnight to give Int-3ca as crude solution. LC/MS: $(M+1)^+$ =464.3. The reaction mixture was cooled to 0° C. and treated with 1 M HCl (40 mL). The mixture was directly used for the next step.

Step B—Synthesis of Int-3c

To crude Int-3ca prepared in the previous step was added $NaHCO_3$ (1.725 g, 20.54 mmol) and Fmoc-OSu (3.81 g, 11.30 mmol) at 0° C. The reaction mixture was stirred at 0° C. for 2 h, treated with 1 M HCl (20.5 mL), and extracted with ethyl acetate (2×200 mL). The combined organic layers were washed with brine (2×100 mL) and dried over anhydrous sodium sulfate, filtered and concentrated under reduced pressure. The residue was purified by silica gel column chromatography, eluting with a gradient of 2% to 5% MeOH in DCM, to afford Int-3c. LC/MS: $(M+1)^+$=686.4.

Preparation of Intermediate Int-4b

Intermediate Int-4b was prepared in accordance with the following scheme:

Step A—Synthesis of Int-4ba from tert-butyl-3-(2-hydroxyethoxy)proponate

To a solution of tert-butyl 3-(2-hydroxyethoxy)propanoate (500.0 mg, 2.63 mmol) in DCM (2 mL) were added $CBr_4$ (1395 mg, 4.21 mmol) and $PPh_3$ (965 mg, 3.68 mmol) at 0° C. The mixture was stirred at room temperature for 2 h. The resulting mixture was concentrated under reduced pressure and the residue was purified by silica gel column chromatography, eluting with a gradient 1%-15% of ethyl acetate in petroleum ether. The fractions containing the desired product were combined and concentrated to afford tert-butyl 6-bromohexanoate. Thus prepared, a solution of tert-butyl 6-bromohexanoate (5 g, 19.91 mmol) in acetonitrile (10 ml) was treated with trimethylamine (13.56 ml, 59.7 mmol) and the resulting solution was heated at 50° C. overnight. The solution was concentrated to give Int-4ba. LC/MS: $M^+$=230.3.

Step B—Synthesis of Int-4b

To a solution of Int-4ba (6.8 g, 21.92 mmol) in DCM (6 ml) was added 4N HCl in dioxane (27.4 ml, 110 mmol), and the resulting solution was stirred at rt for 3 h. The mixture was then concentrated to give Int-4b. LC/MS: $M^+$=174.3.

The preparation of intermediate Int-2d is described above for use in the preparation of Ex-01 and Ex-25. This portion of the molecule may be described as a "linker" which cyclizes the lower peptide ring bearing the $R^1$, $R^2$ and $R^8$ substituents. Other similar "linkers" may be used in place of Int-2d. Following is a description of other "linkers" which may be used to prepare examples of the invention described herein.

Preparation of Intermediate Int-2e

Intermediate Int-2e, useful as a "linker" in the preparation of compounds of the invention, was prepared in accordance with the following scheme:

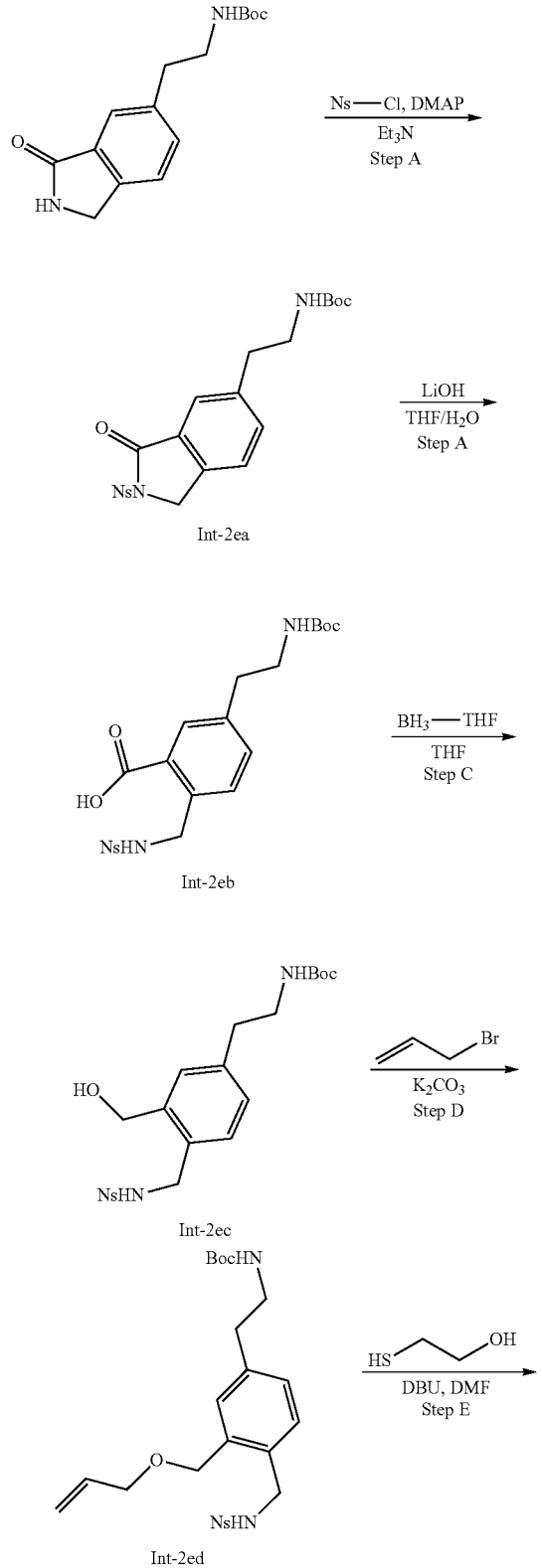

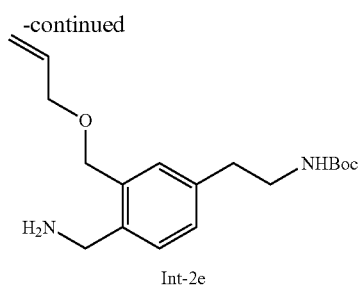

Step A—Synthesis of Intermediate Int-2ea

To a solution of tert-butyl (2-(3-oxoisoindolin-5-yl)ethyl) carbamate (1.60 g, 5.79 mmol) in DCE (20 mL) were added NsCl (1.93 g, 8.69 mmol), triethylamine (1.76 g, 17.4 mmol) and DMAP (0.141 g, 1.16 mmol). The reaction mixture was stirred for 14 h at 40° C. The reaction was cooled to room temperature and concentrated under reduced pressure. The residue was purified by column chromatography over silica gel (eluting with a 1%-40% gradient of EtOAc in PE) to give Int-2ea. LC/MS: $(M+Na)^+:=484.4$.

Step B—Synthesis of Intermediate Int-2eb

To a solution of Int-2ea (11.3 g, 24.5 mmol) in THF (100 mL) and water (100 mL) was added LiOH (1.76 g, 73.5 mmol). The reaction mixture was stirred for 5 h at 25° C. then the resulting solution was adjusted to pH 4-5 with HCl (1M). The solution was extracted with EtOAc and the combined organic layers were washed with brine, dried over anhydrous $Na_2SO_4$ and filtered. The filtrate was concentrated under reduced pressure and the residue was purified by column chromatography over silica gel (eluting with a 1%-6% gradient of MeOH in DCM) to afford Int-2eb. LC/MS: $(M+Na)^+:=502.2$.

Step C—Synthesis of Intermediate Int-2ec

To a solution of Int-2eb (1.70 g, 3.55 mmol) in THF (8 mL) was added borane (0.147 g, 10.6 mmol) at 0° C. The reaction mixture was stirred for 14 h at 25° C. then the resulting solution was concentrated under reduced pressure. The residue was purified by column chromatography over silica gel (eluting with a 1%-50% gradient of EtOAc in PE) to give Int-2ec. LC/MS: $(M+NH_4)^+=483.2$.

Step D—Synthesis of Intermediate Int-2ed

To a solution of Int-2ec (4.50 g, 9.67 mmol) in DMF (150 mL) was added $K_2CO_3$ (2.01 g, 14.5 mmol) and 3-bromoprop-1-ene (1.41 g, 11.6 mmol). The reaction mixture was stirred for 5 h at room temperature then diluted with water and extracted with EtOAc. The combined organic layers were washed with brine, dried over anhydrous $Na_2SO_4$ and filtered. The filtrate was concentrated under reduced pressure and the residue was purified by column chromatography over silica gel (eluting with a 1%-50% gradient of EtOAc in PE) to afford Int-2ed. LC/MS: $(M+H)^+:=506.2$.

Step E—Synthesis of Intermediate Int-2e

To a solution of Int-2ed (4.50 g, 8.90 mmol) in DMF (35 mL) was added DBU (1.35 g, 8.90 mmol) and 2-mercaptoethanol (2.08 g, 26.7 mmol). The reaction mixture was stirred for 14 h at room temperature then purified by column chromatography over C18 (Column: 330 g; Mobile Phase A: water/0.05% TFA, Mobile Phase B: ACN; Flow rate: 85 mL/min; Gradient: 10% B to 20% B in 15 min, 20% B to 45% B in 15 min Detector: UV 210 nm; Rt=20 min) to afford Int-2e. LC/MS: $(M+H)^+:=321.2$. 1H NMR (300 MHz, CDCl3) δ 7.21-7.13 (m, 2H), 7.10-7.01 (m, 1H), 5.96-5.79

(m, 1H), 5.30-5.09 (m, 2H), 4.58 (s, 2H), 3.84 (s, 2H), 3.43-3.19 (m, 4H), 2.76 (t, J=7.1 Hz, 2H), 1.41 (s, 9H).

Preparation of Intermediate Int-2f-1

Intermediate Int-2f-1, useful as a "linker" in the preparation of compounds of the invention, was prepared in accordance with the following scheme:

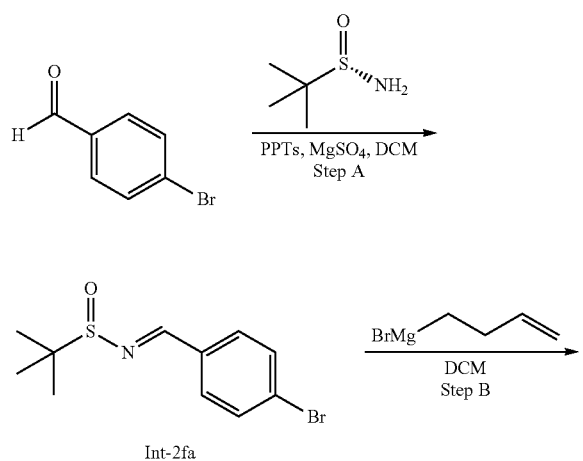

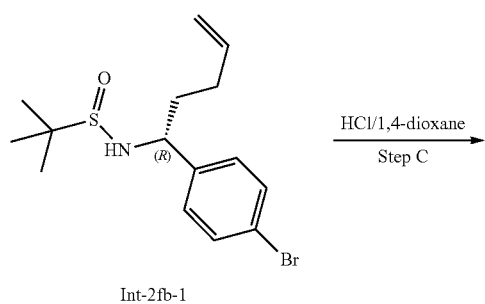

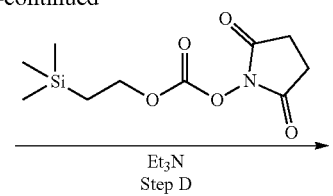

Step A—Synthesis of Intermediate Int-2fa

To a solution of 4-bromobenzaldehyde (20.0 g, 108 mmol), (S)-2-methylpropane-2-sulfinamide (12.5 g, 103 mmol), MgSO₄ (130 g, 1081 mmol) in DCM (225 mL) was added pyridine 4-methylbenzenesulfonate (1.35 g, 5.40 mmol) under nitrogen protection. This mixture was stirred at 25° C. for 72 h then the resulting solution was filtered, and the filtrate was concentrated under reduced pressure. The resulting residue was purified by column chromatography over silica gel (eluting with a 1%-15% gradient of EtOAc in PE) to give Int-2fa. LC/MS: (M+H)⁺:=287.9, 289.9.

Step B—Synthesis of Intermediate Int-2fb (Racemate) and Separation into Enantiomers Int-2fb-1 and Int-2fb-2

To a solution of Int-2fa (20.0 g, 65.9 mmol) in dry DCM (200 mL) was added but-3-en-1-ylmagnesium bromide (15.7 g, 99 mmol) slowly at −48° C. under nitrogen protection. The mixture was stirred at −48° C. for 2 h then quenched with saturated NH$_4$Cl (400 mL) aqueous solution and extracted with DCM. The combined organic layers were washed with brine, dried over anhydrous Na$_2$SO$_4$ and filtered. The filtrate was concentrated under reduced pressure and the resulting residue (containing Int-2fb racemic mixture) was purified by column chromatography over silica gel (eluting with a 1%-35% gradient of EtOAc in PE) to give Int-2fb-1 and Int-2fb-2. LC/MS: (M+H)$^+$:=344.0, 346.0.

Step C—Synthesis of Intermediate Int-2fc-1

To a solution of HCl (100 mL, 4 N in 1,4-dioxane) at room temperature was added Int-2fb-1 (17.0 g, 46.9 mmol). The reaction solution was stirred for 1 h then concentrated under reduced pressure to afford Int-2fc-1. LC/MS: (M+H−HCl)$^+$:=240.0, 242.0.

Step D—Synthesis of Intermediate Int-2fd-1

To a solution of Int-2fc-1 (8.20 g, 28.2 mmol) and Teoc-OSu (8.03 g, 31.0 mmol) in 1,4-dioxane (200 mL) was added TEA (8.55 g, 84 mmol) at 25° C. This mixture was stirred for 2 hours then quenched with water and extracted with petroleum ether (PE). The combined organic layers were concentrated under reduced pressure and the residue was purified by column chromatography over silica gel (eluting with a 1%-10% gradient of EtOAc in PE) to give Int-2fd-1. LC/MS: (M+Na+CH$_3$CN)$^+$:=447.3, 449.3.

Step E—Synthesis of Intermediate Int-2fe-1

To a solution of Int-2fd-1 (15.1 g, 37.3 mmol), potassium (2-((tert-butoxycarbonyl)amino)ethyl) trifluoroborate (18.7 g, 74.6 mmol), Cs$_2$CO$_3$ (36.5 g, 112 mmol) in toluene (285 mL) and water (95 mL) was added PdCl$_2$(dppf) (1.37 g, 1.87 mmol) under nitrogen protection. The mixture was stirred at 80° C. for 40 h. The resulting solution was quenched with water and extracted with EtOAc. The combined organic layers were dried over Na$_2$SO$_4$ and filtered. The filtrate was concentrated under reduced pressure and the residue was purified by column chromatography over silica gel (eluting with a 1%-40% gradient of EtOAc in PE) to afford Int-2fe-1. LC/MS: (M+Na)$^+$:=471.4.

Step F—Synthesis of Intermediate Int-2f-1

To a solution of Int-2fe1 (10.6 g, 22.4 mmol) in THF (100 mL) was added 1N TBAF in THF (44.9 mL, 44.9 mmol). This mixture was stirred at room temperature for 16 h then quenched with water and extracted with EtOAc. The combined organic layers were washed with brine, dried over anhydrous Na$_2$SO$_4$ and filtered. The filtrate was concentrated under reduced pressure and the residue was purified by column chromatography over silica gel (eluting with a 1%-70% gradient of EtOAc in PE) then by column chromatography over C18 (Column: 330 g; Mobile Phase A: water (10 mm NH4HCO3), Mobile Phase B: ACN; Flow rate: 80 mL/min; Gradient: 10% B to 10% B in 10 min, 20% B to 45% B in 10 min, 45% B to 70% B in 20 min Detector: UV 210 nm; Rt=25 min) to provide Int-2f-1. LC/MS: (M+H)$^+$:=305.1. 1H NMR (300 MHz, CD$_3$OD) δ 7.27-7.16 (m, 4H), 5.85-5.75 (m, 1H), 5.00-4.85 (m, 2H), 3.79 (t, J=7.0 Hz, 1H), 3.32-3.21 (m, 2H), 2.75 (t, J=7.4 Hz, 2H), 2.98-1.72 (m, 4H), 1.42 (s, 9H).

Example 2 Preparation of Ex-50 and Ex-52

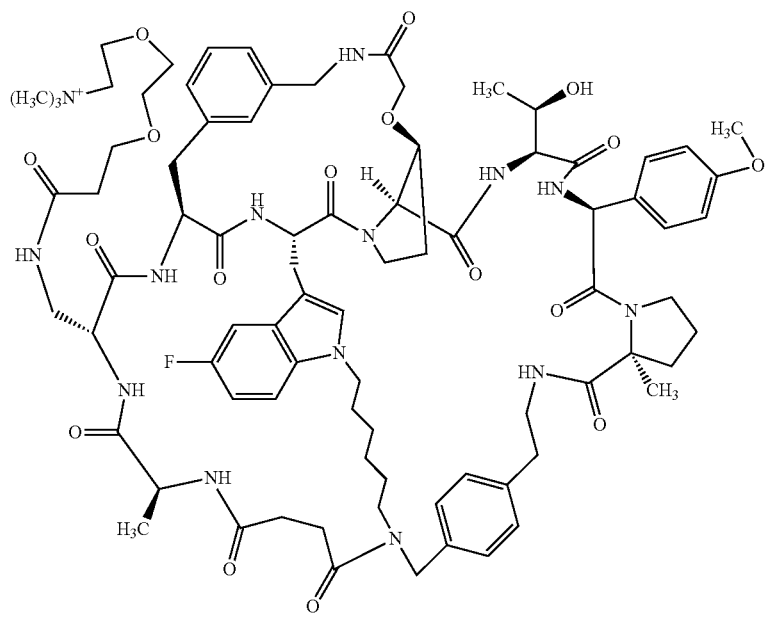

Ex-50

Ex-52

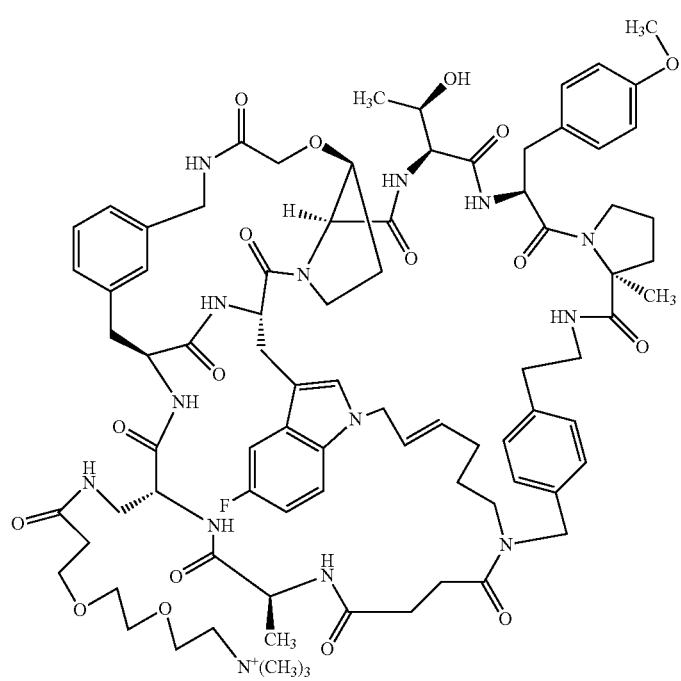

The compound Ex-50 is prepared in accordance with the scheme below from compound Ex-01, the preparation of which is described herein in Example 1, by reacting it under appropriate conditions with intermediate Int 32, prepared in accordance with the following Scheme:

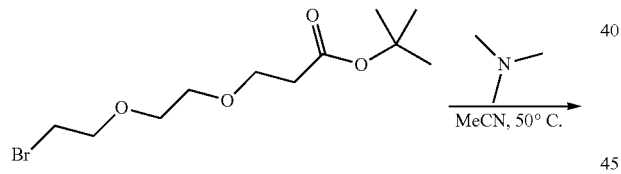

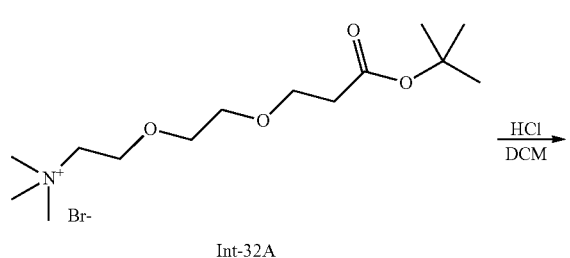

Int-32A

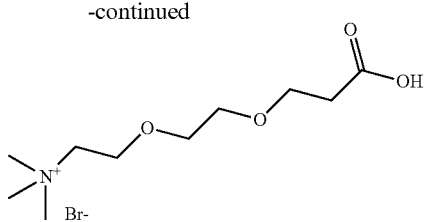

Int-32

Step A: Preparation of Intermediate Int-32A

To a solution of tert-butyl 3-(2-(2-bromoethoxy)ethoxy)propanoate (5 g, 16.82 mmol) in acetonitrile (10 ml) was added trimethylamine (33% in ethanol, 11.46 ml, 50.5 mmol), and the resulting solution was heated at 50° C. overnight. The solution was concentrated to give 2-(2-(3-(tert-butoxy)-3-oxopropoxy)ethoxy)-N,N,N-trimethyl-ethanaminium bromide (Int 32A). LC/MS: (M)$^+$: 276.5.

Step B: Preparation of Intermediate Int-32

To a solution of 2-(2-(3-(tert-butoxy)-3-oxopropoxy)ethoxy)-N,N,N-trimethylethanaminium bromide (Int-32A) (5.99 g, 16.81 mmol) in DCM (20 ml) was added HCl (4N in dioxane) (21.01 ml, 84 mmol), and the resulting solution was stirred at rt overnight. The solution was concentrated to give 2-(2-(2-carboxyethoxy)ethoxy)-N,N,N-trimethylethanaminium bromide (Int-32). LC/MS: (M)$^+$: 220.1.

Preparation of Example Compound Ex-50
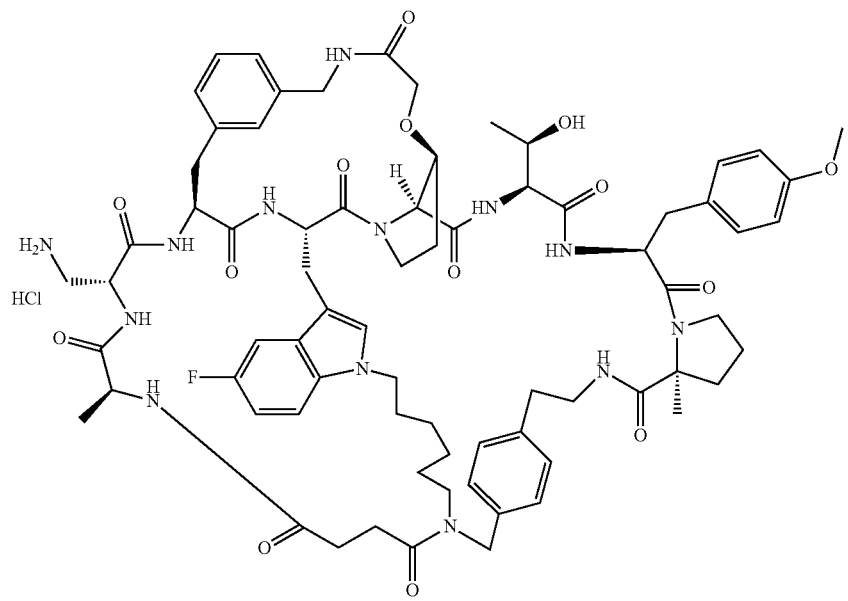
Ex-01
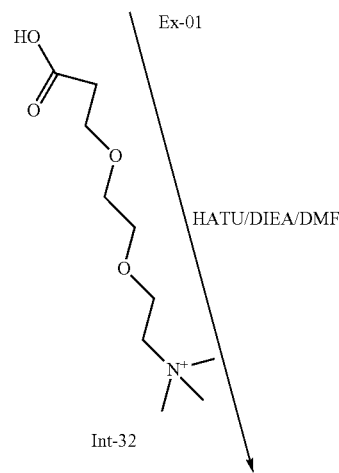
Int-32
HATU/DIEA/DMF
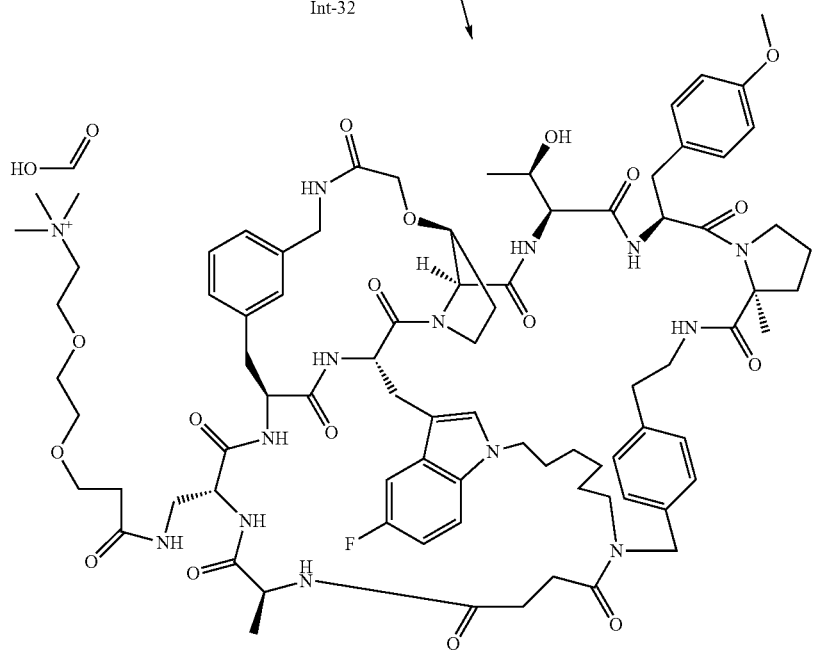

To a solution of Ex-01 (crude) (17.4 mg, 0.012 mmol) and 2-(2-(2-carboxyethoxy)ethoxy)-N,N,N-trimethyl-ethanaminium bromide (Int-32) (4.49 mg, 0.015 mmol) in DMF (2 ml) was added HATU (5.69 mg, 0.015 mmol) and DIEA (6.54 μl, 0.037 mmol), and the resulting solution was stirred at rt for 50 min, then purified by reverse phase HPLC using acetonitrile (0.1% formic acid)/water (0.1% formic acid) as mobile phase to give Ex-50. LC/MS: M+=1596.3.

Preparation of Example Compound Ex-52

Compound Ex-52 was prepared in an analogous manner to the preparation of compound Ex-50 but using Ex-51 instead of Ex-01. Ex-52 was purified using reverse phase HPLC, in accordance with the methods described herein. LC/MS: M+=1593.8.

Example 3 Preparation of Ex-53, Ex-54 and Ex-55

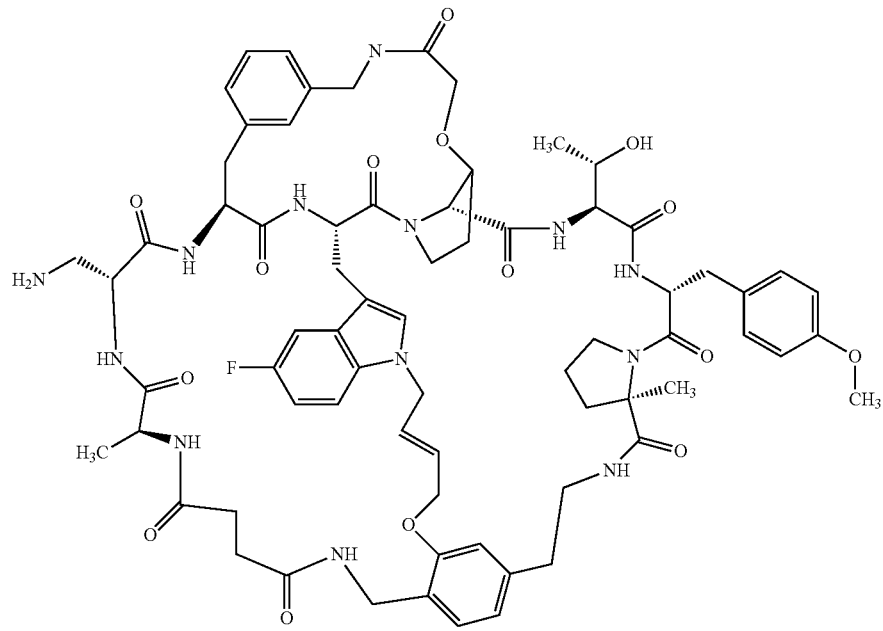

Ex-53

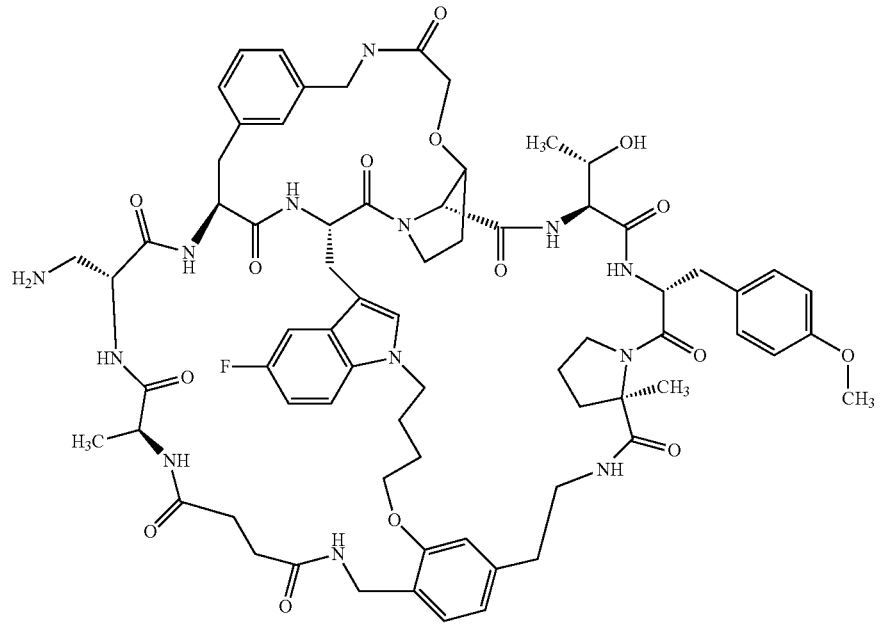

Ex-54

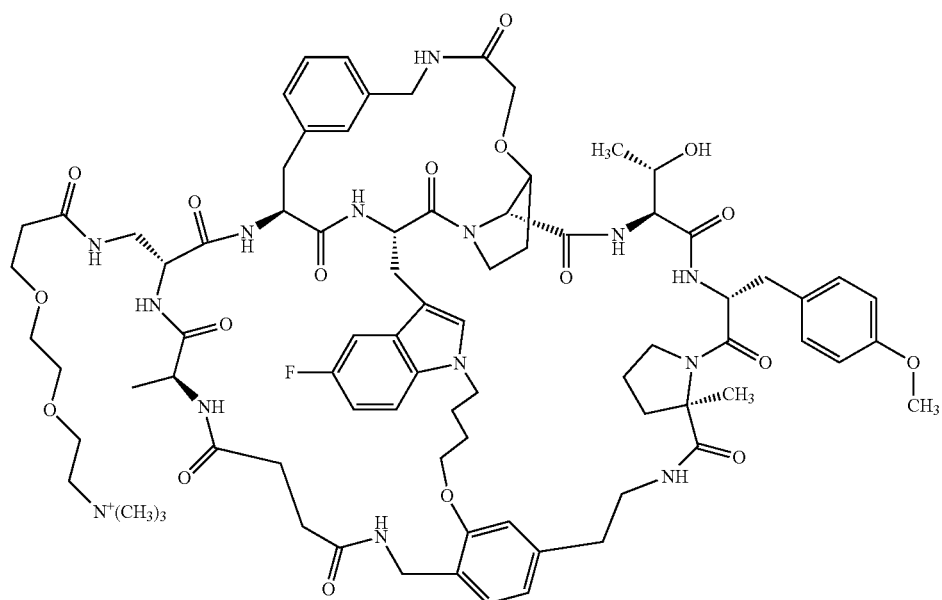
Ex-55
Compounds Ex-53, Ex-54 and Ex-55 were prepared in a manner analogous to the compounds described above from intermediate 115 (preparation described below), according to the following schemes and synthesis description:
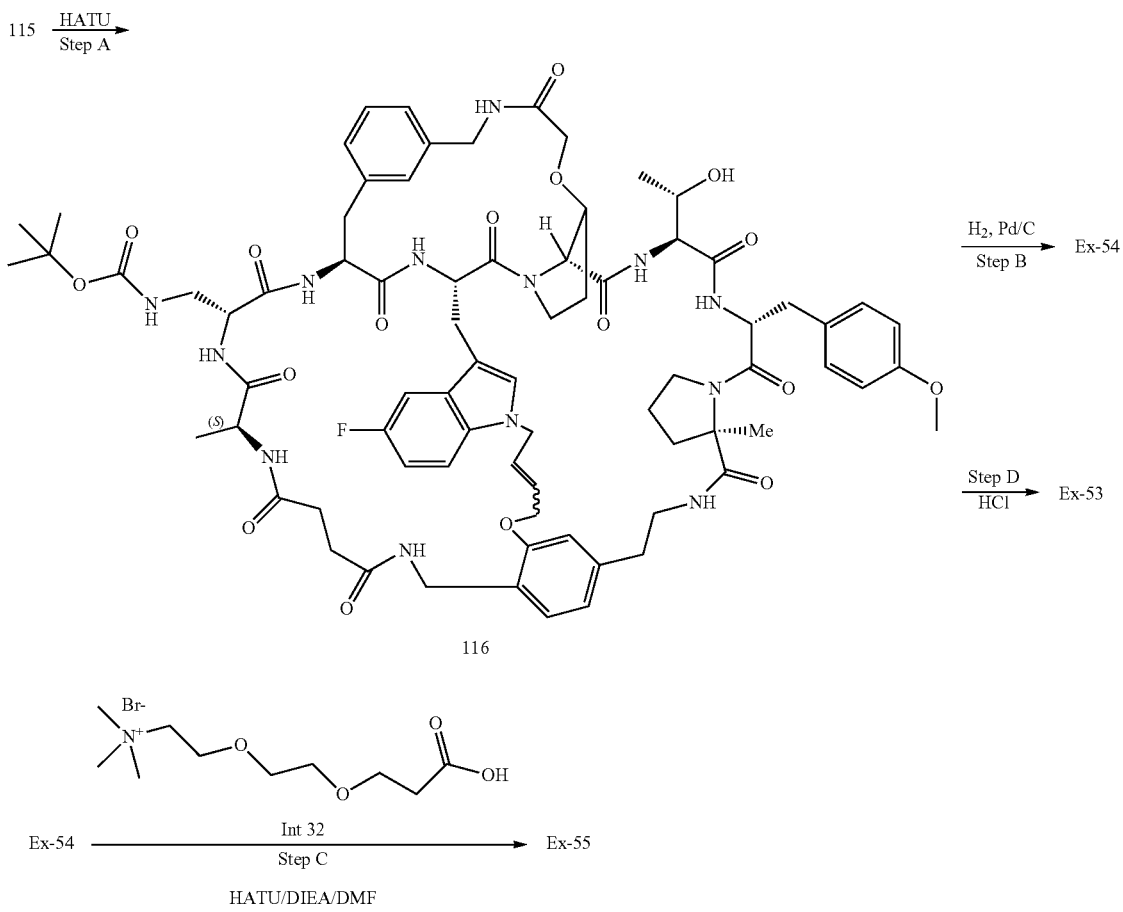

Step A—Synthesis of Intermediate 116

To a solution of 115 (66.3 mg, 0.044 mmol) in DMF (1.5 ml), DCM (10 ml) and water (0.5 ml) at 0° C. was added DIPEA (0.030 ml, 0.173 mmol) followed by HATU (18.50 mg, 0.049 mmol) and the mixture was stirred for 30 min. The mixture was concentrated in vacuo and directly purified by column chromatography over C18 (30 g, eluting with acetonitrile+0.05% TFA/water+0.05% TFA 90:10 to 40:60) to provide 116 as a mixture of E and Z isomers as well as 116 as pure fractions of E or Z isomer. LC/MS (major isomer) LC/MS: M$^+$=1481.19; LC/MS (minor isomer): LC/MS: M+=1480.

Step B—Synthesis of Compound Ex-54

A solution of 116 (25.1 mg, 0.017 mmol) and Pd—C 10% (3.61 mg, 3.39 μmol) in MeOH (10 ml) was hydrogenated at 1 atm for 1 h. The reaction was filtered over Celite and concentrated. The residue was treated with DCM/TFA 1:1 for 30 min then concentrated, treated with 4N HCl in dioxane (100 uL) then concentrated to provide Ex-54 in the form of the HCl salt. LC/MS: M$^+$=1383.44.

Step C—Synthesis of Compound Ex-55

Example compound Ex-55 was prepared in the form of the formate salt from Ex-54 in a manner identical to that described in Example 2 for the synthesis of Compound Ex-50. LC/MS: M$^+$=1583.69.

Step D—Synthesis of Compound Ex-53

Example compound Ex-53 was prepared in the form of the HCl salt from intermediate compound 116 in a manner identical to that described in Example 1 for the synthesis of compound Ex-51. LC/MS: M$^+$=1381.33.

Preparation of the intermediates needed to provide intermediate compound 115 from which compounds Ex-53, Ex-54, and Ex-55 are ultimately prepared is described in the schemes and synthesis below beginning with the preparation of intermediate compound 103.

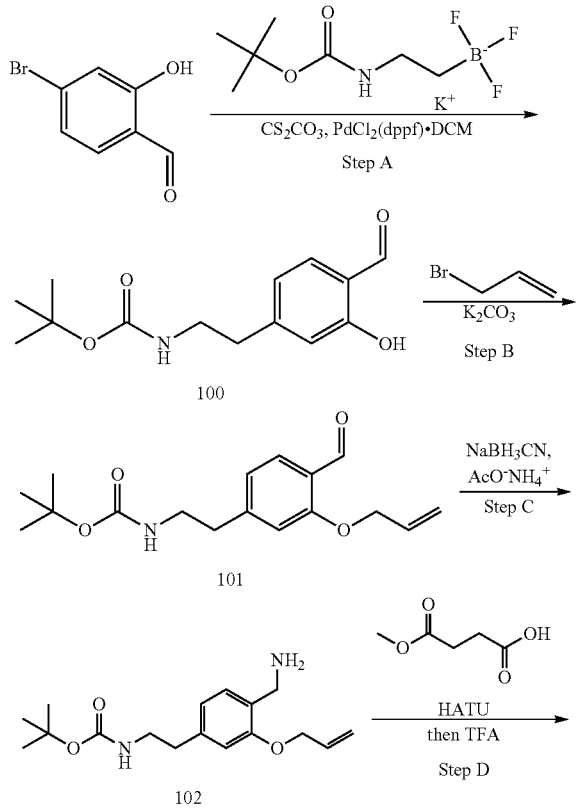

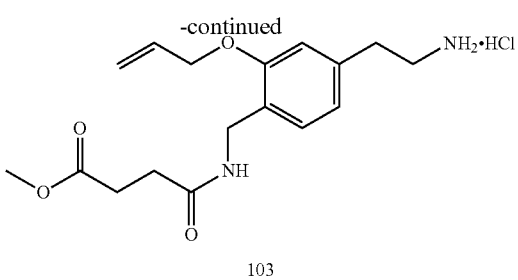

Step A—Synthesis of Intermediate 100

A solution of 4-bromo-2-hydroxybenzaldehyde (3.00 g, 14.92 mmol), potassium tert-butyl N-[2-trifluoroboraniudyl)ethyl]carbamate (3.82 g, 15.22 mmol), cesium carbonate (17.02 g, 52.2 mmol) and 1,1'-bis(diphenylphosphino)ferrocene-palladium(ii)dichloride dichloromethane complex (0.611 g, 0.746 mmol) in degassed toluene (45 ml) and water (15 ml) was warmed to 75° C. and stirred overnight. The mixture was quenched at room temperature with half-saturated aqueous sodium bicarbonate and extracted with EtOAc. The combined organic fractions were washed with brine, dried over Na$_2$SO$_4$, filtered and concentrated in vacuo. The residue was purified by column chromatography over silica gel (eluting with Hexanes/EtOAc 99:1 to 60:40) to give 100. LC/MS: (M−55)$^+$=210.25.

Step B—Synthesis of Intermediate 101

To a solution of 100 (1.70 g, 6.41 mmol) and allyl bromide (0.832 ml, 9.61 mmol) in DMF (10 ml) at room temperature was added potassium carbonate (1.328 g, 9.61 mmol) and the mixture was warmed to 50° C. and stirred for 1 h. The mixture was quenched at room temperature with half-saturated aqueous sodium bicarbonate and extracted with EtOAc. The combined organic fractions were washed with brine, dried over Na$_2$SO$_4$, filtered and concentrated in vacuo. The residue was purified by column chromatography over silica gel (eluting with Hexanes/EtOAc 99:1 to 70:30) to give 101. LC/MS: (M−55)$^+$=250.29.

Step C—Synthesis of Intermediate 102

To a solution of 101 prepared in the previous step (1.76 g, 5.76 mmol), 4 A molecular sieves (2 g) and ammonium acetate (4.44 g, 57.6 mmol) in MeOH (100 ml) at room temperature was added sodium cyanoborohydride (0.380 g, 6.05 mmol) and the mixture was shaken overnight. The mixture was concentrated, quenched at room temperature with water and extracted with DCM. The combined organic fractions were dried over Na$_2$SO$_4$, filtered and concentrated in vacuo. The residue was purified by column chromatography over silica gel (eluting with DCM/MeOH 99:1 to 30:70) to provide 102. LC/MS: (2M+H)$^+$=613.56.

Step D—Synthesis of Intermediate 103

To a solution of 102 (220 mg, 0.718 mmol) and succinic acid mono-methyl ester (114 mg, 0.862 mmol) in DMF (4 ml) at room temperature was added HATU (300 mg, 0.790 mmol) and DIPEA (0.314 ml, 1.795 mmol) and the mixture was stirred for 30 min. The mixture was quenched at room temperature with saturated aqueous sodium bicarbonate and extracted with EtOAc. The combined organic fractions were washed with brine, dried over Na$_2$SO$_4$, filtered and concentrated in vacuo. The residue was purified by column chromatography over silica gel (eluting with Hexanes/EtOAc 99:1 to 30:70) to give an intermediate that was treated with 20% TFA in DCM for 1 h. The reaction was concentrated then treated with 4N HCl (1.5 mL) and concentrated to provide 103. LC/MS: (M+H)$^+$=321.29.

Preparation of Intermediate 109

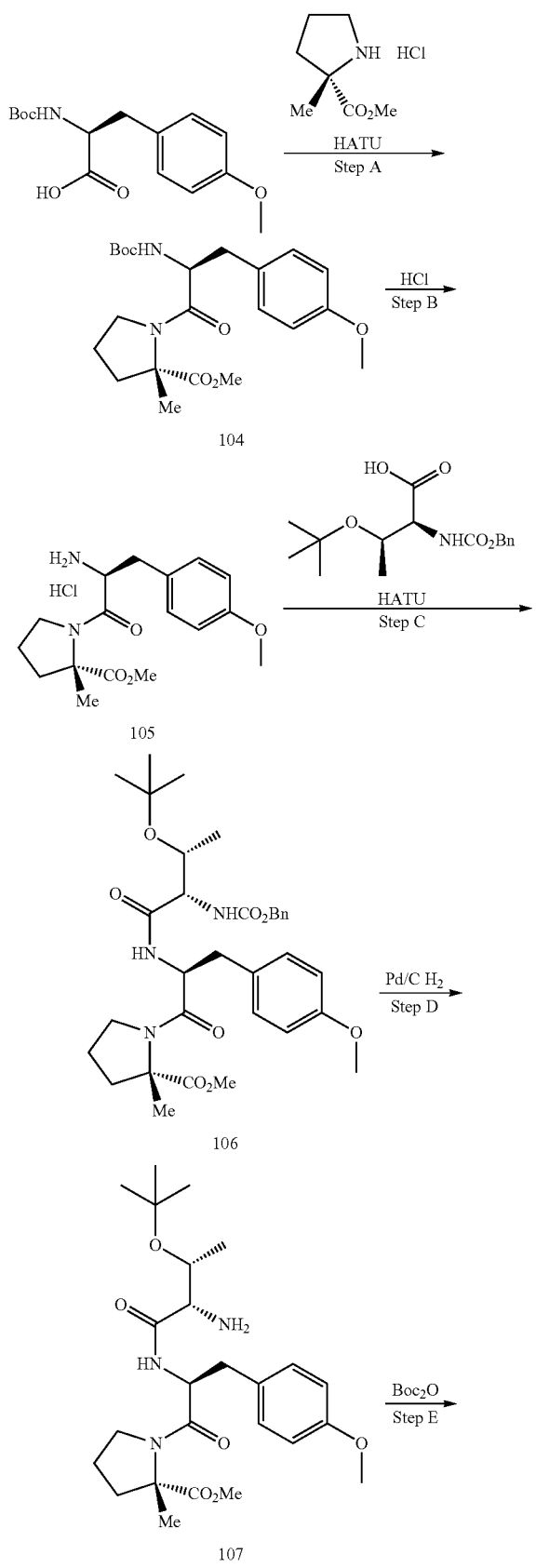

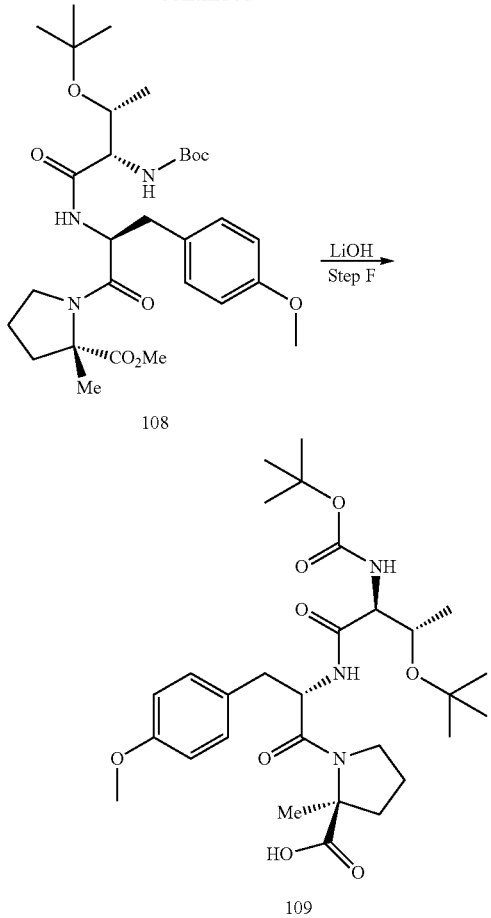

Step A—Synthesis of Intermediate 104

To a stirred solution of methyl (S)-2-methylpyrrolidine-2-carboxylate hydrochloride (7.00 g, 39 mmol) and (S)-2-((tert-butoxycarbonyl)amino)-3-(4-methoxyphenyl)propanoic acid (12.08 g, 40.9 mmol) in DMF (100 ml) at 0° C. was added DIPEA (17.01 ml, 97.0 mmol) followed by HATU (19.26 g, 50.7 mmol). The resulting mixture was allowed to warm to room temperature and stirred overnight. The reaction was quenched with a 10% aqueous LiCl solution and extracted with EtOAc. The organic extract was washed with 10% aqueous LiCl and dried over MgSO4. The solvent was removed under reduced pressure and the residue purified by column chromatography over silica gel (eluting with Hexanes/EtOAc 80:20 to 40:60) to provide 104.

Step B—Synthesis of Intermediate 105

To a solution of 104 (16.4 g, 39.0 mmol) in EtOAc (100 ml) was added 4 N HCl in dioxane (48.8 ml, 195 mmol). The resulting mixture was stirred at room temperature for 18 h and was concentrated under reduced pressure to give 105 that was used in the next step without further purification.

Step C—Synthesis of Intermediate 106

To a solution of 105 (13.2 g, 37.0 mmol) and N-((benzyloxy)carbonyl)-O-(tert-butyl)-L-threonine (18.15 g, 37.0 mmol) in DMF at 0° C. was added DIPEA (16.15 ml, 92 mmol) followed by HATU (18.28 g, 48.1 mmol). The resulting mixture was allowed to warm to room temperature and stirred overnight. The reaction was quenched with 10% aqueous LiCl solution and extracted with EtOAc. The organic extract was washed with 10% aqueous LiCl and dried over MgSO$_4$. The solvent was removed under reduced pressure and the residue purified by column chromatography over silica gel (eluting with Hexanes/EtOAc 80:20 to 40:60) to provide 106.

Step D—Synthesis of Intermediate 107

To a solution of 106 (16.5 g, 27.0 mmol) in MeOH was added a slurry of 10% Pd/C and the mixture was hydrogenated at 20 psi for 4 h. The reaction mixture was filtered over Celite and concentrated under reduced pressure. The crude product was then re-dissolved in DCM and the solution was filtered through a 2 μm filter and concentrated to give 107.

Step E—Synthesis of Intermediate 108

To a solution of 107 (3.2 g, 6.70 mmol) in DCM was added DIPEA (1.52 ml, 8.71 mmol) followed by di-tert-butyl dicarbonate (1.90 g, 8.71 mmol). The resulting mixture was stirred at room temperature for 2 h then concentrated under reduced pressure. The residue was purified by column chromatography over silica gel (eluting with Hexanes/EtOAc 100:0 to 40:60) to afford 108.

Step F—Synthesis of Intermediate 109

A solution of 108 (1.43 g, 2.475 mmol) and 1 N aqueous LiOH (9.90 ml, 9.90 mmol) in THF (15 ml) and MeOH (15 ml) was warmed to 45° C. and stirred for 4 h then at 32° C. for 48 h. The reaction was concentrated, quenched at 0° C. with 0.5 M aqueous hydrochloric acid until pH ~2-3 and extracted with EtOAc. The combined organic fractions were dried over Na$_2$SO$_4$, filtered and concentrated in vacuo. The residue was purified by column chromatography over silica gel (eluting with Hexanes/EtOAc-EtOH 99:1 to EtOAc-EtOH 3:1) to give 109. LC/MS: (M+H)$^+$=564.49.

Preparation of Intermediate Compounds 110 to 115

Step A—Synthesis of Intermediate 110

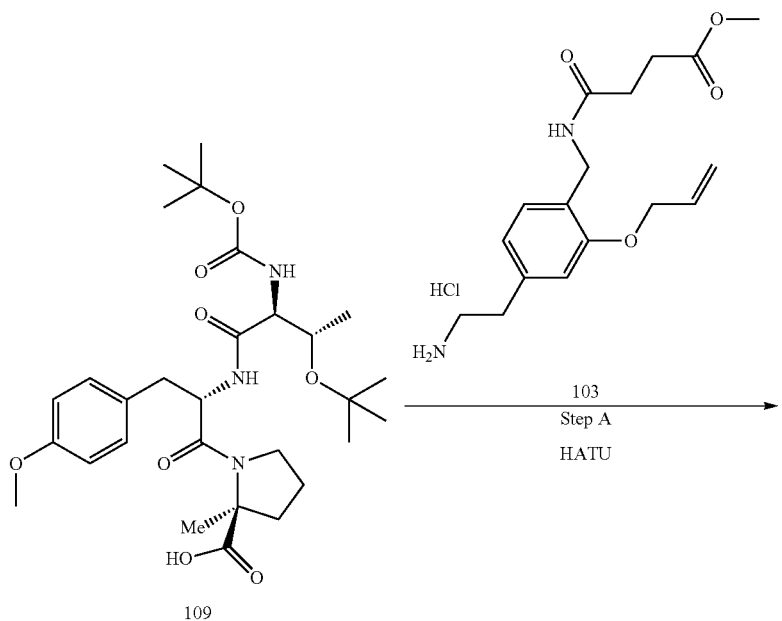

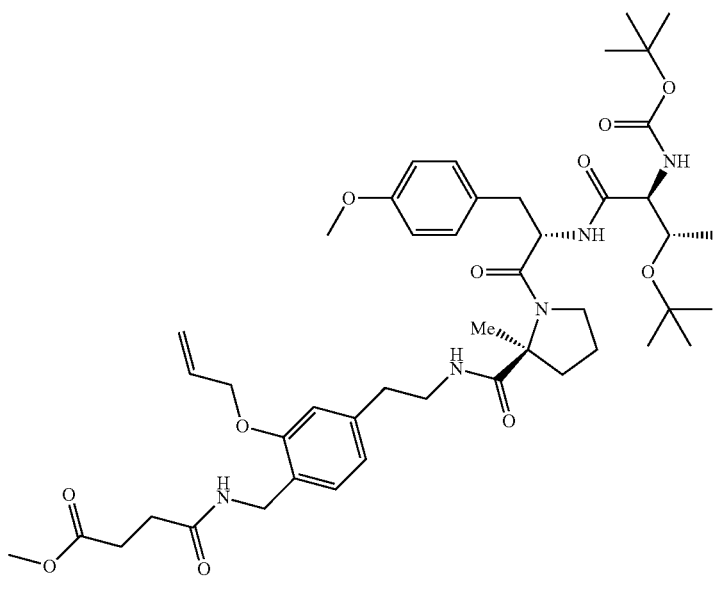

A solution of 109 (217 mg, 0.385 mmol), HATU (133 mg, 0.350 mmol) and DIPEA (0.245 ml, 1.400 mmol) in DMF (2.5 ml) was treated with 103 (217 mg, 0.385 mmol) at 0° C. and the mixture was allowed to warm to room temperature and stirred for 30 min. The mixture was quenched at 0° C. with saturated aqueous sodium bicarbonate and extracted with EtOAc. The combined organic fractions were washed with brine, dried over $Na_2SO_4$, filtered and concentrated in vacuo. The residue was purified by column chromatography over silica gel (eluting with Hexanes/EtOAc-EtOH 3:1 99:1 to EtOAc-EtOH 3:1) to give 110. LC/MS: $(M+H)^+=866.21$.

Steps B and C—Synthesis of Intermediate Compounds 111 and 112

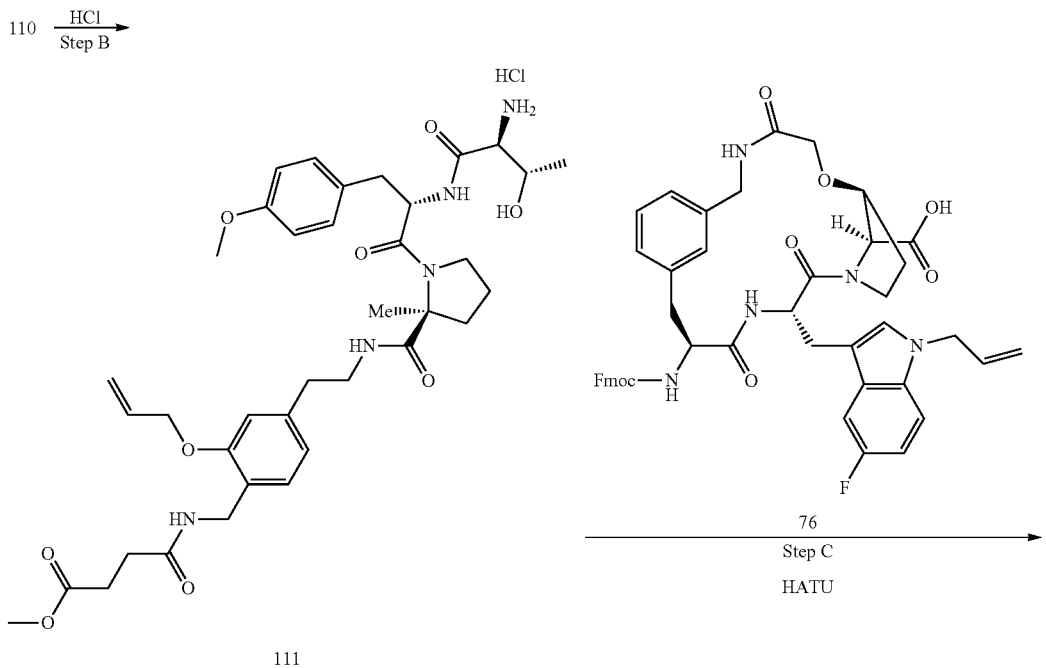

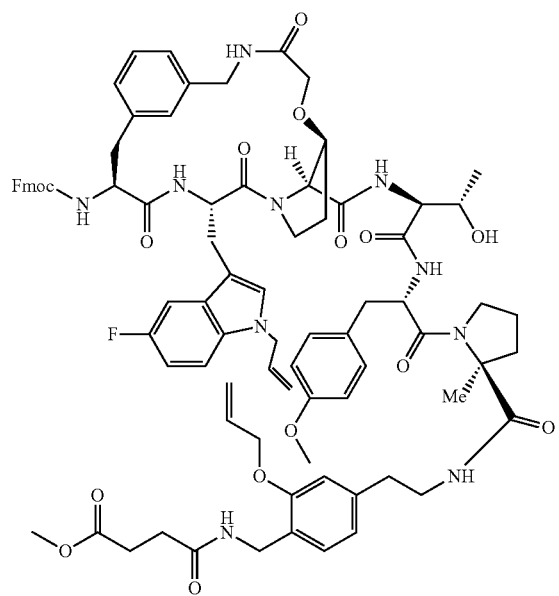

To a solution of 110 (249 mg, 0.288 mmol) in DCM (1 ml) at room temperature was added HCl 4 N in dioxane (0.359 ml, 1.438 mmol) and the mixture was stirred for 6 h then concentrated to provide 111. LC/MS: (M+H)⁺=710.19.

To a solution of 111 (219 mg, 0.293 mmol) and 76 (232 mg, 0.285 mmol) in DMF (3 ml) and water (0.15 ml) at 0° C. was added DIPEA (0.128 ml, 0.734 mmol) and HATU (123 mg, 0.323 mmol) and the mixture was stirred for 30 min. The mixture was quenched at 0° C. with brine and extracted with EtOAc. The combined organic fractions were dried over Na₂SO₄, filtered and concentrated in vacuo. The residue was purified by column chromatography over silica gel (eluting with Hexanes/EtOAc-EtOH 3-1 99:1 to 30:70 then DCM/MeOH 99:1 to 70:30) to afford 112. LC/MS: (M+H)⁺=1506.11.

Step D—Synthesis of Intermediate 113

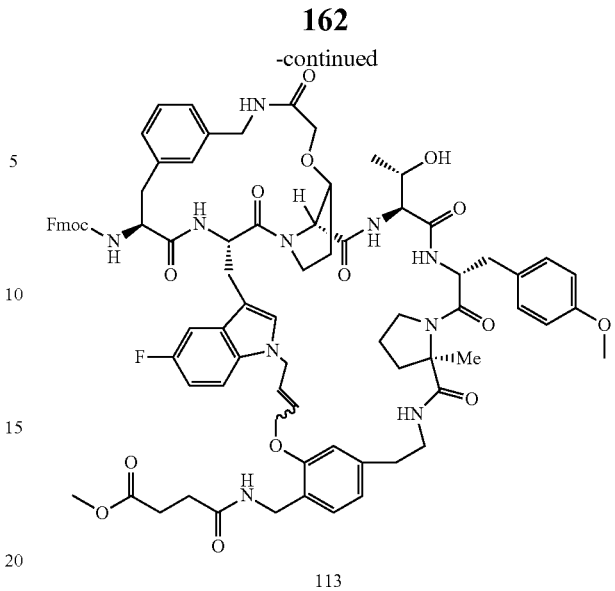

113

To a solution of 112 (173 mg, 0.115 mmol) in DCM (180 ml) and AcOH (15 ml) degassed with nitrogen for 30 min was added Zhan's Catalyst (59.0 mg, 0.080 mmol) and the mixture was warmed to 50° C. and stirred for 3 h. The mixture was filtered over Celite, washing with DCM then concentrated in vacuo. The residue was purified by column chromatography over silica gel (eluting with DCM/MeOH 99:1 to 80:20) to afford 113 as a mixture of E and Z isomers. LC/MS (major isomer): (M)⁺=1477.80; LC/MS (minor isomer): (M)⁺=1478.28.

Step E—Synthesis of Intermediate 114

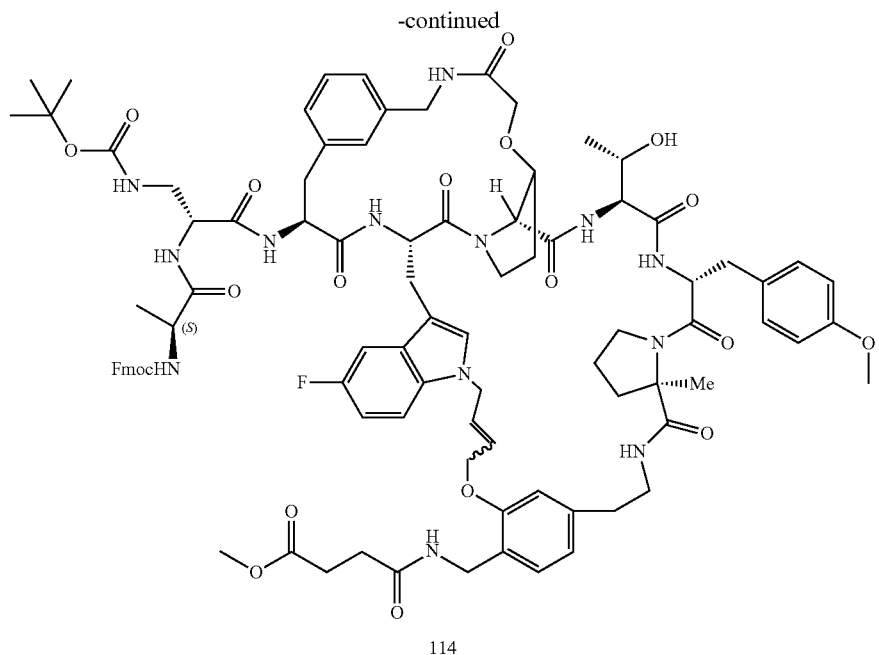

114

To a solution of 113 (141 mg, 0.095 mmol)) in acetonitrile (2 ml) was added piperidine (0.066 ml, 0.668 mmol) and the mixture was stirred for 45 min. The mixture was concentrated in vacuo, co-evaporated with acetonitrile trice to give a crude. To a slurry of this crude (119 mg, 0.095 mmol) and intermediate compound 88 (52.0 mg, 0.105 mmol) in DMF (2 ml) and water (0.1 ml) at 0° C. was added HATU (39.7 mg, 0.105 mmol) and DIPEA (0.037 ml, 0.209 mmol) and the mixture was stirred for 30 min. The mixture was purified by column chromatography over C18 (eluting with acetonitrile+0.05% TFA/water+0.05% TFA 90:10 to 30:70) to give 114 as a mixture of E and Z isomers. LC/MS major isomer: $(M)^+=1735.28$; LC/MS (minor isomer): $(M)^+=1735.25$.

Step F—Synthesis of Intermediate Compound 115

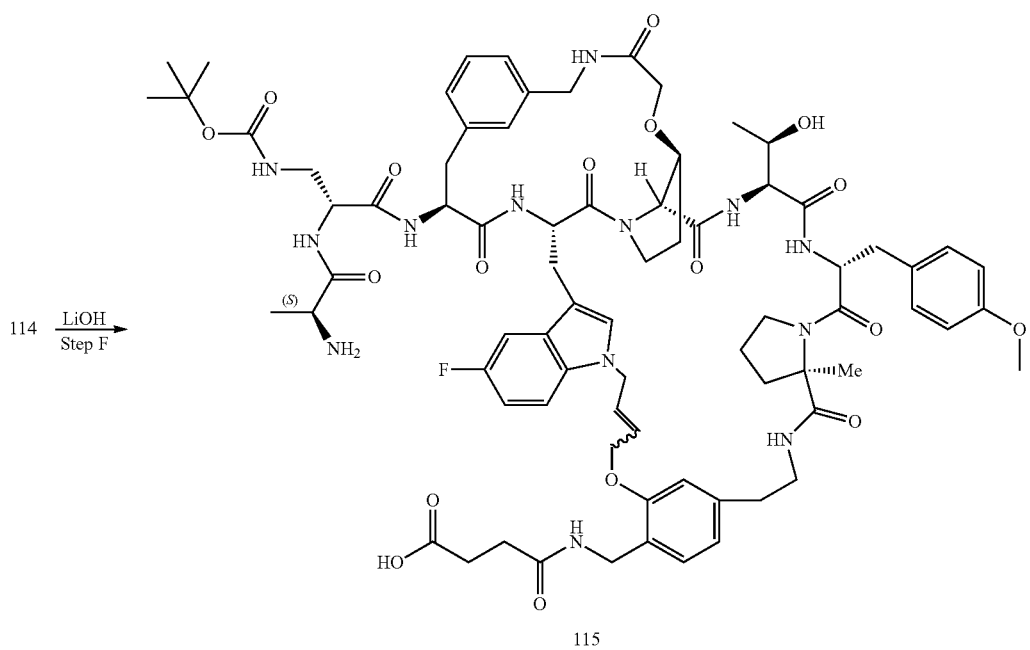

115

To a solution of 114 (134 mg, 0.077 mmol) in THF (1.5 ml) and MeOH (1.5 ml) at 0° C. was added 1 N aqueous LiOH (0.386 ml, 0.386 mmol) dropwise and the mixture was stirred for 2 h. The reaction was treated at 0° C. dropwise with 0.5 N HCl until pH~7, concentrated from organic solvents, then the slurry was dissolved with ~1 mL of DMF and directly purified by column chromatography over C18

(eluting with acetonitrile+0.05% TFA/water+0.05% TFA 90:10 to 50:50) to give 115 as a mixture of E and Z isomers. LC/MS major isomer: (M)⁺=1498.71; LC/MS (minor isomer): (M)⁺=1499.48.

As described above in the preparation of Ex-50 from Ex-01, and Ex-55 from Ex-54 by reaction of the $R^2$ amide thereof in the respective starting compounds with an acidic substituent precursor, the following intermediate compounds may be employed in analogous reactions to provide useful compounds of the invention.

Synthesis of $R^1/R^2$ Substituent Precursors

Preparation of 5-carboxy-N-(3-methoxypropyl)-N, N-dimethylpentan-1-aminium Chloride (Intermediate Z-1a)

Step A: Preparation of Intermediate Z-1

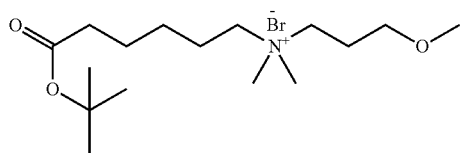

Z-1

To a stirred solution of tert-butyl 6-(dimethylamino) hexanoate (300 mg, 1.393 mmol) in acetonitrile (1 mL) was added 1-bromo-3-methoxypropane (853 mg, 5.57 mmol). The reaction mixture was stirred at 50° C. for 16 h. The resulting mixture was concentrated under reduced pressure to afford Z-1. LC/MS: (M−Br)⁺=288.4. ¹H NMR (300 MHz, CDCl₃): δ 3.76-3.47 (m, 6H), 3.38 (d, J=28.9 Hz, 9H), 2.25 (t, J=7.2 Hz, 2H), 2.12-1.95 (m, 2H), 1.87-1.55 (m, 4H), 1.45 (s, 11H).

Step B: Synthesis of Intermediate Compound Z-1a

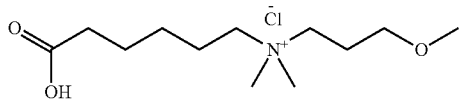

Z-1a

To a stirred solution of Z-1 (460 mg, 1.249 mmol) in DCM (0.5 mL) was added 4 M HCl in dioxane (2 mL) at room temperature. The reaction mixture was stirred at room temperature for 4 h and concentrated under reduced pressure. The residue was re-dissolved in DCM (5 mL) and concentrated under reduced pressure to afford intermediate compound Z-1a. LC/MS: (M−Cl)⁺=232.3.

Preparation of Intermediate Z-2b

Step A: Preparation of Intermediate Z-2

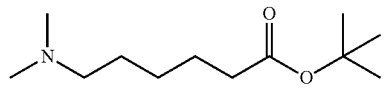

Z-2

To a stirred solution of tert-butyl 6-bromohexanoate (1.0 g, 3.98 mmol) in THF (10 mL) was added dimethylamine (2 M in THF) (7.96 mL, 15.93 mmol). The reaction mixture was stirred at room temperature for 16 h. The resulting mixture was concentrated under reduced pressure and the residue was purified by silica gel column chromatography, eluting with a gradient 1%-15% MeOH in DCM. The fractions containing the desired product were combined and concentrated to afford Z-2. LC/MS: (M+H)⁺=216.2. ¹H NMR (300 MHz, CDCl₃): δ 2.35-2.17 (m, J=8.5, 6.5 Hz, 10H), 1.67-1.47 (m, 4H), 1.45 (s, 9H), 1.42-1.23 (m, 2H).

Step B: Preparation of Intermediate Z-2a

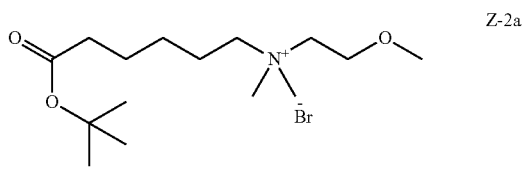 [SMILES: COCC[N+](C)(C)CCCCCC(=O)OC(C)(C)C ; Br]

Z-2a

To a stirred solution of Z-2 (250 mg, 1.161 mmol) in ACN (1 mL) was added 1-bromo-2-methoxyethane (645 mg, 4.64 mmol). The reaction mixture was stirred at 50° C. for 16 h. The resulting mixture was concentrated under reduced pressure to afford Z-2a. LC/MS: (M−Br)⁺=274.3. ¹H NMR (300 MHz, CDCl₃): δ 4.02-3.80 (m, 4H), 3.70-3.54 (m, 2H), 3.42 (d, J=13.0 Hz, 9H), 2.24 (t, J=7.2 Hz, 2H), 1.85-1.75 (m, 2H), 1.72-1.55 (m, 2H), 1.44 (s, 11H).

Step C: Preparation of Intermediate Z-2b

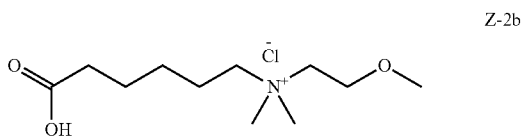

Z-2b

To a stirred solution of Z-2a (450 mg, 1.270 mmol) in DCM (0.5 mL) was added 4 M HCl in dioxane (2 mL) at room temperature. The reaction mixture was stirred at room temperature for 4 h and concentrated under reduced pressure. The residue was re-dissolved in DCM (5 mL) and concentrated under reduced pressure to afford Z-2b. LC/MS: (M−Cl)⁺=218.3.

Preparation of Intermediate Z-3b

Step A: Preparation of Intermediate Z-3

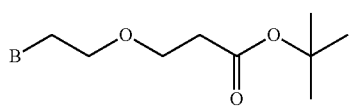

Z-3

To a solution of tert-butyl 3-(2-hydroxyethoxy)propanoate (500.0 mg, 2.63 mmol) in DCM (2 mL) were added CBr₄ (1395 mg, 4.21 mmol) and PPh₃ (965 mg, 3.68 mmol) at 0° C. The mixture was stirred at room temperature for 2 h. The resulting mixture was concentrated under reduced pressure and the residue was purified by silica gel column chromatography, eluted with gradient 1%-15% EA in PE. The fractions containing desired product were combined and concentrated to afford Z-3. ¹H NMR (400 MHz, CDCl₃): δ 3.78 (dt, J=11.1, 6.3 Hz, 4H), 3.47 (t, J=6.3 Hz, 2H), 2.53 (t, J=6.4 Hz, 2H), 1.48 (s, 9H).

Step B: Synthesis of Intermediate Z-3a

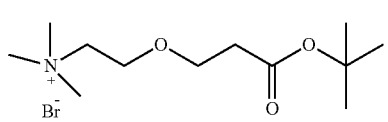
Z-3a

To a stirred solution of tert-butyl 3-(2-bromoethoxy)propanoate Z-3 (450 mg, 1.778 mmol) in ACN (2 mL) was added trimethylamine (955 mg, 5.33 mmol) (33% Wt, in EtOH). The reaction mixture was stirred at 50° C. for 16 h. The resulting mixture was concentrated under reduced pressure to afford Z-3a. LC/MS: (M–Br)$^+$=232.3. $^1$H NMR (400 MHz, CDCl$_3$): δ 5.32 (s, 1H), 4.04-3.94 (m, 4H), 3.73 (t, J=5.7 Hz, 2H), 3.50 (s, 10H), 2.50 (t, J=5.7 Hz, 2H), 1.44 (s, 9H).

Step C: Synthesis of Intermediate Z-3b

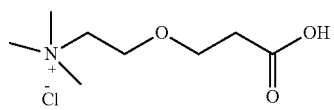
Z-3b

To a solution of Z-3a (550 mg, 1.761 mmol) in DCM (0.6 mL) was added 4 M HCl in dioxane (2.5 mL) at room temperature. The mixture was stirred at room temperature for 4 h. The resulting mixture was concentrated under reduced pressure and the residue was re-dissolved in DCM (3 mL) and toluene (3 mL). The mixture was then concentrated under reduced pressure to afford Z-3b. LC/MS: (M–Cl)$^+$=176.2.

Preparation of Intermediate Z-4b

Step A: Preparation of Intermediate Z-4

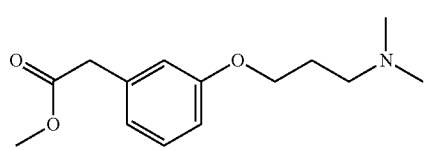
Z-4

To a solution of DIAD (1.755 mL, 9.03 mmol) in THF (30 mL) was added Ph$_3$P (2.368 g, 9.03 mmol). The mixture was stirred at room temperature for 10 min, then methyl 2-(3-hydroxyphenyl)acetate (1.0 g, 6.02 mmol) and 3-(dimethylamino)propan-1-ol (0.931 g, 9.03 mmol) were added to the solution. The mixture was stirred at 50° C. for 1 h. The resulting solution was concentrated under reduced pressure and the residue was purified by silica gel column chromatography, eluting with a gradient 1%-10% MeOH in DCM. The fractions containing the desired product were combined and concentrated to afford Z-4. LC/MS: (M+H)$^+$=252.2. $^1$H NMR (300 MHz, CDCl$_3$): δ 7.23-7.18 (m, 1H), 6.82 (td, J=8.7, 4.1 Hz, 3H), 4.01 (t, J=6.4 Hz, 2H), 3.69 (s, 3H), 3.59 (s, 2H), 2.46 (t, J=7.3 Hz, 2H), 2.27 (s, 6H), 1.97 (dt, J=7.9, 6.5 Hz, 2H).

Step B: Preparation of Intermediate Z-4a

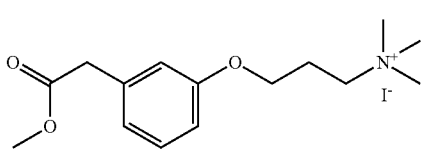
Z-4a

To a solution of Z-4 (600 mg, 2.268 mmol) in ACN (12 mL) was added MeI (1.288 g, 9.07 mmol). The mixture was stirred at room temperature for 1 h. The resulting solution was concentrated under reduced pressure to afford Z-4a. LC/MS: (M–I)$^+$=266.2.

Step C: Preparation of Intermediate Z-4b

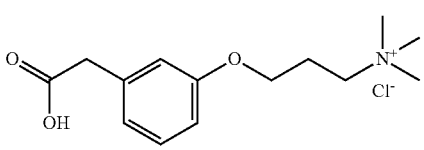
Z-4b

To a solution of Z-4a (800 mg, 1.729 mmol) in THF (12 mL) was added 2 M LiOH (1.729 mL, 3.46 mmol). This mixture was stirred at room temperature for 2 h. The pH value of the solution was adjusted to 4 with HCl (1 M) and the solution was concentrated under reduced pressure. The crude product was purified by reverse phase chromatography over C18 (Mobile Phase A: water, Mobile Phase B: ACN; Flow rate: 60 mL/min; Gradient: 1% B to 25% B in 25 min; 25% B to 95% B in 15 min; 95% B to 95% B in 10 min) to afford Z-4b. LC/MS: (M–Cl)$^+$=252.2. $^1$H NMR (300 MHz, CD$_3$OD): δ 7.21 (t, J=7.9 Hz, 1H), 6.95-6.75 (m, 3H), 4.12 (t, J=5.7 Hz, 2H), 3.63-3.50 (m, 4H), 3.18 (s, 9H), 2.35-2.20 (m, 2H).

Example 4 Preparation of Ex-23

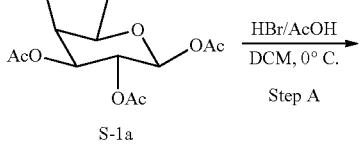
S-1a

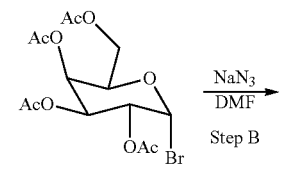
S-1b

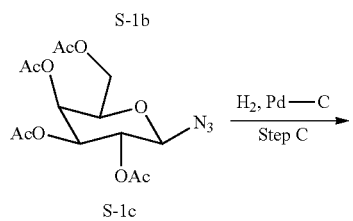
S-1c

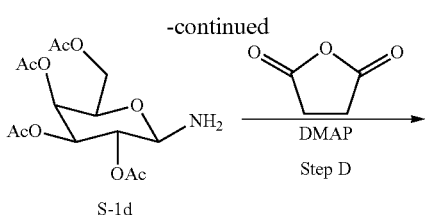

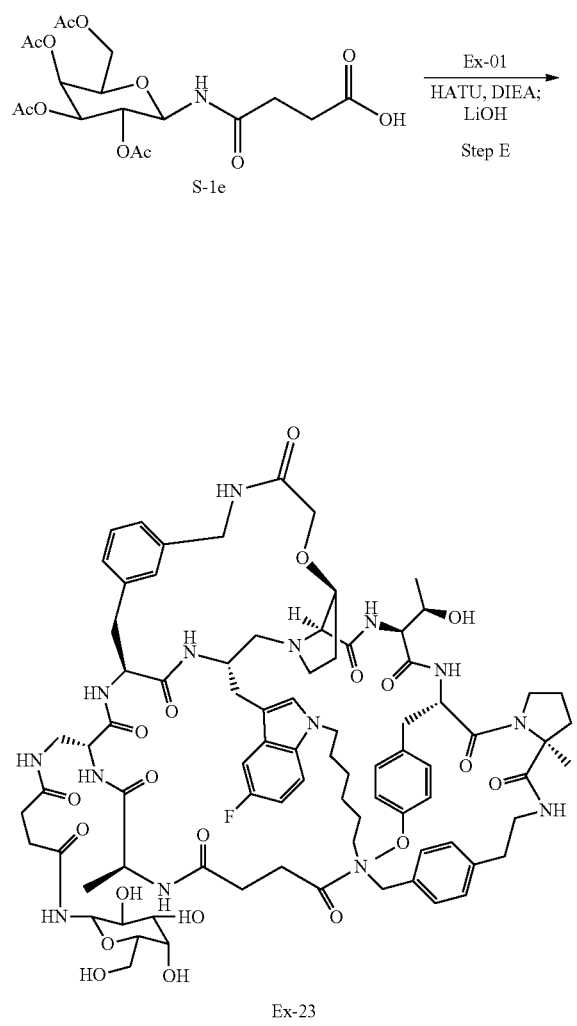

Step A: Preparation of Intermediate S-1b (2S,3R,4S,5S,6R)-6-(acetoxymethyl)tetrahydro-2H-pyran-2,3,4,5-tetrayltetraacetate S-1a (5 g, 12.81 mmol) was added to a solvent of 48% HBr (7.25 mL, 64.0 mmol) in AcOH and DCM (40 mL) at 0° C. and the mixture was stirred at 0° C. for 1 hour. The reaction mixture was poured into aqueous saturated sodium hydrogen carbonate cooled on ice and the mixture was extracted with DCM (3×60 mL).

The organic layer was washed with brine, dried over $Na_2SO_4$, filtered and concentrated then the crude product was purified by flash chromatography over silica gel (eluting with 0-30% EtOAc/PE) to S-1b.

Step B: Preparation of Intermediate S-1c

To a solution of S-1b (4.5 g, 10.94 mmol) in dry DMF (45 mL) was added sodium azide (0.854 g, 13.13 mmol) and the reaction was stirred at 18° C. for 30 min. The reaction mixture was diluted with water (30 mL) and extracted with EtOAc (3×80 mL). The organic layer was dried over $Na_2SO_4$ and evaporated to dryness. The crude product was purified by flash chromatography over silica gel (eluting with 0-30% EtOAc/PE) to give S-1c.

Step C: Preparation of Intermediate S-1d

To a solution of S-1c (3.15 g, 8.44 mmol) in EtOH (60 mL) were added 10% Pd—C (0.898 g, 0.844 mmol). The reaction vessel was purged from air and filled with $H_2$ under 50 psi. The reaction was stirred at 18° C. for 5 h. The reaction mixture was diluted with EtOAc, filtered through Celite, and concentrated, to give S-1d which was used for the next step.

Step D: Preparation of Intermediate S-1e

To a solution of S-1d (2.34 g, 6.74 mmol) in anhydrous THF (20 mL) was added dihydrofuran-2,5-dione (0.742 g, 7.41 mmol) and Et3N (0.939 mL, 6.74 mmol). The reaction was stirred for 3 h until complete consumption of the starting material then evaporated. The resulting crude product was purified by flash chromatography over silica gel (eluting with 0~10% DCM/MeOH) to give 5-1e. MS (ESI): m/z $(M+H)^+$ 448.1. 1HNMR (400 MHz, CDCl3) δ: 6.48 (d, J=9.04 Hz, 1H), 5.43 (s, 1H), 5.24 (t, J=8.93 Hz, 1H), 5.07-5.17 (m, 2H), 4.08-4.18 (m, 2H), 4.04 (q, J=6.69 Hz, 1H), 2.72-2.84 (m, 1H), 2.58-2.69 (m, 2H), 2.43-2.53 (m, 2H), 2.15 (s, 3H), 2.06 (s, 3H), 2.04 (s, 4H), 2.00 (s, 3H).

Step E: Preparation of Ex-23

To a solution of Ex-01 (300 mg, 0.215 mmol) and S-1e (115 mg, 0.258 mmol) in DMF (8 ml) and water (0.4 ml) was added DIEA (0.150 ml, 0.860 mmol) and HATU (98 mg, 0.258 mmol) and the resulting solution was stirred at rt for 1 h. The reaction was quenched with 1N LiOH (2.58 ml, 2.58 mmol) dropwise, the resulting solution was stirred at rt for 2 h then filtered and the filtrate was purified on reverse phase HPLC C18 column using a 29-34% gradient of acetonitrile (0.05% TFA) in water (0.05% TFA) to give Ex-23. LC/MS: [M+1]+=1657.1.

Example 5 Preparation of Ex-14

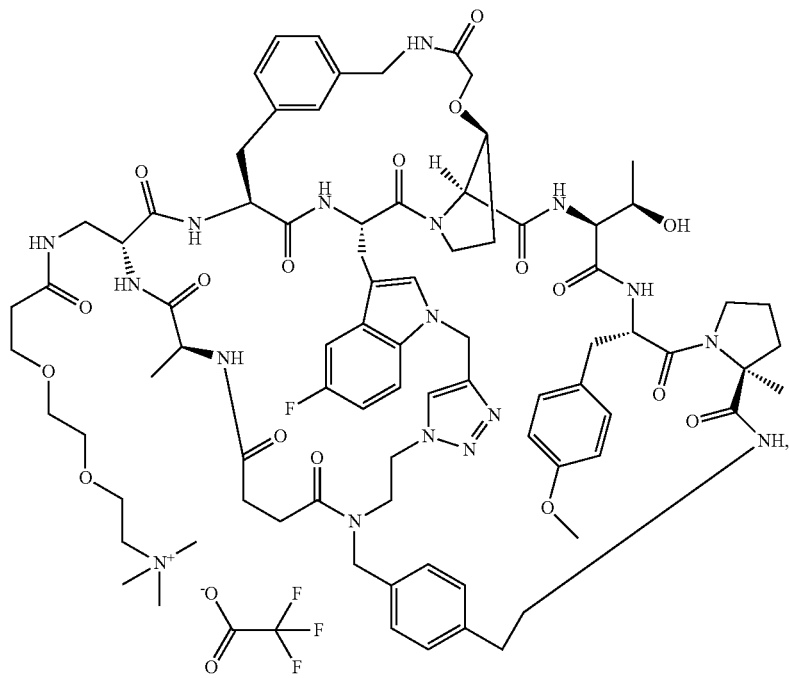

Ex-14

Compound Ex-14 was prepared in a manner analogous to procedures described in Example 1 but using different "linkers" and alternate synthetic steps. Synthesis of these "linkers", alternative steps and main assembly is described below.

Preparation of Intermediate Int-2g

Intermediate Int-2g, useful as a "linker" in the preparation of compounds of the invention, was prepared in accordance with the following scheme:

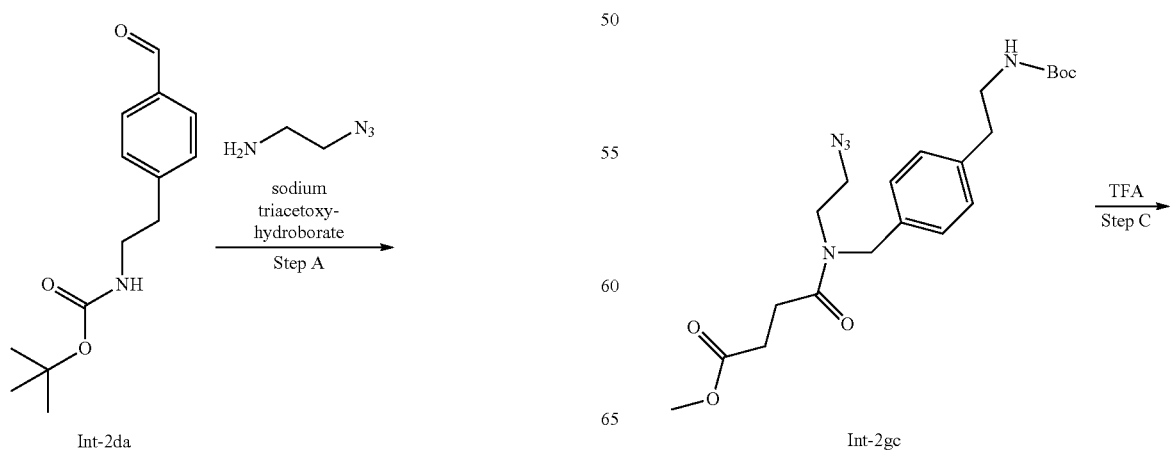

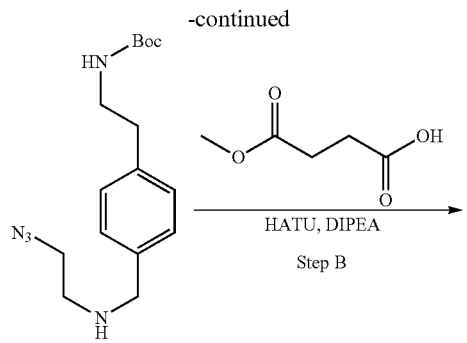

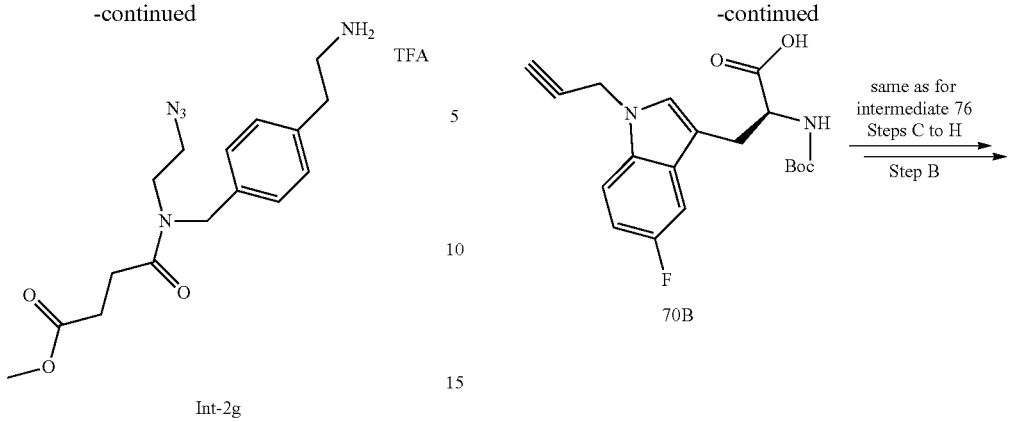

Int-2g

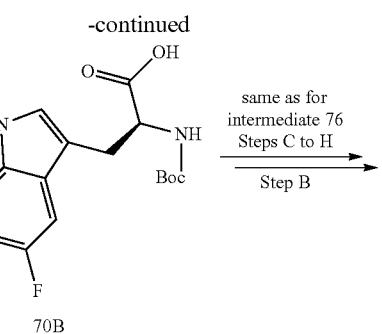

70B

Step A—Synthesis of Int-2gb

To a solution of Int-2da (0.5 g, 2 mmol) and 2-azidoethanamine, HCl (0.246 g, 2 mmol) in THF (16 ml) at room temperature in a water bath was added sodium triacetoxyhydroborate (1.06 g, 5 mmol) portion wise and the mixture was stirred for 2 h. The reaction was slowly quenched with aqueous saturated NaHCO$_3$ solution, then extracted with DCM and washed with brine. The combined organic layers were dried over MgSO$_4$ and concentrated to give Int-2gb. LC/MS: (M+1)$^+$=320.3.

Step B—Synthesis of Int-2gc

To a solution of Int-2gb (0.64 g, 2 mmol) and monomethyl succinate (0.3 g, 2.3 mmol) in DMF (4 ml) and DCM (8 ml) was added HATU (0.914 g, 2.4 mmol) and DIPEA (0.7 ml, 4.01 mmol) at −15° C. The resulting solution was stirred at −15° C. for 2 hours, then quenched with water and concentrated. The residue was purified by reverse-phase chromatography over C18 (eluting with acetonitrile/water+0.1% TFA) to give Int-2gc. LC/MS: (M+1)$^+$=434.3.

Step C—Synthesis of Int-2g

To a solution of Int-2gc (0.52 g, 1.2 mmol) in DCM (9 mL) was added TFA (3 mL, 38.9 mmol) at room temperature. The reaction mixture was stirred at room temperature for 2 h. The mixture was concentrated under reduced pressure to afford Int-2g. LC/MS: (M+1)$^+$=334.3.

Preparation of Intermediate Compounds 70B and 76C

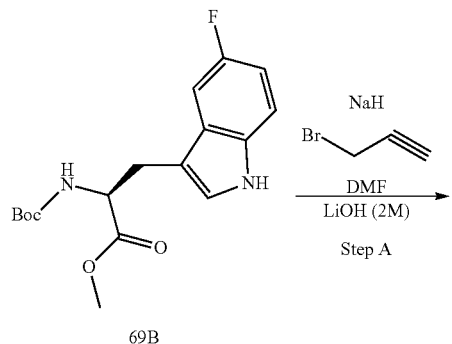

69B

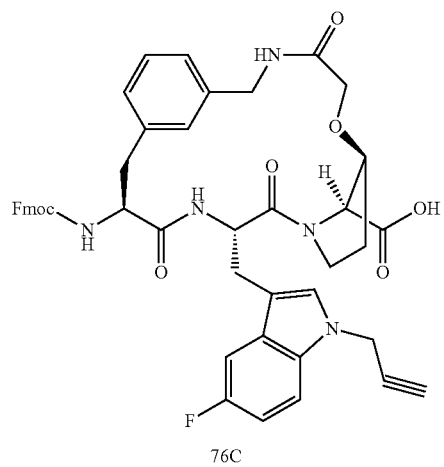

76C

Step A—Synthesis of Intermediate 70B

To a solution of 69B (1.5 g, 4.46 mmol) in DMF (17.8 ml) at 0° C. was added 95% NaH (0.141 g, 5.56 mmol), and the resulting solution was stirred at 0° C. for 20 min followed by addition of 3-bromoprop-1-yne (80% in toluene) (0.596 ml, 5.35 mmol) dropwise. To the resulting solution was added aqueous lithium hydroxide (2M) (3345 µl, 6.69 mmol) dropwise. The reaction was stirred at room temperature for 2 h, filtered and purified by reverse phase HPLC (eluting with acetonitrile/water+0.1% TFA) to give 70B. LC/MS: (M+1)$^+$: 361.0, (M+Na)$^+$: 383.0.

Step B—Synthesis of Intermediate 76C

Conversion of 70B to intermediate 76C proceeded according to procedures analogous to those described in the preparation of intermediate 76 Steps C to H. LC/MS: [M+1]+=812.16.

Assembly into Example Ex-14:
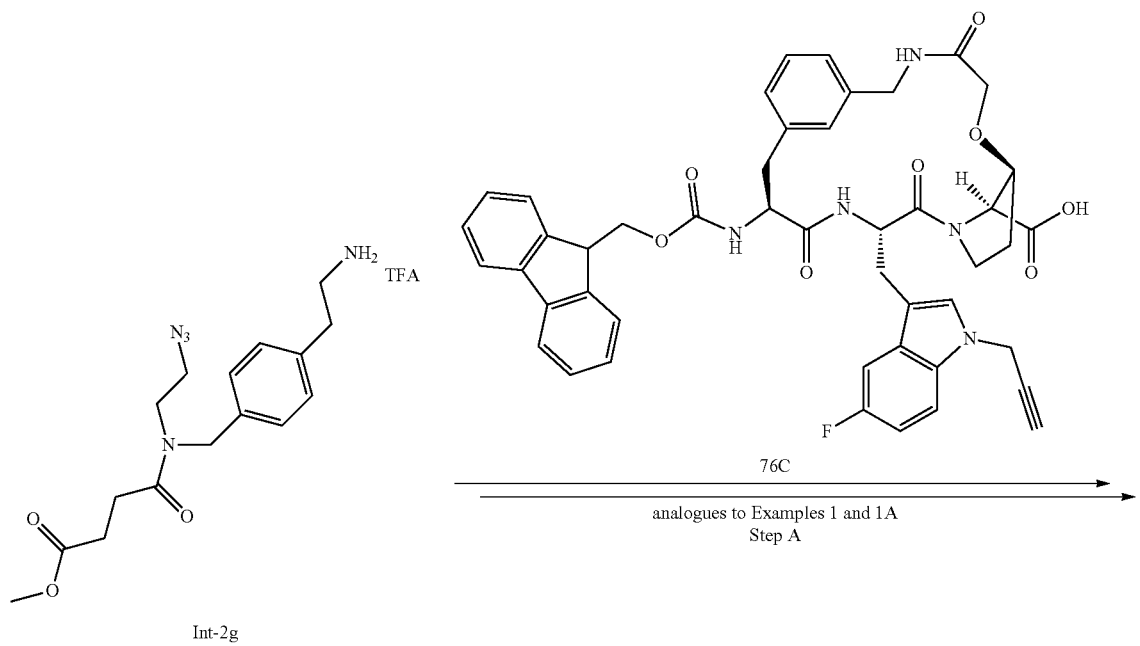
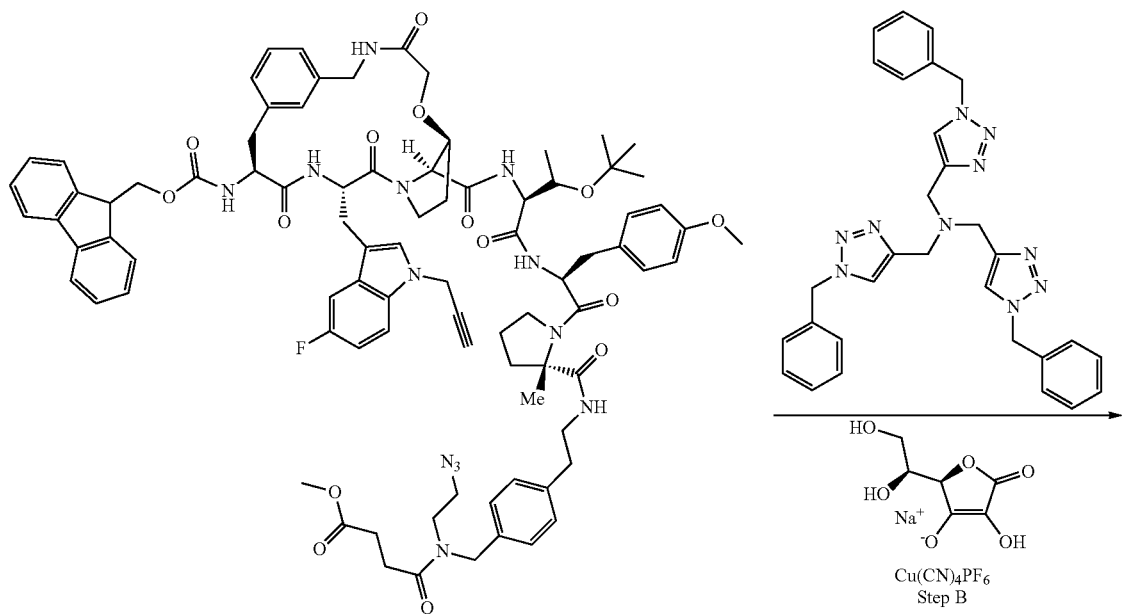

-continued

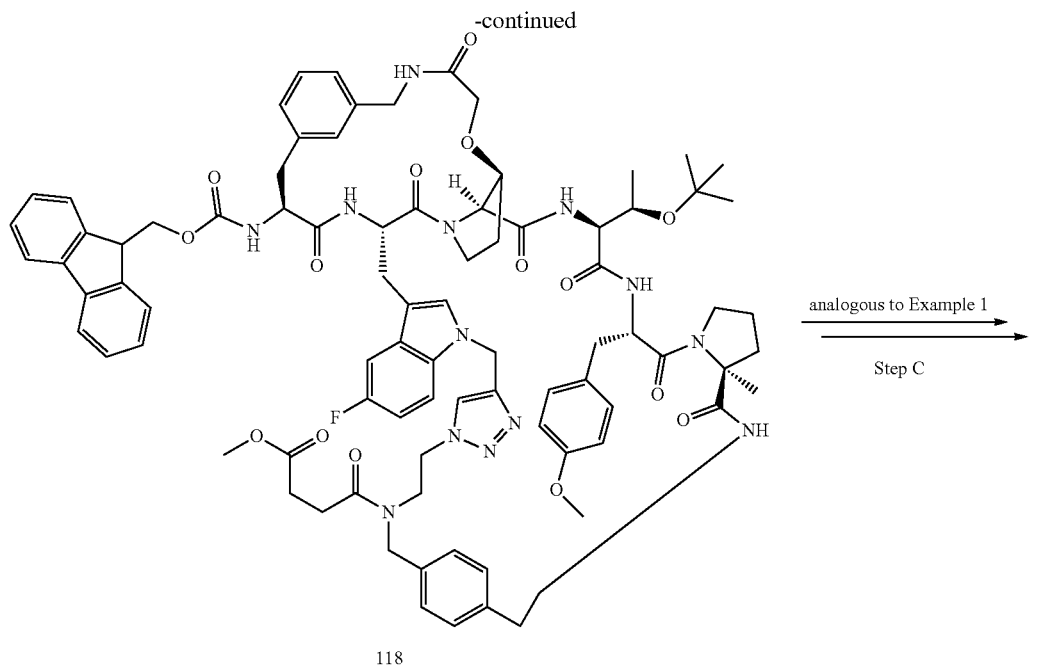

118

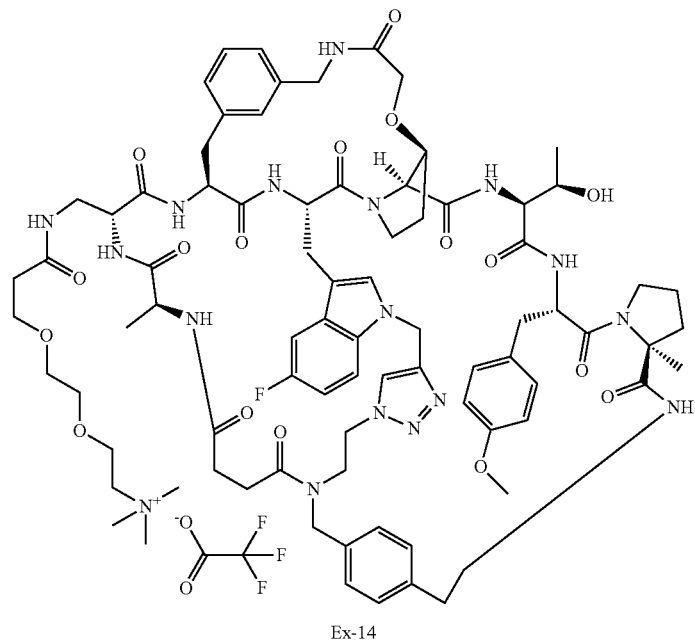

Ex-14

Step A—Synthesis of Intermediate 117

Intermediate 117 was prepared from intermediates Int-2g and 76C according to procedures analogous to those described in Example 1 and 1A. More specifically Int-2g was functionalized following reagents and procedures for the preparation of intermediate 77B Steps A to B, further elaborated following procedures for the preparation of intermediate 86 Steps G to J, then finally coupled with intermediate 76C following procedures for the preparation of Example 1A Steps B to C, to provide 117. LC/MS: (M+1)+: 1573.36.

Step B—Synthesis of Intermediate 118

Tetrakis(acetonitrile)copper(I) hexafluorophosphate (51.6 mg, 0.138 mmol), tris[(1-benzyl-1h-1,2,3-triazol-4-yl)methyl]amine (73.4 mg, 0.138 mmol) and sodium ascorbate (137 mg, 0.692 mmol) in BuOH (185.00 mL)/water (93 mL) were bubbled with nitrogen and then heated at 50° C. Intermediate 117 (435.3 mg, 0.277 mmol) was added into the reaction as a solid. After 1 h, the reaction was treated with aqueous pH 4 buffer and extracted with EtOAc. The combined organic layers were evaporated, and the residue was purified by reverse phase chromatography (eluting with a gradient of acetonitrile/water+0.1% formic acid) to provide intermediate 118. LC/MS: (M+1)$^+$: 1573.2.

Step C—Synthesis of Ex-14

Synthesis of Example Ex-14 proceeded from intermediate 118 according to procedures analogous to those described in Example 1, including the use of alternate spacers for the assembly. LC/MS: [M+1]+=1621.01.

Using the synthetic schemes described above, and as will be appreciated, in some instances with appropriate substitution of certain intermediates including the use of alternate spacers apparent to those skilled in the art, the preparation of which may be described above, the following compounds of the invention, listed in Table 2 below, were prepared. Additionally, alternate salt forms of compounds of the instant invention may also be described in this application:

TABLE 2

| Ex-No/ | Structure | LC/MS: (M)+ |
|---|---|---|
| Ex-01 ACOH salt | 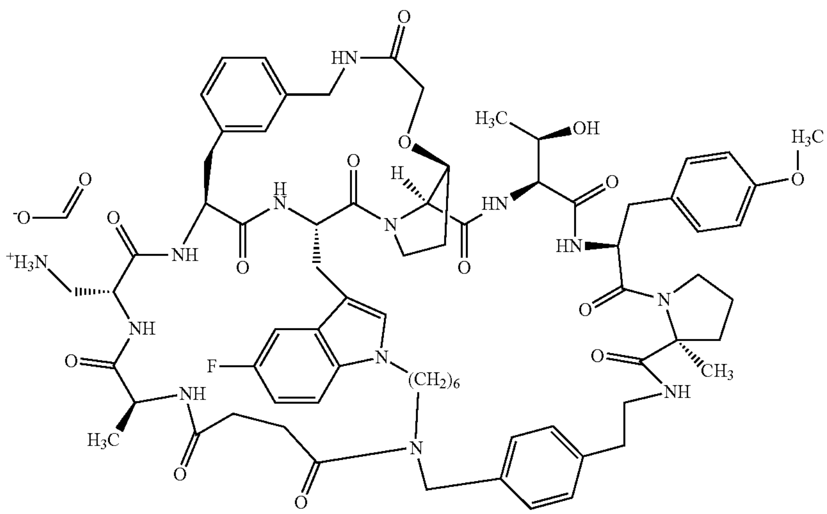 | 1394.4 |
| Ex-02 TFA salt | 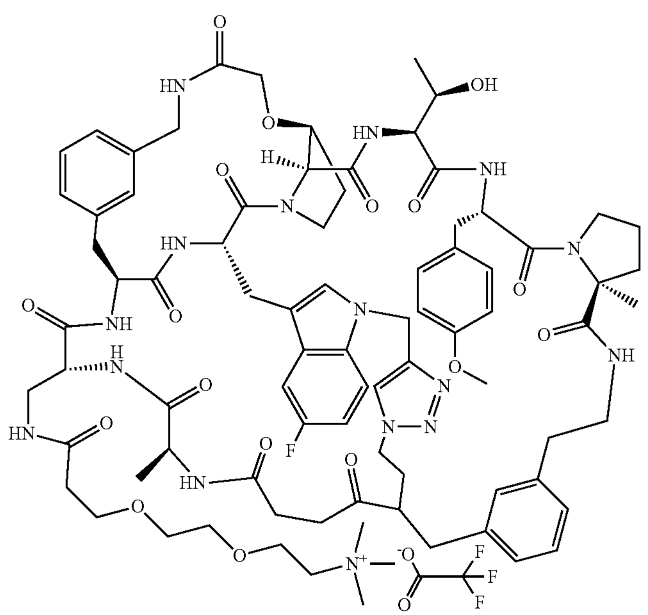 | 1622.12 |

TABLE 2-continued

| Ex-No/ | Structure | LC/MS: (M)+ |
|---|---|---|
| Ex-03 TFA salt | 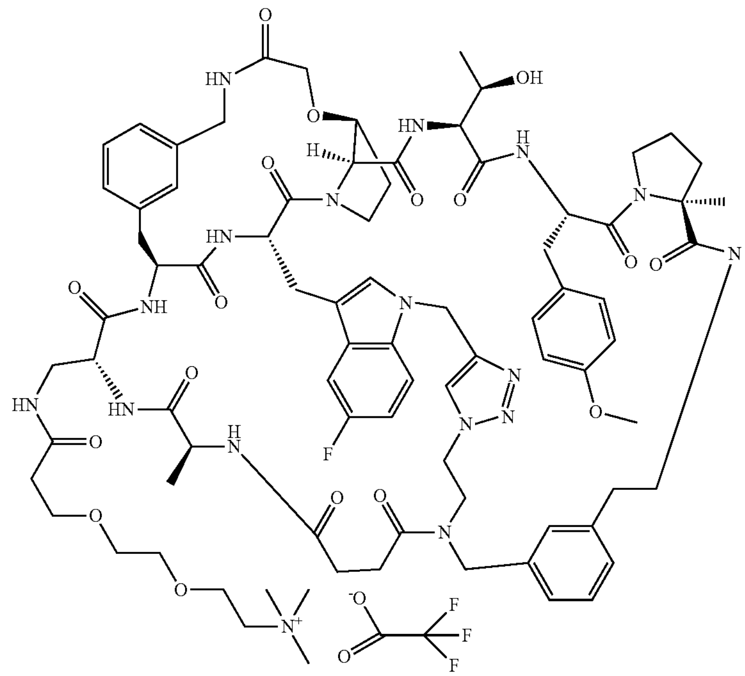 | 1622.06 |
| Ex-04 TFA salt | 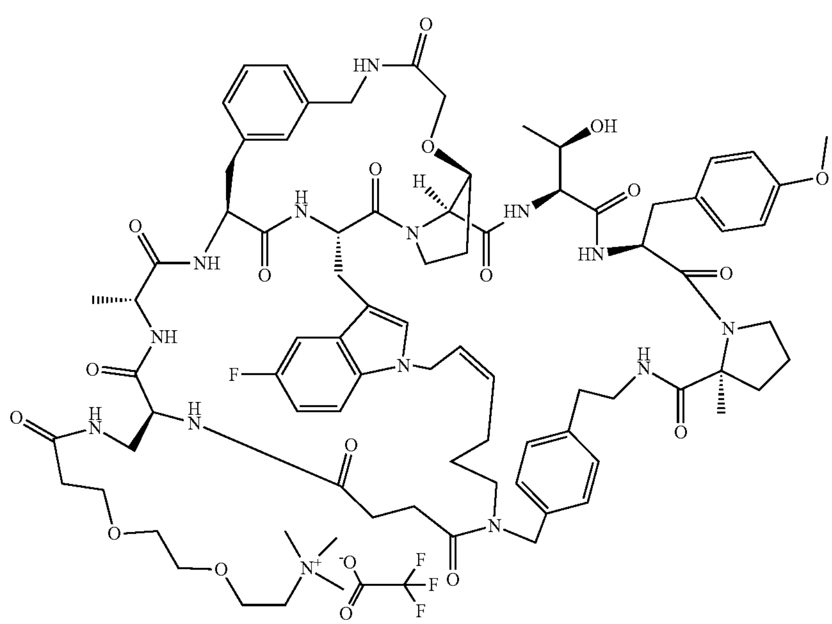 | 1595.04 |

TABLE 2-continued
| Ex-No/ | Structure | LC/MS: (M)+ |
|---|---|---|
| Ex-05 TFA salt | 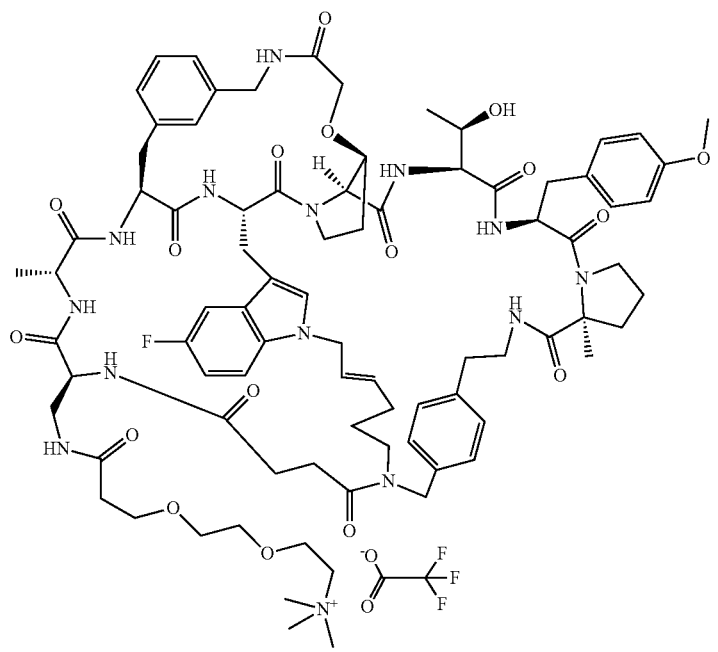 | 1594.54 |
| Ex-06 TFA salt | 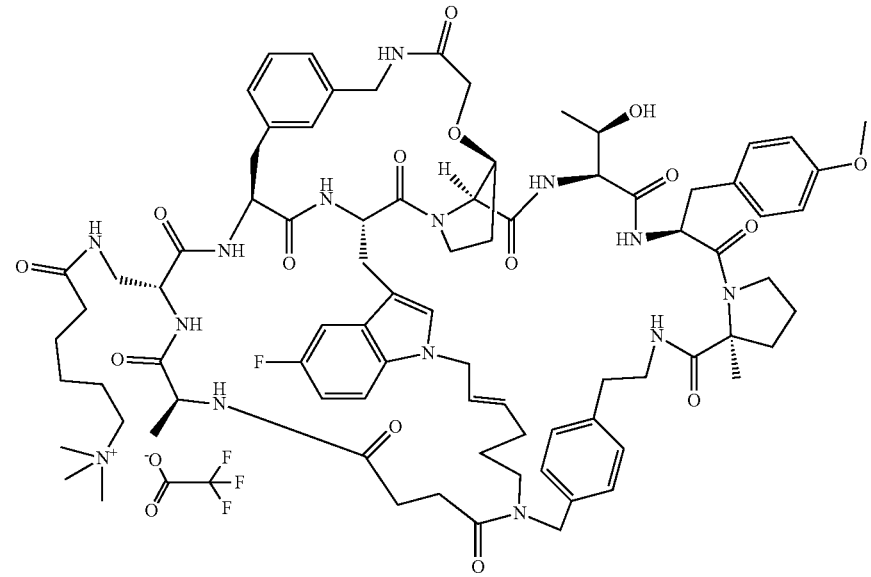 | 1549.44 |

TABLE 2-continued
| Ex-No/ | Structure | LC/MS: (M)+ |
|---|---|---|
| Ex-07 TFA salt | 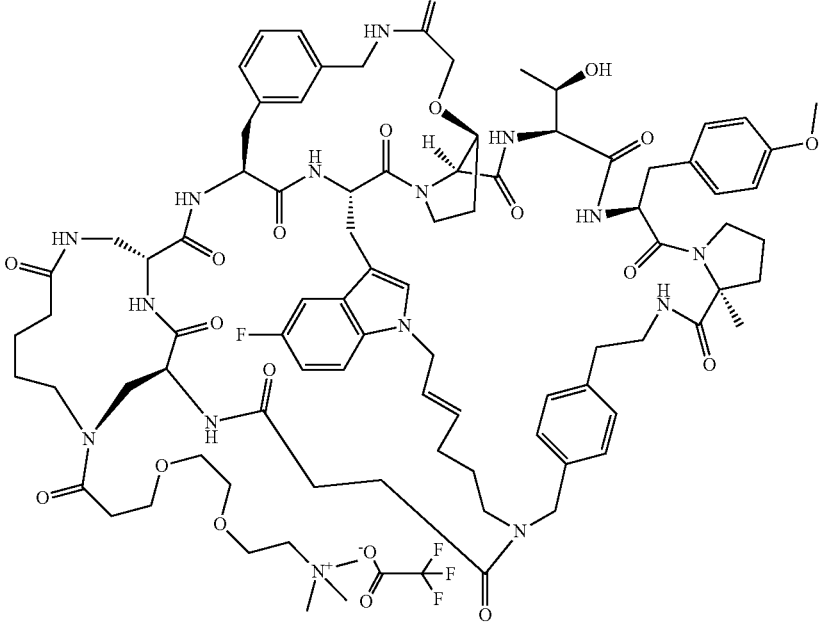 | 1692.66 |
| Ex-08 TFA salt | 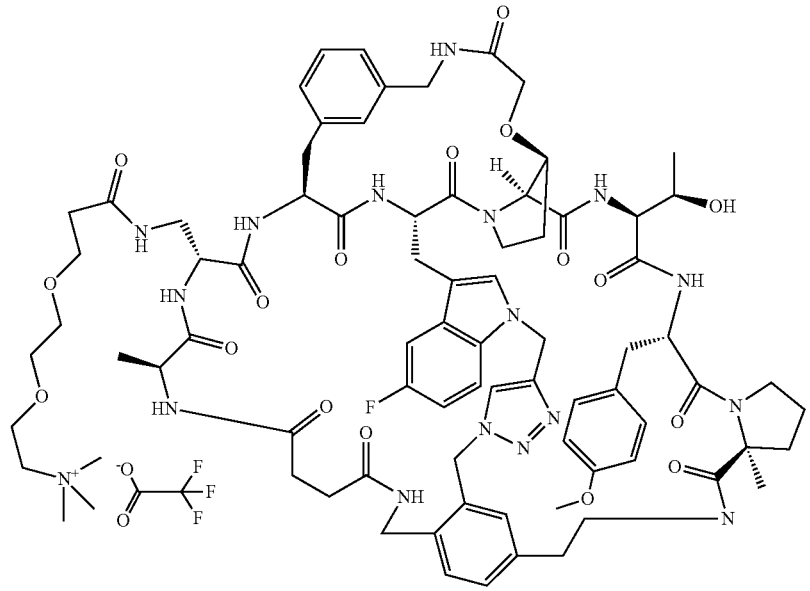 | 1608.46 |

TABLE 2-continued

| Ex-No/ | Structure | LC/MS: (M)+ |
|---|---|---|
| Ex-09 Cl salt | 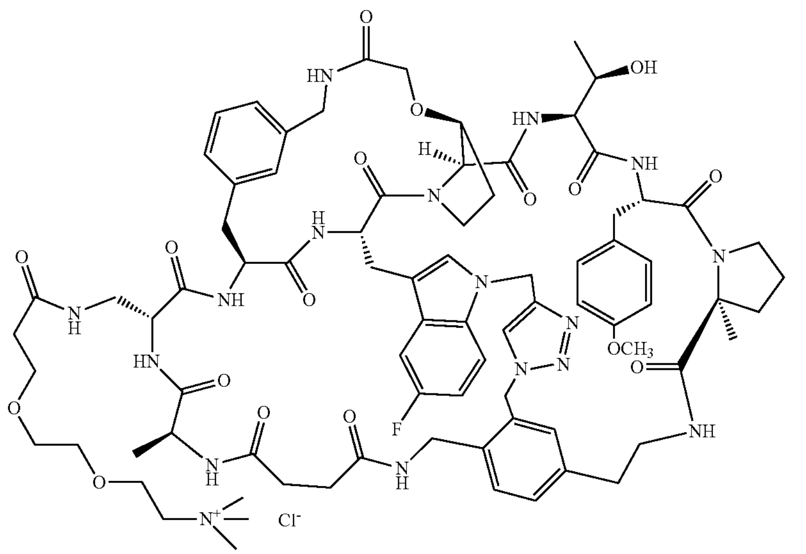 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)Cc5cn(nn5)Cc5cc(ccc5CNC(=O)CCC(=O)N[C@@H](C)C(=O)N[C@H](CNC(=O)CCOCCOCC[N+](C)(C)C)C(=O)N[C@@H](Cc5cccc(c5)CNC(=O)CO4)C(=O)N3)CCNC(=O)[C@]3(C)CCCN3C2=O)cc1 ; [Cl-]] | 1608.30 |
| Ex-10 TFA salt | 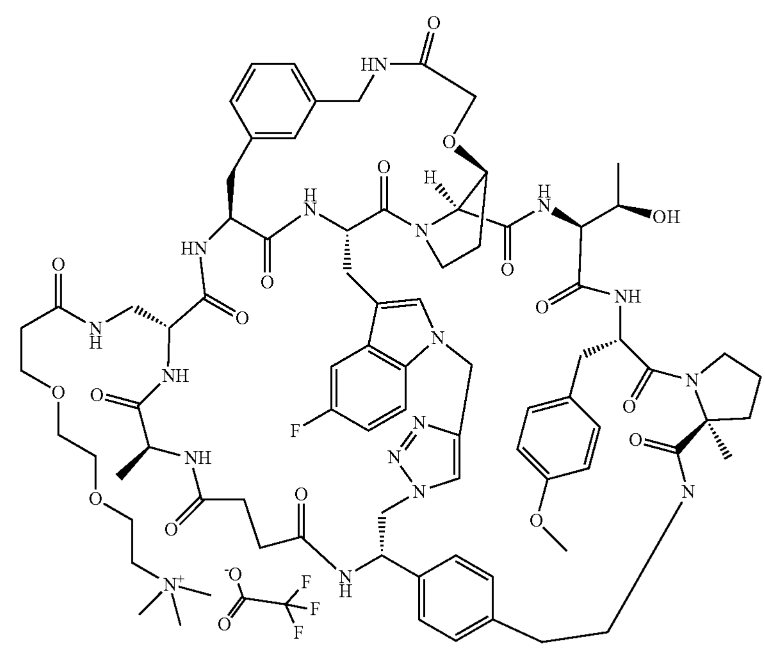 | 1608.40 |

TABLE 2-continued
| Ex-No/ | Structure | LC/MS: (M)+ |
|---|---|---|
| Ex-11 TFA salt | 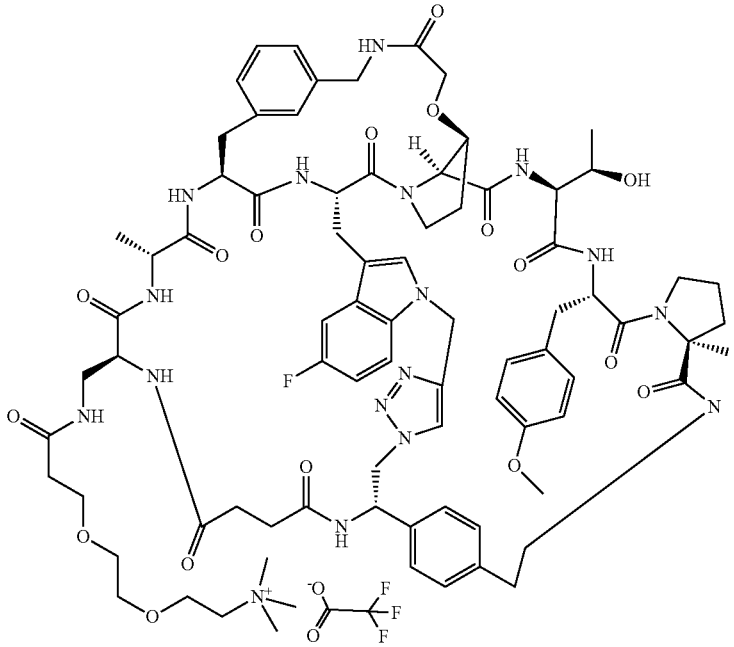 | 1608.84 |
| Ex-12 TFA Salt | 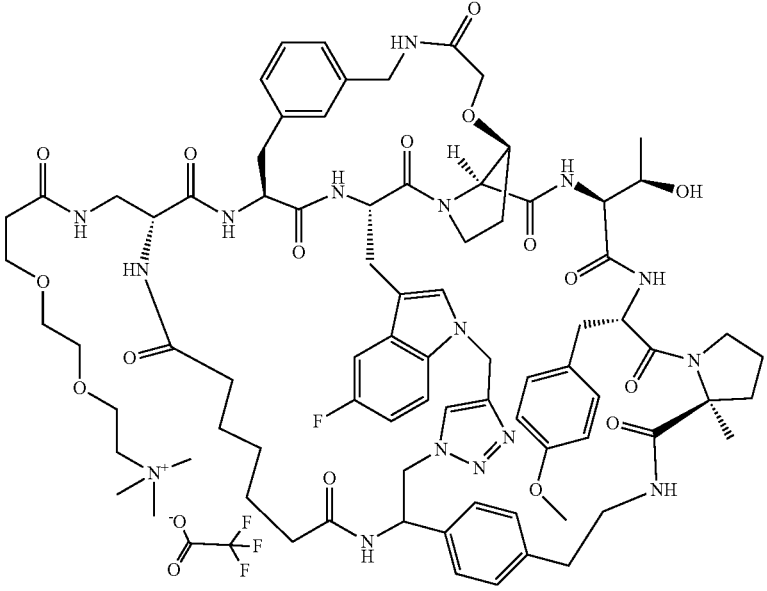 | 1579.54 |

TABLE 2-continued

| Ex-No/ | Structure | LC/MS: (M)+ |
|---|---|---|
| Ex-13 TFA salt | 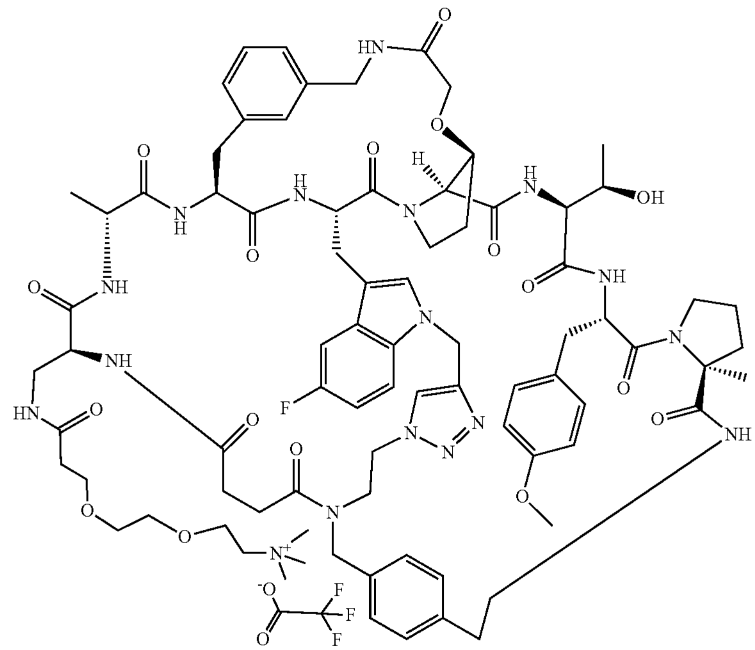 | 1621.74 |
| Ex-14 TFA salt | 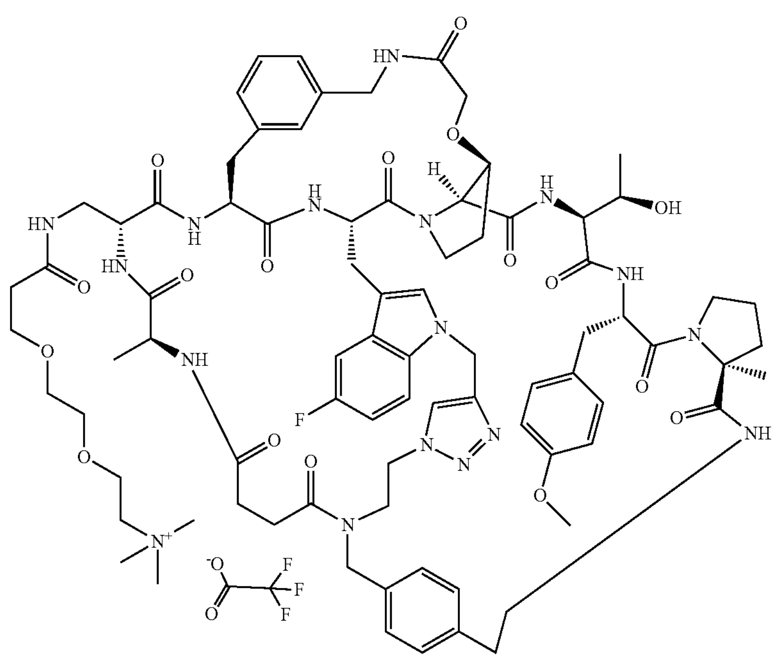 | 1622.28 |

TABLE 2-continued
| Ex-No/ | Structure | LC/MS: (M)+ |
|---|---|---|
| Ex-15 TFA salt | 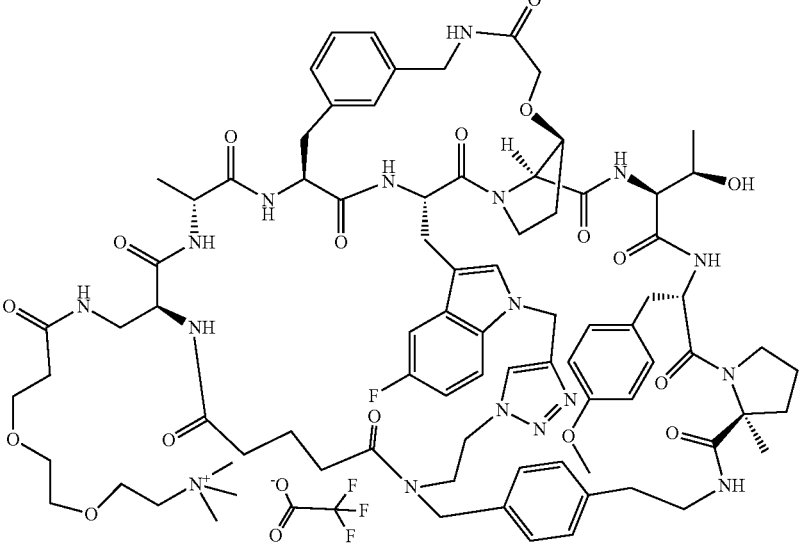 | 1636.54 |
| Ex-16 TFA salt | 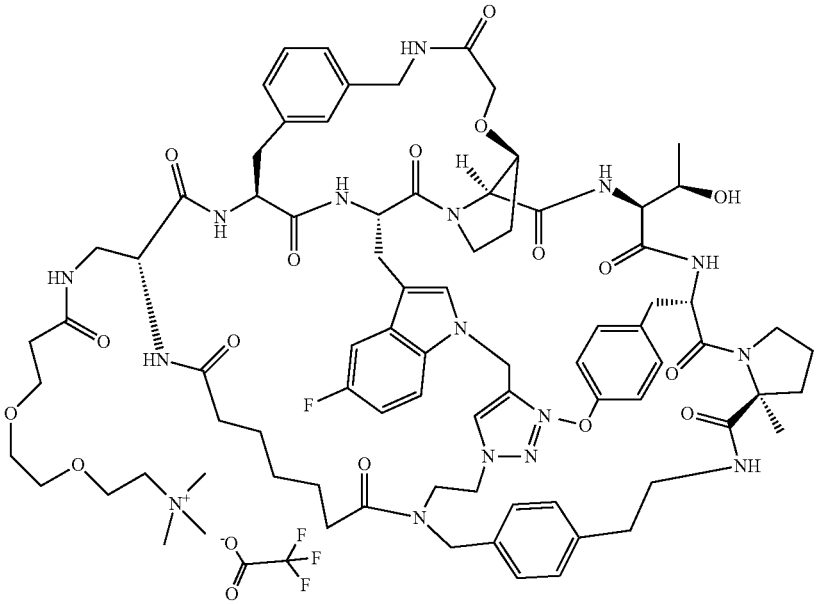 | 1592.52 |

TABLE 2-continued

| Ex-No/ | Structure | LC/MS: (M)+ |
|---|---|---|
| Ex-17 TFA salt | 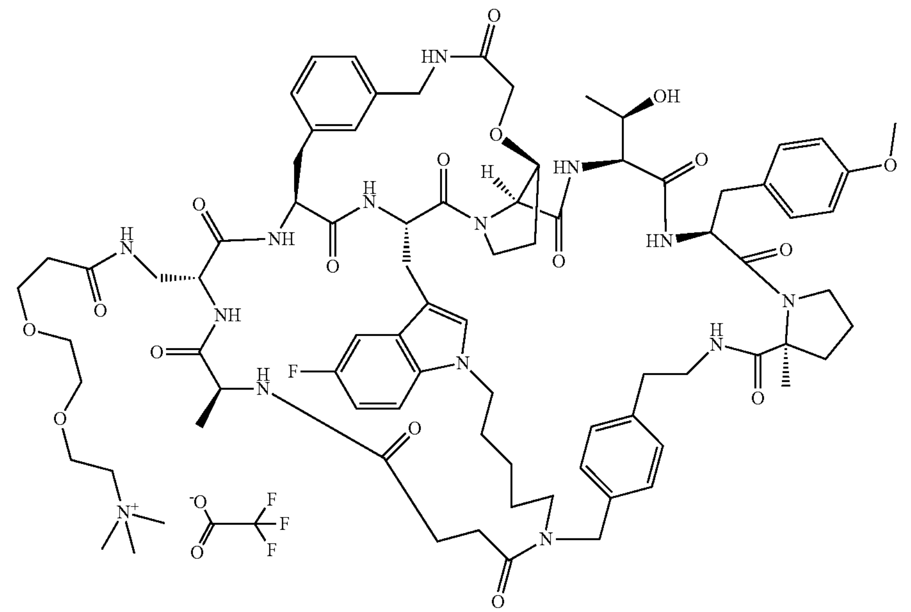 | 1582.68 |
| Ex-18 TFA salt | 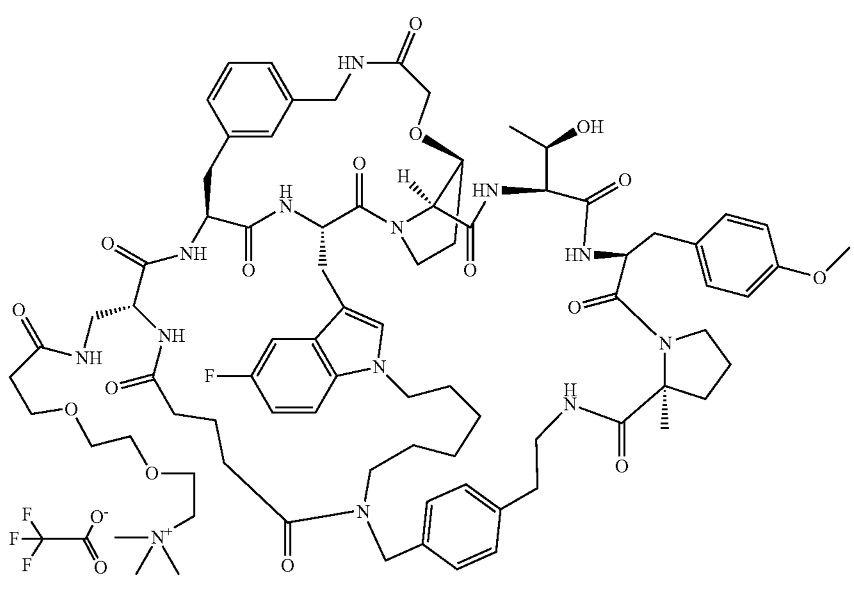 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCCC(=O)N[C@H](CNC(=O)CCOCCOCC[N+](C)(C)C)C(=O)N[C@@H](Cc2cccc(c2)CNC(=O)CO4)C(=O)N3)cc1 ; O=C([O-])C(F)(F)F] | 1539.75 |

TABLE 2-continued
| Ex-No/ | Structure | LC/MS: (M)+ |
|---|---|---|
| Ex-19 TFA salt | 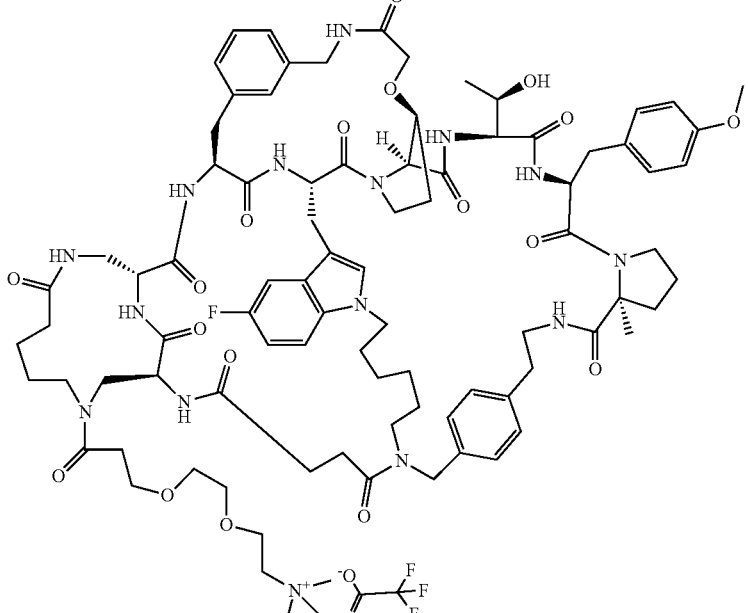 | 1692.91 |
| Ex-20 TFA salt | 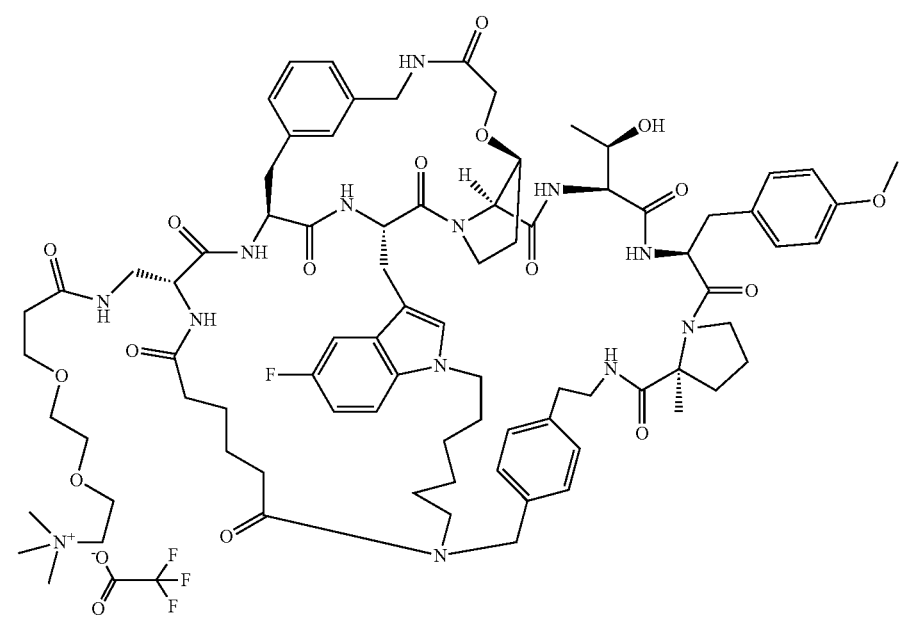 | 1553.62 |

TABLE 2-continued
| Ex-No/ | Structure | LC/MS: (M)+ |
|---|---|---|
| Ex-21 Cl salt | 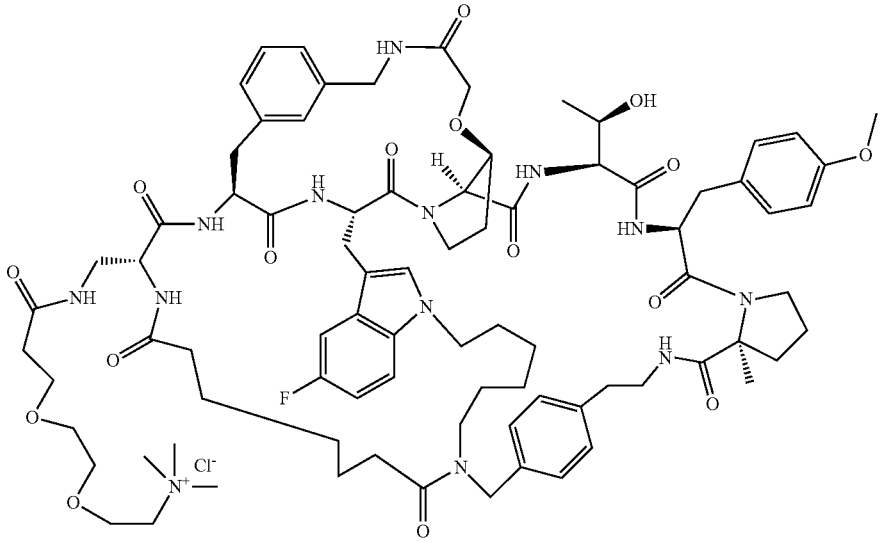 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCCCCC(=O)N[C@H](CNC(=O)CCOCCOCC[N+](C)(C)C)C(=O)N[C@@H](Cc2cccc(c2)CNC(=O)CO4)C(=O)N3)cc1 ; [Cl-]] | 1566.91 |
| Ex-22 TFA salt | 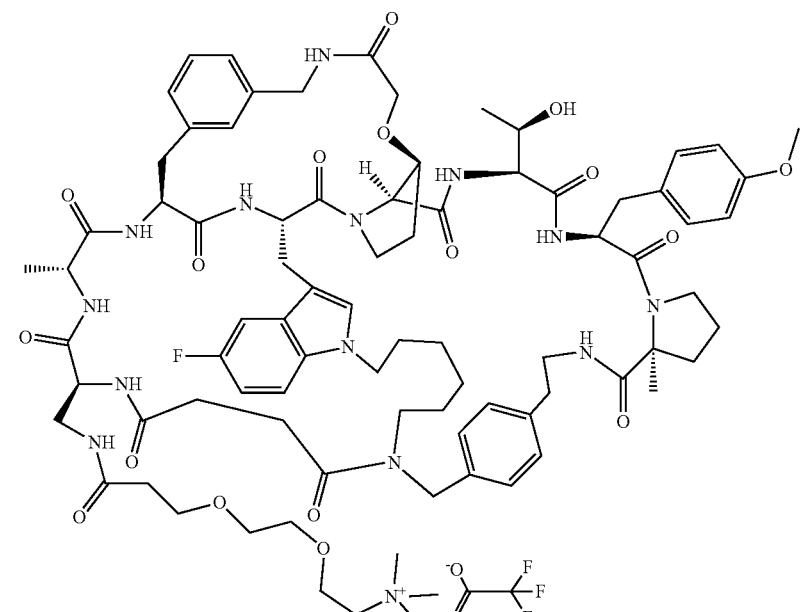 | 1596.66 |

TABLE 2-continued

| Ex-No/ | Structure | LC/MS: (M)+ |
|---|---|---|
| Ex-23 | 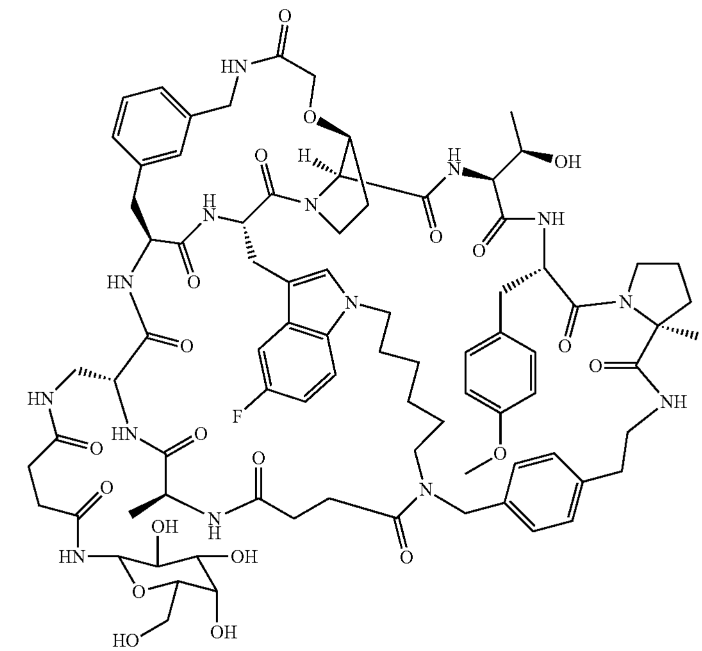 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCC(=O)NC2OC(CO)C(O)C(O)C2O)C(=O)N[C@@H](Cc2cccc(c2)CNC(=O)CO4)C(=O)N3)cc1] | 1656.57 |
| Ex-24 TFA salt | 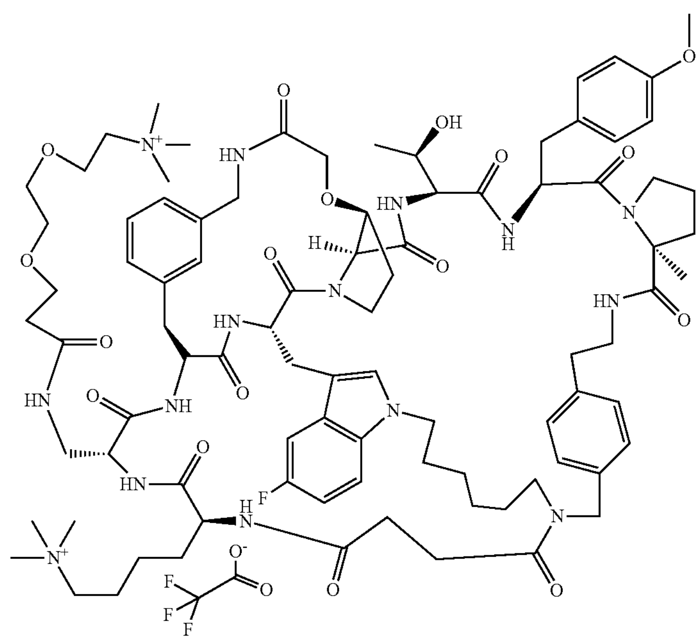 | 1810.06 (half mass 848.64) |

TABLE 2-continued

| Ex-No/ | Structure | LC/MS: (M)+ |
|---|---|---|
| Ex-25 TFA salt | 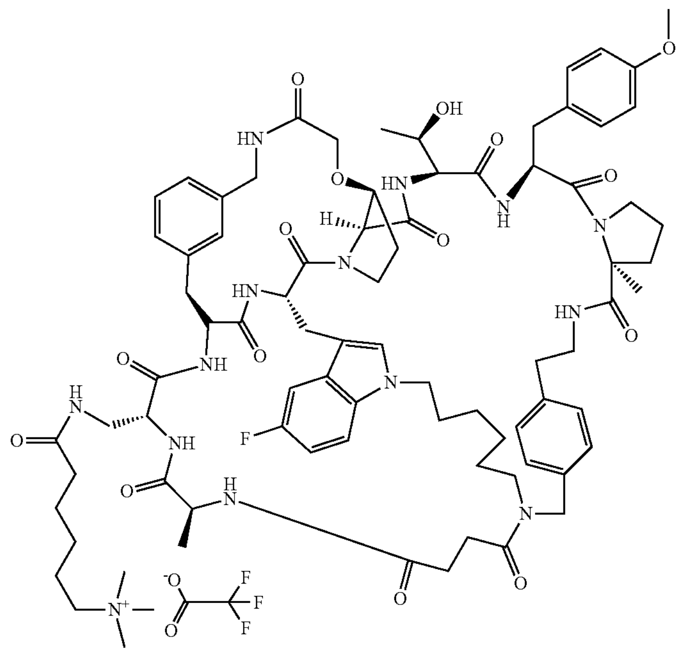 | 1550.6 |
| Ex-25 Cl Salt | 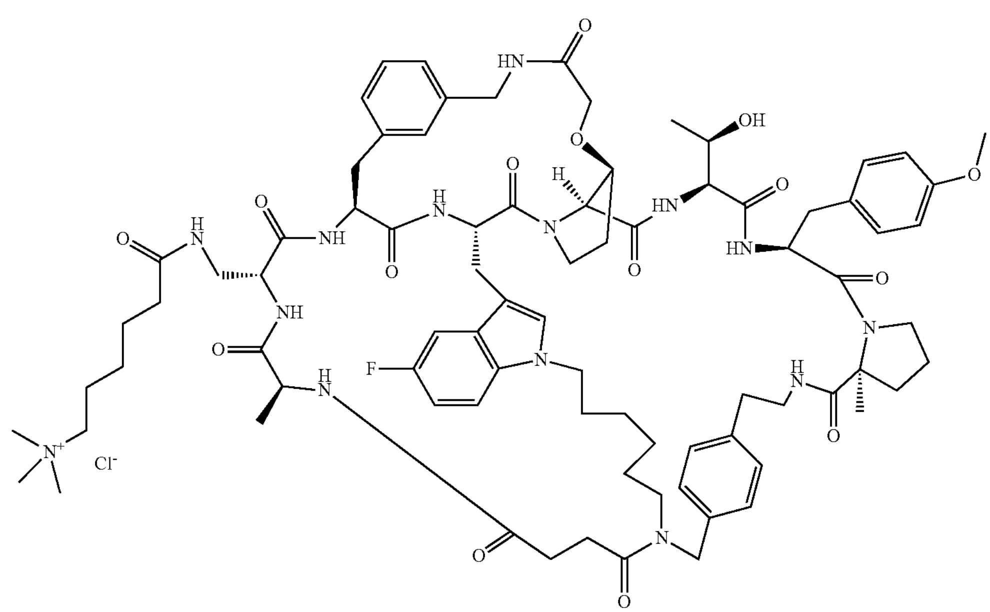 | 1550.6 |

TABLE 2-continued
| Ex-No/ | Structure | LC/MS: (M)+ |
|---|---|---|
| Ex-26 | 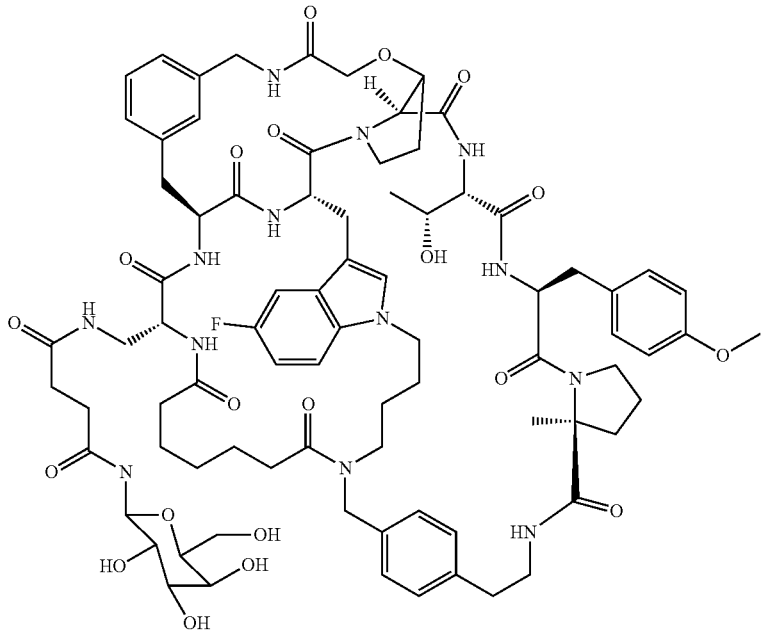 [SMILES: COc1ccc(C[C@@H]2NC(=O)[C@H]([C@@H](C)O)NC(=O)[C@@H]3C4CCN3C(=O)[C@@H]3Cc5cn(c6ccc(F)cc56)CCCCN(Cc5ccc(cc5)CCNC(=O)[C@]5(C)CCCN5C2=O)C(=O)CCCCCC(=O)N[C@H](CNC(=O)CCC(=O)NC2OC(CO)C(O)C(O)C2O)C(=O)N[C@@H](Cc2cccc(c2)CNC(=O)CO4)C(=O)N3)cc1] | 1599.19 |
| Ex-27 | 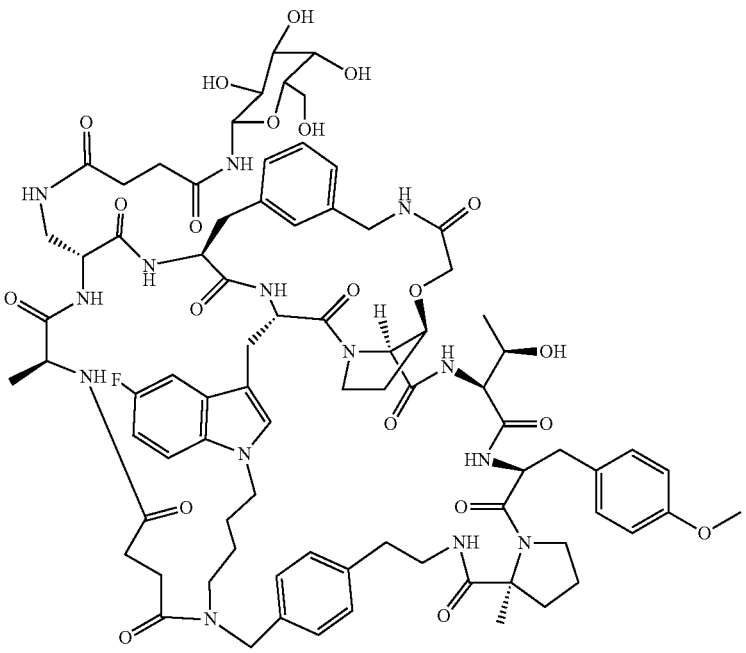 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCN(Cc5ccc(cc5)CCNC(=O)[C@]5(C)CCCN5C2=O)C(=O)CCC(=O)N[C@@H](C)C(=O)N[C@H](CNC(=O)CCC(=O)NC2OC(CO)C(O)C(O)C2O)C(=O)N[C@@H](Cc2cccc(c2)CNC(=O)CO4)C(=O)N3)cc1] | 1628.74 |

TABLE 2-continued

| Ex-No/ | Structure | LC/MS: (M)+ |
|---|---|---|
| Ex-28 TFA salt | 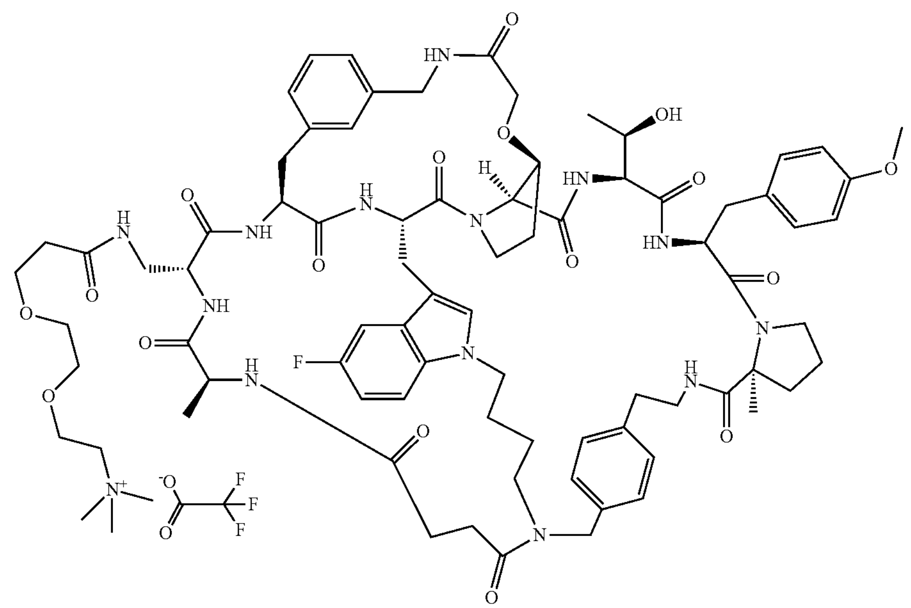 | 1568.63 |
| Ex-29 TFA salt | 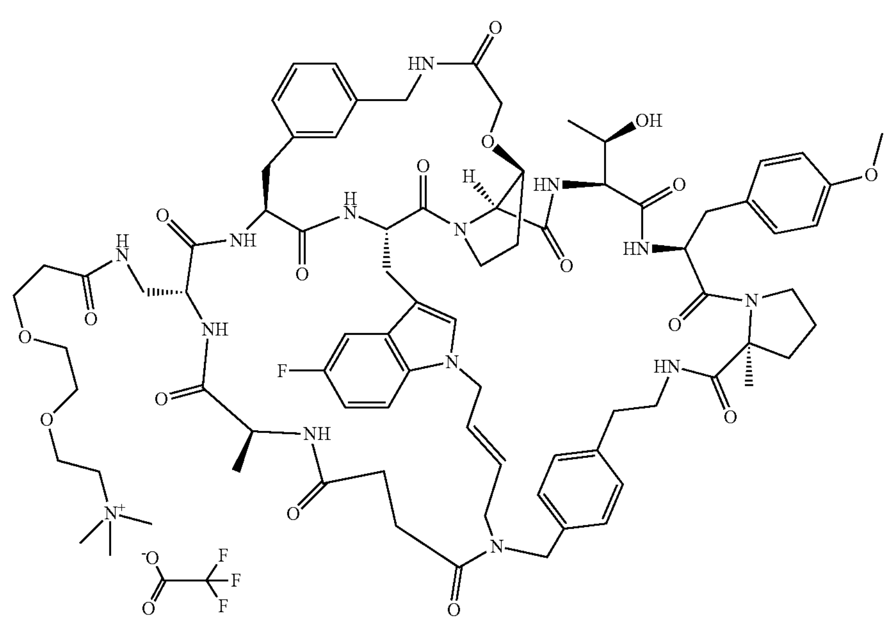 | 1566.60 |

| Ex-No/ | Structure | LC/MS: (M)+ |
|---|---|---|
| Ex-31 Cl salt | 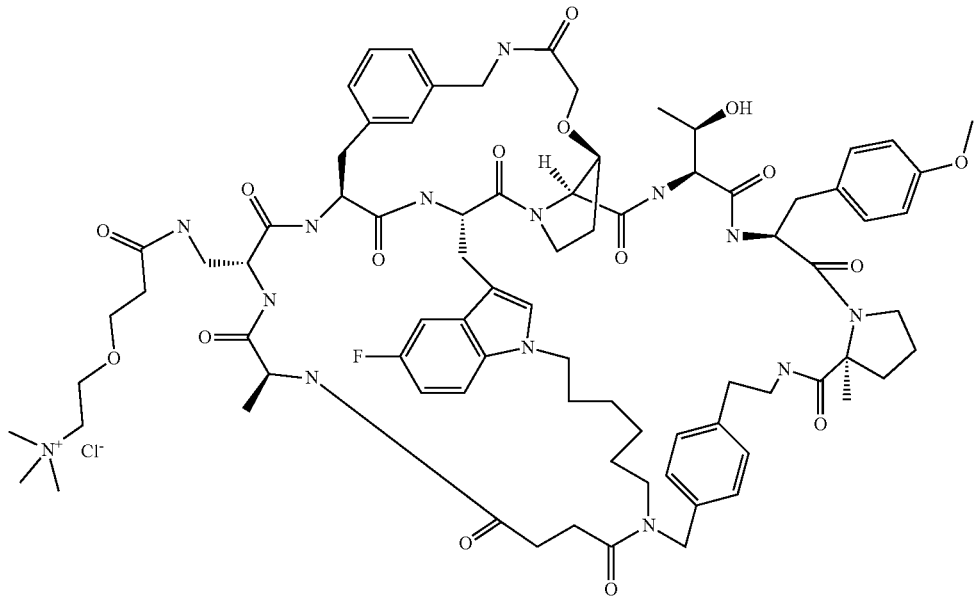 | 1552.85 |
| Ex-35 Cl salt | 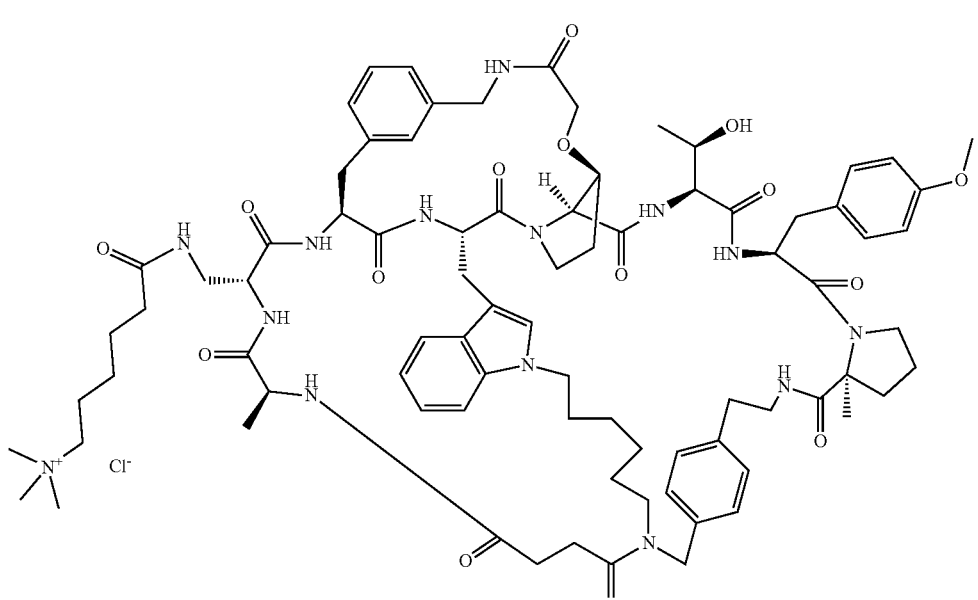 | 1533.40 |

211 212
TABLE 2-continued
| Ex-No/ | Structure | LC/MS: (M)+ |
|---|---|---|
| Ex-36 Cl salt | 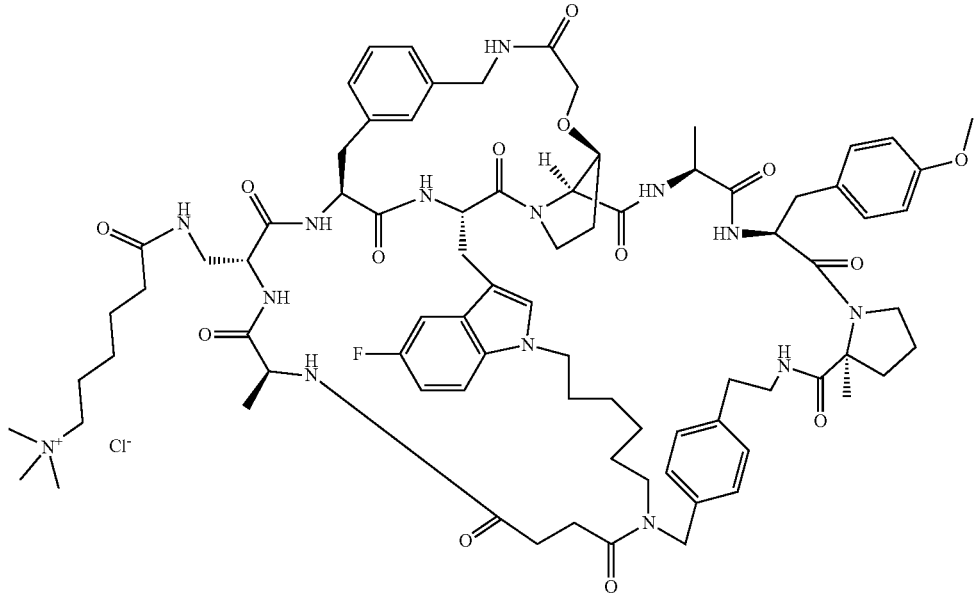 | 1520.60 |
| Ex-38 TFA salt | 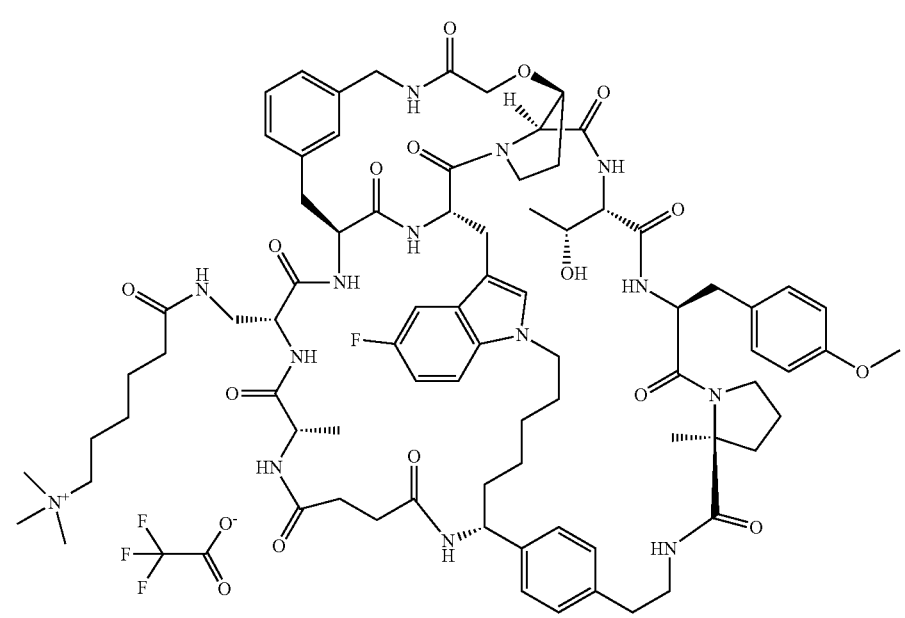 | 1536.21 |

TABLE 2-continued

| Ex-No/ | Structure | LC/MS: (M)+ |
|---|---|---|
| Ex-39 TFA salt | 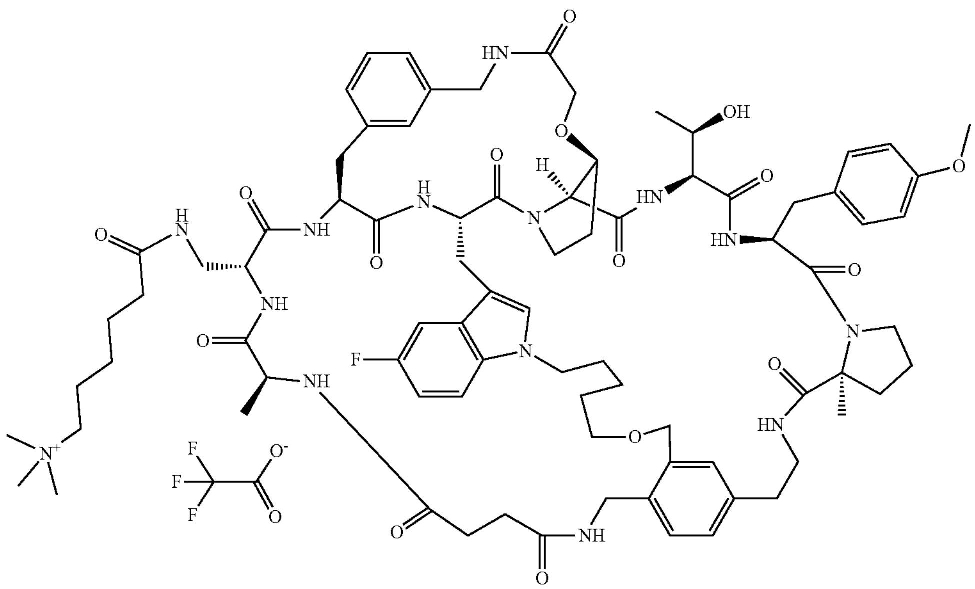 | 1551.21 |
| Ex-40 Cl salt | 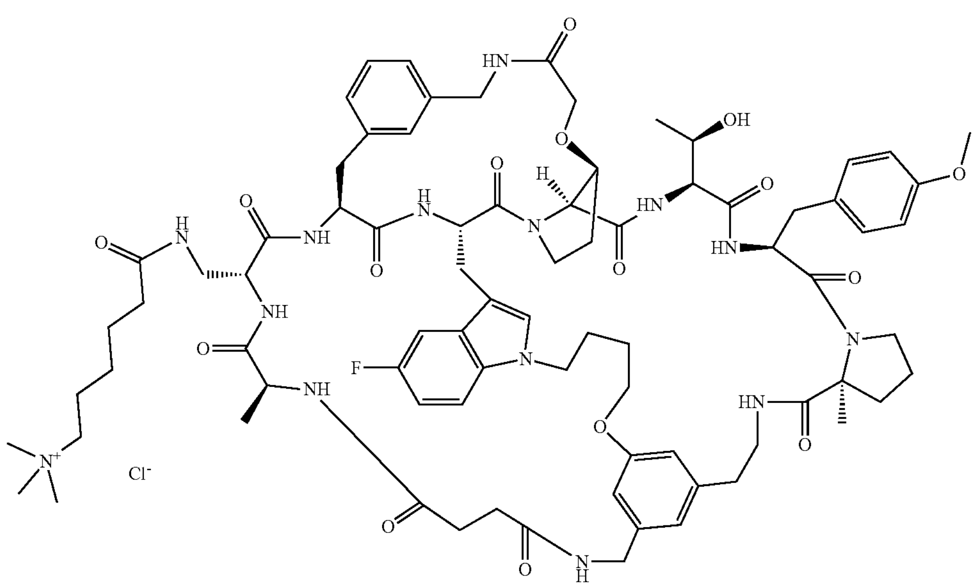 | 1538.60 |

TABLE 2-continued

| Ex-No/ | Structure | LC/MS: (M)+ |
|---|---|---|
| Ex-41 Cl salt | 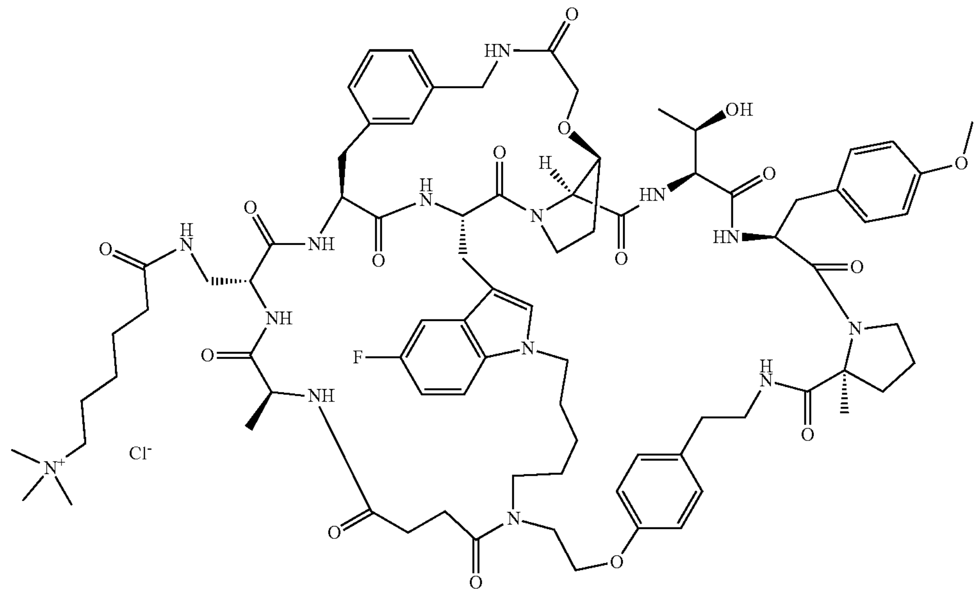 | 1566.40 |
| Ex-44 TFA salt | 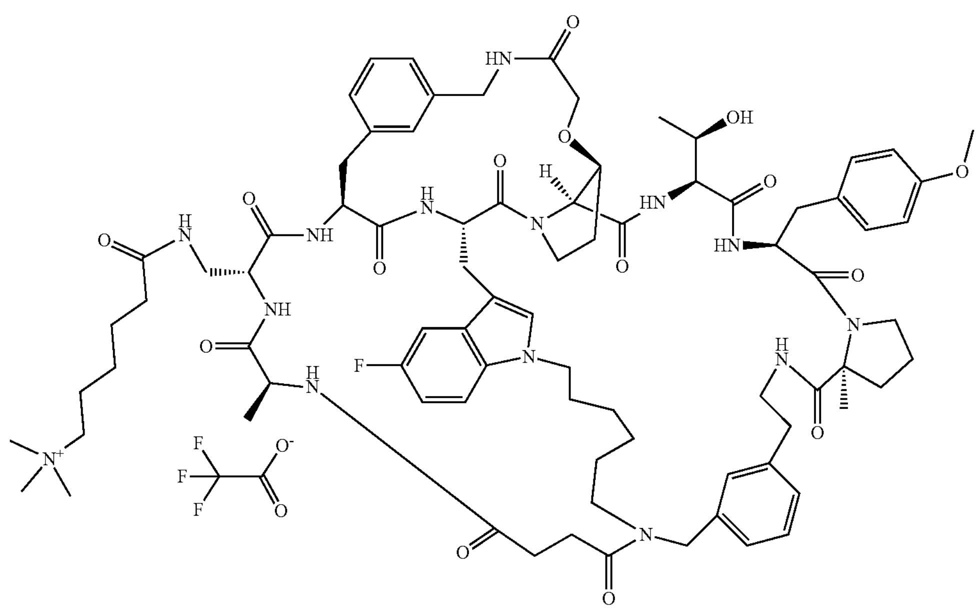 | 1549.49 |

TABLE 2-continued

| Ex-No/ | Structure | LC/MS: (M)+ |
|---|---|---|
| Ex-47 TFA salt | 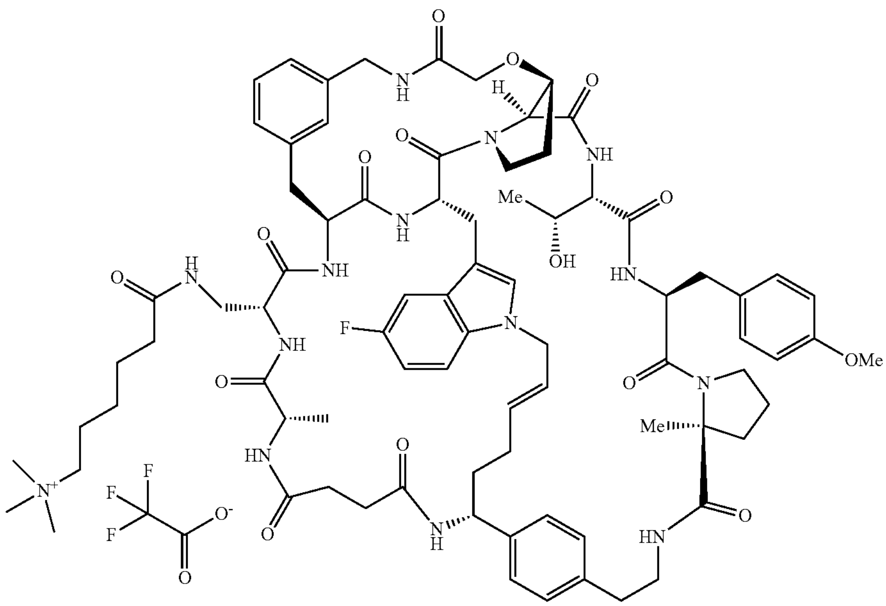 | 1534.27 |
| Ex-48 TFA salt | 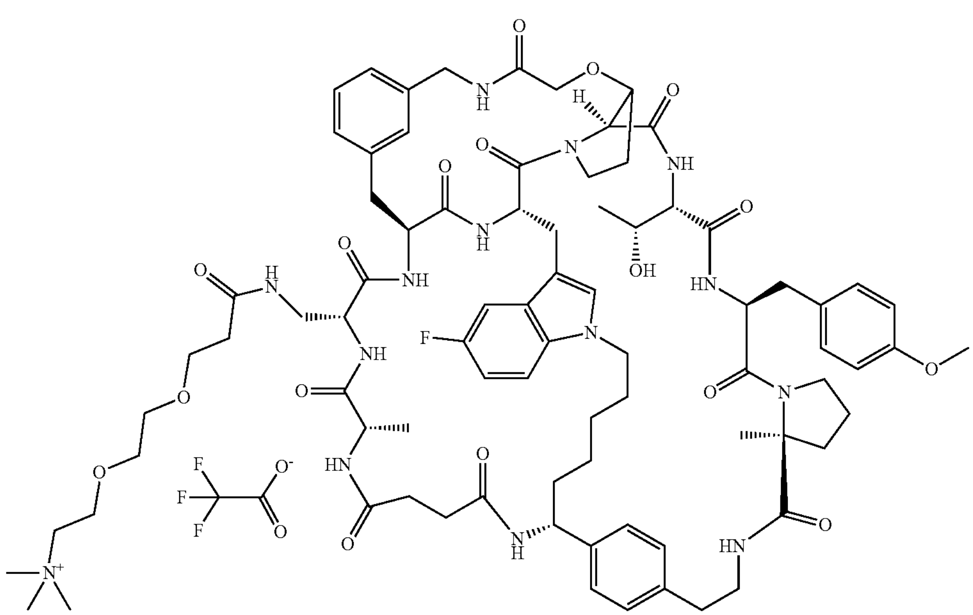 | 1582.20 |

TABLE 2-continued
| Ex-No/ | Structure | LC/MS: (M)+ |
|---|---|---|
| Ex-49 TFA salt | 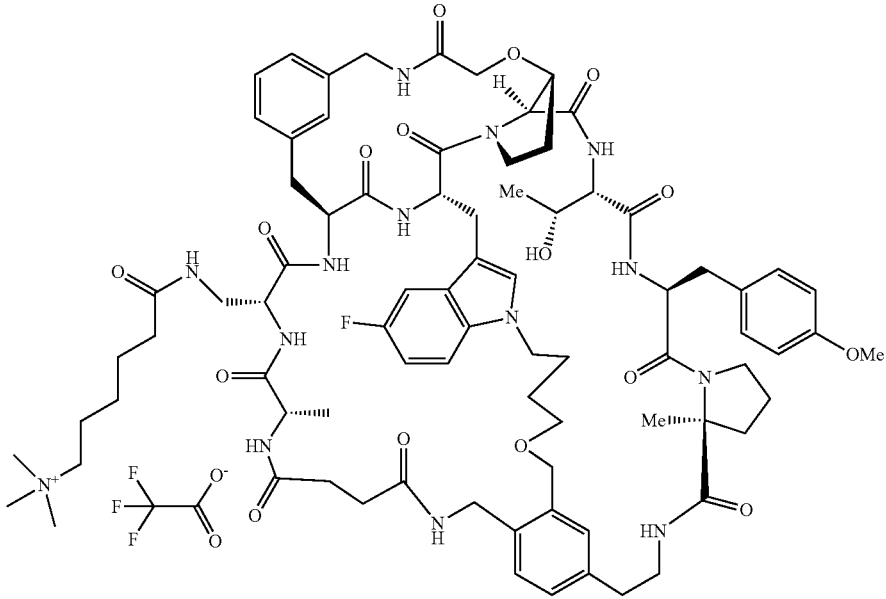 | 1551.21 |
| Ex-50 ACOH salt | 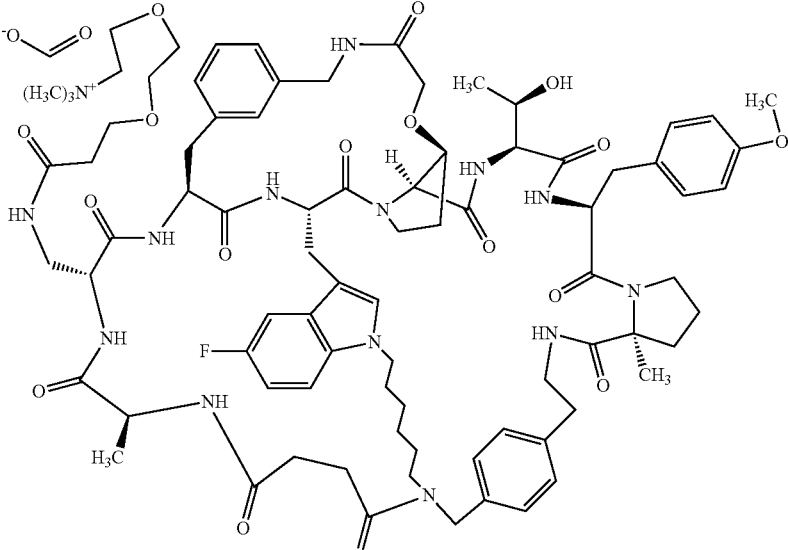 | 1596.3 |

TABLE 2-continued

| Ex-No/ | Structure | LC/MS: (M)+ |
|---|---|---|
| Ex-51 ACOH salt | 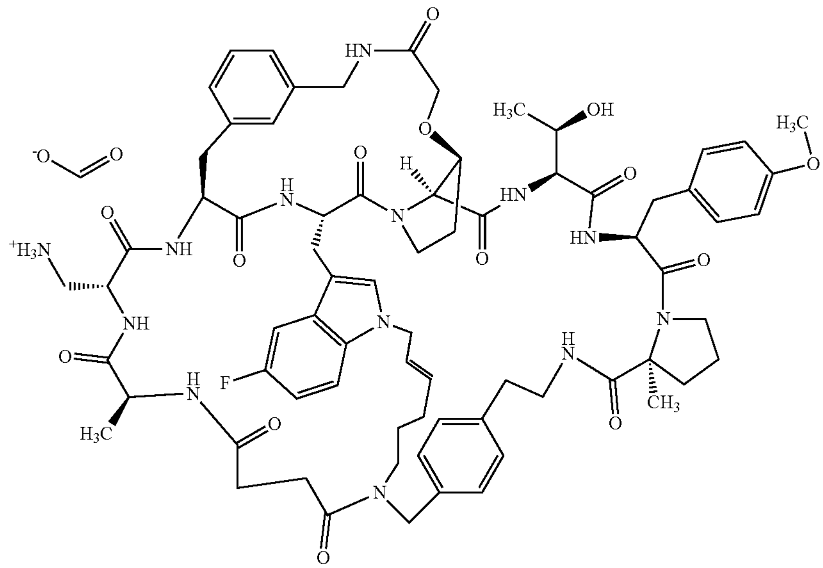 | 1392.0 |
| Ex-52 ACOH salt | 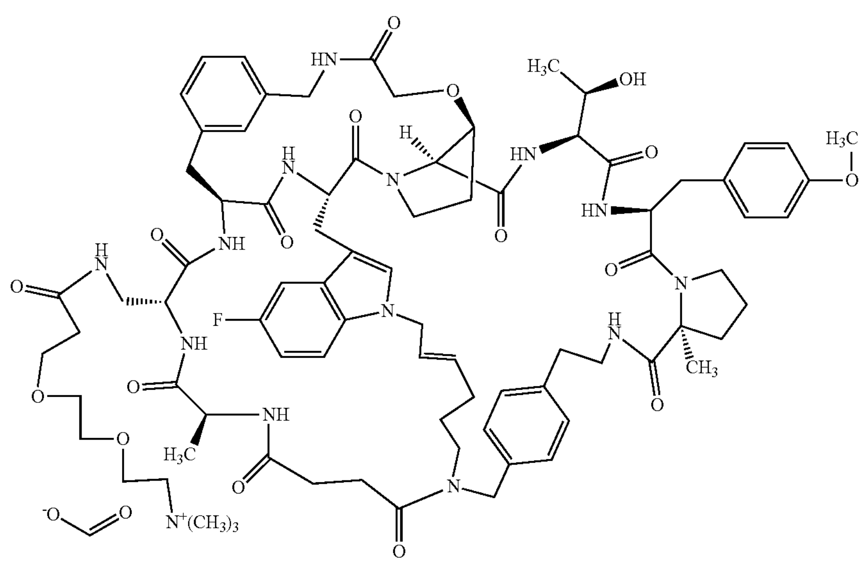 | 1593.8 |

TABLE 2-continued
| Ex-No/ | Structure | LC/MS: (M)+ |
|---|---|---|
| Ex-53 Cl salt | 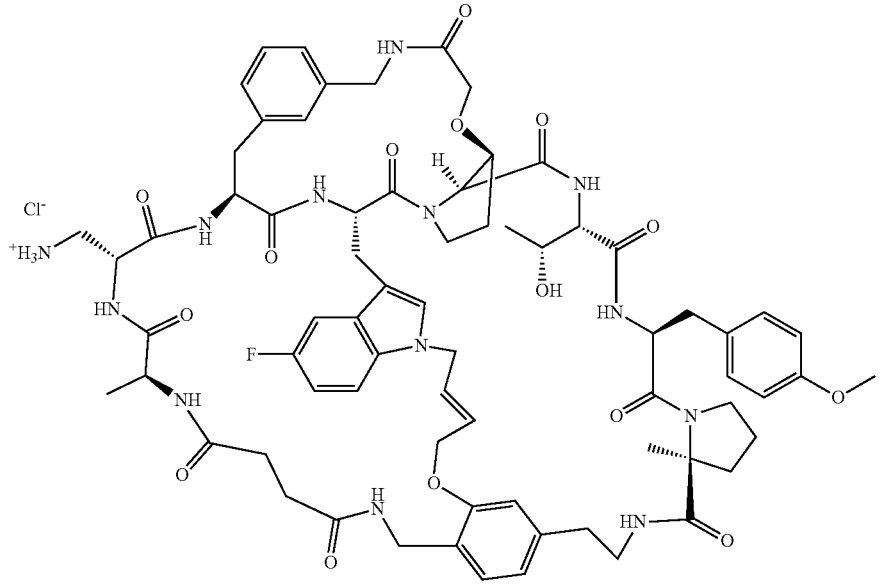 [SMILES: [Cl-] ; COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)C/C=C/COc5cc(ccc5CNC(=O)CCC(=O)N[C@@H](C)C(=O)N[C@H](C[NH3+])C(=O)N[C@@H](Cc5cccc(c5)CNC(=O)CO4)C(=O)N3)CCNC(=O)[C@]3(C)CCCN3C2=O)cc1] | 1381.33 |
| Ex-54 Cl salt | 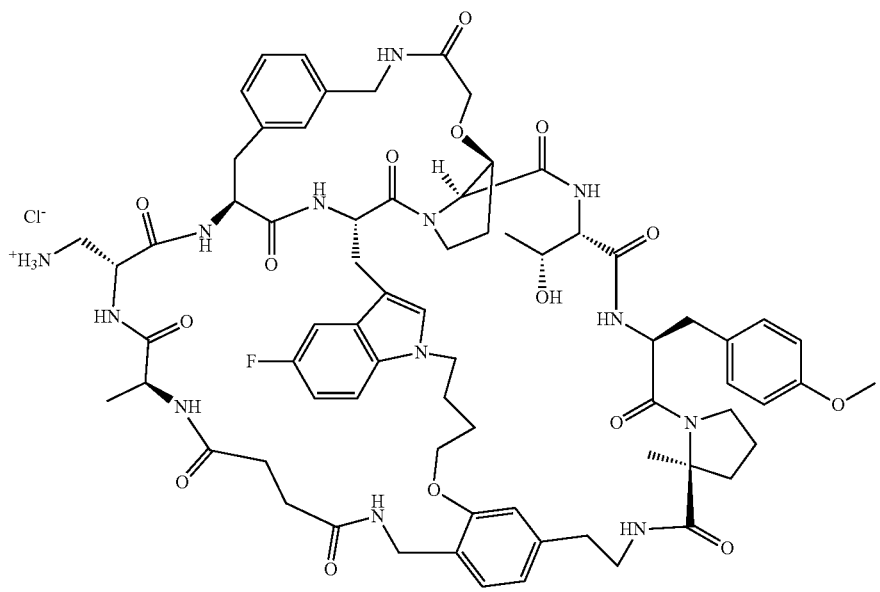 [SMILES: [Cl-] ; COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCOc5cc(ccc5CNC(=O)CCC(=O)N[C@@H](C)C(=O)N[C@H](C[NH3+])C(=O)N[C@@H](Cc5cccc(c5)CNC(=O)CO4)C(=O)N3)CCNC(=O)[C@]3(C)CCCN3C2=O)cc1] | 1383.44 |

TABLE 2-continued

| Ex-No/ | Structure | LC/MS: (M)+ |
|---|---|---|
| Ex-55 ACOH salt | 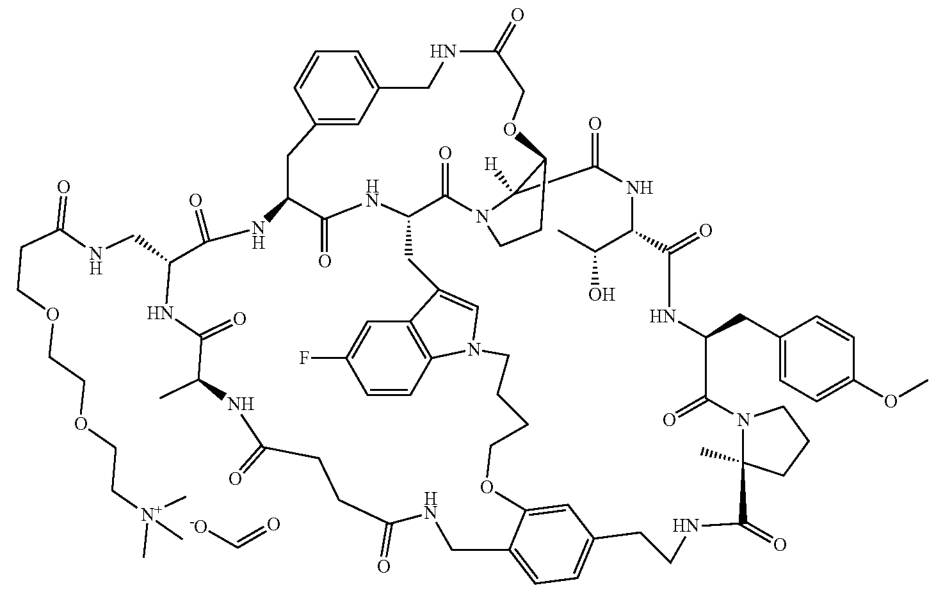 | 1583.69 |
| Ex-56 Cl salt | 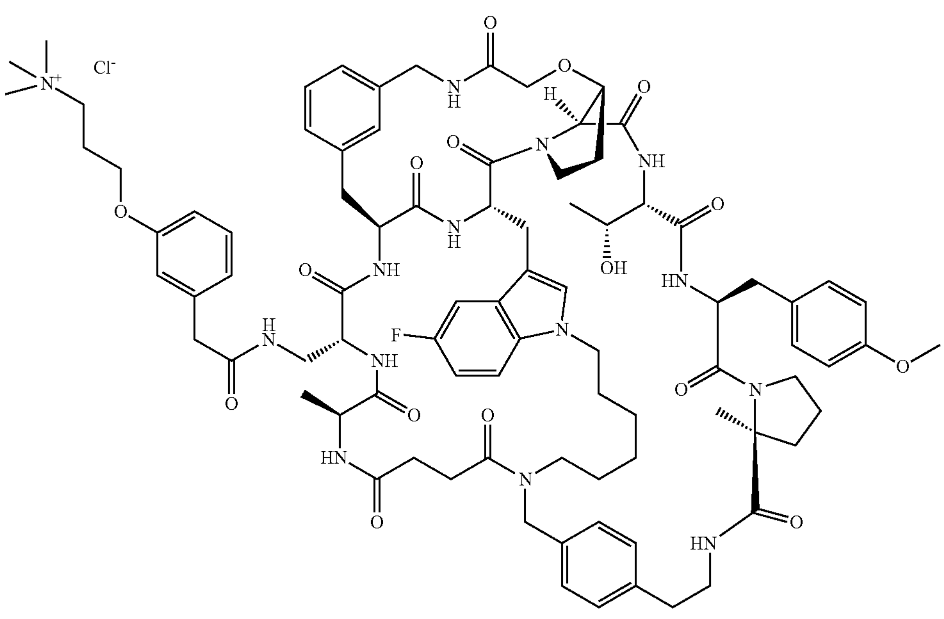 | 1628.95 |

TABLE 2-continued

| Ex-No/ | Structure | LC/MS: (M)+ |
|---|---|---|
| Ex-57 Cl salt | 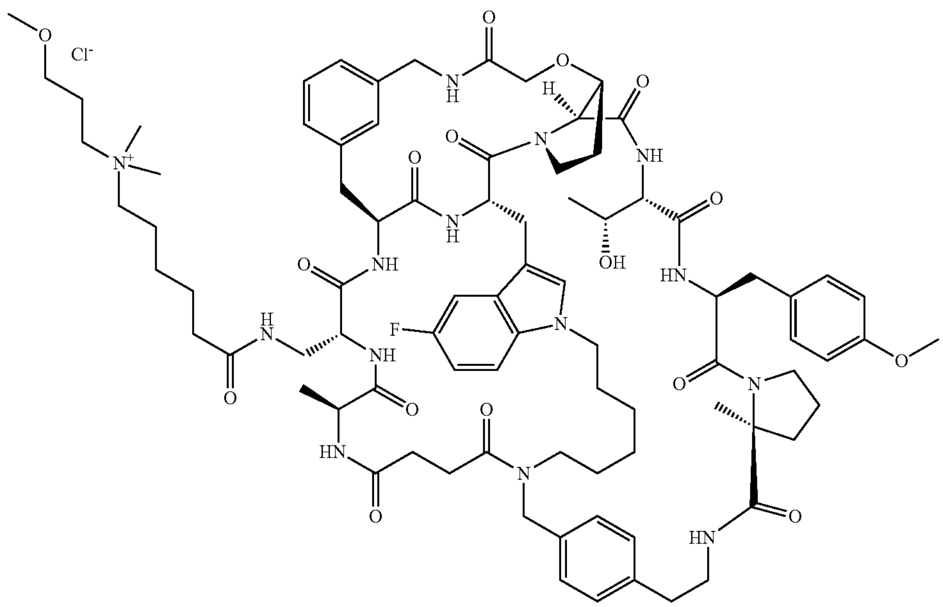 | 1608.95 |
| Ex-58 Cl salt | 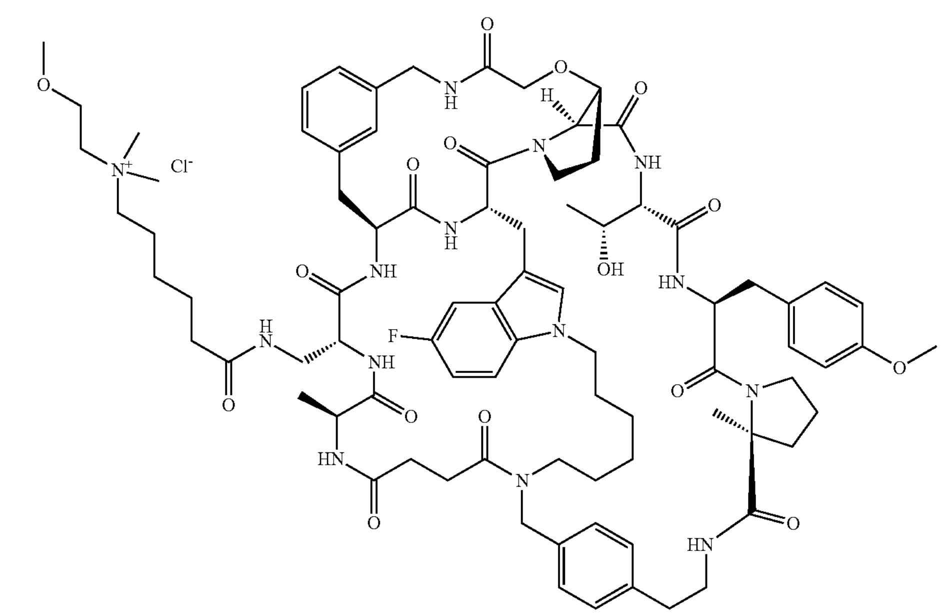 | 1594.93 |

TABLE 2-continued
| Ex-No/ | Structure | LC/MS: (M)+ |
|---|---|---|
| Ex-59 Cl salt | 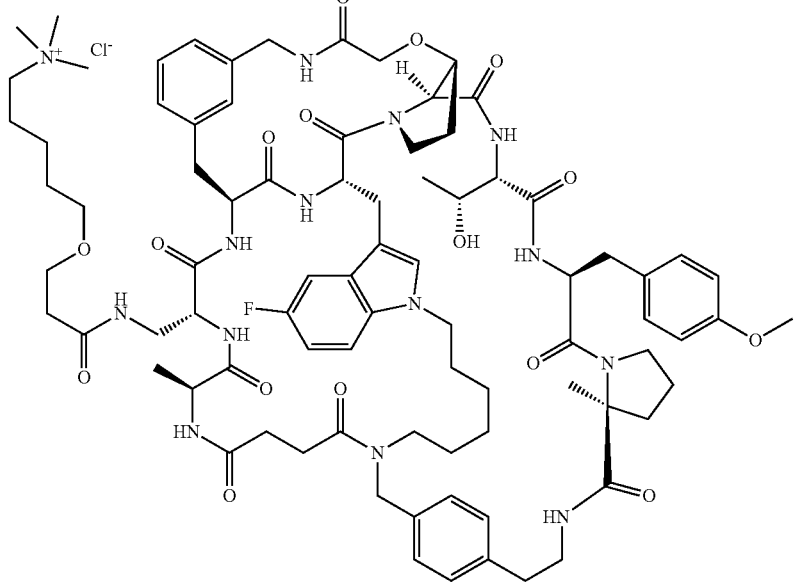 | 1593.7 |
| Ex-60 Cl salt | 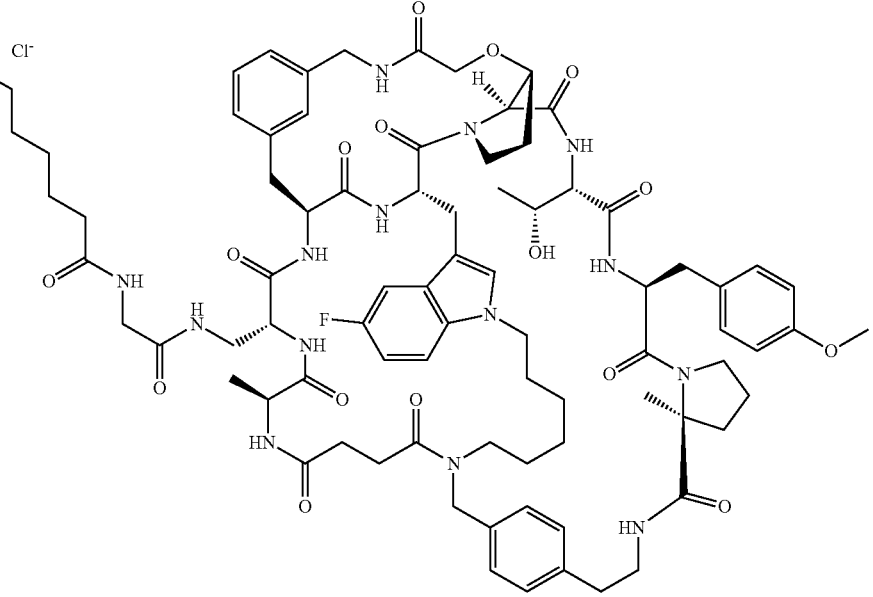 | 1607.4 |

TABLE 2-continued

| Ex-No/ | Structure | LC/MS: (M)+ |
|---|---|---|
| Ex-61 Cl salt | 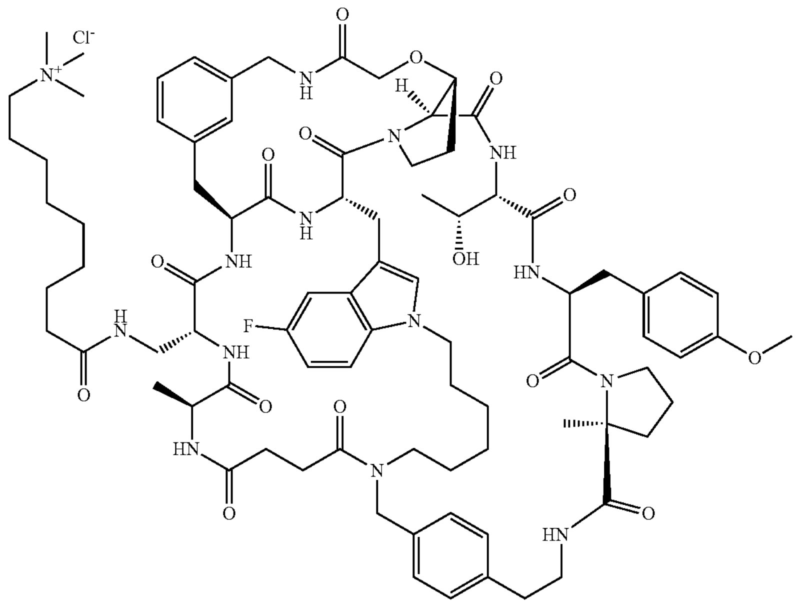 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCCCCCCC[N+](C)(C)C)C(=O)N[C@@H](Cc2cccc(c2)CNC(=O)CO4)C(=O)N3)cc1 ; [Cl-]] | 1592.4 |

Activity Determination

Selected compounds of the invention were subjected to one or more of the following procedures to assay their activity for antagonism of PCSK9 activity.

The following is a description of the assays used to determine activity of compounds of the invention, and any comparator compounds reported, toward PCSK9 antagonism. Biotinylated PCSK9 was obtained commercially.

LDLR TR-FRET

The PCSK9 TR-FRET assay measures the interaction between PCSK9 and LDLR. A solution containing 40 nM biotinylated PCSK9+10 nM Lance ULight Streptavidin is made in 50 mM HEPES pH 7.4, 0.15 M NaCl, 5 mM CaCl2, 0.01% BSA, and 0.01% Surfactant P20. A separate solution containing 40 nM rhLDLR-6xHis+10 nM Eu-W1024 anti-6xHis is made in the same buffer system. An Echo is used to transfer 0.750 ul of compound to an assay plate followed by the addition of 15 ul of PCSK9+Ulight and 15 ul of LDLR+Eu. The final assay volume is 30.750 ul containing 20 nM PCSK9, 5 nM Ulight, 20 nM LDLR, and 5 nM Eu. The reaction is incubated at room temperature for at least two hours prior to fluorescence measurements using an Envision Multilabel Reader. 1050 values are determined by fitting data to a sigmoidal dose-response curve using nonlinear regression. Counts (B-counts) of the europium-labeled LDLR are followed to observe if compounds are adversely affecting LDLR. A fall off of the B-counts is likely indicates a false positive of inhibition.

Alexa FRET Standard TR-FRET

The PCSK9 Alexa FRET Standard assay measures the interaction between PCSK9 and an AlexaFluor647 (AF) tagged cyclic peptide, Reagent A ($K_D$=83 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 40 nM of the AlexaFluor tagged cyclic peptide is made in the same buffer system. An Echo is used to transfer 0.750 ul of compound to an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 20 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the IC50 and the $K_D$ of AF cyclic peptide. Counts (B-counts) of the europium-labeled PCSK9 are followed to observe if compounds are adversely PCSK9. A fall off of the B-counts likely indicates a false positive of inhibition. Data from this procedure is reported as "A='numerical value' (nanomolar)"

Reagent A was prepared in accordance with the following method:

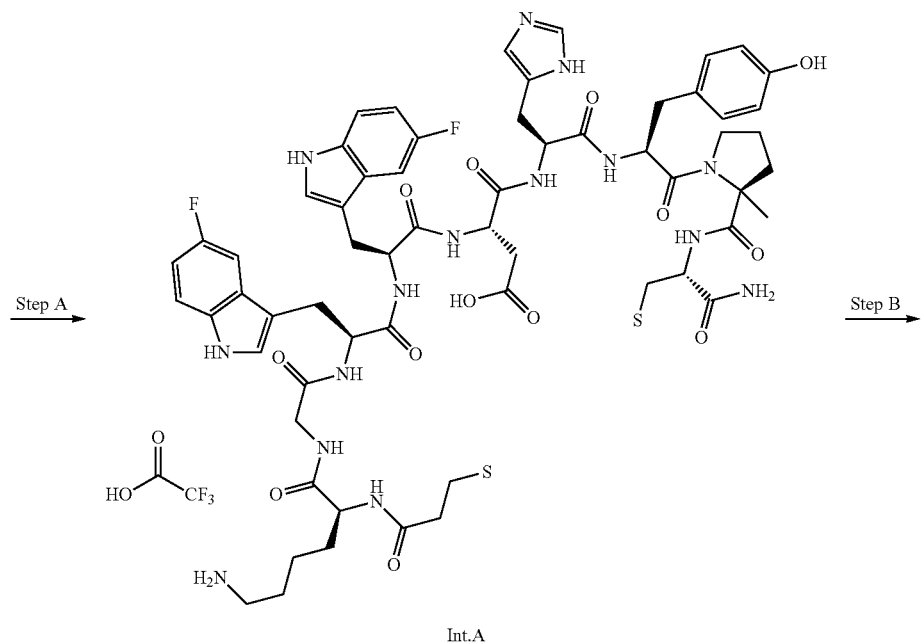 [SMILES: O=C(O)C(F)(F)F ; C[C@@]1(C(=O)N[C@@H](CS)C(N)=O)CCCN1C(=O)[C@H](Cc1ccc(O)cc1)NC(=O)[C@H](Cc1cnc[nH]1)NC(=O)[C@H](CC(=O)O)NC(=O)[C@H](Cc1c[nH]c2ccc(F)cc12)NC(=O)[C@H](Cc1c[nH]c2ccc(F)cc12)NC(=O)CNC(=O)[C@H](CCCCN)NC(=O)CCS]
Step A →
Int.A
Step B →
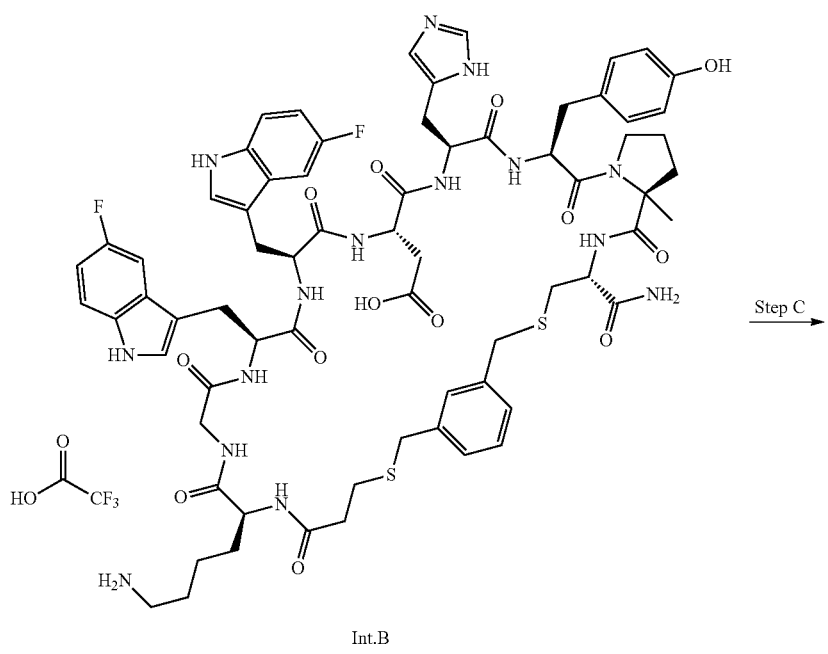
Int.B
Step C →

-continued

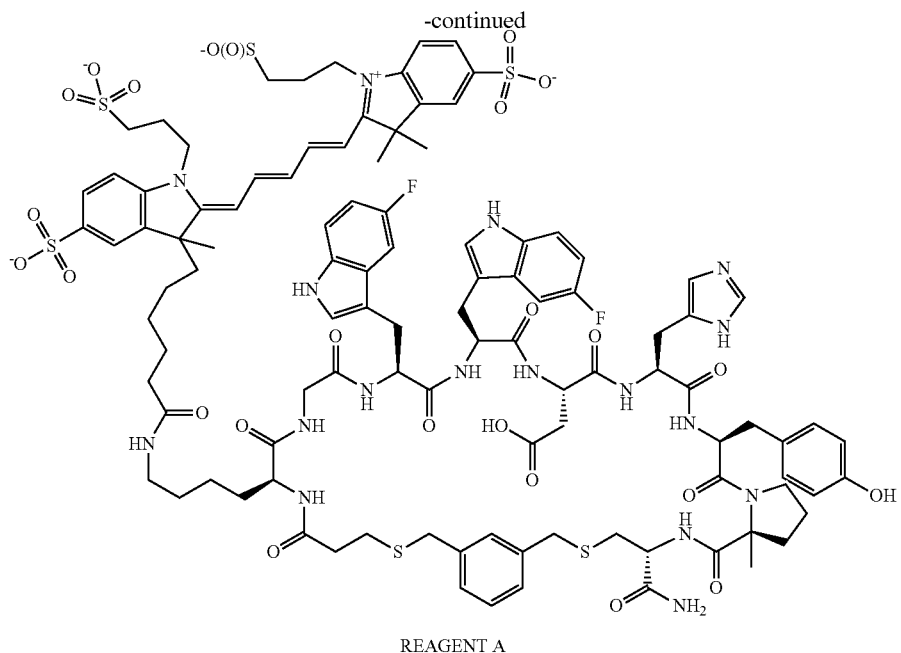

REAGENT A

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4 eq of Fmoc protected amino acid 0.2M in DMF, 4 eq of 0.5M HATU in DMF, 4 eq of 2M DIPEA (double coupling for Tyr). Fmoc deprotection cycles were performed using 20% (V/V) piperidine in DMF.

The sequence of Fmoc protected amino acids and building blocks used are:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (((9H-fluoren-9-yl)methoxy)carbonyl)-L-tyrosine
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)glycine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (399 mg), which was used as crude in the next step. LCMS anal. calcd. C61H75F2N15O13S2: 1328.48, found: 1328.2 (M+1)$^+$ Step B—Synthesis of Intermediate Compound Int-B: As Described for Reagent B Purified by RP-HPLC (Waters Deltapak C4, double cartridge, 40×100 mm, 15□m, 300 A; 15% to 35% ACN/water+0.1% TFA modifier over 20 min). Collected fractions lyophilized to afford 35 mg of Intermediate Compound Int-B. LCMS anal. calcd. for C69H81F2N15O13S2: 1430.62; found: 1430.9 (M+1)$^+$.

Step C—Synthesis of Compound Reagent A: As Described for Reagent B

LCMS anal. calcd. for C105H122F2N17O26S6$^{3-}$: 2268.58; 1135.8 (M+2)$^{2+}$

Alexa FRET Plus TR-FRET

The PCSK9 Alexa FRET Plus assay measures the interaction between PCSK9 and an AlexaFluor647 (AF) tagged cyclic peptide, Reagent B (K$_D$=35 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 1920 nM of the AlexaFluor tagged cyclic peptide is made in the same buffer system. An Echo is used to transfer 0.075 ul of compound plus 0.675 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the IC50 and the K$_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "P='numerical value' (nanomolar)"

Reagent B was prepared by the following procedure.
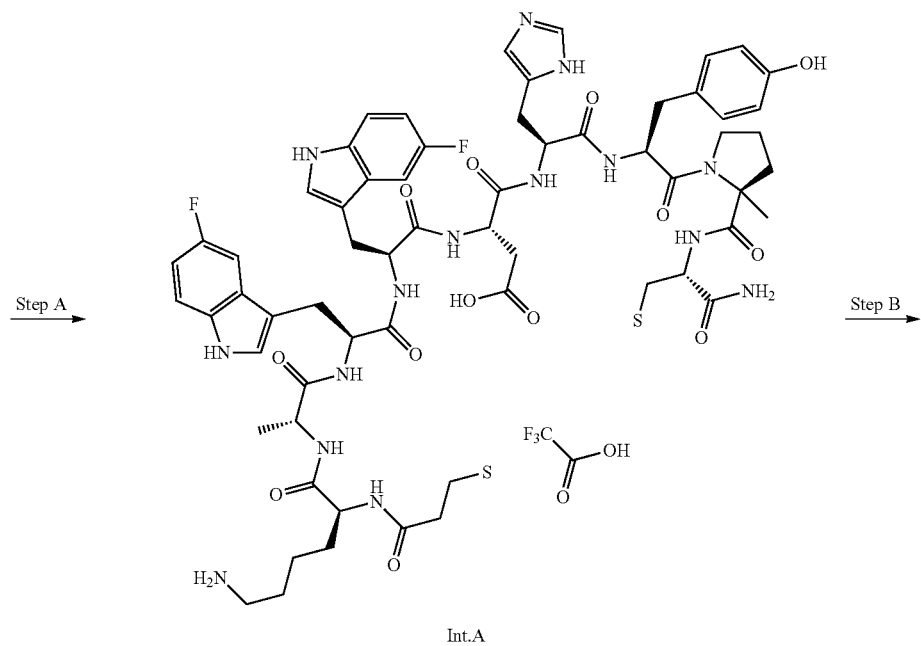 [SMILES: C[C@@H](NC(=O)[C@H](CCCCN)NC(=O)CCS)C(=O)N[C@@H](Cc1c[nH]c2ccc(F)cc12)C(=O)N[C@@H](Cc1c[nH]c2ccc(F)cc12)C(=O)N[C@@H](CC(=O)O)C(=O)N[C@@H](Cc1cnc[nH]1)C(=O)N[C@@H](Cc1ccc(O)cc1)C(=O)N1CCC[C@@]1(C)C(=O)N[C@@H](CS)C(N)=O ; O=C(O)C(F)(F)F]
Int.A
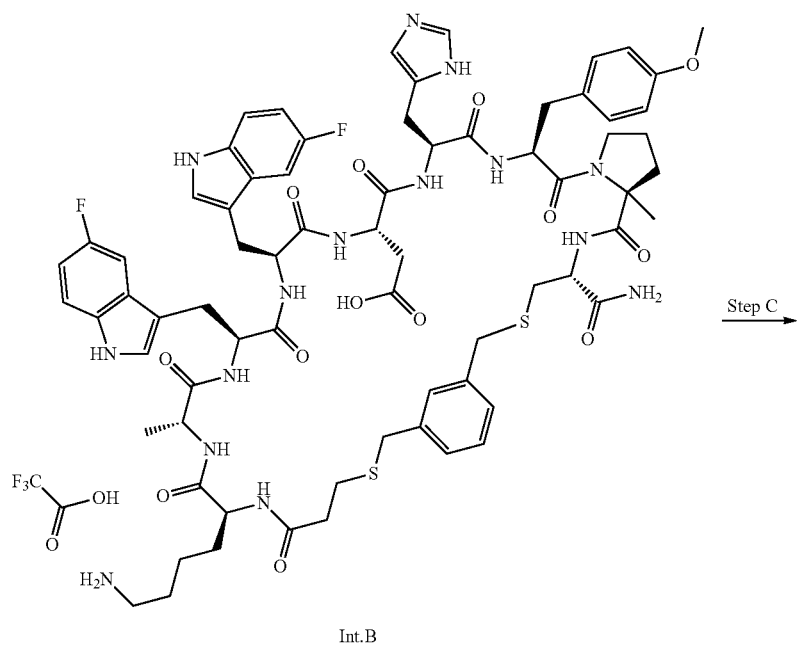
Int.B -continued

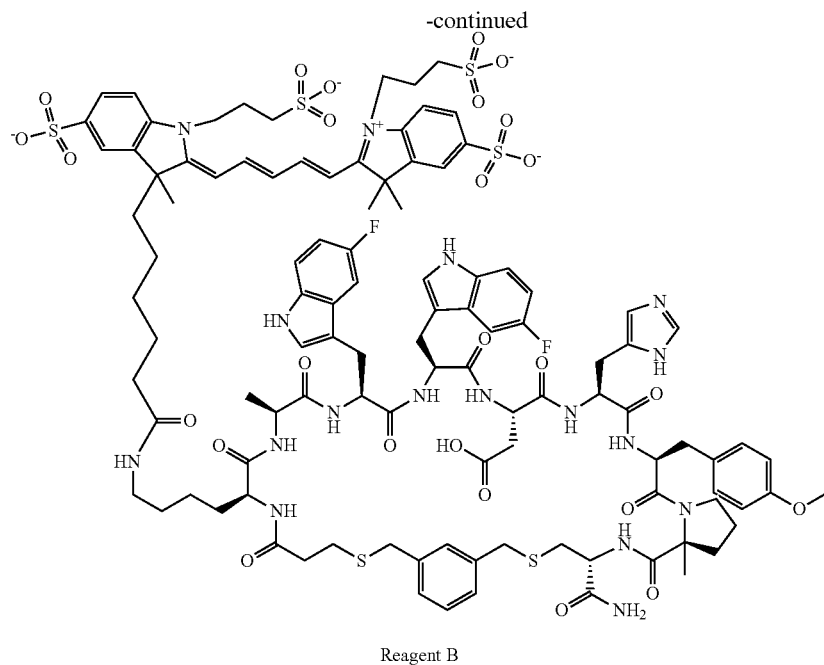

Reagent B

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4 eq of Fmoc protected amino acid 0.2M in DMF, 4 eq of 1M Oxyme in DMF, 4 eq of 0.5M N,N-diisopropylcarbodiimide (DIC) (double coupling for Y01). Fmoc deprotection cycles were performed using 20% (V/V) piperidine in DMF.

The sequence of Fmoc protected amino acids and building blocks used are:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)-D-alanine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (300 mg), which was used as crude in the next step. LCMS anal. calcd. C63H79F2N15O13S2: 1356.53, found: 1356.9 (M+1)$^+$ Step B—Synthesis of Intermediate Compound Int-B Crude Int-A (0.22 mmol) was redissolved in 24 ml of DMF. 6 ml of 1M aqueous solution of sodium bicarbonate was added to raise the pH to 7. Then 0.26 mmol of 1,3-bis(bromomethyl)benzene (0.1 M in DMF) were added dropwise. Reaction was left under stirring at room temperature for 20 min, quenched with TFA (pH to 3-4) and then concentrated in vacuo to provide crude Int-B, which was purified by RP-HPLC (Waters XBridge, C18, 50×150 mm, 5 µm, 130 Å; 25% to 40% ACN/water+0.1% TFA modifier over 20 min). Collected fractions were lyophilized to afford 35 mg of Intermediate Compound Int-B. LCMS anal. calcd. for C71H85F2N15O13S2: 1458.67; found: 1458.8 (M+1)$^+$ Step C—Synthesis of Compound Reagent B Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO were added. 20 uL of dry DIPEA were added. Reaction was left under stirring at room temperature for 12 h under Nitrogen atmosphere in the dark. Quenched with TFA (pH to 3-4) and purified by R-HPLC (Dr Maish, Reprosil Gold C18, 250×20 mm, 120 Å, 10 µm; 20% to 35% of 0.1% TFA in ACN/0.1% TFA in H$_2$O, over 20 min, then 35% to 40% over 5 min at 20 mL/min flow rate). Collected fractions were lyophilized to afford 16.1 mg of Compound Reagent B. LCMS anal. for C107H126F2N17O26S6$^{3-}$: 2296.64, found: 1150.6 (M+2)$^{2+}$ Activity data obtained by one or both of the above-described procedures is reported for selected example compounds of the invention in the following format:
Example No.: A (standard TR Fret)='numerical value'; P (Alexa Fret plus standard TR Fret)='numerical value'/, note that all values reported are nanomolar.
Alexa FRET Ultra TR-FRET The PCSK9 Alexa FRET Ultra assay measures the interaction between PCSK9 and an AlexaFluor647 (AF) tagged cyclic peptide, Reagent B (K$_D$=0.99 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2, 0.01% BSA, and 0.01% Surfactant P20. A separate solution containing 1920 nM of the AlexaFluor tagged cyclic peptide is made in the same buffer system. An Echo is used to transfer 0.015 ul of compound plus 0.735 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the IC50 and the $K_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "Ki Ultra='numerical value' (data reported is nanomolar)"

The following compounds were assessed, as shown in Table 2, using the protocol described above with the results shown:

Ex-01 Ki Plus=<0.00558, Ki Ultra=0.0046/Ex-02 Ki Plus=0.00558, Ki Ultra=0.005933/Ex-03 Ki Plus=0.02535, Ki Ultra=0.06803/Ex-04 Ki Plus≤0.00558, Ki Ultra=0.004711/Ex-05 Ki Plus=0.009621, Ki Ultra=0.03296/Ex-06 Ki Plus=0.00568, Ki Ultra=0.003424/Ex-07 Ki Plus=0.05914, Ki Ultra=0.06753/Ex-08 Ki Plus=0.01574, Ki Ultra=0.06832/Ex-09 Ki Plus=0.09189, Ki Ultra=0.247/Ex-10 Ki Plus=0.005743, Ki Ultra=0.02489/Ex-11 Ki Plus=0.04334, Ki Ultra=0.2067/Ex-12 Ki Plus=0.01448, Ki Ultra=0.02247/Ex-13 Ki Plus=0.1454, Ki Ultra=0.4772/Ex-14 Ki Plus=0.01605, Ki Ultra=0.02099/Ex-15 Ki Plus=0.1027, Ki Ultra=0.2601/Ex-16 Ki Plus=0.01423, Ki Ultra=0.05141/Ex-17 Ki Plus 0.00558, Ki Ultra=0.0028/Ex-18 Ki Plus=0.03356, Ki Ultra=0.1183/Ex-19 Ki Plus=0.01662, Ki Ultra=0.01204/Ex-20 Ki Plus=0.01303, Ki Ultra=0.01711/Ex-21 Ki Plus=0.005692, Ki Ultra=0.001264/Ex-22 Ki Plus=0.00926, Ki Ultra=0.01519/Ex-23 Ki Plus=0.00938, Ki Ultra=0.00239/Ex-24 Ki Plus=0.00812, Ki Ultra=0.00767/Ex-25 Ki Plus=0.01127, Ki Ultra=0.00463/Ex-26 Ki Plus≤0.00558, Ki Ultra=0.002754/Ex-27 Ki Plus≤0.00558, Ki Ultra=0.00301/Ex-28 Ki Plus≤0.00558, Ki Ultra=0.00078/Ex-29 Ki Plus=0.00981, Ki Ultra=0.00614/Ex-31 Ki Plus<0.00558, Ki Ultra=0.00074/Ex-35 Ki Plus=0.04652, Ki Ultra=0.08434/Ex-36 Ki Plus=0.00762, Ki Ultra=0.00507/Ex-38 Ki Plus=0.00904, Ki Ultra=0.01416/Ex-39 Ki Plus=0.00716, Ki Ultra=0.00414/Ex-40 Ki Plus=0.30800, Ki Ultra=0.86010/Ex-41 Ki Plus=0.00697, Ki Ultra=0.00628/Ex-44 Ki Plus=0.01445, Ki Ultra=0.02194/Ex-47 Ki Plus=0.01474, Ki Ultra=0.01193/Ex-48 Ki Plus=0.01169, Ki Ultra=0.01545/Ex-49 Ki Plus=0.00716, Ki Ultra=0.00414/Ex-50 Ki Standard<1.26, Ki Plus=0.01052, Ki Ultra=0.00443/Ex-51 Ki Standard<1.26, Ki Plus<0.00558, Ki Ultra=0.00597/Ex-52 Ki Standard<1.26, Ki Plus<0.00558, Ki Ultra=0.00359/Ex-53 Ki Standard<1.26, Ki Plus=0.09629, Ki Ultra=0.21500/Ex-54 Ki Standard<1.26, Ki Plus=0.36720, Ki Ultra=0.48390/Ex-55 Ki Standard<1.26, Ki Plus=0.07240, Ki Ultra=0.23800/Ex-56 Ki Standard<1.257, Ki Plus=0.02237, Ki Ultra=0.00481/Ex-57 Ki Standard<1.257, Ki Plus<0.00558, Ki Ultra=0.00162/Ex-58 Ki Standard<1.257, Ki Plus=0.00773, Ki Ultra=0.00196/Ex-59 Ki Plus=0.00788, Ki Ultra=0.004959/Ex-60 Ki Plus=0.006515, Ki Ultra=0.005312/Ex-61 Ki Plus=0.00747, Ki Ultra=0.006543.

What is claimed is:
1. A compound of Formula I:

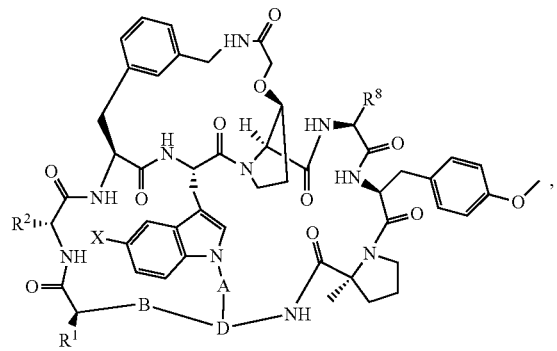

Formula I wherein:
X is H, F, Cl or Br;
$R^1$ is selected from:
(a) —H; or
(b) —(CH$_2$)$_z$—R$^{14A}$, wherein: z is 1-6, and R$^{14A}$ is:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$; or —N$^+$(CH$_3$)$_3$;
  (vi) —NH—C(O)—[(CH$_2$)$_{y12}$—O—]$_2$—(CH$_2$)$_{y13}$R$^{14B}$ wherein:
    y12 and y13 are not both 2 and are independently 2 to 4; and
    R$^{14B}$ is: —NH$_2$; —N$^+$H$_3$; —N(CH$_3$)$_2$; or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{3-4}$—N$^+$(CH$_3$)$_3$; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$;
    (aii) —N$^+$(CH$_3$)$_3$; or
    (aiii) a moiety of the formula:

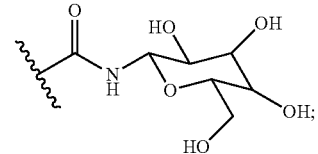 [SMILES: *C(=O)NC1OC(CO)C(O)C(O)C1O]

$R^2$ is selected from:
(a) —H; and
(b) —$(CH_2)_z$—$R^{14A}$, wherein: z is 1-6, and $R^{14A}$ is selected from:
   (i) —H;
   (ii) —$NH_2$;
   (iii) —$N^+H_3$;
   (iv) —$N^+(H_3C)_3$;
   (v) —NH—C(O)—$[(CH_2)_2$—O—$]_2$—$(CH_2)_2R^{14B}$ wherein $R^{14B}$ is: —$NH_2$; —$N^+H_3$; —$N(CH_3)_2$; or —$N^+(CH_3)_3$;
   (vi) —NH—C(O)—$[(CH_2)_{y12}$—O—$]_2$—$(CH_2)_{y13}R^{14B}$ wherein:
      y12 and y13 are not both 2 and are independently 2 to 4; and
      $R^{14B}$ is: —$NH_2$; —$N^+H_3$; —$N(CH_3)_2$, or —$N^+(CH_3)_3$;
   (vii) —NH—C(O)—$(CH_2)_yR^{14C}$, wherein, y=1 to 6 and $R^{14C}$ is —O—$(CH_2)_{3-4}$—$N^+(CH_3)_3$; and
   (viii) —NH—C(O)—$(CH_2)_yR^{14C}$, wherein, y=1 to 6 and $R^{14C}$ is:
      (ai) —O—$(CH_2)_2$—$N^+(CH_3)_3$;
      (aii) —$N^+(CH_3)_2R^{14ca}$, wherein $R^{14ca}$ is —$CH_3$ or —$(CH_2)_{1-4}$—$OCH_3$;
      (aiii) a moiety of the formula:

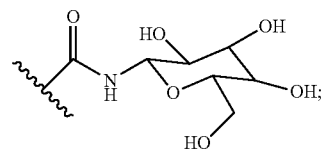 [SMILES: *C(=O)NC1OC(CO)C(O)C(O)C1O]

or
      (aiv) a moiety of the formula:

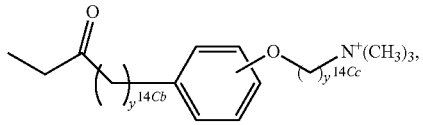

where $y^{14Cb}$ and $y^{14Cc}$ are 1 to 4; or
$R^1$ and $R^2$ may be bonded together to form a moiety of the formula:

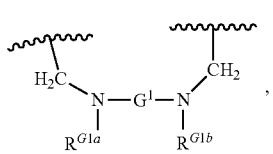

wherein:
$G^1$, $R^{G1a}$ and $R^{G1b}$ are defined as follows:
(a) $G^1$ is a linker moiety of the formula:

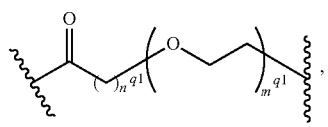

wherein $n^{q1}$ is 1 to 6, $m^{q1}$ is 0, 1 or 2 and together the value of $n^{q1}$ and $m^{q1}$ are selected such that the length of the linker moiety they define does not exceed a total of 8 carbon and/or oxygen atoms comprising the chain including the carbon atom in the chain that forms the carbonyl moiety;
$R^{G1a}$ is selected from: (i) —H; and (ii) alkyl of up to 4 carbon atoms; and
$R^{G1b}$ is selected from:
   (i) a moiety of the formula:

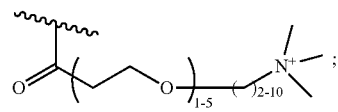

and
   (ii) a moiety of the formula:

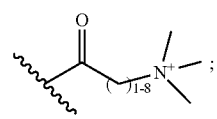

or
(b) $G^1$ is a linker moiety of the formula:

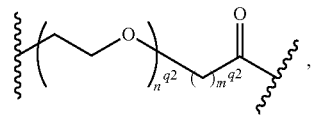

wherein $n^{q2}$ is 0, 1 or 2, $m^{q2}$ is 1 to 6, and together the value of $n^{q2}$ and $m^{q2}$ are selected such that the length of the linker moiety they define does not exceed a total of 8 carbon and/or oxygen atoms comprising the chain including the carbon atom in the chain that forms the carbonyl moiety;
$R^{G1a}$ is selected from:
   (i) a moiety of the formula:

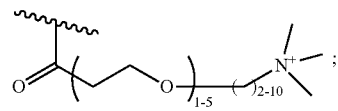

and
   (ii) a moiety of the formula:

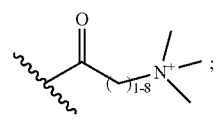

and
$R^{G1b}$ is selected from: (i) —H; and (ii) alkyl of up to 4 carbon atoms;

$R^8$ is —$CH_3$ or a moiety of the formula:

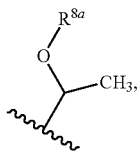

wherein $R^{8a}$ is —H, or a linear, branched or cyclic alkyl of up to four carbon atoms;

A is selected from:

(a) a moiety of the formula:

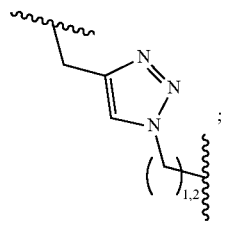

(b) —$CH_2$—$(CH_2)_y$—$CH_2$—, wherein y is 1 to 6;

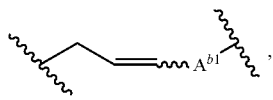

(c) a moiety of the formula:
wherein $A^{b1}$ is:
(i) a moiety of the formula:

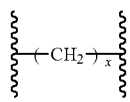

wherein x is 1 to 6; or
(ii) a moiety of the formula:

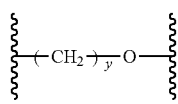

wherein y is 1 to 5;

(d) a moiety of the formula: —$CH_2$—$(CH_2)_m$—O—$(CH_2)_n$—, wherein m=1 to 5, and n=0 or 1 to 4;

B is:
(a) a bond;
(b) —$(CH_2)_{1-2}$—; or
(c) a moiety of the formula:

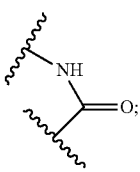 [SMILES: *NC(*)=O]

D is:

(a) a moiety of the Formula:

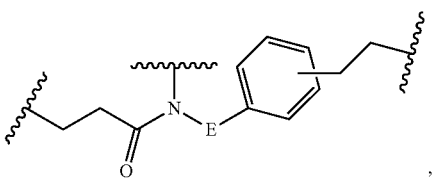

wherein E is —$CH_2$— or —$(CH_2)_{2-4}$—O—;

(b) a moiety of the formula:

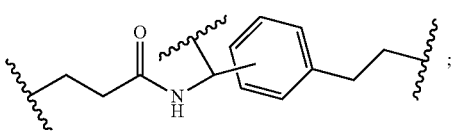

(c) a moiety of the formula:

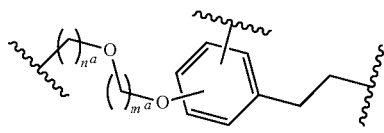

wherein $n^a$ is 1, 2, or 3, $m^a$ is 2, 3, or 4, and $n^a+m^a$ is ≥3;

(d) a moiety of the formula:

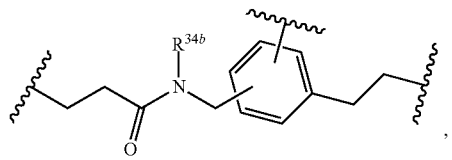

wherein, $R^{34b}$ is —H or a liner, branched or cyclic alkyl of up to four carbon atoms, or a pharmaceutically acceptable salt of any thereof.

2. A compound of claim 1, wherein X is F, or a pharmaceutically acceptable salt of any thereof.

3. A compound of claim 2 wherein D is a moiety of the formula:

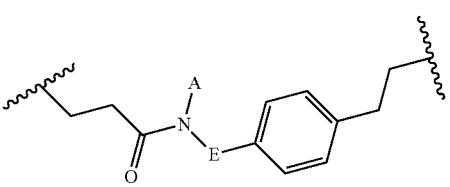

wherein, E is —$CH_2$— or —$(CH_2)_2$—O—, or a pharmaceutically acceptable salt thereof.

4. A compound of claim 2 wherein D is a moiety of the formula:

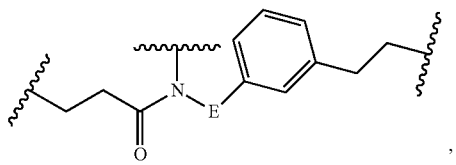

wherein, E is —CH₂— or —(CH₂)₂—O—, or a pharmaceutically acceptable salt thereof.

5. A compound of claim 2 wherein D is a moiety of the formula:

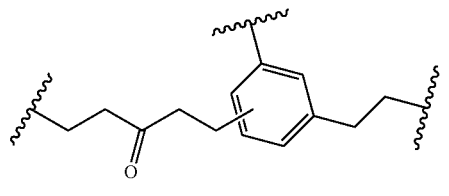

or a pharmaceutically acceptable salt thereof.

6. A compound of claim 2 wherein D is a moiety of the formula:

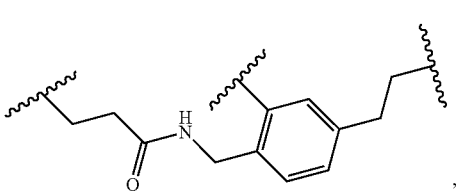 [SMILES: *CCC(=O)NCc1ccc(CC*)cc1*]

or a pharmaceutically acceptable salt thereof.

7. A compound of claim 2 wherein D is a moiety of the formula:

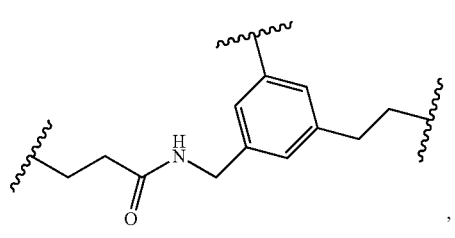 [SMILES: *CCC(=O)NCc1cc(*)cc(CC*)c1]

or a pharmaceutically acceptable salt thereof.

8. A compound of claim 2 wherein D is a moiety of the formula:

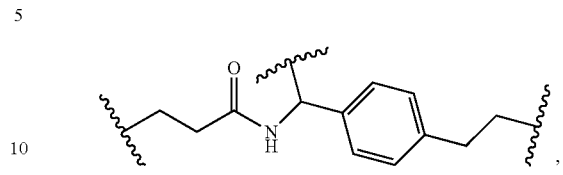

or a pharmaceutically acceptable salt thereof.

9. A compound of claim 2 wherein D is a moiety of the formula:

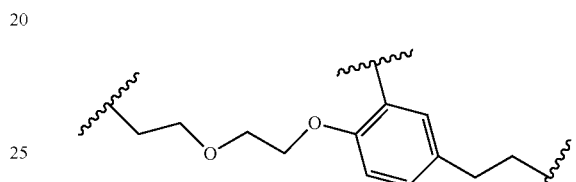

or a pharmaceutically acceptable salt thereof.

10. A compound of claim 2 wherein D is a moiety of the formula:

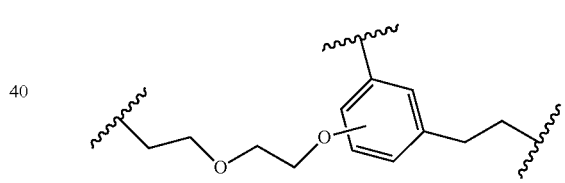

or a pharmaceutically acceptable salt thereof.

11. A compound of claim 2 wherein $R^1$ and $R^2$ are joined together with a moiety of the formula:

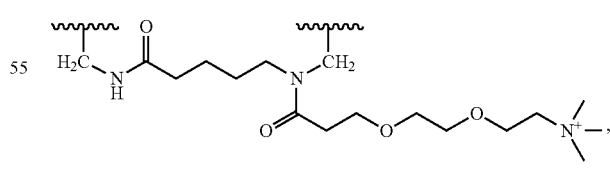

such that together with the cyclopeptide to which $R^1$ and $R^2$ are attached they form a cyclic structure, or a pharmaceutically acceptable salt thereof.

12. A compound of claim 2 having the structure of Formula IIB, or a pharmaceutically acceptable salt thereof:

Formula IIB

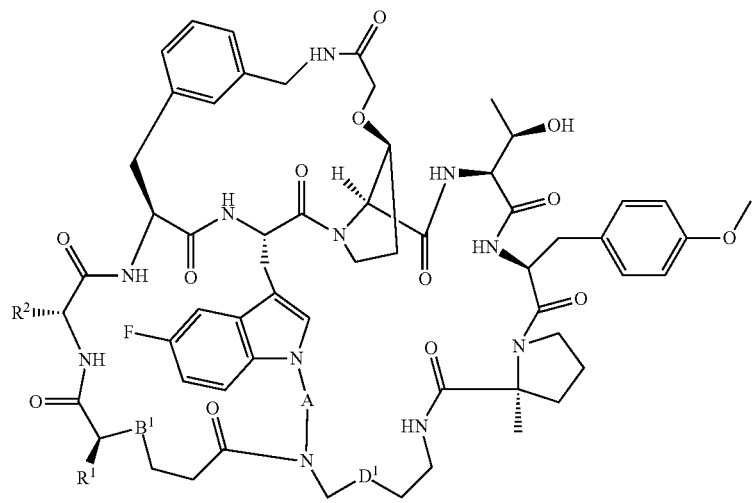

B¹ is —((CH$_2$)$_{0-2}$)—; and

D¹ is:

(a) a moiety of the formula:

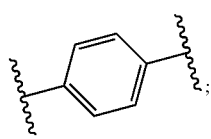 [SMILES: *c1ccc(*)cc1]

(b) a moiety of the formula:

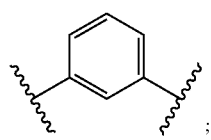

or (c) a moiety of the formula:

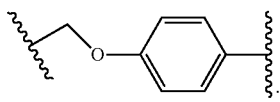

13. A compound of claim 2 having the structure of Formula IIC, or a pharmaceutically acceptable salt thereof:

Formula IIC,

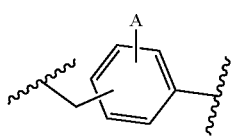

wherein

D² is:

(a) a moiety of the formula:

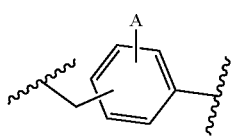

(b) a moiety of the formula:

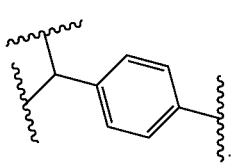 [SMILES: *c1ccc(C(*)*)cc1]

14. A Compound of claim 2 having the structure of Formula IID, or a pharmaceutically acceptable salt thereof:

Formula IID.

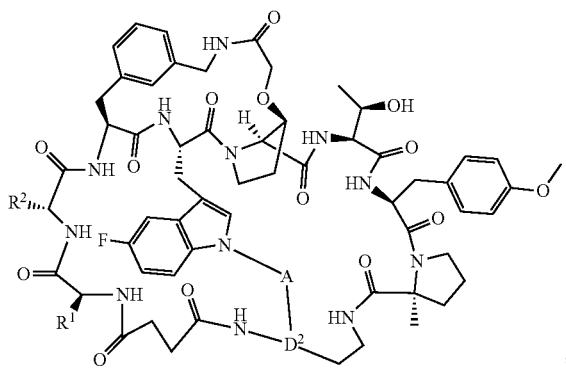

wherein
D² is:
(a) a moiety of the formula:

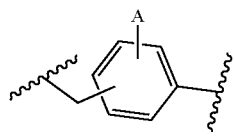

(b) a moiety of the formula:

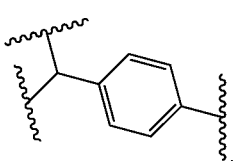 [SMILES: *c1ccc(C(*)*)cc1]

15. A compound of claim 2 having the structure of Formula IIE, or a pharmaceutically acceptable salt thereof:

Formula IIE.

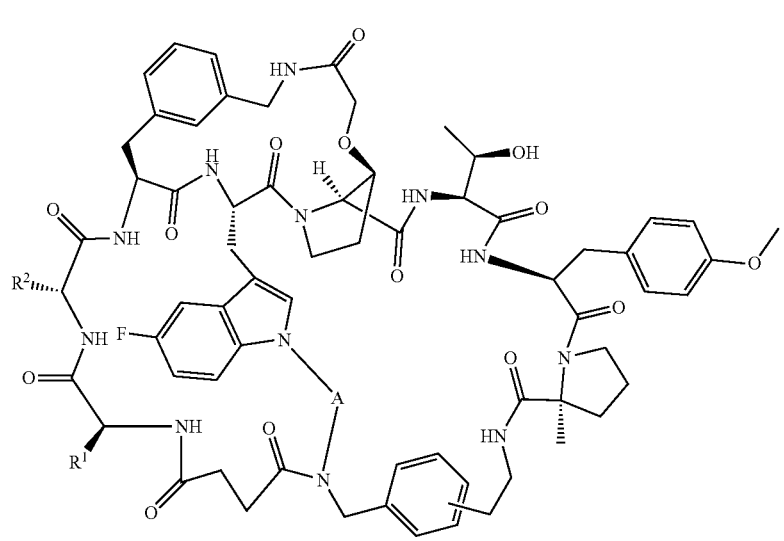

16. A compound of claim 2 having the structure of Formula IIF, or a pharmaceutically acceptable salt thereof:

Formula IIF.

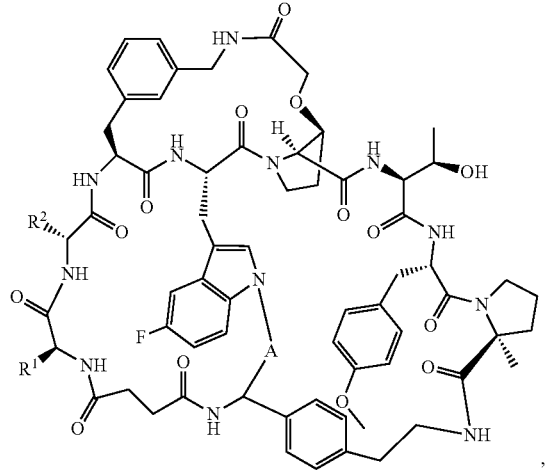

17. A compound of claim 2, or a pharmaceutically acceptable salt thereof, wherein A is:
(a) —$(CH_2)_6$;
(b) a moiety of the formula:

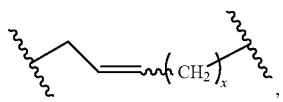

wherein x is 1 to 3; or (c) a moiety of the formula:

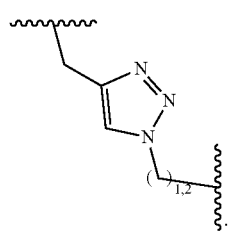

18. A compound of claim 2, or a pharmaceutically acceptable salt thereof, wherein $R^2$ is:

—$(CH_2)_z$—$R^{14A}$, wherein: z is 1-6, and $R^{14A}$ is:

(a) —H;

(b) —$NH_2$;

(c) —$N^+H_3$;

(d) —$N^+(H_3C)_3$;

(e) —NH—C(O)—[$(CH_2)_{2\text{-}4}$—O—]$_2$—$(CH_2)_{2\text{-}4}R^{14B}$ wherein $R^{14B}$ is: —$NH_2$; —$N^+H_3$; —$N(CH_3)_2$; or —$N^+(CH_3)_3$; or (f) —NH—C(O)—[$(CH_2)_y R^{14C}$, wherein, y=1 to 6 and $R^{14C}$ is:

(ai) —O—$(CH_2)_{2\text{-}4}$—$N^+(CH_3)_3$;

(aii) —$N^+(CH_3)_3$; or (aiii) a moiety of the formula:

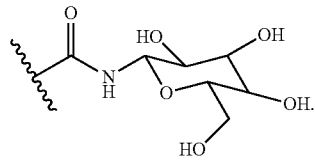 [SMILES: *C(=O)NC1OC(CO)C(O)C(O)C1O]

19. A compound of claim 2, or a pharmaceutically acceptable salt thereof, wherein $R^1$ is selected from:

(a) —H;

(b) —$(CH_2)_z$—$R^{14A}$, wherein: z is 1-6, and $R^{14A}$ is:

(i) —H;

(ii) —$N^+H_3$; or (iii) —NH—C(O)—[$(CH_2)_2$—O—]$_2$—$(CH_2)_2$—$N^+(CH_3)_3$.

20. A compound of claim 2, or a pharmaceutically acceptable salt thereof, wherein $R^8$ is a moiety of the formula:

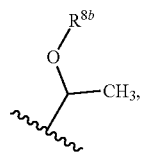

wherein $R^{8b}$ is —H, —$CH_3$, or —$C(CH_3)_3$.

21. A compound of claim 1, which is selected from the group consisting of:

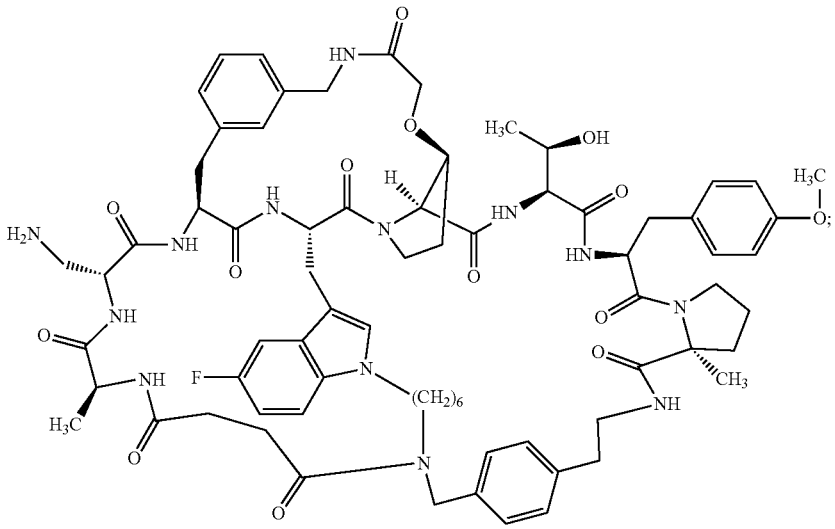

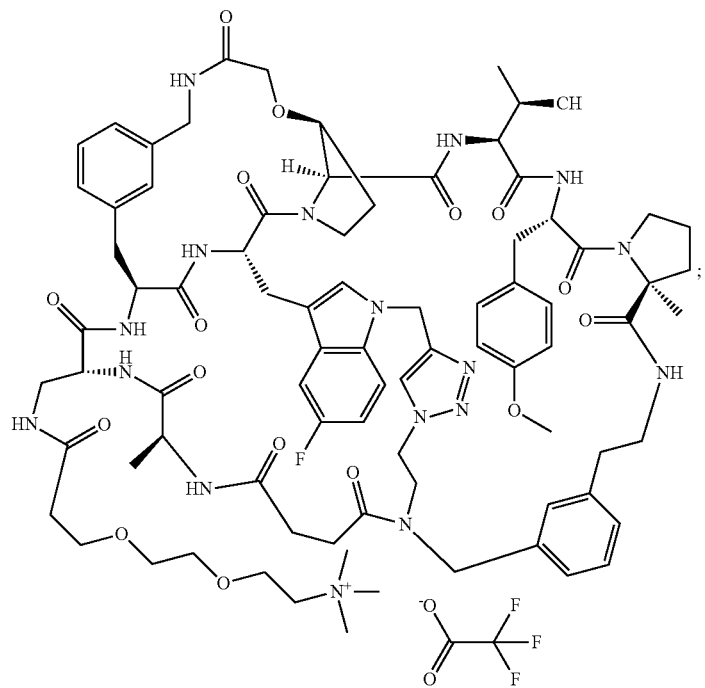
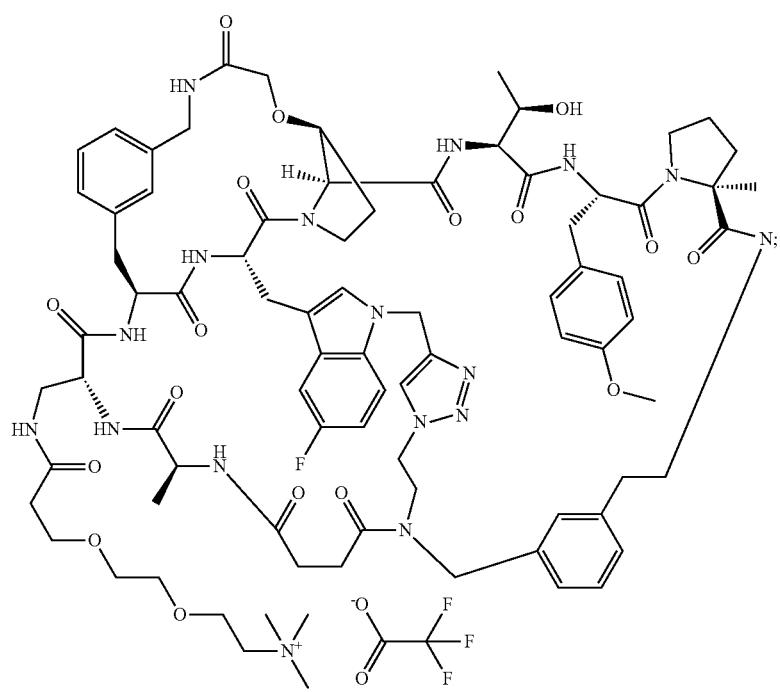

-continued
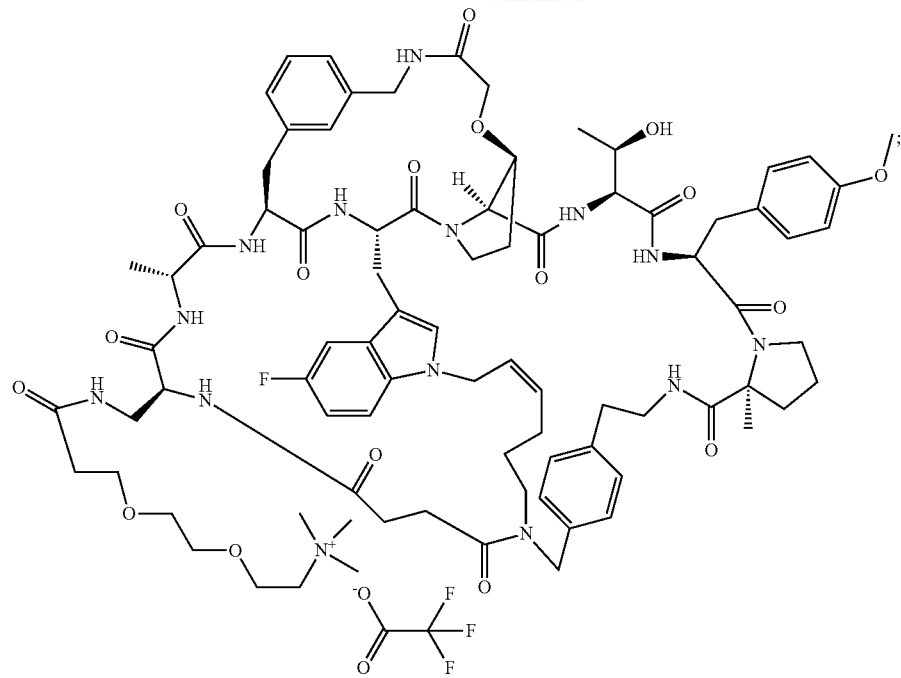
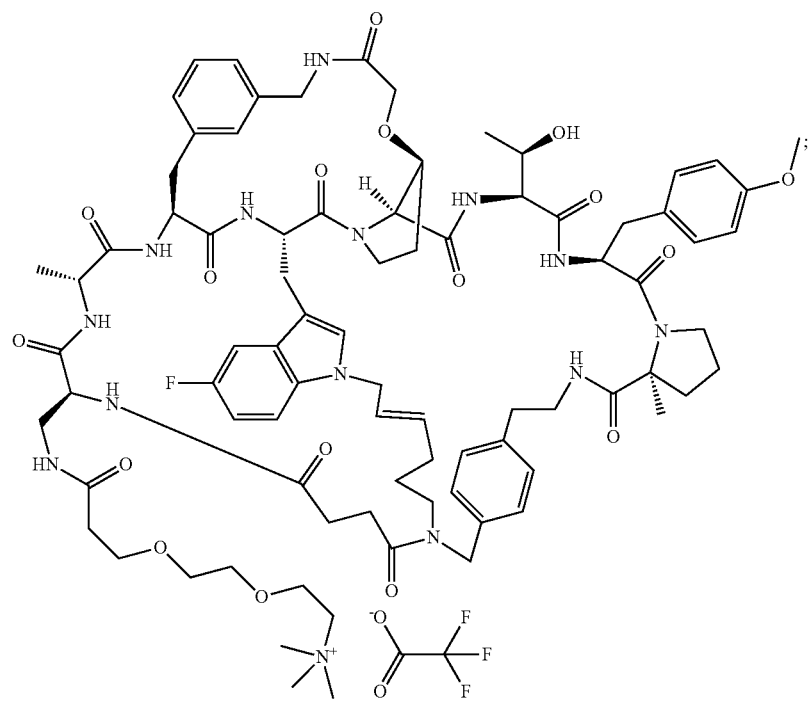

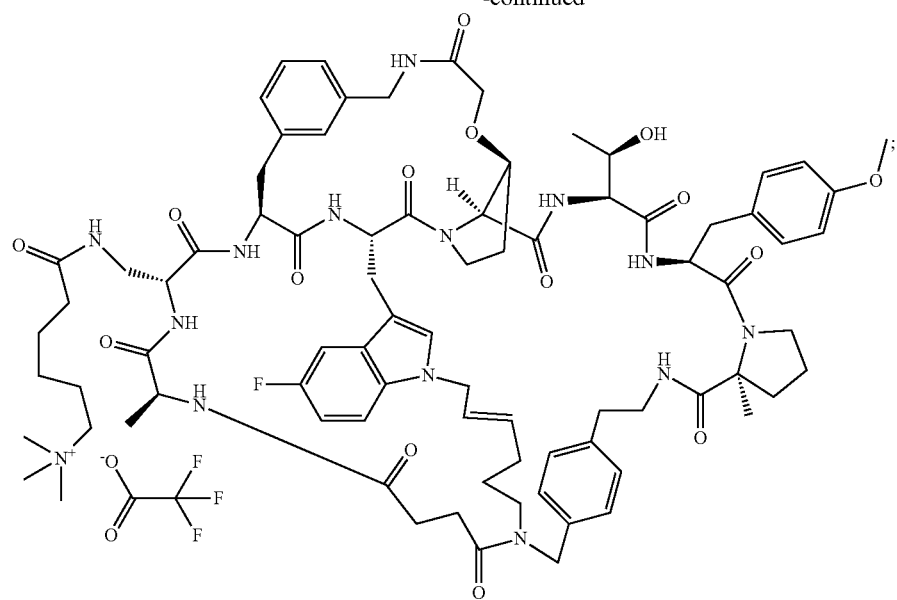
;
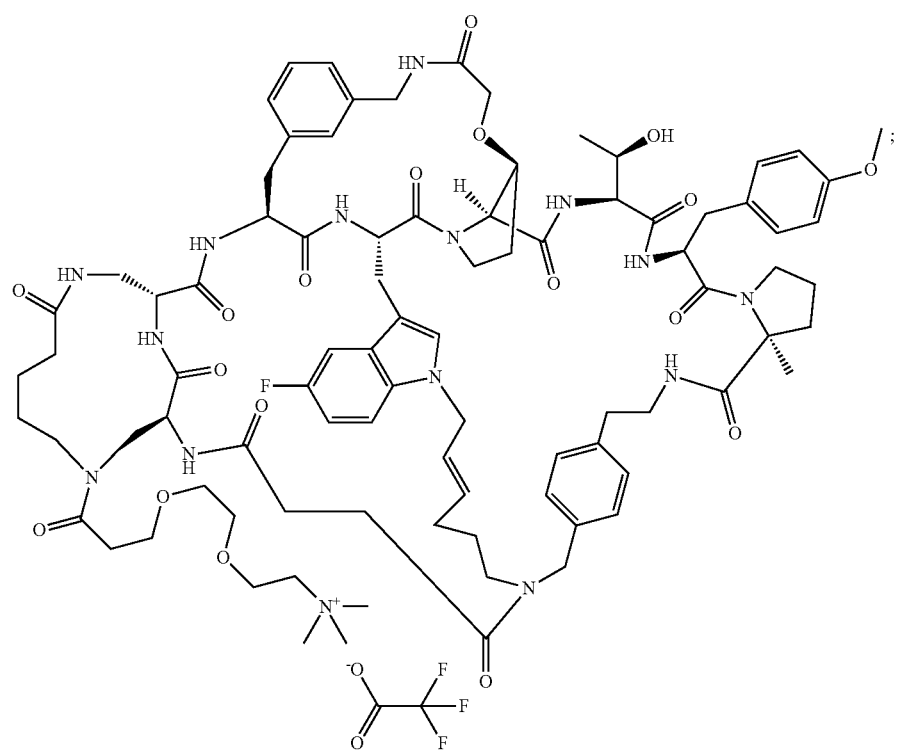
;

-continued
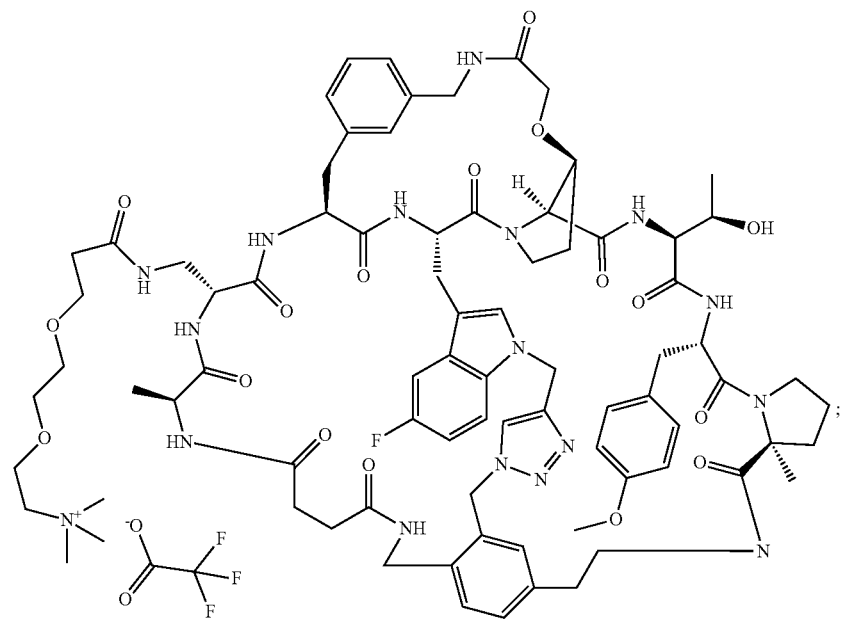
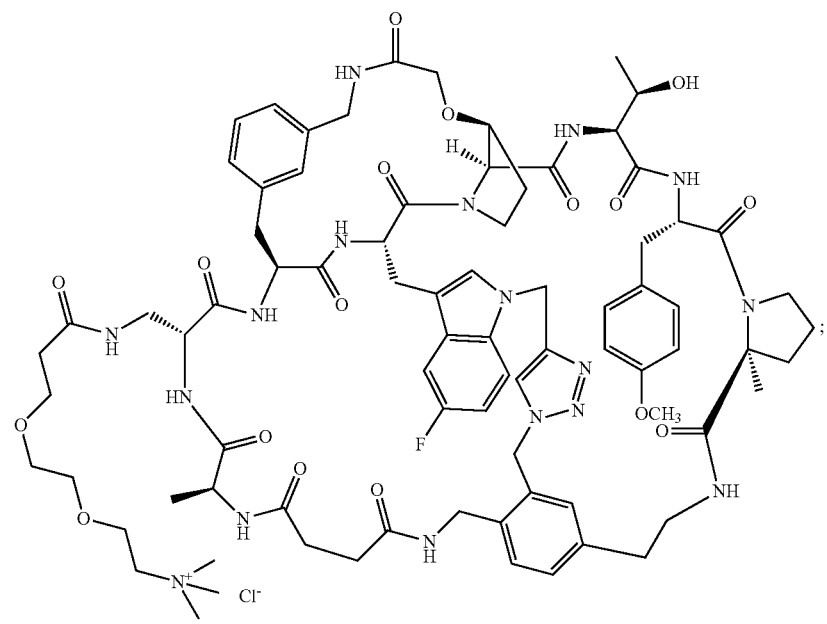

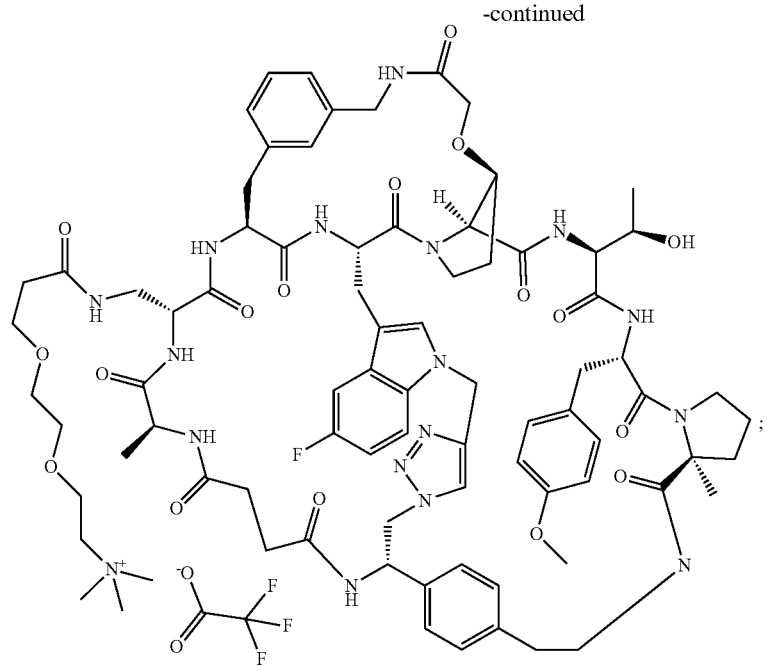
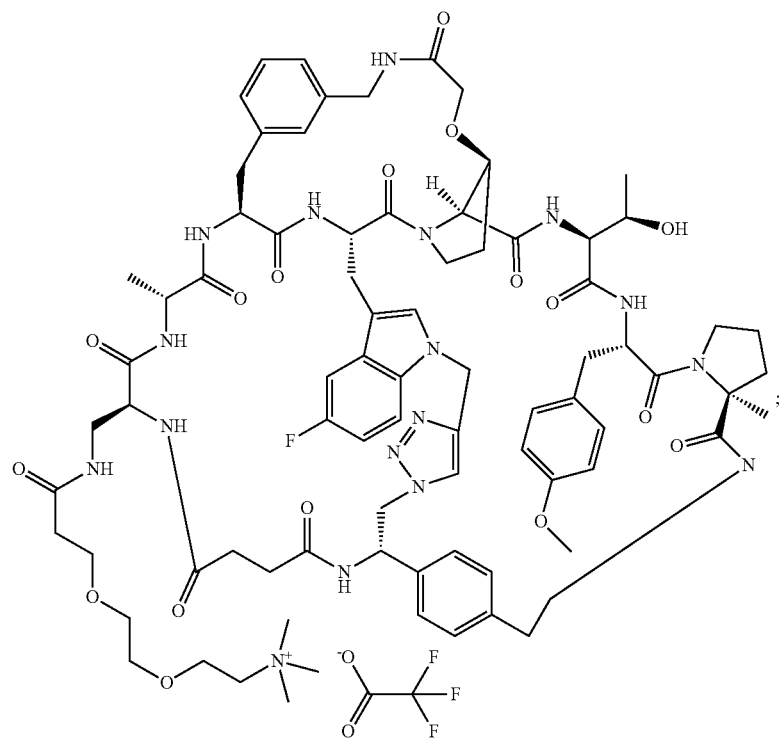

-continued
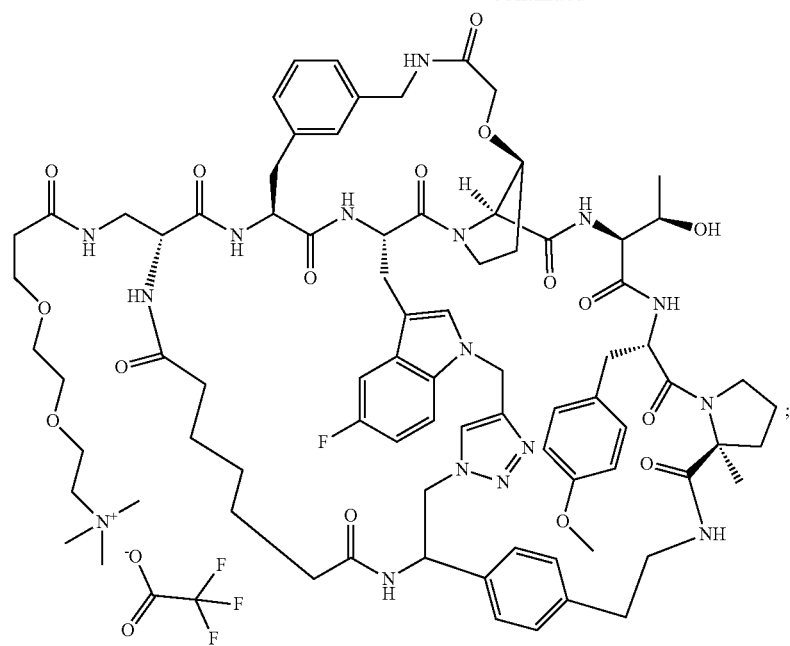
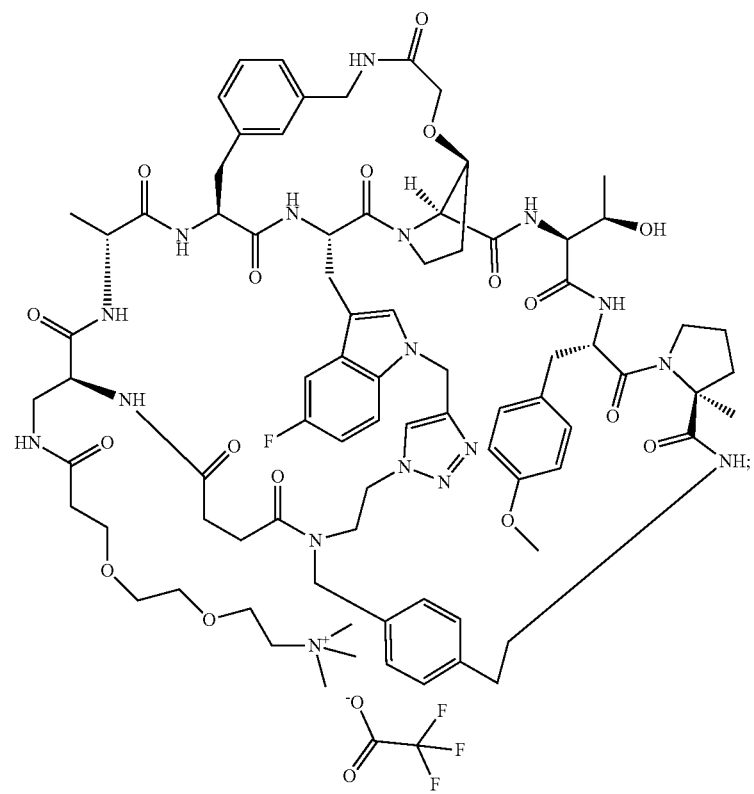

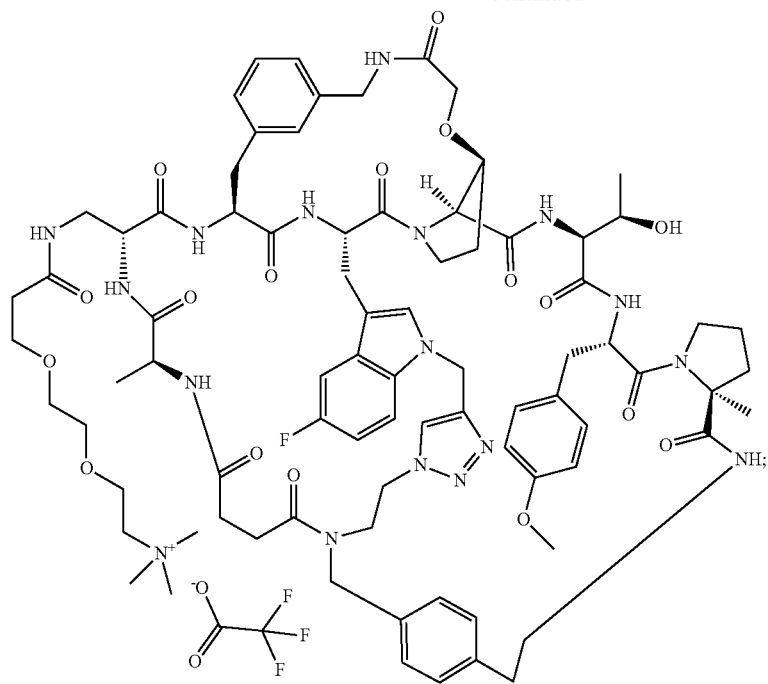
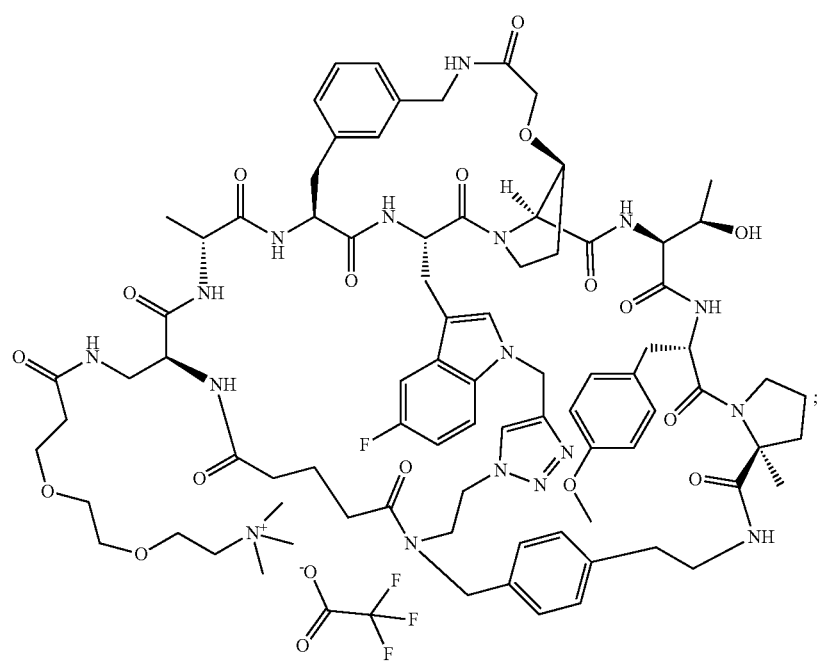

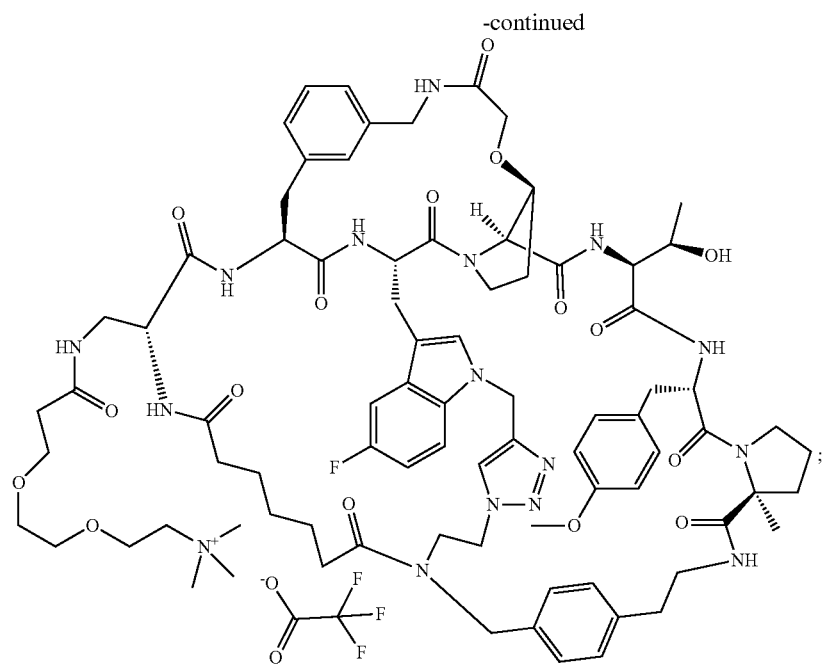
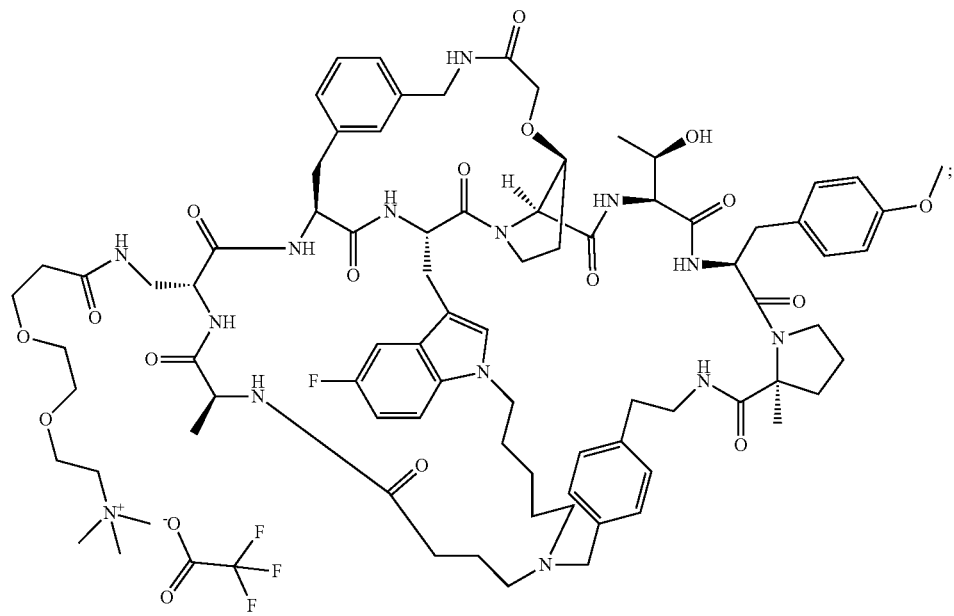

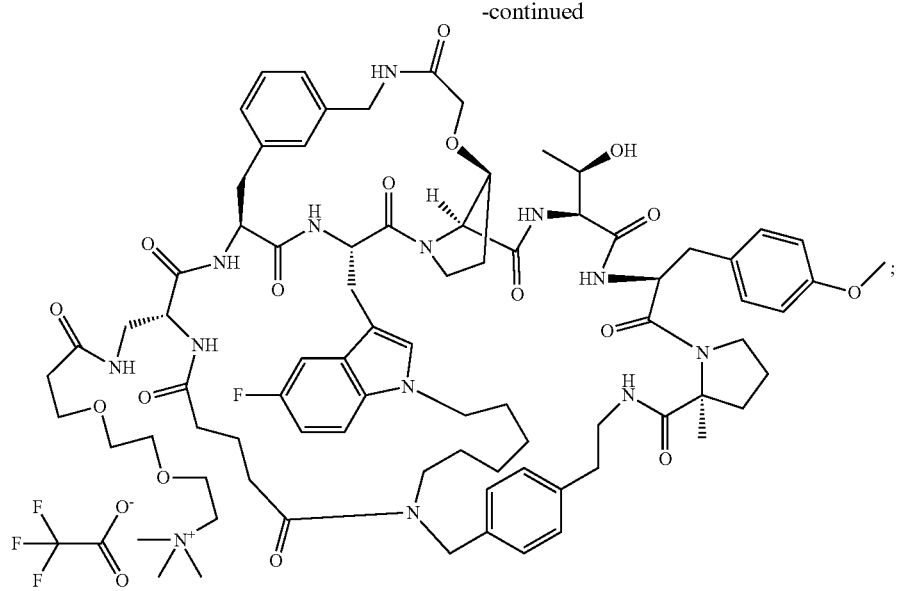
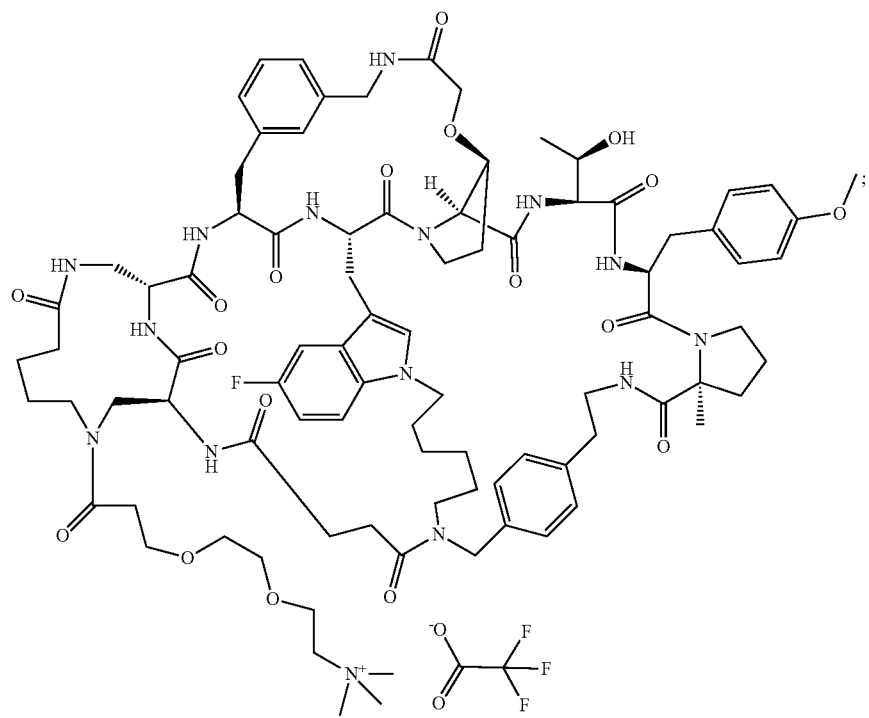

-continued
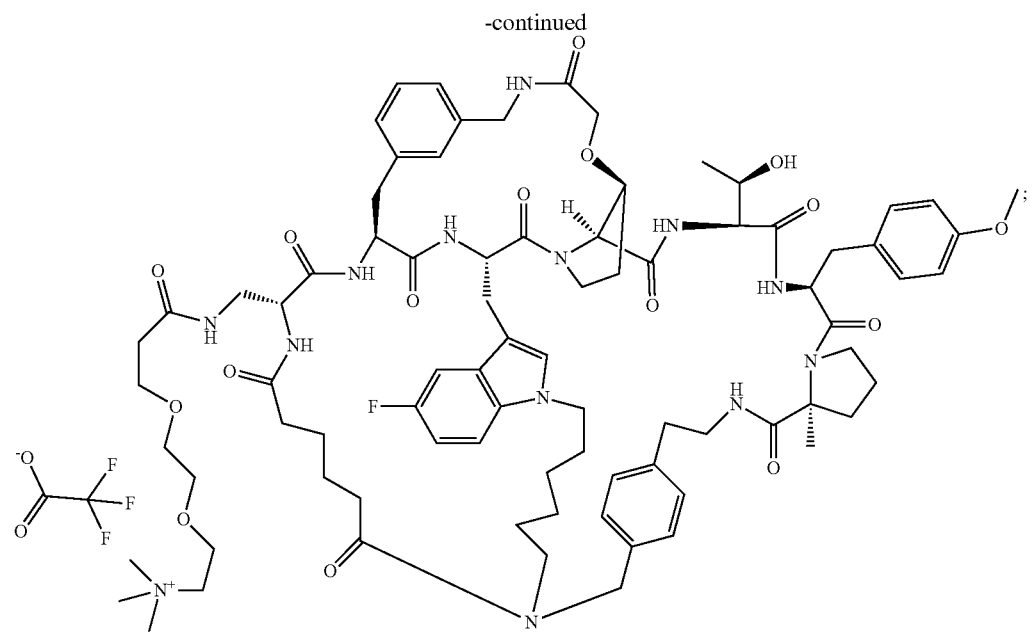
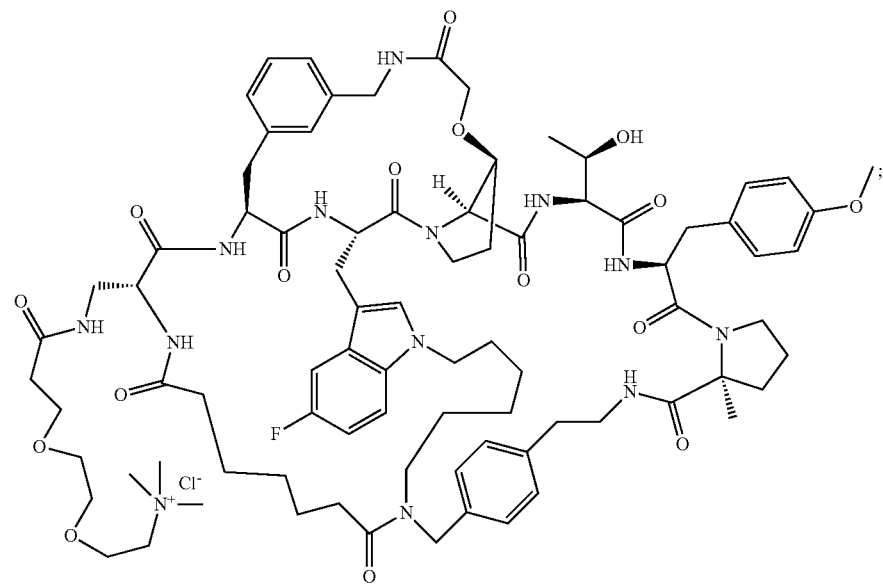

-continued
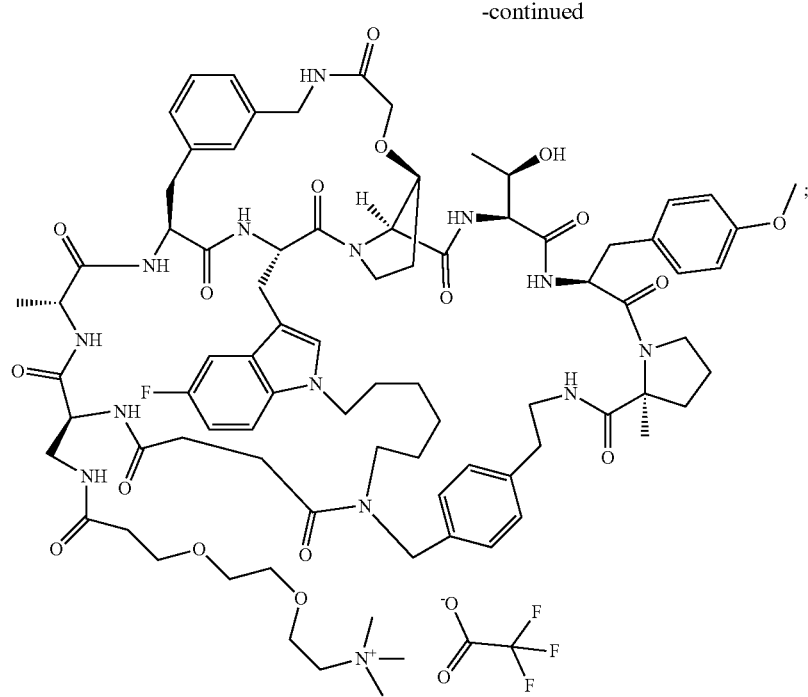
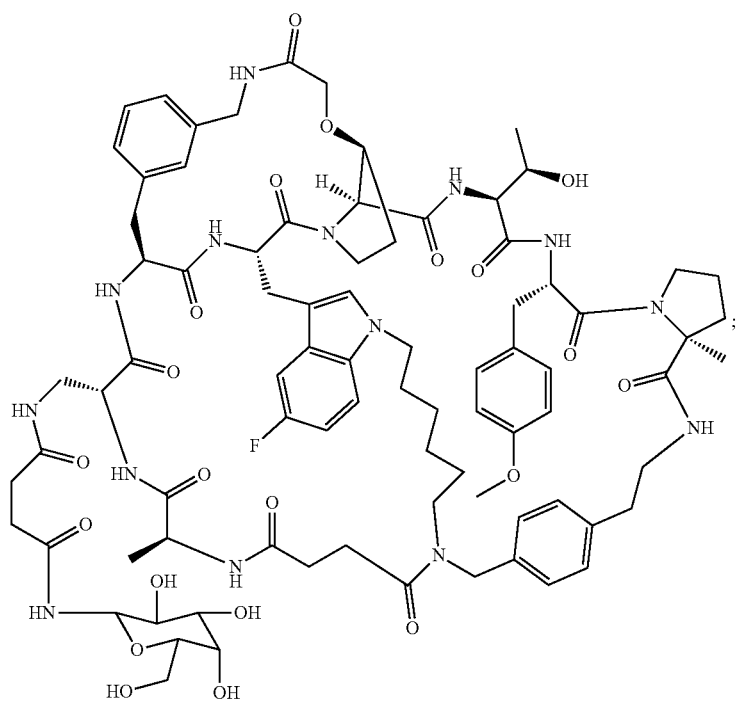

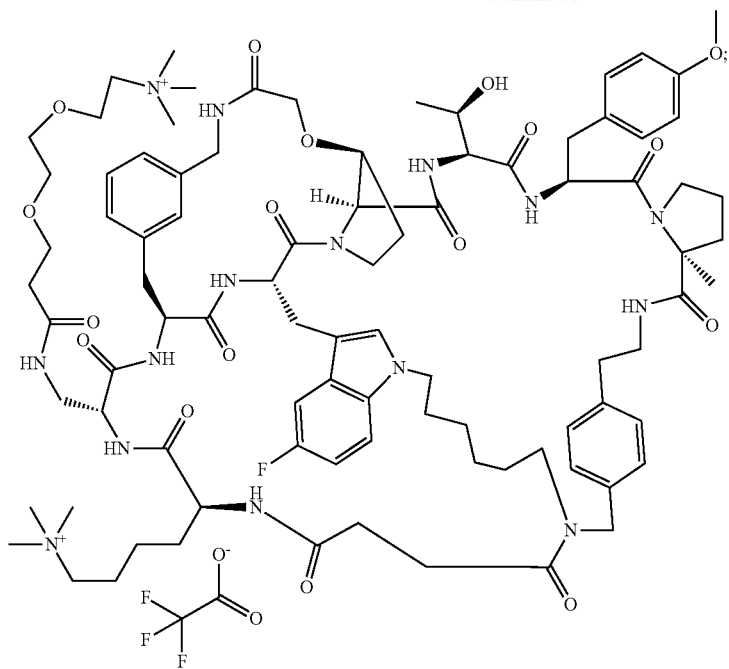
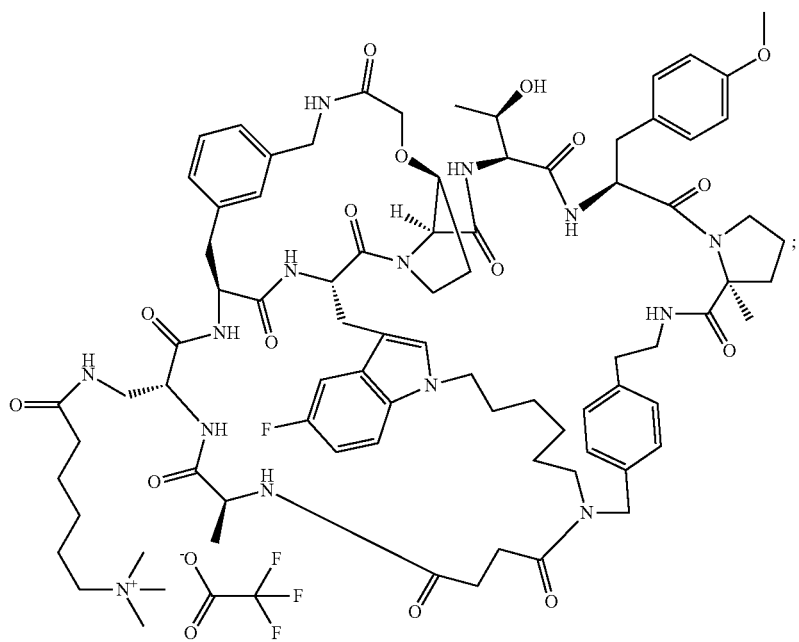

-continued
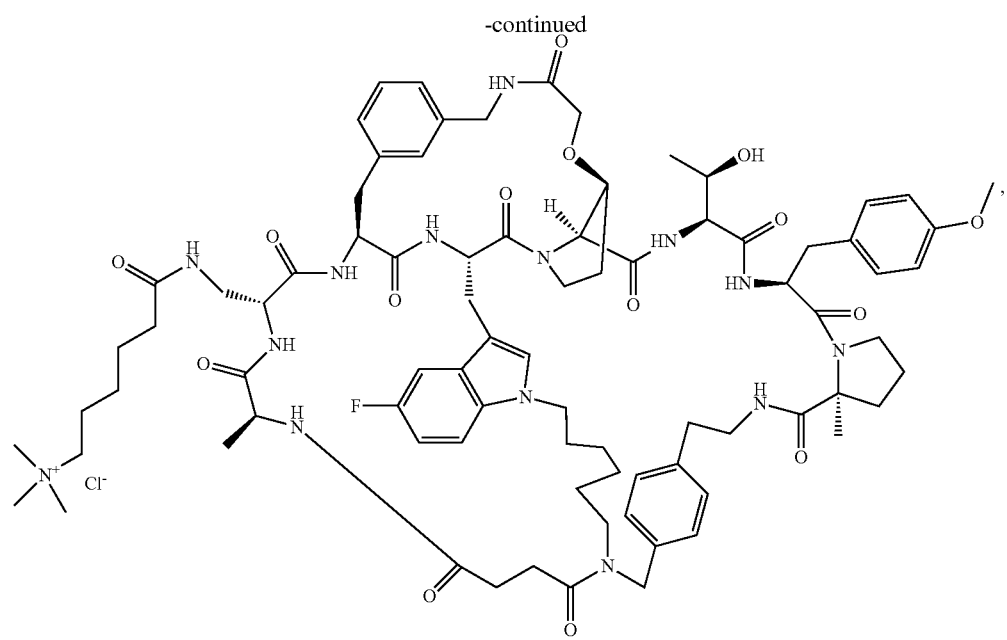
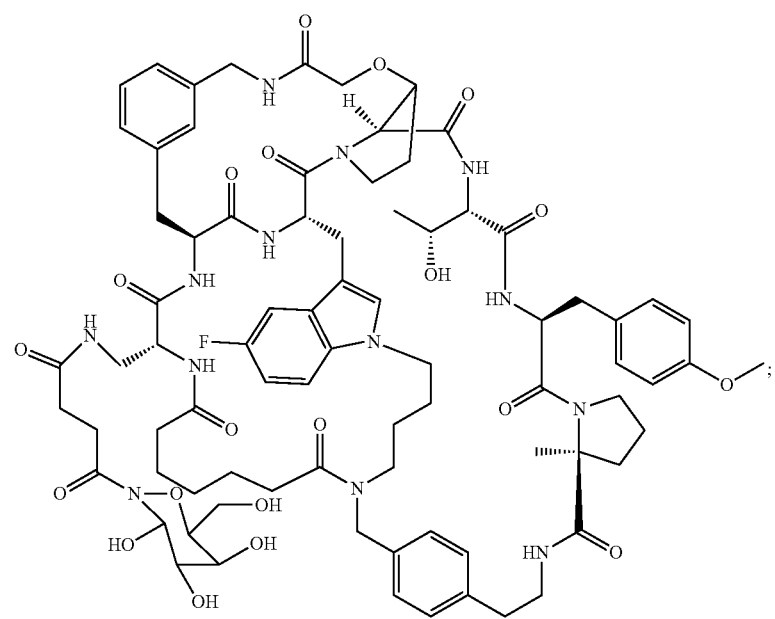

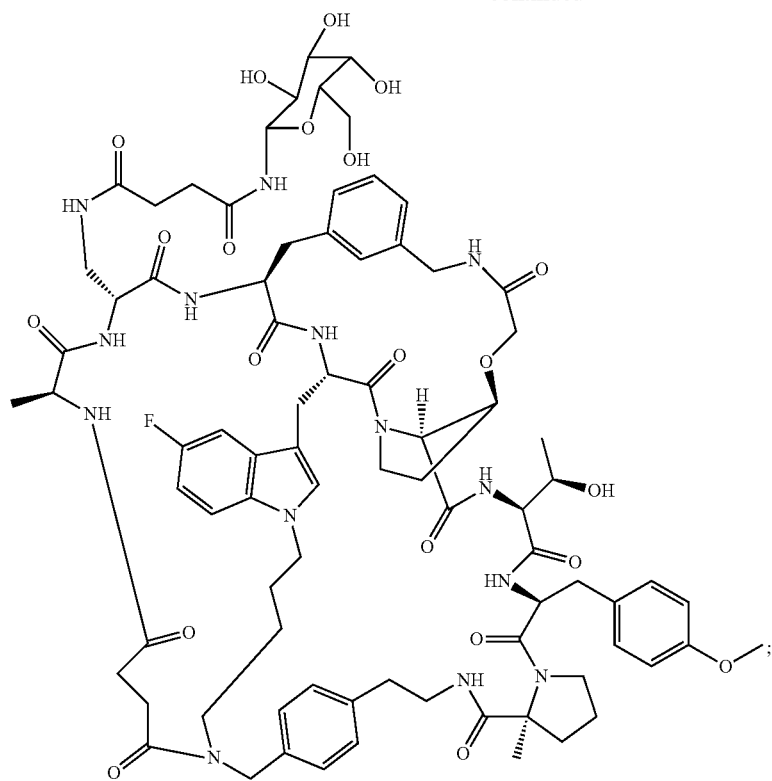
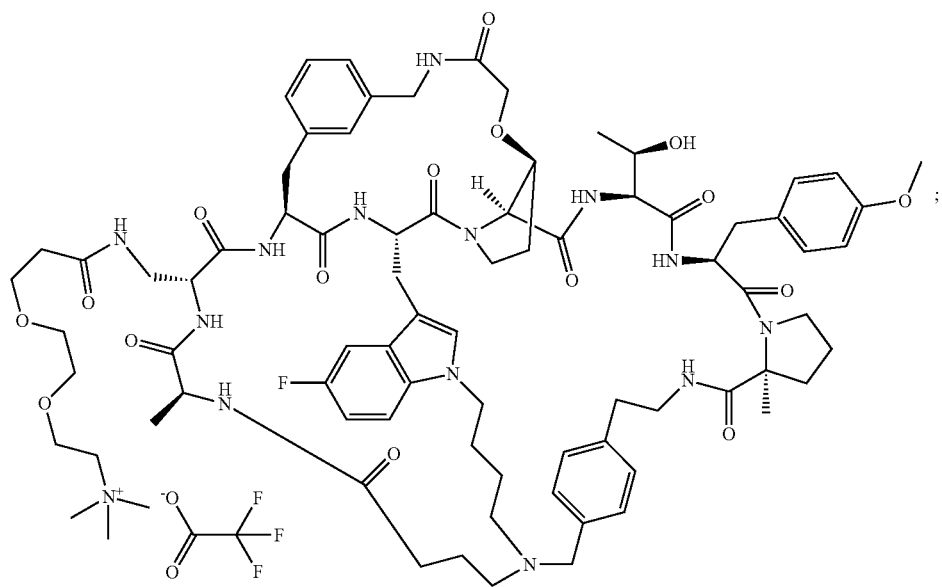

-continued
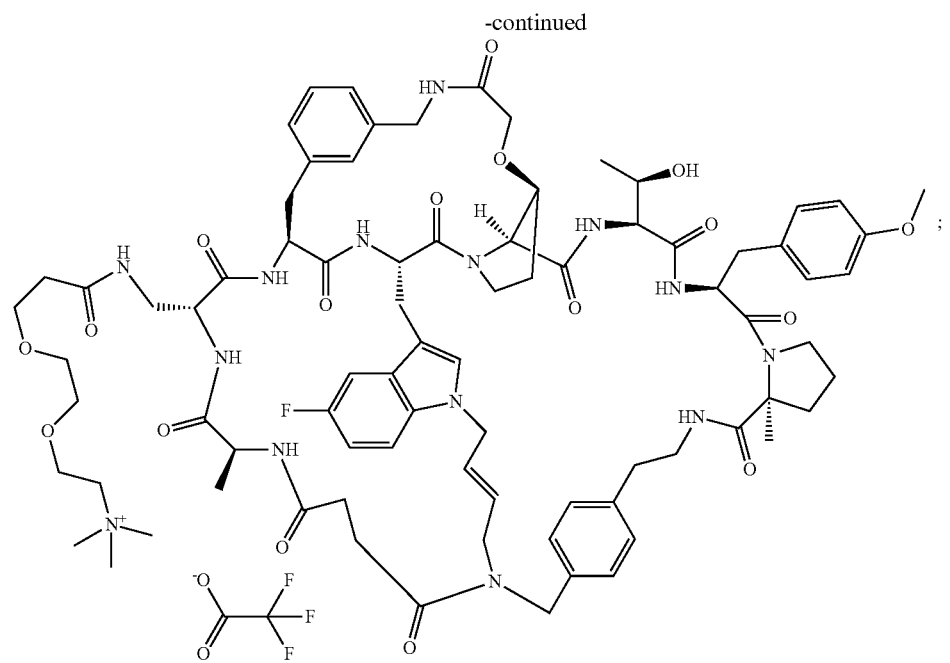
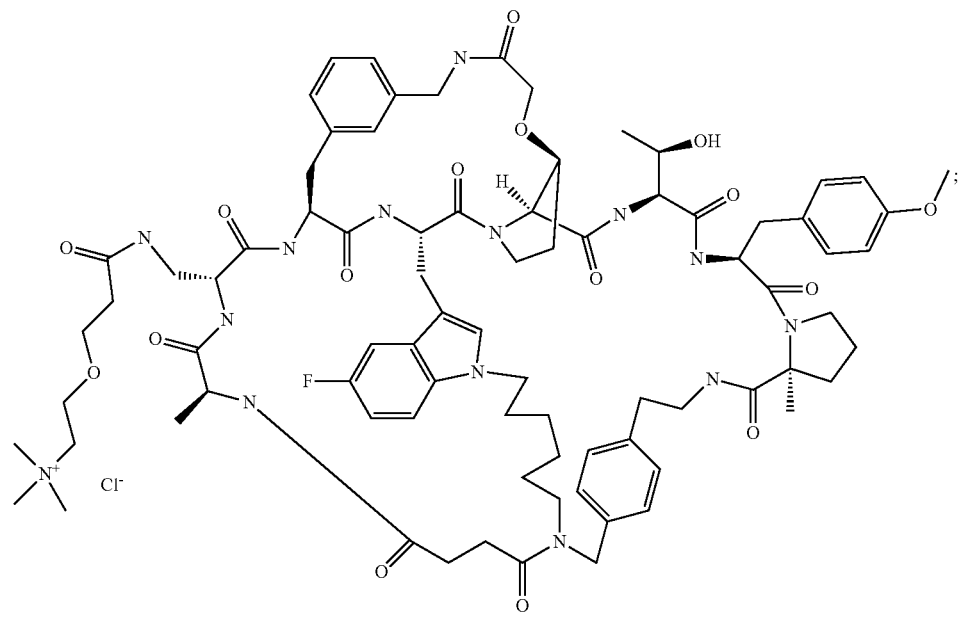

-continued
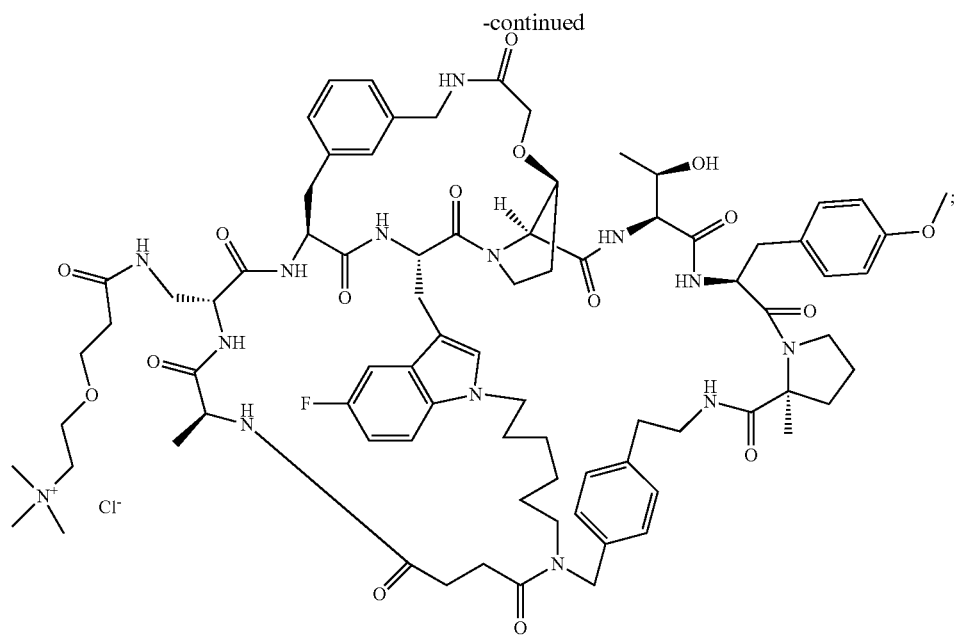
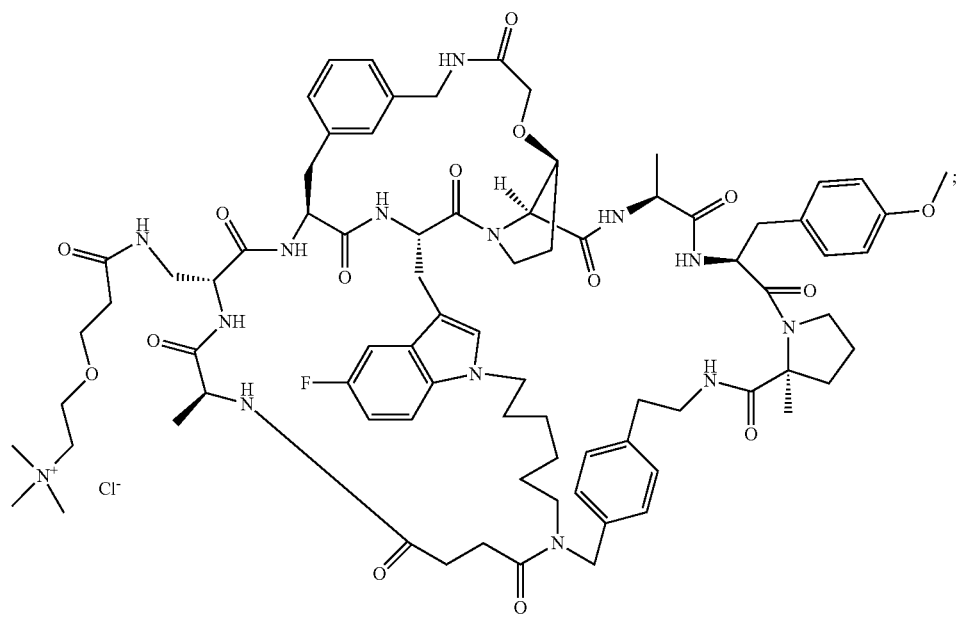

-continued
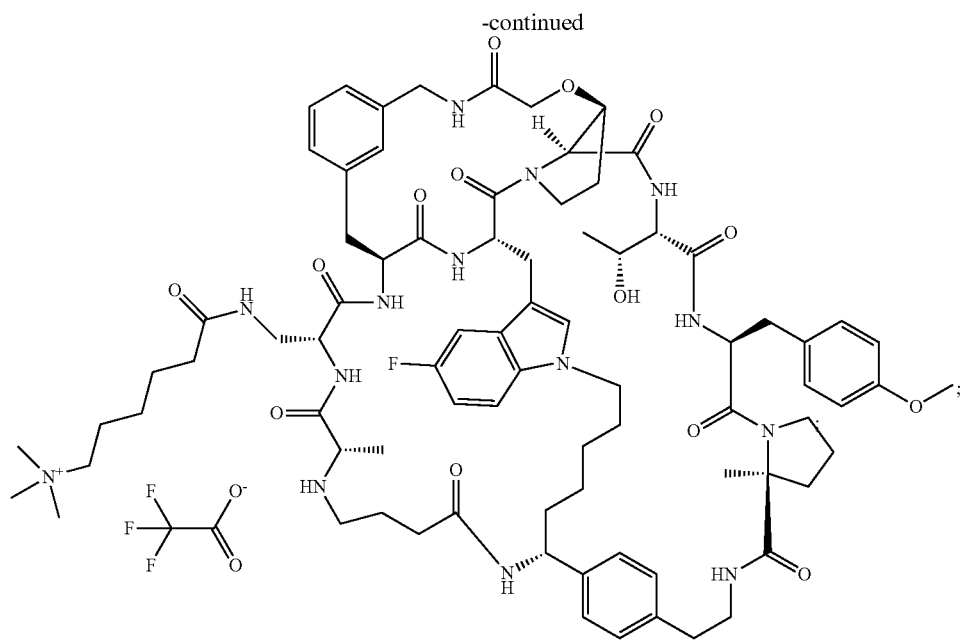
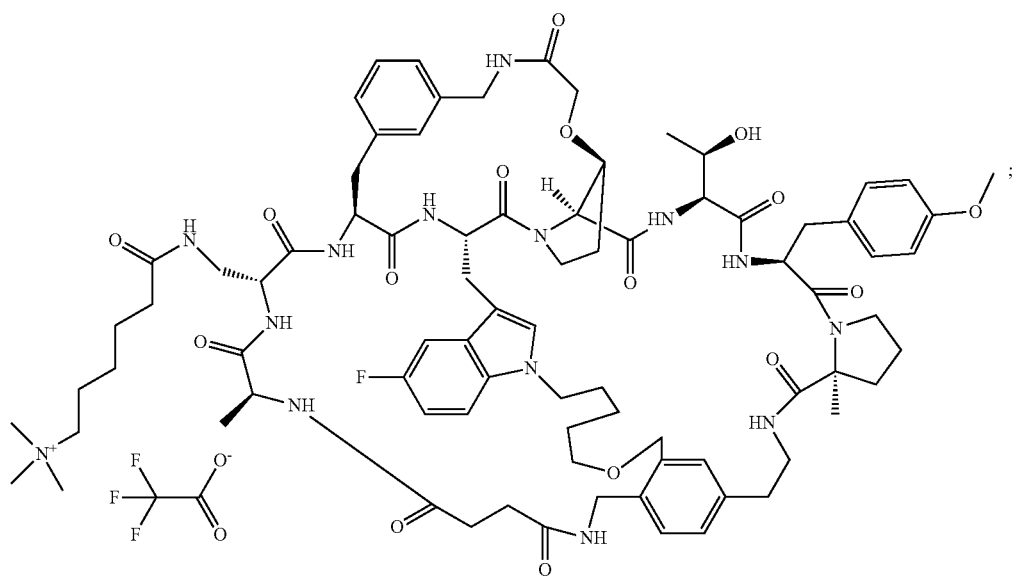

-continued
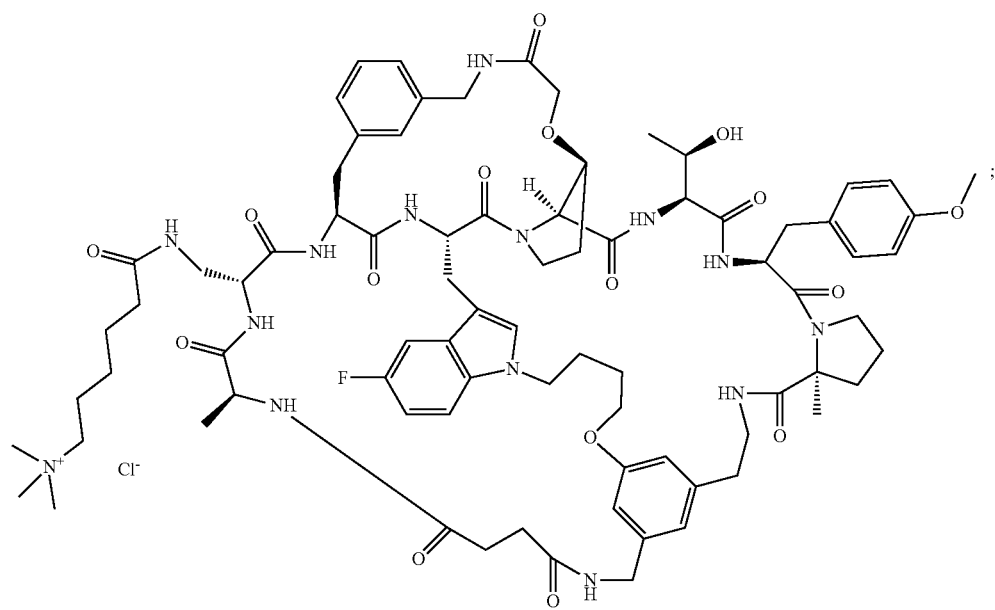
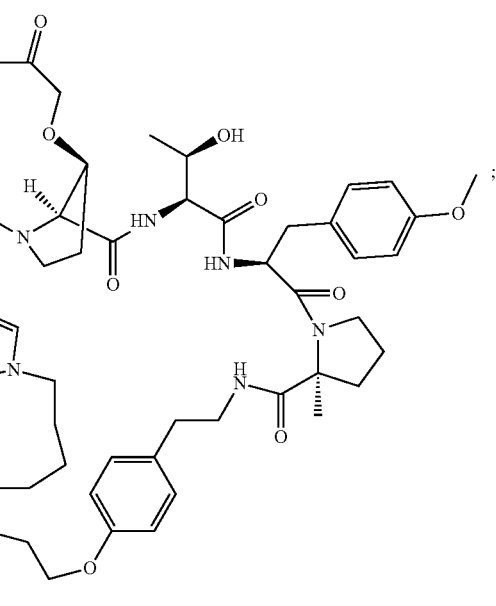

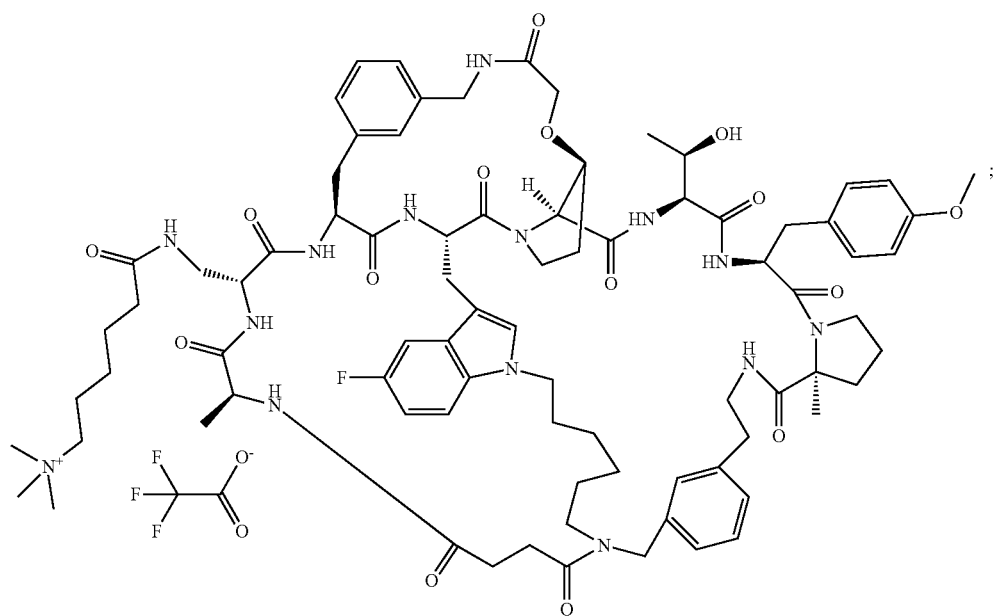
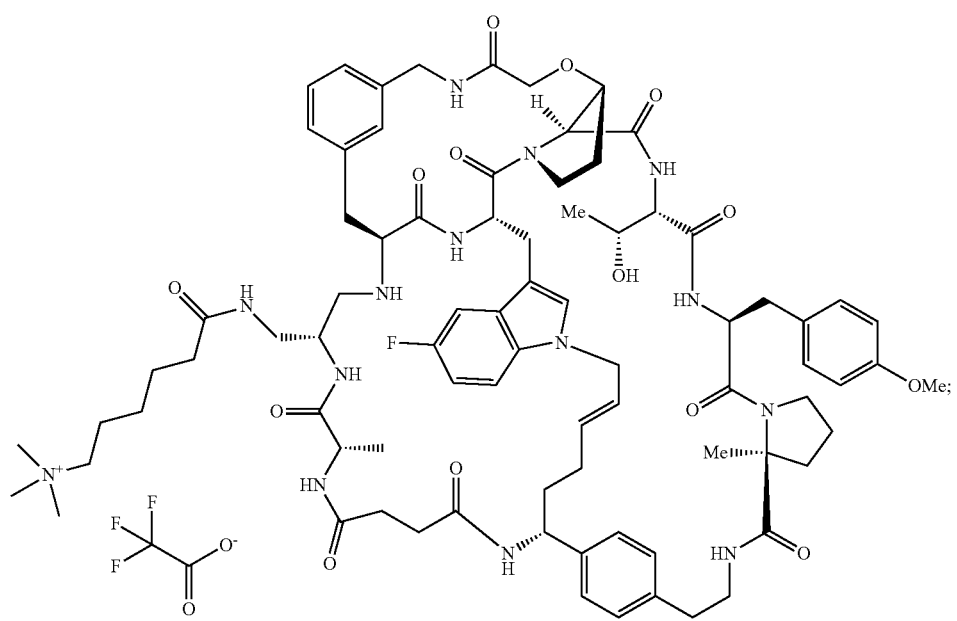

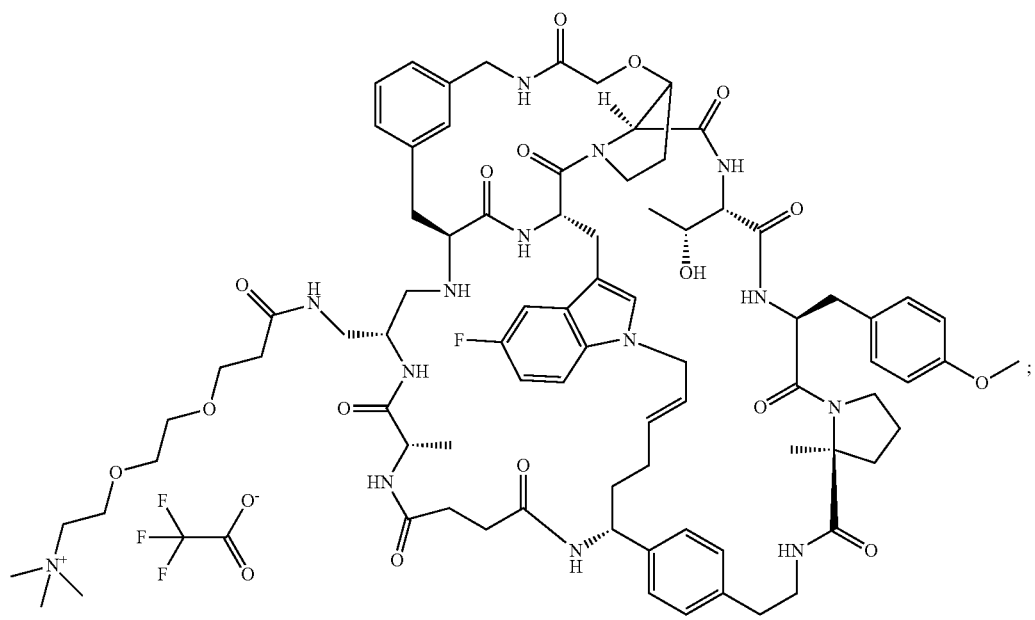
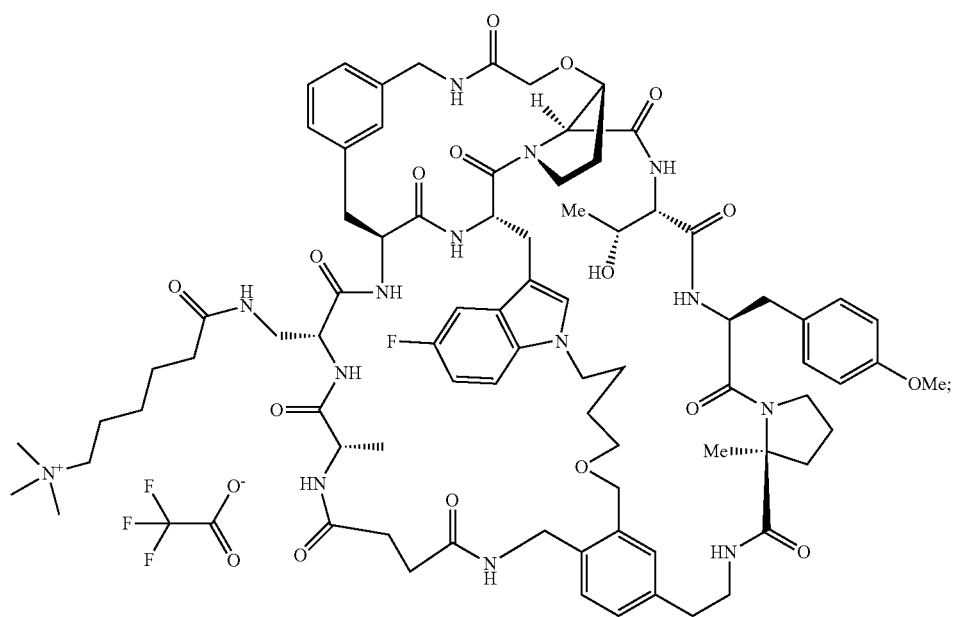

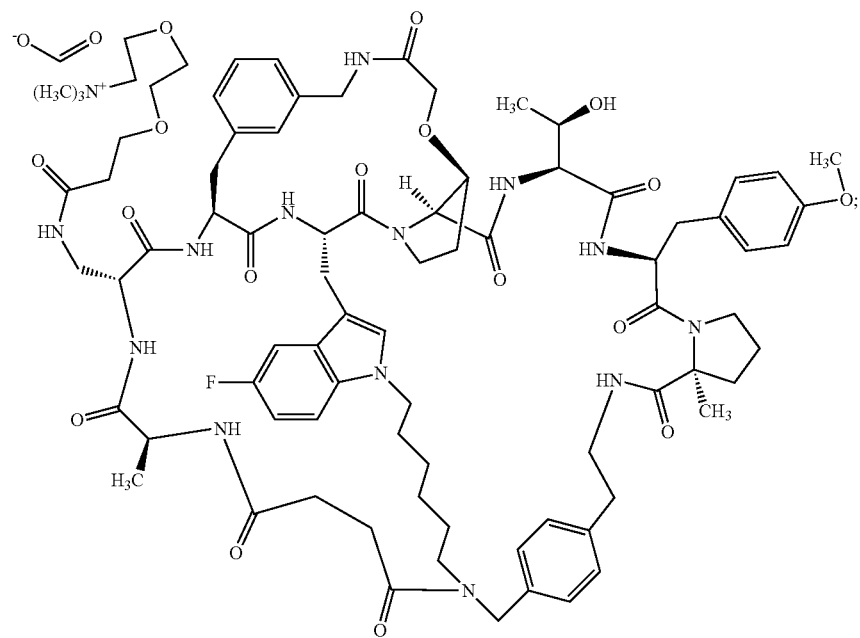
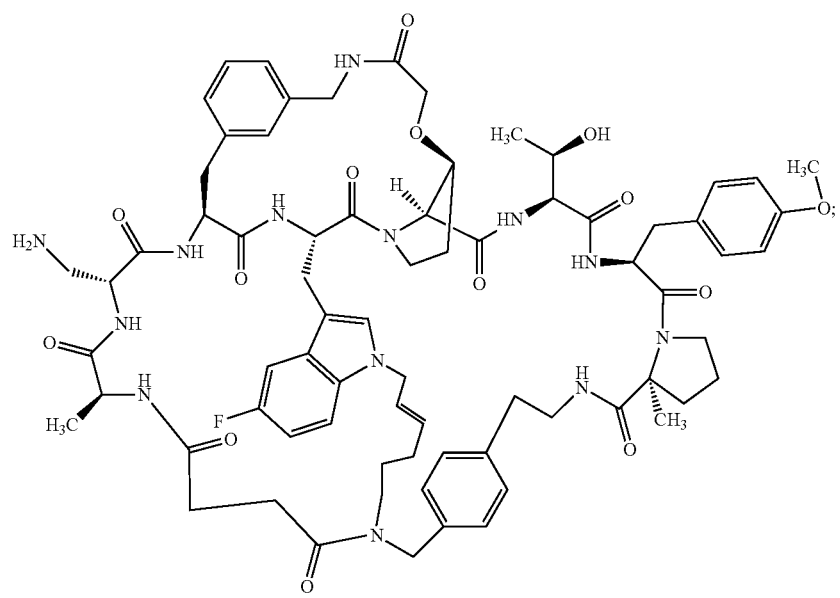

-continued
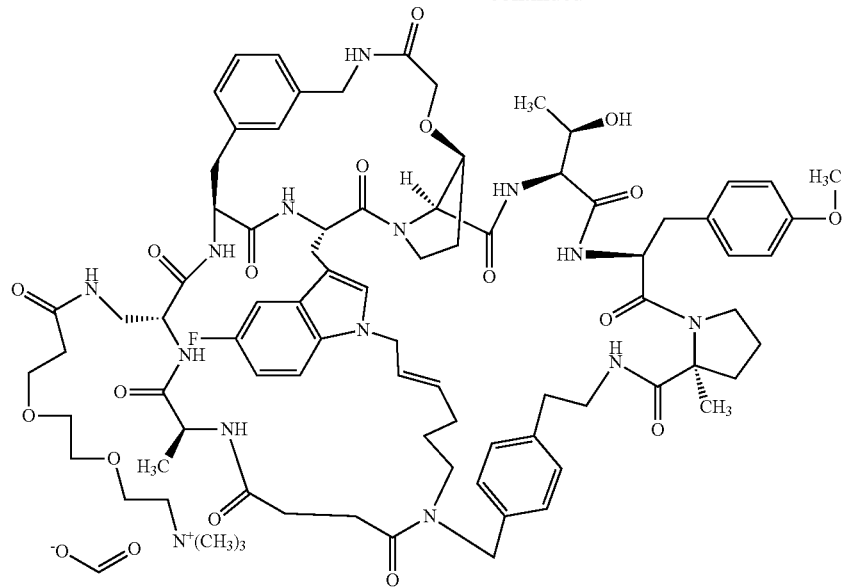
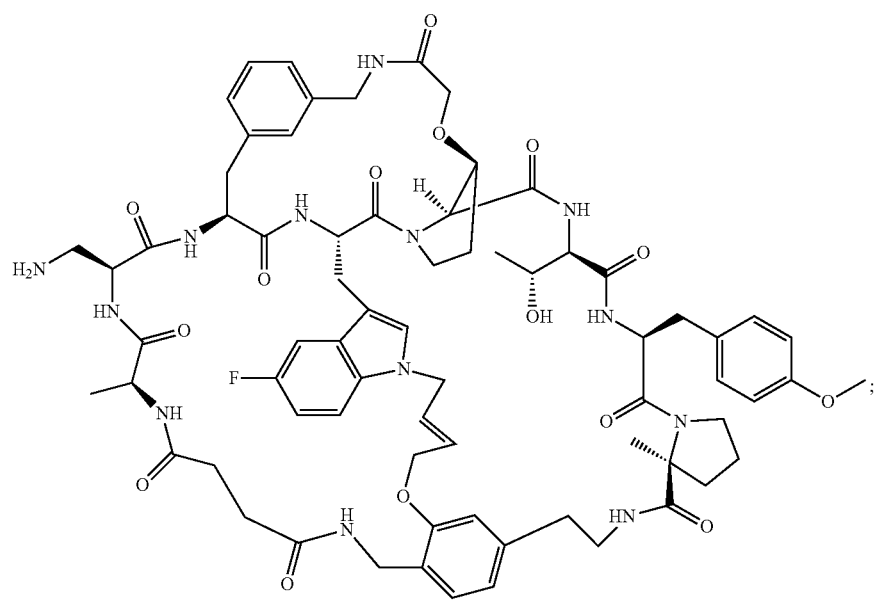

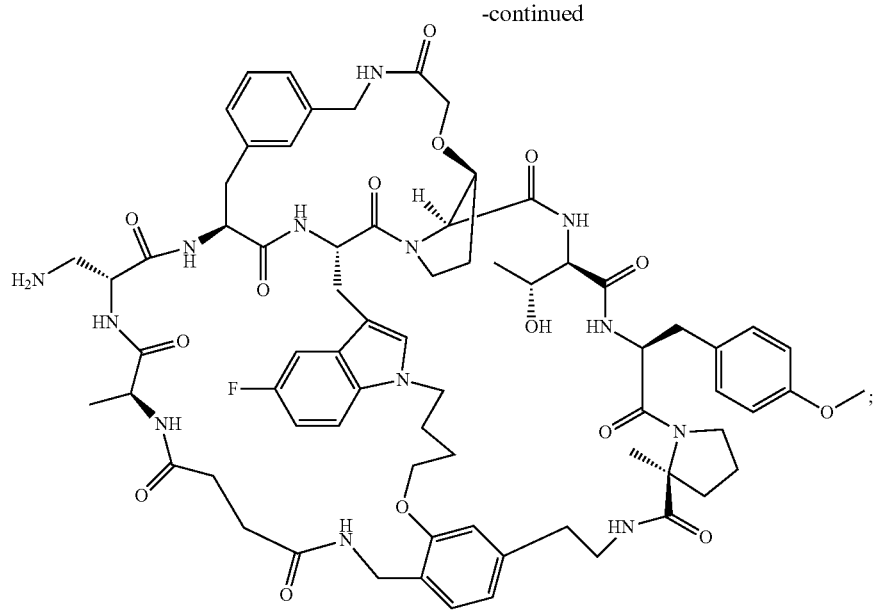
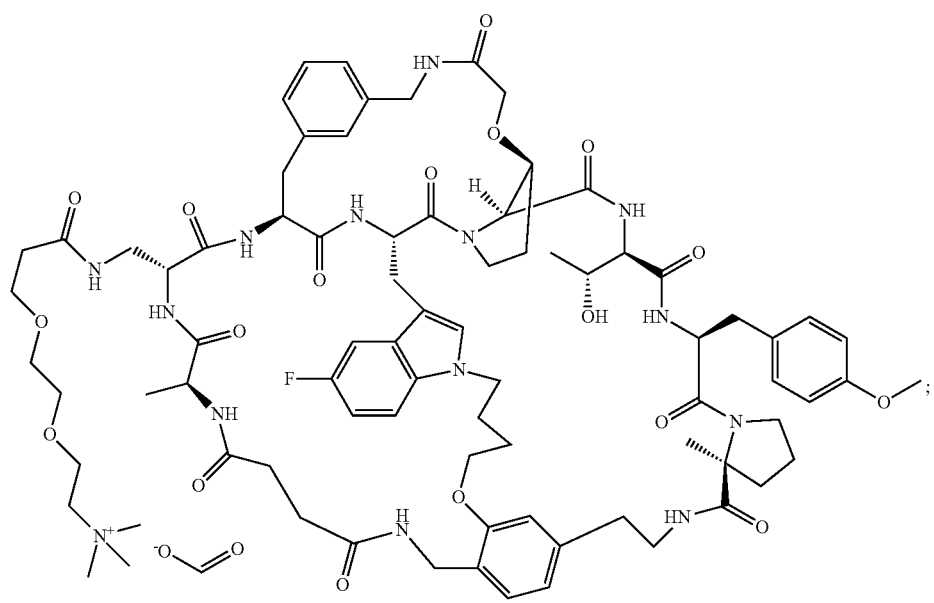

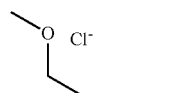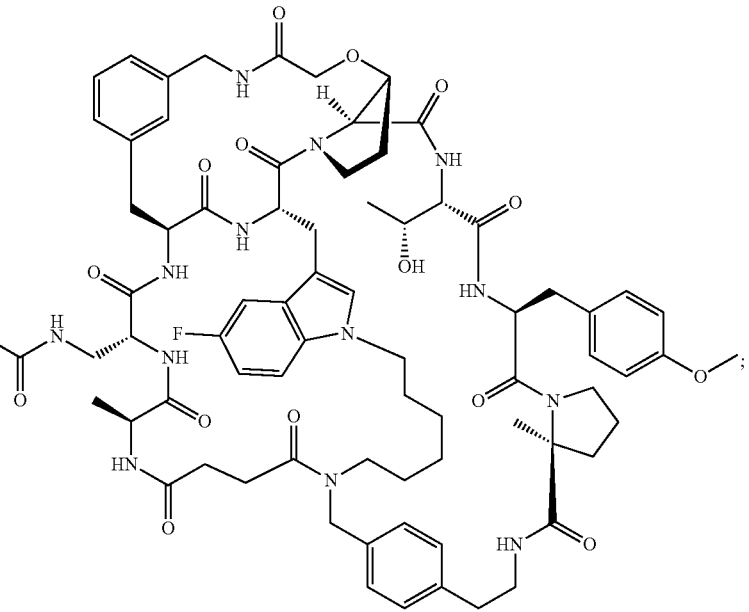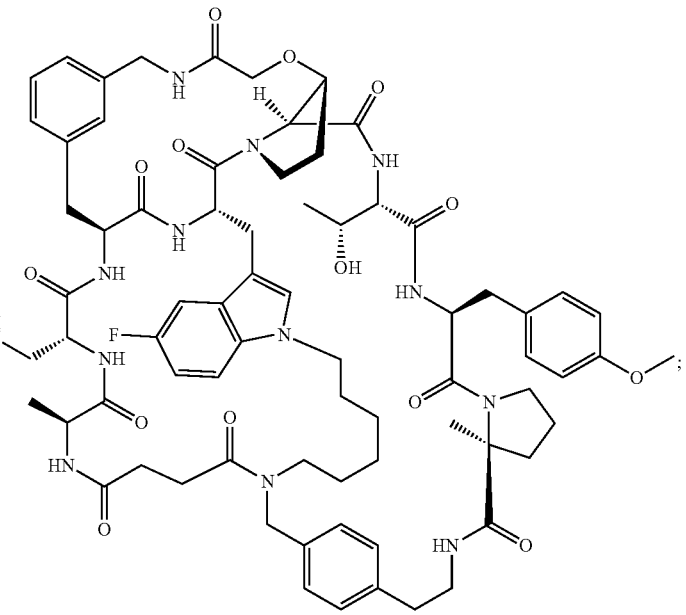

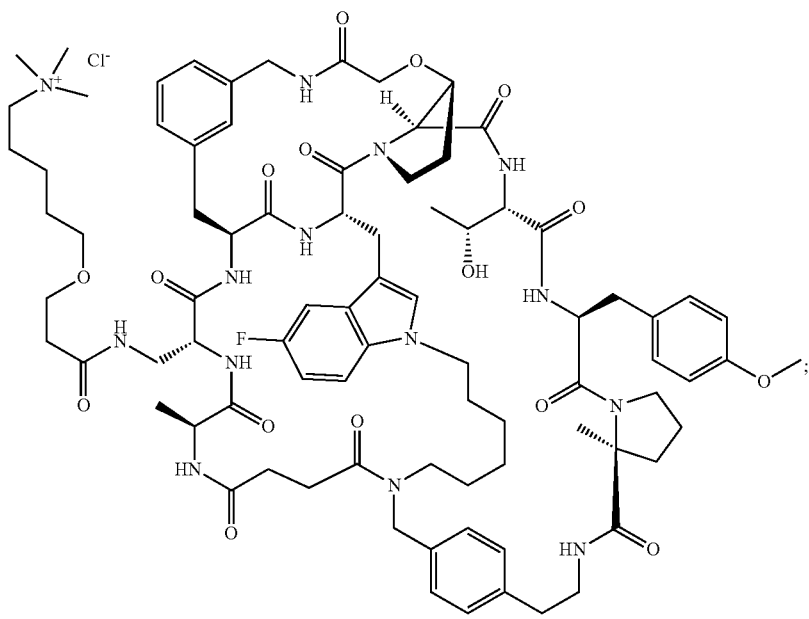
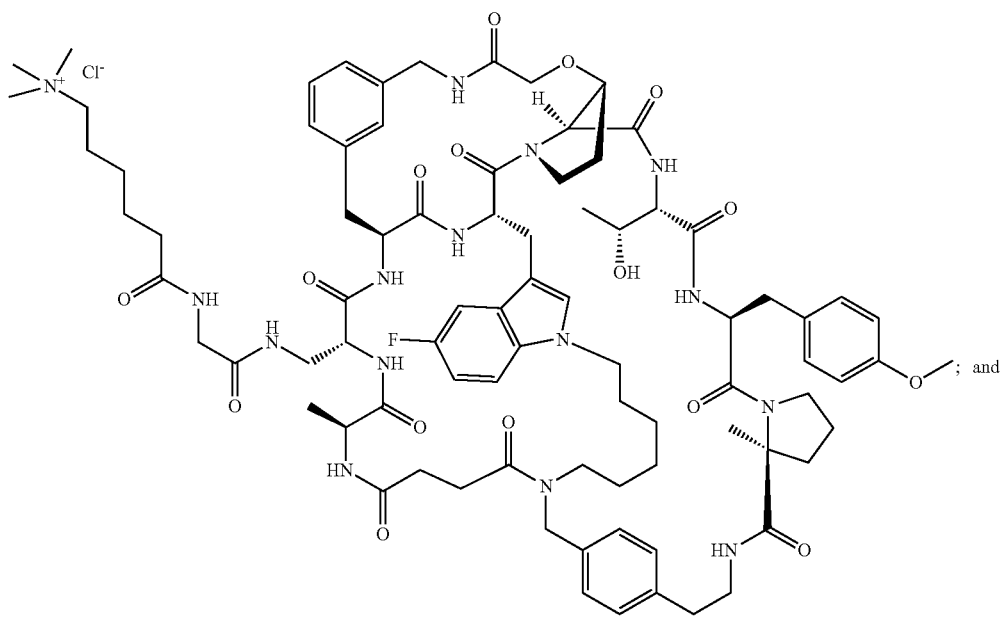

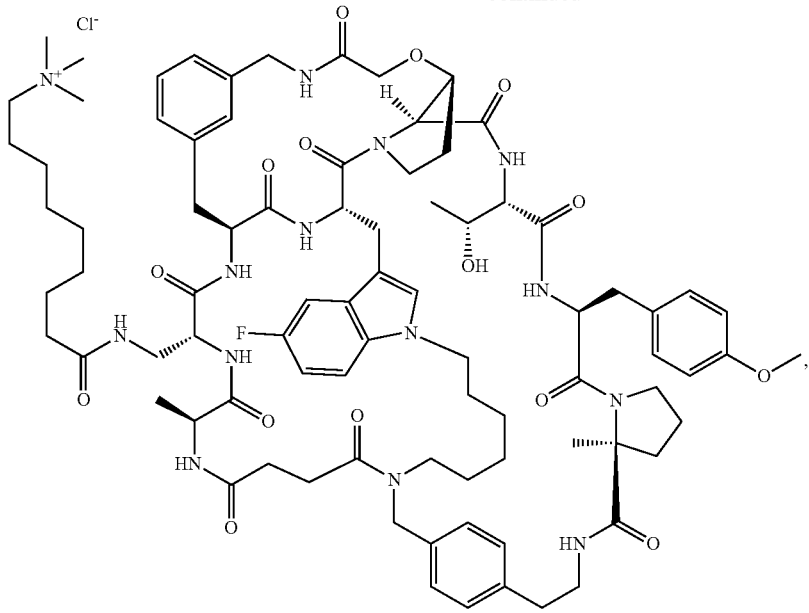 [SMILES: COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCC(=O)N[C@@H](C)C(=O)N[C@H](CNC(=O)CCCCCCCC[N+](C)(C)C)C(=O)N[C@@H](Cc2cccc(c2)CNC(=O)CO4)C(=O)N3)cc1 ; [Cl-]]

or any other pharmaceutically acceptable salt form thereof.

22. A composition comprising at least one compound of claim 2, or a pharmaceutically acceptable salt thereof or freebase form thereof, and at least one pharmaceutically acceptable excipient.

23. A method of treating hypercholesterolemia, comprising administering to a patient in need thereof a therapeutically effective amount of a composition of claim 22.

24. A method of treating hypercholesterolemia, comprising administering to a patient in need thereof a therapeutically effective amount of a compound of claim 2.

25. A compound of claim 15, having the structure of Formula IIE, or a pharmaceutically acceptable salt thereof, Formula IIE

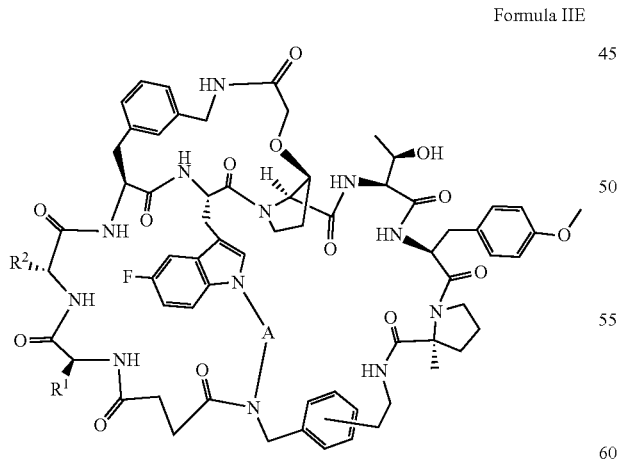

wherein
$R^1$ is selected from:
(a) —H; or
(b) —$(CH_2)_z$—$R^{14A}$, wherein: z is 1-6, and $R^{14A}$ is:
(i) —H;
(ii) —$NH_2$;

(iii) —$N^+H_3$;
(iv) —$N^+(H_3C)_3$;
(v) —NH—C(O)—[$(CH_2)_2$—O—]$_2$—$(CH_2)_2R^{14B}$ wherein $R^{14B}$ is: —$NH_2$; —$N^+H_3$; —$N(CH_3)_2$; or —$N^+(CH_3)_3$;
(vi) —NH—C(O)—[$(CH_2)_{y12}$—O—]$_2$—$(CH_2)_{y13}R^{14B}$ wherein:
y12 and y13 are not both 2 and are independently 2 to 4; and
$R^{14B}$ is: —$NH_2$; —$N^+H_3$; —$N(CH_3)_2$; or —$N^+(CH_3)_3$;
(vii) —NH—C(O)—$(CH_2)_yR^{14C}$, wherein, y=1 to 6 and $R^{14C}$ is —O—$(CH_2)_{3-4}$—$N^+(CH_3)_3$; and
(viii) —NH—C(O)—$(CH_2)_yR^{14C}$, wherein, y=1 to 6 and $R^{14C}$ is:
(ai) —O—$(CH_2)_2$—$N^+(CH_3)_3$;
(aii) —$N^+(CH_3)_3$; or
$R^2$ is selected from:
(a) —H; and
(b) —$(CH_2)_z$—$R^{14A}$, wherein: z is 1-6, and $R^{14A}$ is selected from:
(i) —H;
(ii) —$NH_2$;
(iii) —$N^+H_3$;
(iv) —$N^+(H_3C)_3$;
(v) —NH—C(O)—[$(CH_2)_2$—O—]$_2$—$(CH_2)_2R^{14B}$ wherein $R^{14B}$ is: —$NH_2$; —$N^+H_3$; —$N(CH_3)_2$; or —$N^+(CH_3)_3$;
(vi) —NH—C(O)—[$(CH_2)_{y12}$—O—]$_2$—$(CH_2)_{y13}R^{14B}$ wherein:
y12 and y13 are not both 2 and are independently 2 to 4; and
$R^{14B}$ is: —$NH_2$; —$N^+H_3$; —$N(CH_3)_2$; or —$N^+(CH_3)_3$;
(vii) —NH—C(O)—$(CH_2)_yR^{14C}$, wherein, y=1 to 6 and $R^{14C}$ is —O—$(CH_2)_{3-4}$—$N^+(CH_3)_3$; and (viii) —NH—C(O)—(CH$_2$)$_y$R$^{14C}$, wherein, y=1 to 6 and R$^{14C}$ is:
  (ai) —O—(CH$_2$)$_2$—N$^+$(CH$_3$)$_3$;
  (aii) —N$^+$(CH$_3$)$_2$R$^{14ca}$, wherein R$^{14ca}$ is —CH$_3$ or —(CH$_2$)$_{1-4}$—OCH$_3$;
A is selected from:
(a) —CH$_2$—(CH$_2$)$_y$—CH$_2$—, wherein y is 1 to 6;
(b) a moiety of the formula:

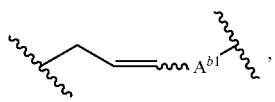

wherein A$^{b1}$ is:
(i) a moiety of the formula:

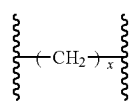

wherein x is 1 to 6; or
(ii) a moiety of the formula:

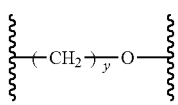

wherein y is 1 to 5; and
(c) a moiety of the formula: —CH$_2$—(CH$_2$)$_m$—O—(CH$_2$)$_n$—, wherein m=1 to 5, and n=0 or 1 to 4.

26. A compound of claim 25, or a pharmaceutically acceptable salt thereof,
wherein
R$^1$ is —(CH$_2$)$_z$—R$^{14A}$, wherein: z is 1-6, and R$^{14A}$ is:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$; or —N$^+$(CH$_3$)$_3$;
  (vi) —NH—C(O)—[(CH$_2$)$_{y12}$—O—]$_2$—(CH$_2$)$_{y13}$R$^{14B}$ wherein:
    y12 and y13 are not both 2 and are independently 2 to 4; and
    R$^{14B}$ is: —NH$_2$; —N$^+$H$_3$; —N(CH$_3$)$_2$; or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{3-4}$—N$^+$(CH$_3$)$_3$; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$;
    (aii) —N$^+$(CH$_3$)$_3$; or
R$^2$ is —(CH$_2$)$_z$—R$^{14A}$, wherein: z is 1-6, and R$^{14A}$ is selected from:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$; or —N$^+$(CH$_3$)$_3$;
  (vi) —NH—C(O)—[(CH$_2$)$_{y12}$—O—]$_2$—(CH$_2$)$_{y13}$R$^{14B}$ wherein:
    y12 and y13 are not both 2 and are independently 2 to 4; and
    R$^{14B}$ is: —NH$_2$; —N$^+$H$_3$; —N(CH$_3$)$_2$; or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{3-4}$—N$^+$(CH$_3$)$_3$; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$;
    (aii) —N$^+$(CH$_3$)$_2$R$^{14ca}$, wherein R$^{14ca}$ is —CH$_3$ or —(CH$_2$)$_{1-4}$—OCH$_3$;
A is —CH$_2$—(CH$_2$)$_y$—CH$_2$—, wherein y is 1 to 6.

27. A compound of claim 26, or a pharmaceutically acceptable salt thereof,
wherein
R$^1$ is —(CH$_2$)$_z$—R$^{14A}$, wherein: z is 1-6, and R$^{14A}$ is:
  (i) —H;
R$^2$ is —(CH$_2$)$_z$—R$^{14A}$, wherein: z is 1-6, and R$^{14A}$ is selected from:
  (i) —H;
  (ii) —NH$_2$;
  (iii) —N$^+$H$_3$;
  (iv) —N$^+$(H$_3$C)$_3$;
  (v) —NH—C(O)—[(CH$_2$)$_2$—O—]$_2$—(CH$_2$)$_2$R$^{14B}$ wherein R$^{14B}$ is: —NH$_2$; —N$^+$H$_3$; —N(CH$_3$)$_2$; or —N$^+$(CH$_3$)$_3$;
  (vi) —NH—C(O)—[(CH$_2$)$_{y12}$—O—]$_2$—(CH$_2$)$_{y13}$R$^{14B}$ wherein:
    y12 and y13 are not both 2 and are independently 2 to 4; and
    R$^{14B}$ is: —NH$_2$; —N$^+$H$_3$; —N(CH$_3$)$_2$; or —N$^+$(CH$_3$)$_3$;
  (vii) —NH—C(O)—(CH$_2$)$_y$R$^{14C}$, wherein, y=1 to 6 and R$^{14C}$ is —O—(CH$_2$)$_{3-4}$—N$^+$(CH$_3$)$_3$; and
  (viii) —NH—C(O)—(CH$_2$)$_y$R$^{14C}$, wherein, y=1 to 6 and R$^{14C}$ is:
    (ai) —O—(CH$_2$)$_2$—N$^+$(CH$_3$)$_3$;
    (aii) —N$^+$(CH$_3$)$_2$R$^{14ca}$, wherein R$^{14ca}$ is —CH$_3$ or —(CH$_2$)$_{1-4}$—OCH$_3$;
A is —CH$_2$—(CH$_2$)$_y$—CH$_2$—, wherein y is 1 to 6.

28. A compound of claim 1, which is selected from the group consisting of:

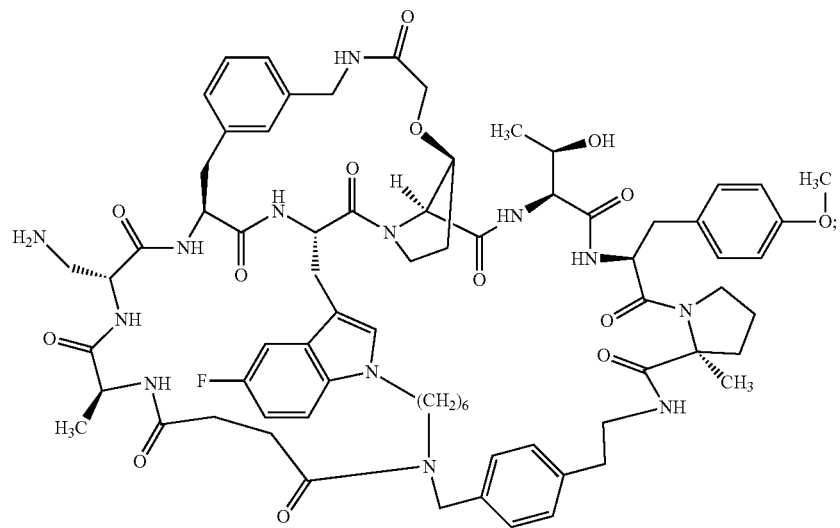
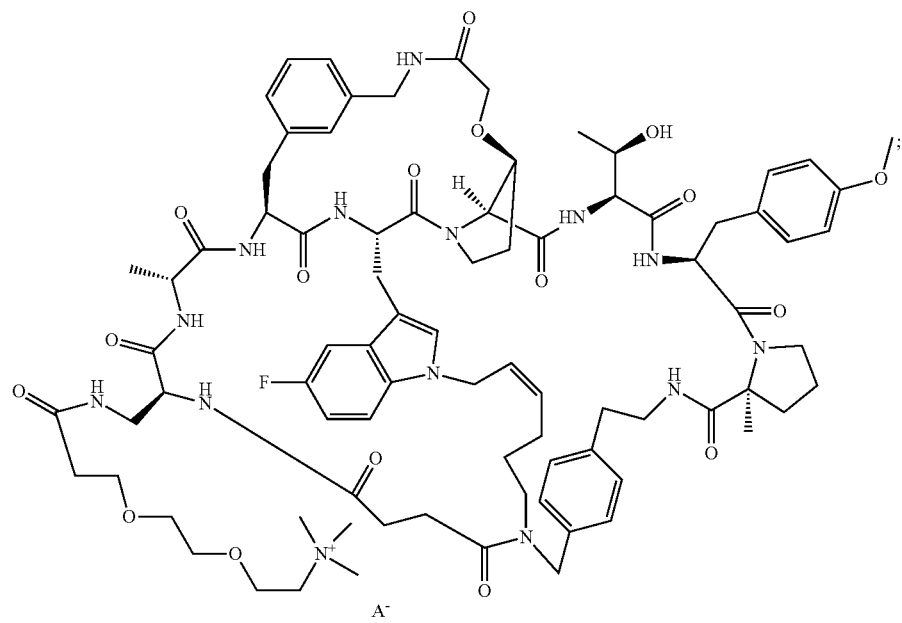

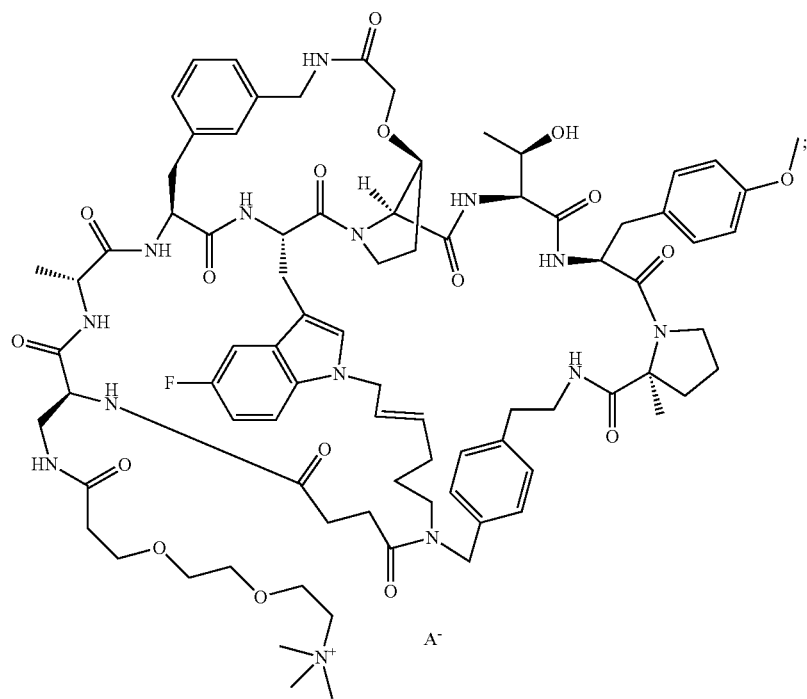
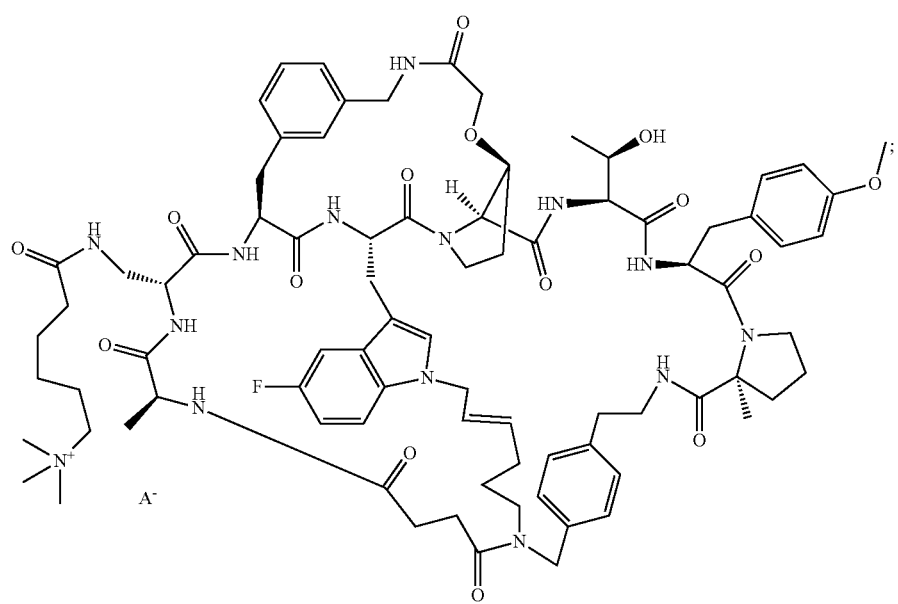

-continued
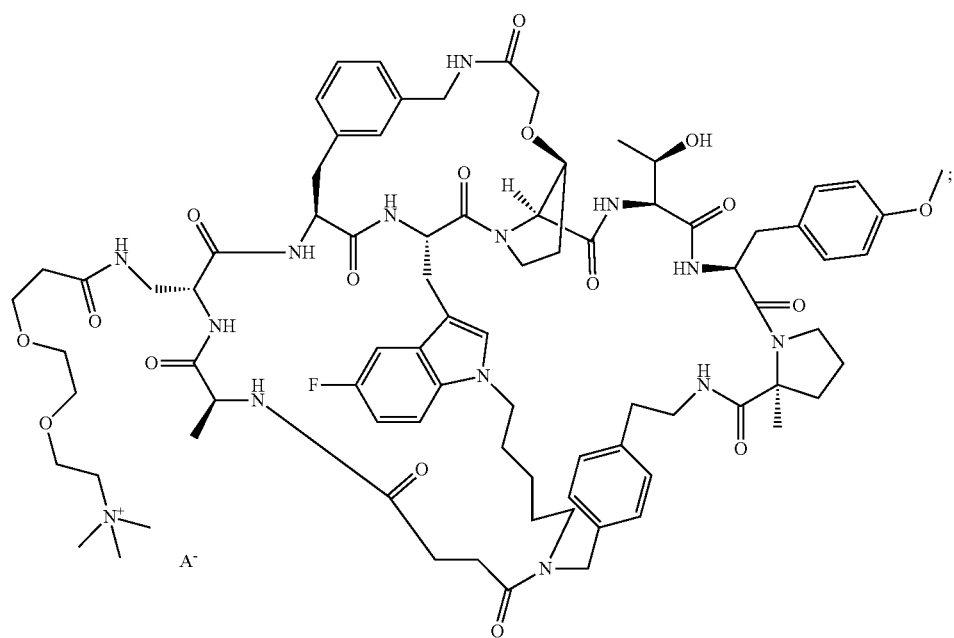
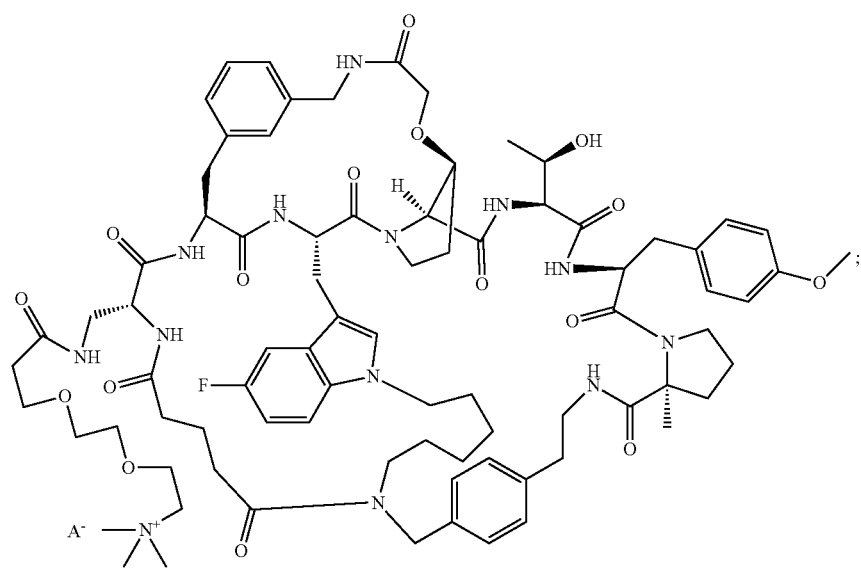

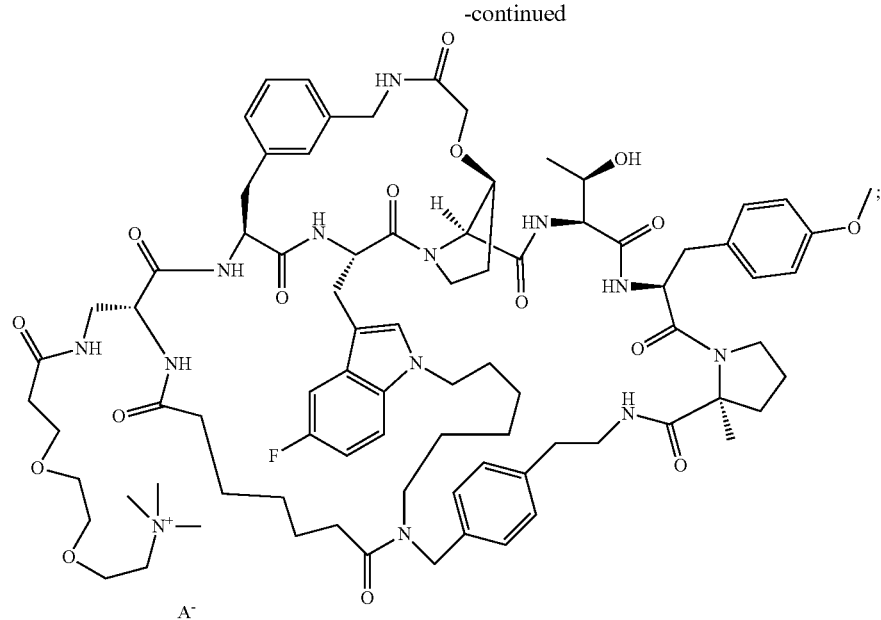
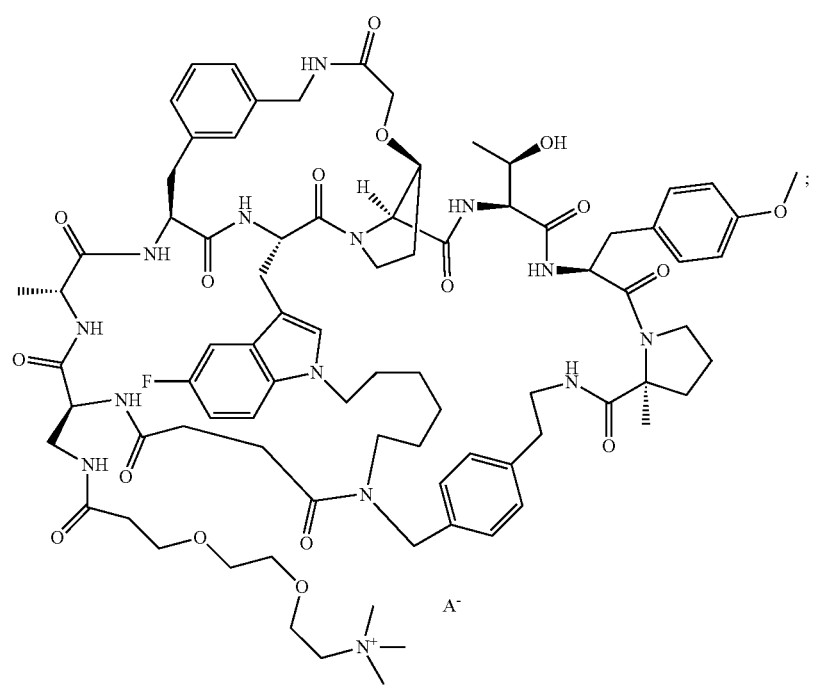

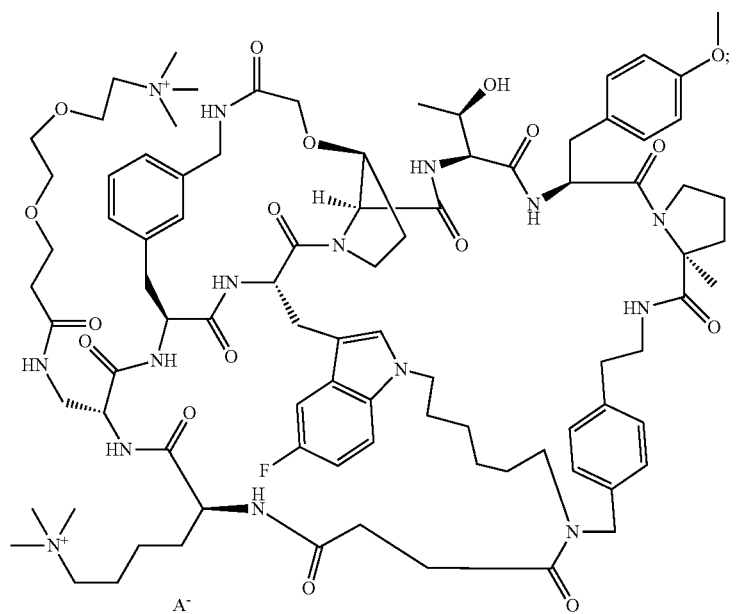
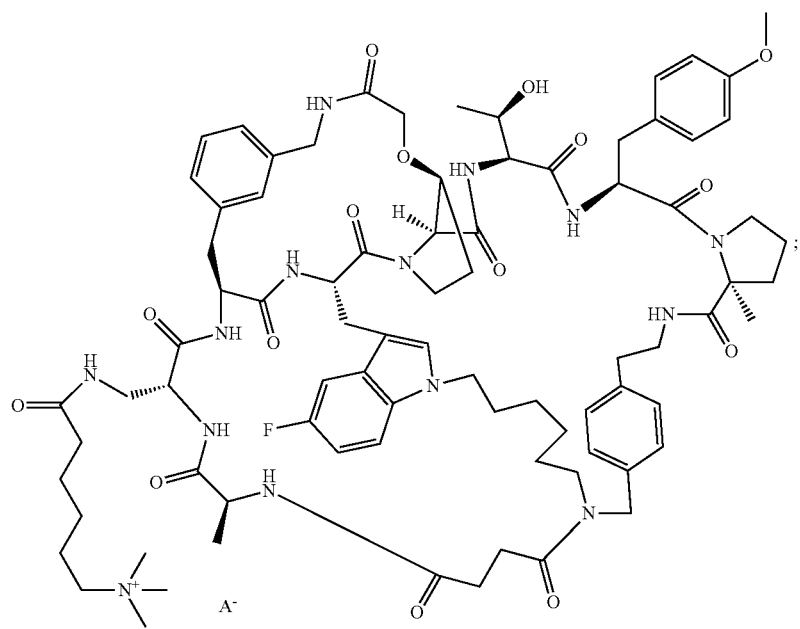

-continued
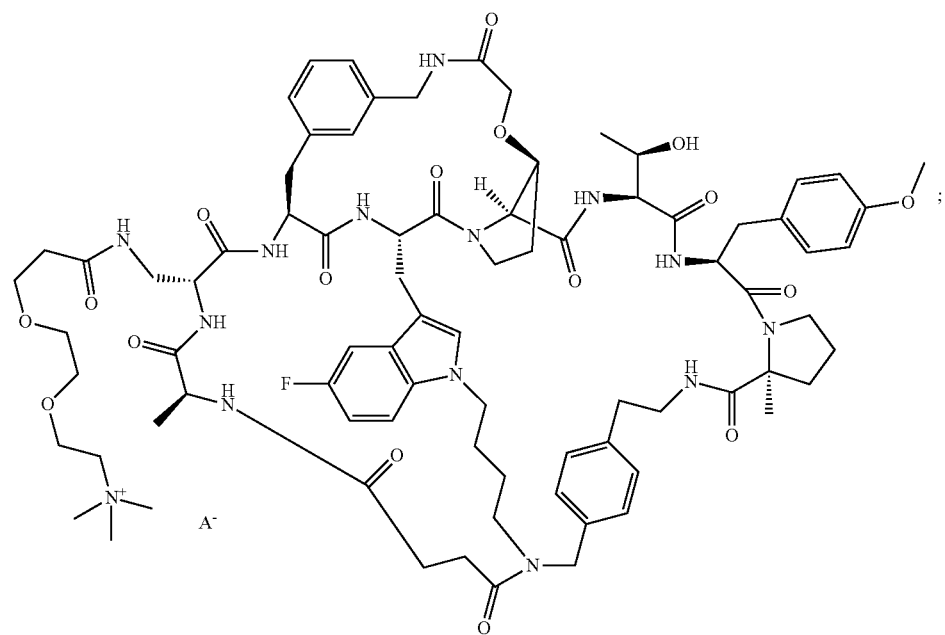
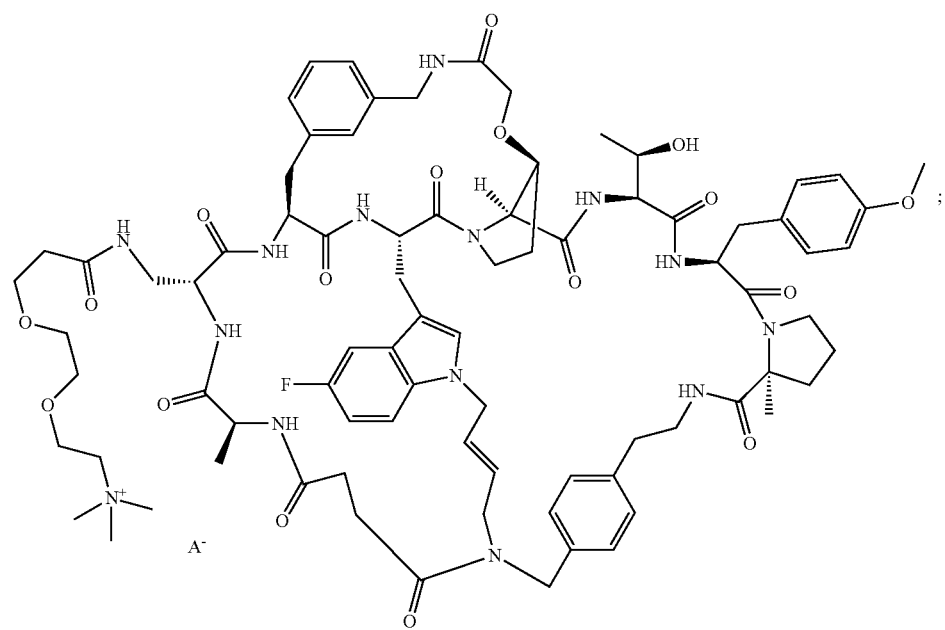

-continued
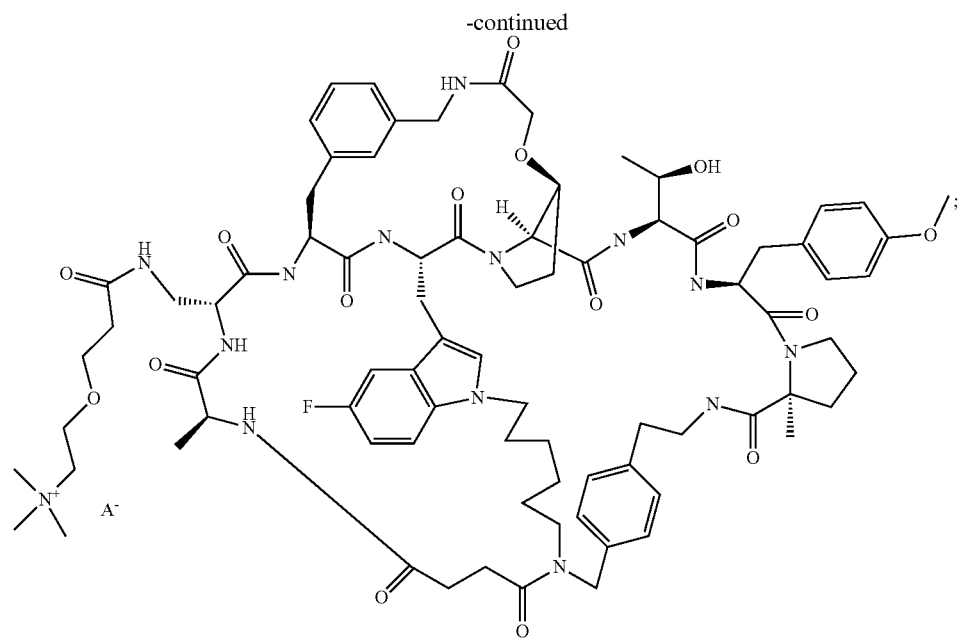
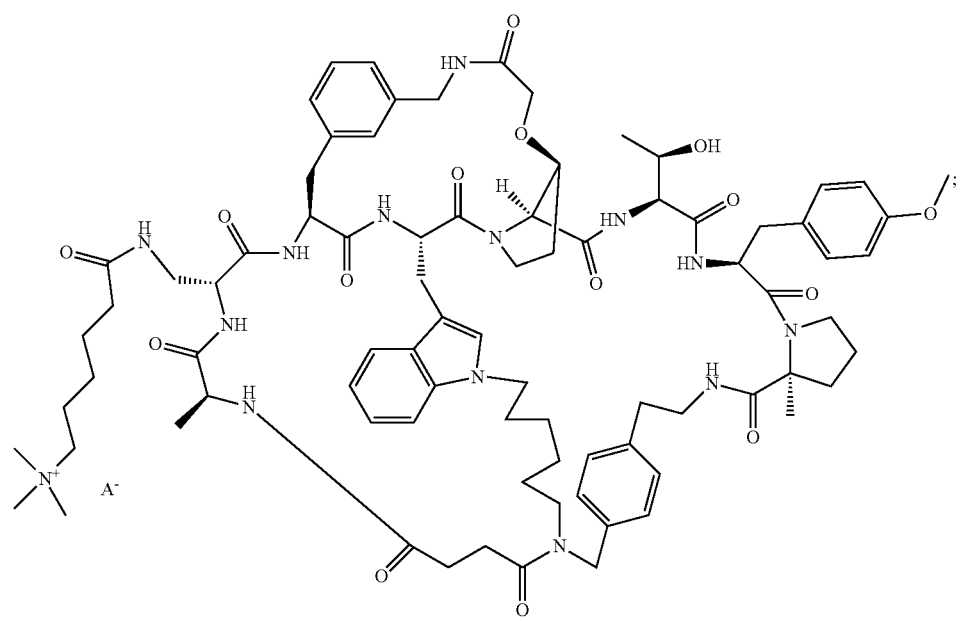

-continued
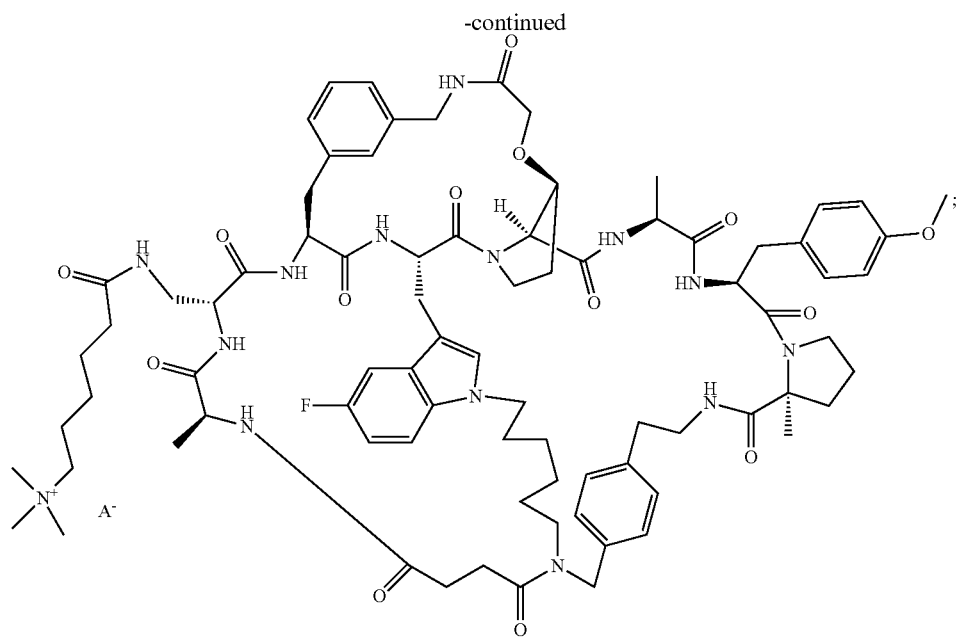
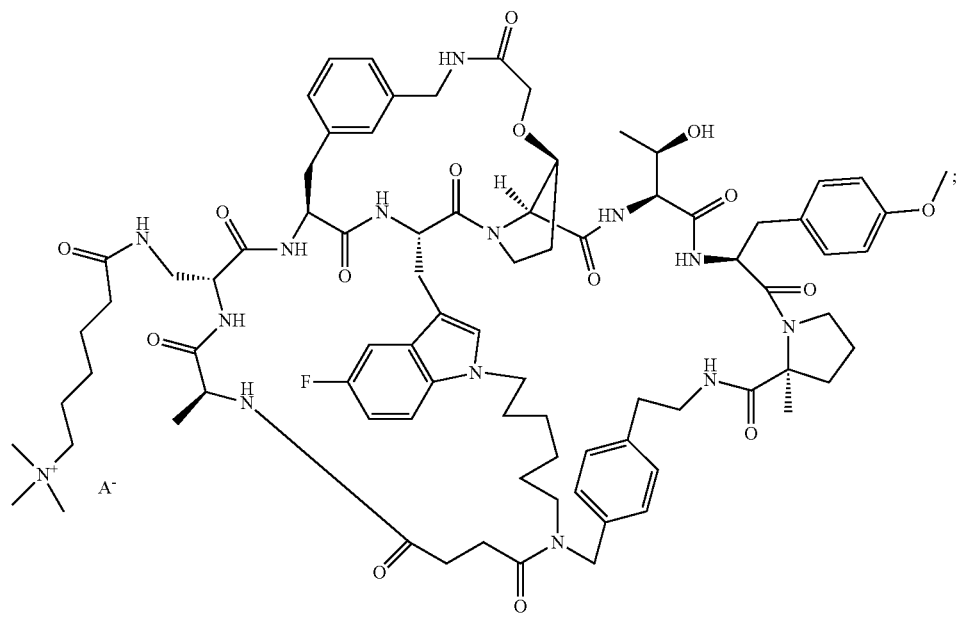

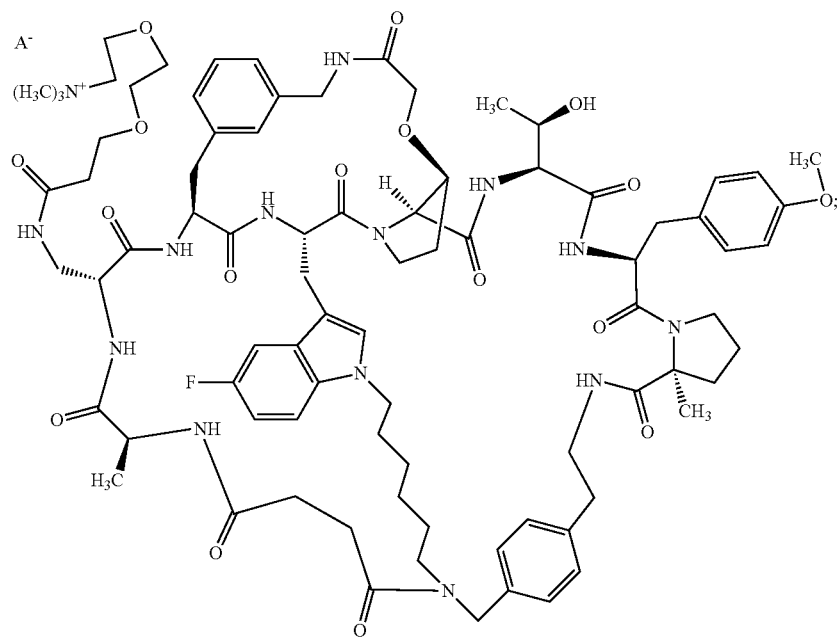
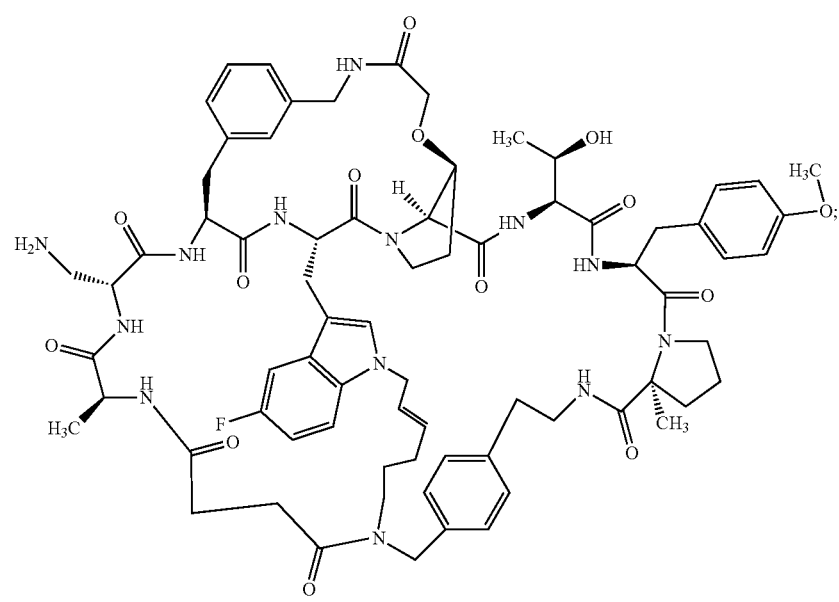

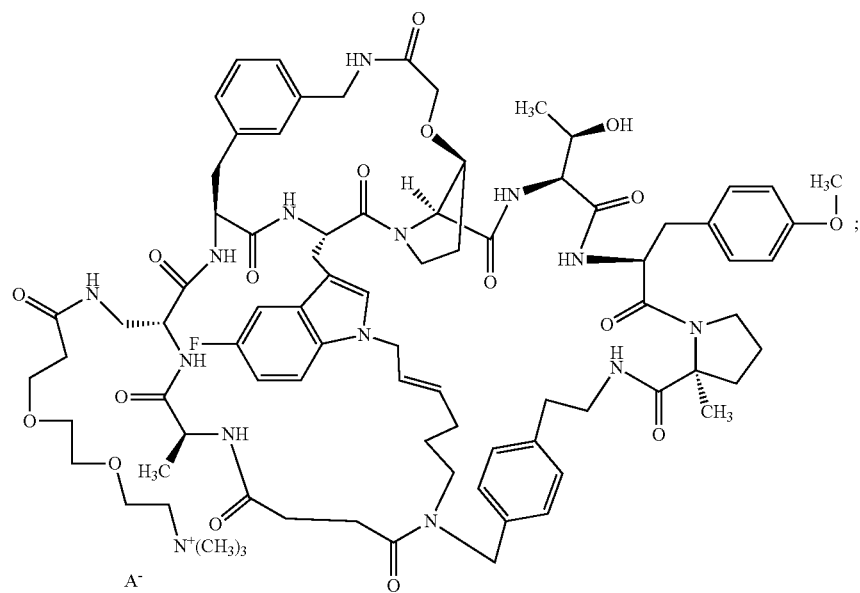
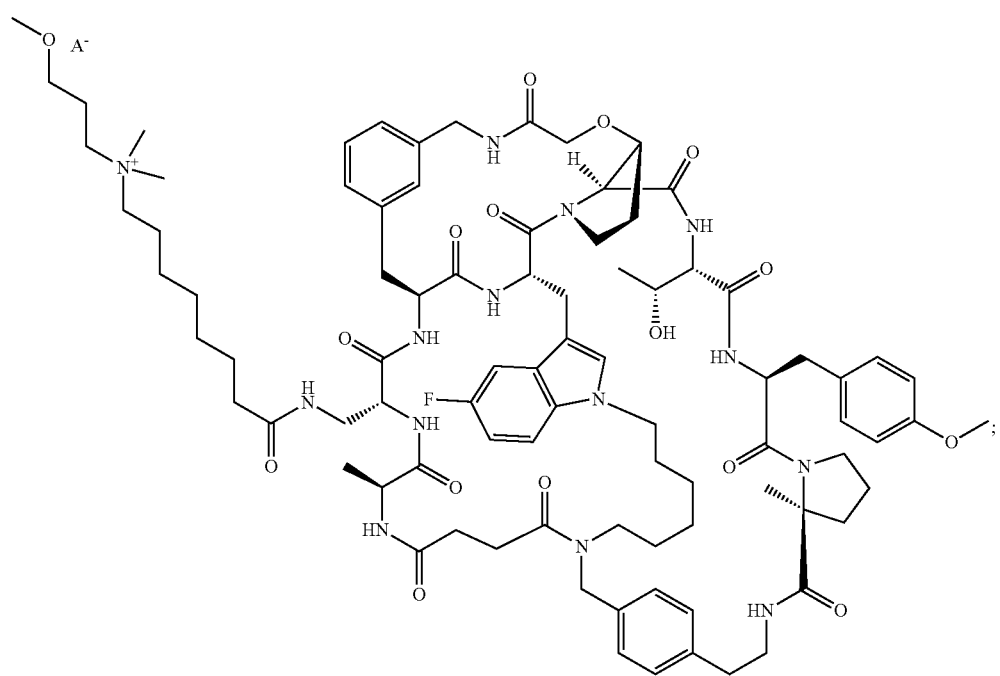

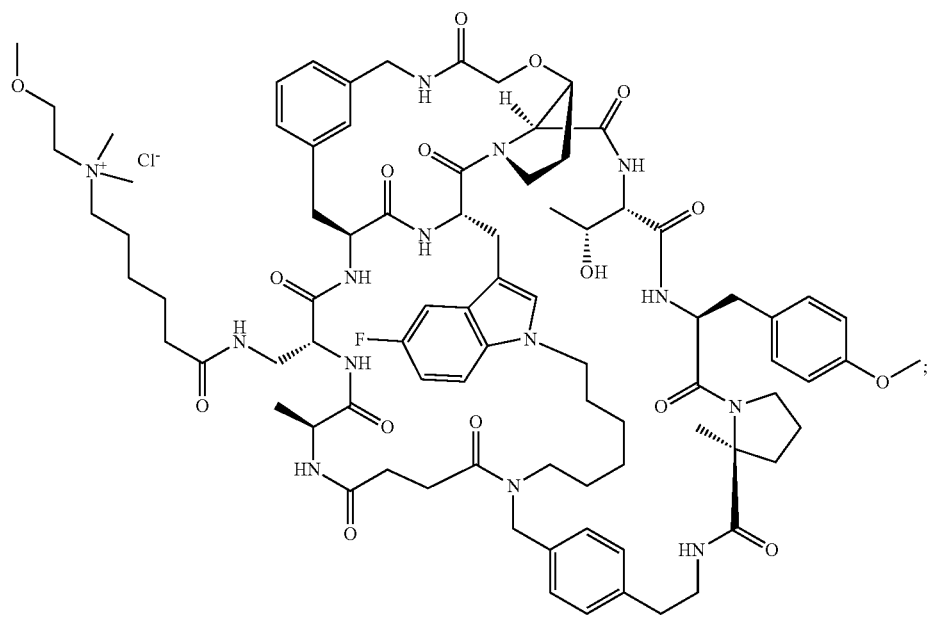
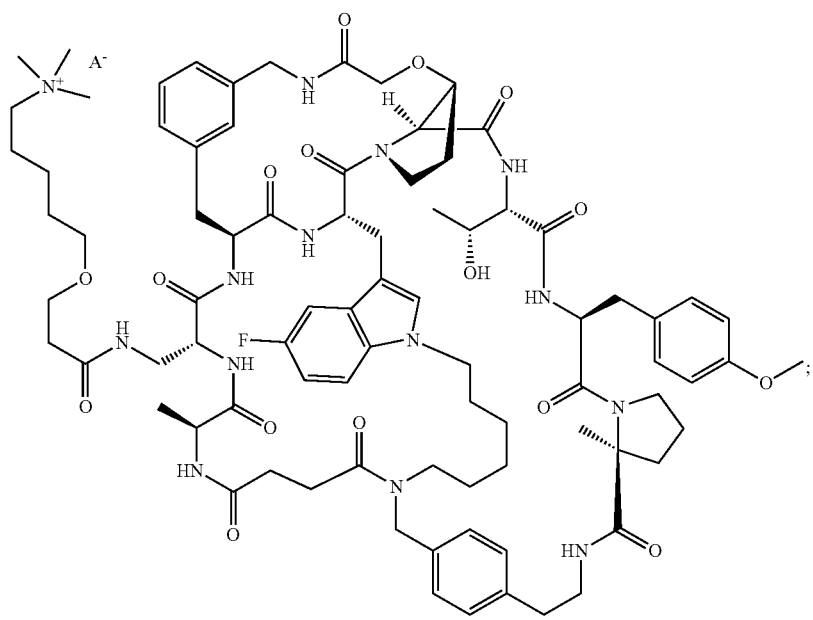

-continued
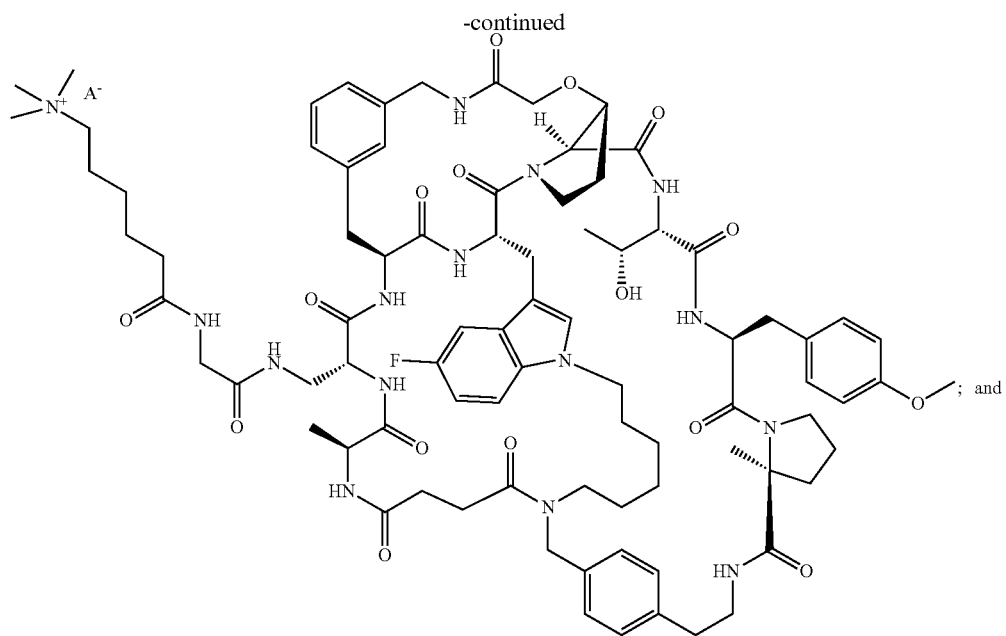
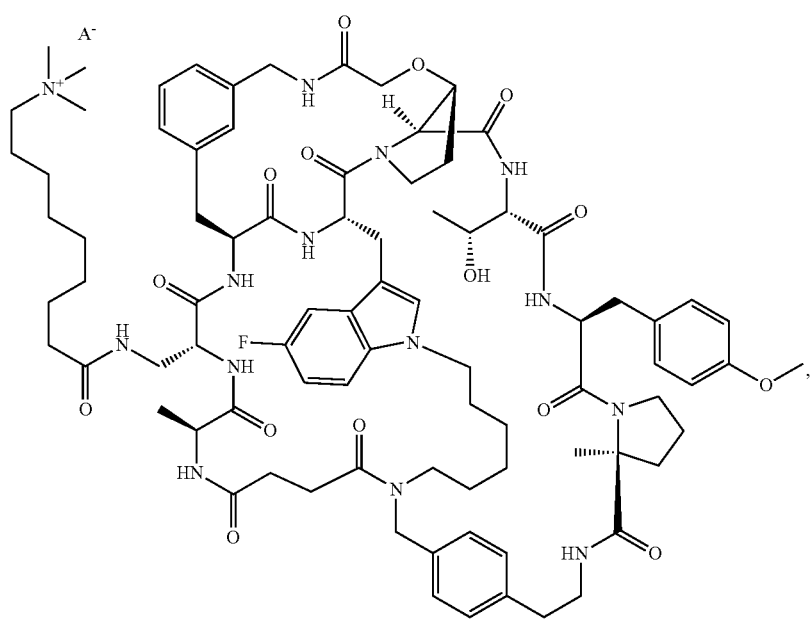
wherein A⁻ is a pharmaceutically acceptable anion.

29. The compound having the structure:

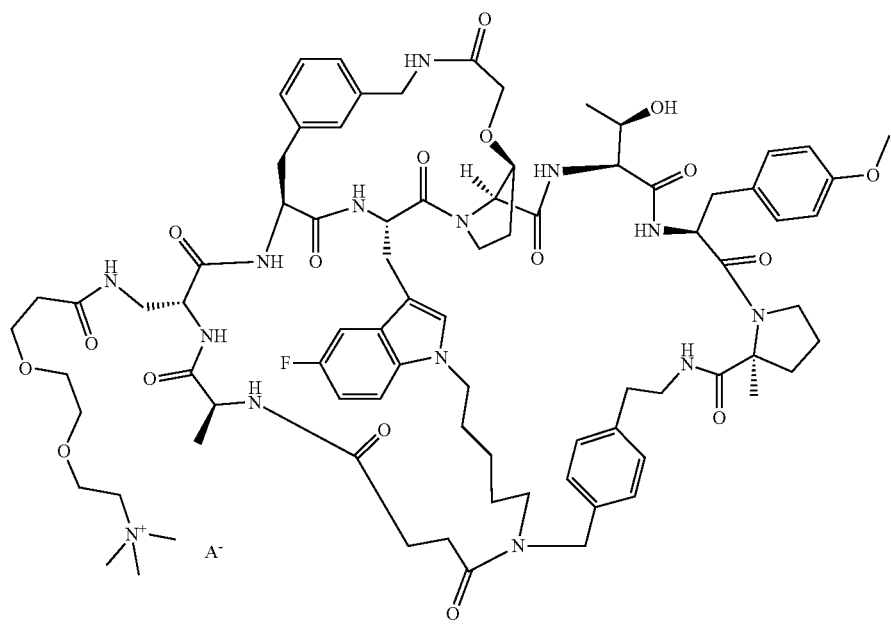

wherein A⁻ is a pharmaceutically acceptable anion.

30. A composition comprising the compound of claim 29, and at least one pharmaceutically acceptable excipient.

31. A method of treating hypercholesterolemia, comprising administering to a patient in need thereof a therapeutically effective amount of a composition of claim 30.

32. A compound of claim 29, wherein the compound is:

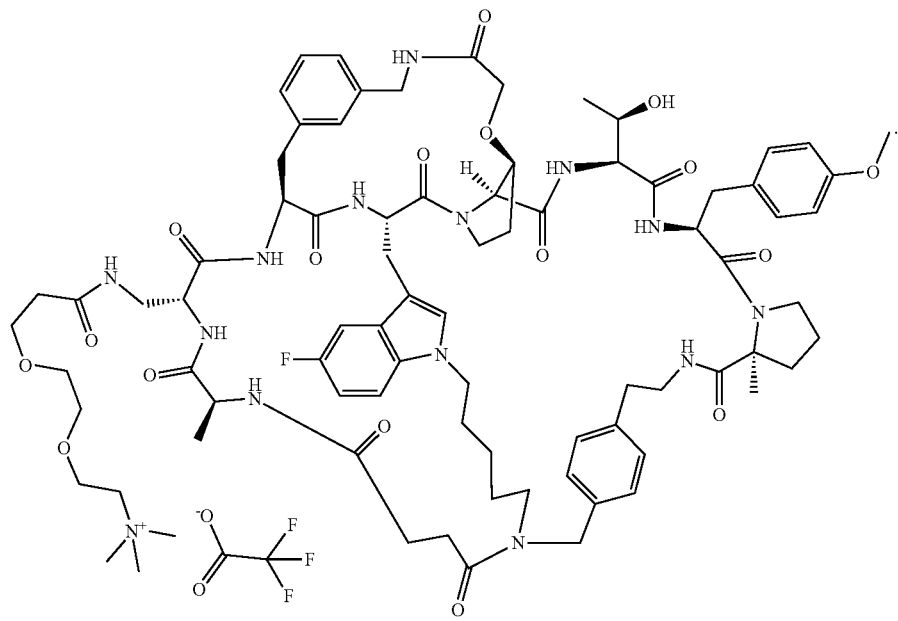

33. A composition comprising the compound of claim 32, and at least one pharmaceutically acceptable excipient.

34. A method of treating hypercholesterolemia, comprising administering to a patient in need thereof a therapeutically effective amount of a composition of claim 33.

35. The compound having the structure:

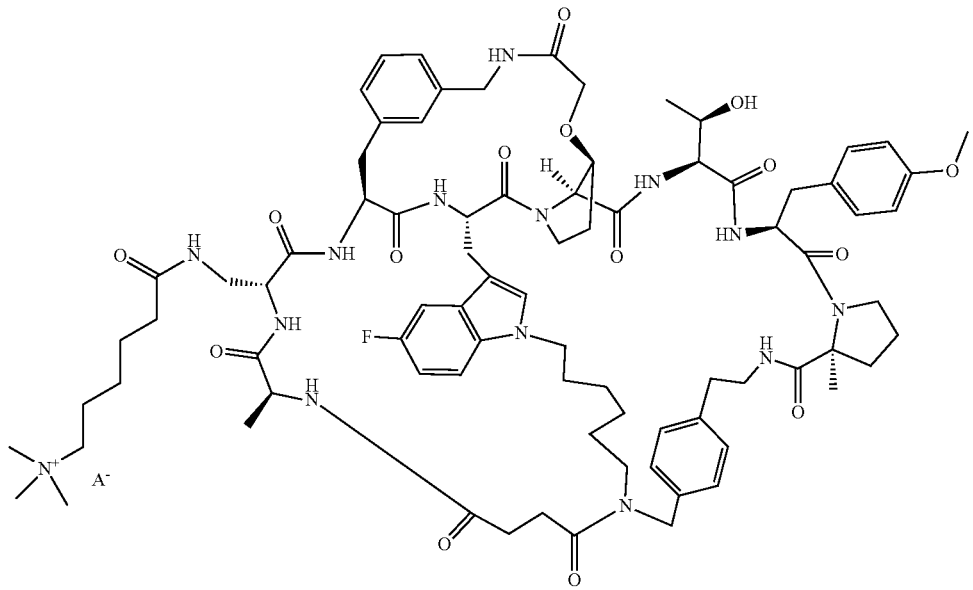

wherein A⁻ is a pharmaceutically acceptable anion.

36. A composition comprising the compound of claim 35, and at least one pharmaceutically acceptable excipient.

37. A method of treating hypercholesterolemia, comprising administering to a patient in need thereof a therapeutically effective amount of a composition of claim 36.

38. A compound of claim 35, wherein the compound is:

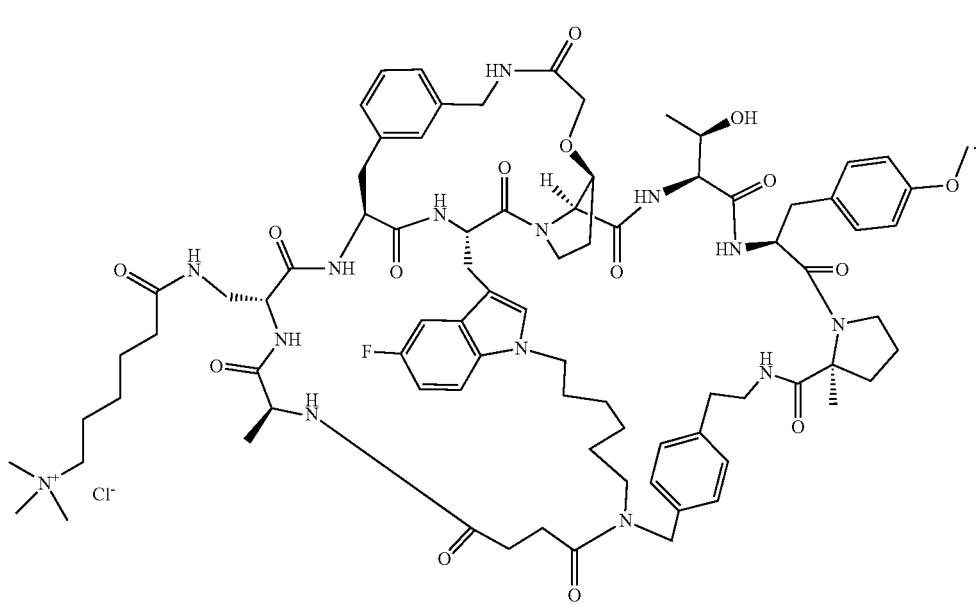

39. A composition comprising the compound of claim 38, and at least one pharmaceutically acceptable excipient.

40. A method of treating hypercholesterolemia, comprising administering to a patient in need thereof a therapeutically effective amount of a composition of claim 39.

41. The compound having the structure:

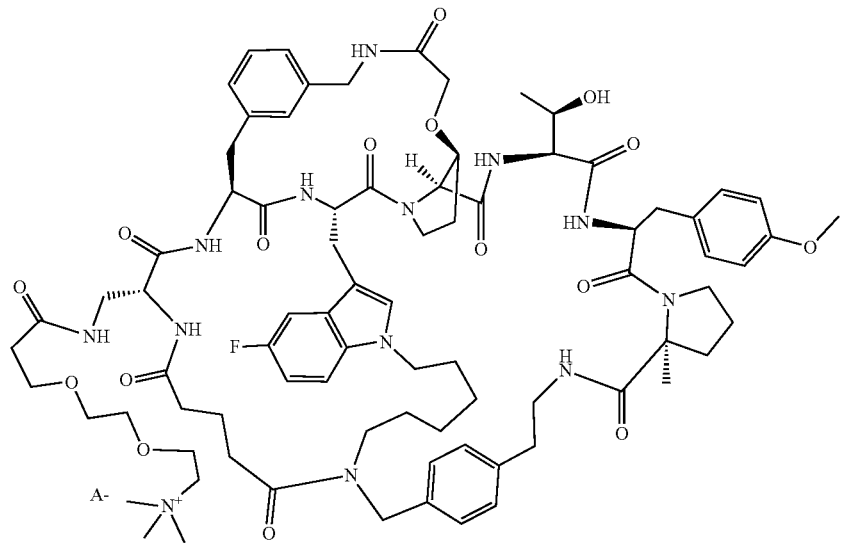

wherein A⁻ is a pharmaceutically acceptable anion.

42. A composition comprising the compound of claim 41, and at least one pharmaceutically acceptable excipient.

43. A method of treating hypercholesterolemia, comprising administering to a patient in need thereof a therapeutically effective amount of a composition of claim 42.

44. A compound of claim 41, wherein the compound is:

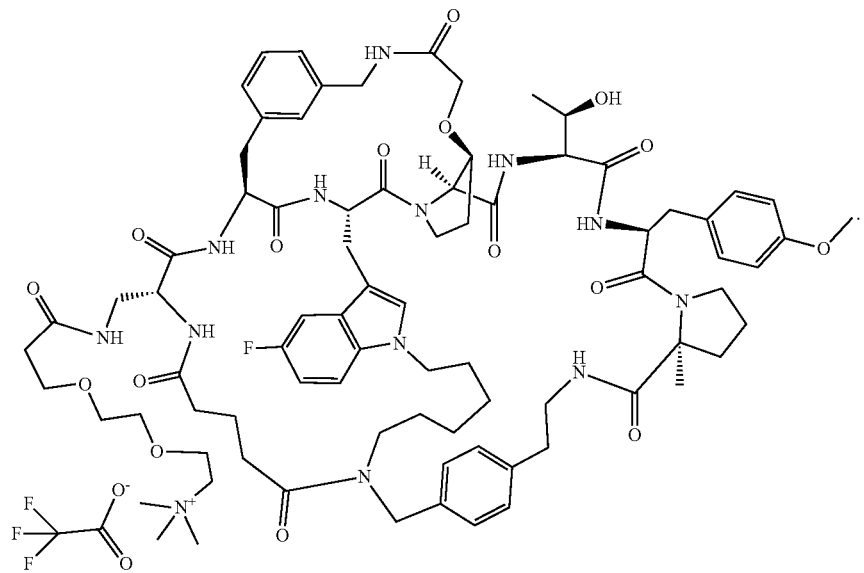 [SMILES: O=C([O-])C(F)(F)F ; COc1ccc(C[C@@H]2NC(=O)[C@H]([C@@H](C)O)NC(=O)[C@@H]3[C@@H]4CCN3C(=O)[C@@H]3Cc5cn(c6ccc(F)cc56)CCCCCCN(Cc5ccc(cc5)CCNC(=O)[C@]5(C)CCCN5C2=O)C(=O)CCCC(=O)N[C@H](CNC(=O)CCOCCOCC[N+](C)(C)C)C(=O)N[C@@H](Cc2cccc(c2)CNC(=O)CO4)C(=O)N3)cc1]

45. A composition comprising the compound of claim 44, and at least one pharmaceutically acceptable excipient.

46. A method of treating hypercholesterolemia, comprising administering to a patient in need thereof a therapeutically effective amount of a composition of claim 45.

47. A compound of claim 13 wherein $D^2$ is:

(a) a moiety of the formula:

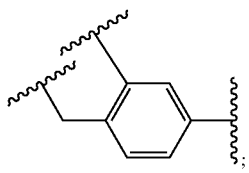

or (b) a moiety of the formula:

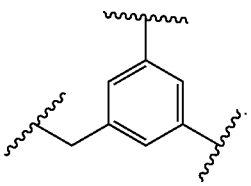

48. A compound of claim 14 wherein $D^2$ is:

(a) a moiety of the formula:

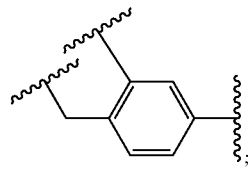 [SMILES: *Cc1ccc(*)cc1*]

or (b) a moiety of the formula:

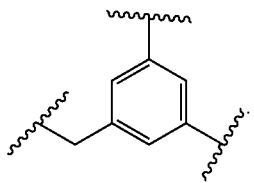 [SMILES: *Cc1cc(*)cc(*)c1]

* * * * *

Disclaimer

11,427,616 B2 - Harold B. Wood, Westfield, NJ (US); Hubert B. Josien, Jersey City, NY (US); Thomas Joseph Tucker, North Wales, PA (US); Angela Dawn Kerekes, Plainfiled, NY (US); Ling Tong, Warren, NJ (US); Abbas M. Walji, Lansdale, PA (US); Anilkumar G. Nair, Rahway, NY (US); Fa-Xiang Ding, Staten Island, NY (US); Elisabetta Bainchi, Rome IT); Danila Branca, Pomezia (IT)); Chengwei Wu, Ambler, PA (US); Yusheng Xiong, Plainsboro, NJ(US); Sookhee Nicole Ha, Warren, NJ (US) Jian Liu, Edison, NJ (US); Sobhana Babu Boga, Karnataka (IN). PCSK9 ANTAGONIST COMPOUNDS. Patent dated August 30, 2022. Disclaimer filed May 8, 2023, by the assignee, Merck Sharp & Dohme LLC.

I hereby disclaim the following complete Claims 21 and 28 of said patent.

*(Official Gazette, June 25, 2024)*